US012637408B2

(12) United States Patent
Petrie et al.

(10) Patent No.: US 12,637,408 B2
(45) Date of Patent: May 26, 2026

(54) LIPID COMPOSITIONS COMPRISING TRIACYLGLYCEROL WITH LONG-CHAIN POLYUNSATURATED FATTY ACIDS

(71) Applicants: Commonwealth Scientific and Industrial Research Organisation, Acton (AU); Grains Research and Development Corporation, Barton (AU); Nuseed Nutritional Australia Pty Ltd, Laverton North (AU)

(72) Inventors: James Robertson Petrie, Goulburn (AU); Surinder Pal Singh, Downer (AU); Pushkar Shrestha, Lawson (AU); Jason Timothy McAllister, Portarlington (AU); Robert Charles de Feyter, Monash (AU); Malcolm David Devine, Vernon (CA); Xue-Rong Zhou, Harrison (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barlon (AU); NUSEED NUTRITIONAL AUSTRALIA PTY LTD., Laverton North (AU)

( * ) Notice: Subject to any disclaimer, the term of this patent is extended or adjusted under 35 U.S.C. 154(b) by 84 days.

(21) Appl. No.: 18/334,880

(22) Filed: Jun. 14, 2023

(65) Prior Publication Data

US 2023/0416186 A1      Dec. 28, 2023

Related U.S. Application Data

(60) Continuation of application No. 17/063,678, filed on Oct. 5, 2020, now Pat. No. 11,718,577, which is a
(Continued)

(30) Foreign Application Priority Data

Dec. 18, 2013 (AU) ................................ 2013905033
Jun. 27, 2014 (AU) ................................ 2014902471

(51) Int. Cl.
*C11B 1/10* (2006.01)
*A01H 5/00* (2018.01)
(Continued)

(52) U.S. Cl.
CPC ............. *C07C 69/587* (2013.01); *A01H 5/00* (2013.01); *A23D 9/00* (2013.01); *A61K 31/20* (2013.01);
(Continued)

(58) Field of Classification Search
CPC ...... C07C 69/587; C12N 15/8247; C11B 1/10
See application file for complete search history.

(56) References Cited

U.S. PATENT DOCUMENTS

| | | | | |
|---|---|---|---|---|
| 7,834,250 B2 * | 11/2010 | Singh | ........................ | A61P 3/02 |
| | | | | 800/306 |
| 2010/0227924 A1 * | 9/2010 | Cirpus | ............... | C12N 15/8247 |
| | | | | 536/23.6 |

FOREIGN PATENT DOCUMENTS

WO      WO-2013185184 A2 *  12/2013   .............  A01H 1/104

OTHER PUBLICATIONS

Feb. 25, 2023 First Office Action issued in connection with Chinese Patent Application 202010034905.6 including English language translation thereof.

(Continued)

*Primary Examiner* — Yate' K Cutliff
(74) *Attorney, Agent, or Firm* — Gary J. Gershik

(57) ABSTRACT

The present invention relates to lipid comprising docosapentaenoic acid and/or docosahexaenoic acid wherein the
(Continued)

Figure 1:
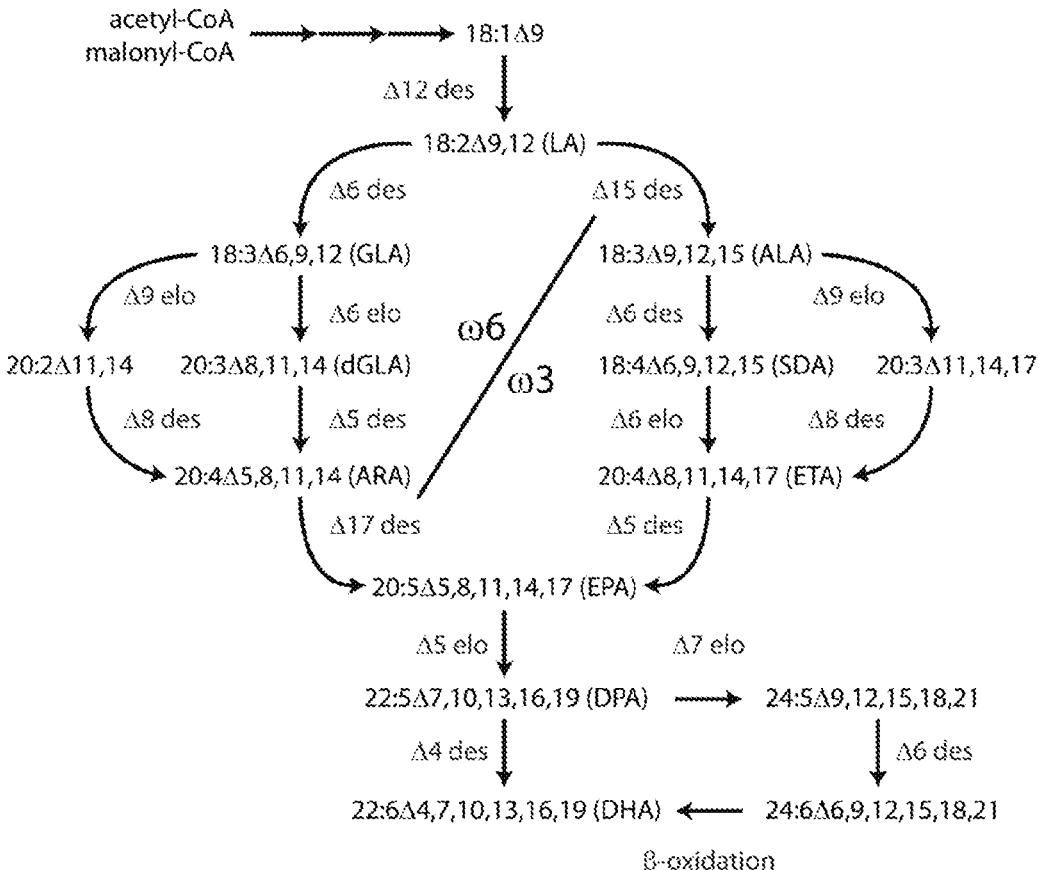

docosapentaenoic acid and/or docosahexaenoic acid may be preferentially esterified at the sn-2 position of triacylglycerol, and processes for producing and using the lipid.

9 Claims, 10 Drawing Sheets

Specification includes a Sequence Listing.

Related U.S. Application Data continuation-in-part of application No. 15/982,634, filed on May 17, 2018, now Pat. No. 10,793,507, and a continuation-in-part of application No. 16/220,695, filed on Dec. 14, 2018, now Pat. No. 10,800,729, said application No. 15/982,634 is a continuation of application No. 14/975,333, filed on Dec. 18, 2015, now Pat. No. 10,005,713, which is a continuation-in-part of application No. PCT/AU2015/050340, filed on Jun. 18, 2015, and a continuation-in-part of application No. 14/743,531, filed on Jun. 18, 2015, now Pat. No. 9,718,759, which is a division of application No. 14/575,756, filed on Dec. 18, 2014, now Pat. No. 9,725,399, and a continuation-in-part of application No. PCT/AU2014/050433, filed on Dec. 18, 2014, said application No. 16/220,695 is a continuation of application No. 15/406,099, filed on Jan. 13, 2017, now Pat. No. 10,190,073, which is a division of application No. 14/575,756, filed on Dec. 18, 2014, now Pat. No. 9,725,399.

(51) Int. Cl.

| | |
|---|---|
| *A23D 9/00* | (2006.01) |
| *A61K 31/20* | (2006.01) |
| *A61K 31/201* | (2006.01) |
| *A61K 31/202* | (2006.01) |
| *A61K 31/23* | (2006.01) |
| *A61K 31/232* | (2006.01) |
| *A61K 36/31* | (2006.01) |
| *C07C 69/587* | (2006.01) |
| *C11B 3/02* | (2006.01) |
| *C11B 3/04* | (2006.01) |
| *C11B 3/10* | (2006.01) |
| *C11B 3/12* | (2006.01) |
| *C11B 7/00* | (2006.01) |
| *C11C 3/00* | (2006.01) |
| *C12N 15/52* | (2006.01) |
| *C12N 15/82* | (2006.01) |

(52) U.S. Cl.
  CPC .......... *A61K 31/201* (2013.01); *A61K 31/202* (2013.01); *A61K 31/23* (2013.01); *A61K 31/232* (2013.01); *A61K 36/31* (2013.01); *C11B 1/10* (2013.01); *C11B 3/02* (2013.01); *C11B 3/04* (2013.01); *C11B 3/10* (2013.01); *C11B 3/12* (2013.01); *C11B 7/0075* (2013.01); *C11C 3/003* (2013.01); *C12N 15/52* (2013.01); *C12N 15/8247* (2013.01); *A61K 2236/00* (2013.01)

(56) References Cited

OTHER PUBLICATIONS

Jul. 18, 2023 Rejection Decision issued in connection with Brazilian Patent Application BR1120160145089 including English language translation thereof.
Oct. 10, 2023 Written Opinion issued in connection with Brazilian Patent Application Brazilian Patent Application 1220230128060 (Divisional of BR BR1120160145089) including English language translation thereof.
Mar. 12, 2024 Office Action issued in connection with Japanese patent application 2023-017919 (Divisional of JP 7225293) including English language translation thereof.
Feb. 20, 2024 Written Opinion issued in connection with Chilean Patent Application 201903105 (Divisional of CL 64970) including English language translation thereof.
May 7, 2024 Written Opinion issued in connection with Brazilian patent application 1220230128060 (Divisional of Br BR1120160145089) including English language translation thereof.
May 31, 2024 Office Action issued in connection with European Patent Application 14870813.4.
Jul. 10, 2024 Office Action issued in connection with Argentine Patent Application P190102974 (Divisional of AR AR098831B1) including English language translation thereof.
Jul. 11, 2024 Office Action issued in connection with Argentine Patent Application P190102975 (Divisional of AR AR098831B1) including English language translation thereof.
Sep. 30, 2024 Response to the May 31, 2024 Office Action filed in connection with European patent application 14870813.4.
Oct. 29, 2024 Office Action issued in connection with Brazilian patent application 1220230128060 (Divisional of BR BR1120160145089) including English language translation thereof.
First Information Disclosure Statement Substitute Form PTO-1449 submitted Jun. 29, 2022 and initialed by Examiner on Aug. 29, 2022 in connection with U.S. Appl. No. 17/063,678.
Second Information Disclosure Statement Substitute Form PTO-1449 submitted June 29, 2022 and initialed by Examiner on August 29, 2022 in connection with U.S. Appl. No. 17/063,678.
Third Information Disclosure Statement Substitute Form PTO-1449 submitted Jun. 29, 2022 and initialed by Examiner on Aug. 29, 2022 in connection with U.S. Appl. No. 17/063,678.
Fourth Information Disclosure Statement Substitute Form PTO-1449 submitted Mar. 1, 2023 and initialed by Examiner on Mar. 15, 2023 in connection with U.S. Appl. No. 17/063,678.
Jan. 20, 2022 Notice of References Cited issued in connection with U.S. Appl. No. 17/063,678.

* cited by examiner

A)

B)

Figure 7

LIPID COMPOSITIONS COMPRISING TRIACYLGLYCEROL WITH LONG-CHAIN POLYUNSATURATED FATTY ACIDS

CROSS-REFERENCE TO RELATED APPLICATIONS

This application is a continuation of U.S. application Ser. No. 17/063,678, filed Oct. 5, 2020, now allowed, which is a continuation-in-part of (i) U.S. application Ser. No. 15/982, 634, filed May 17, 2018, now U.S. Pat. No. 10,793,507, issued Oct. 6, 2020, which is a continuation of U.S. application Ser. No. 14/975,333, filed Dec. 18, 2015, now U.S. Pat. No. 10,005,713, issued Jun. 26, 2018, which is a continuation-in-part of (a) PCT International Application No. PCT/AU2015/050340, filed Jun. 18, 2015; and (b) U.S. application Ser. No. 14/743,531, filed Jun. 18, 2015, now U.S. Pat. No. 9,718,759, issued Aug. 1, 2017, which is a continuation-in-part of (a) PCT International Application No. PCT/AU2014/050433, filed Dec. 18, 2014; and (b) U.S. application Ser. No. 14/575,756, filed Dec. 18, 2014, now U.S. Pat. No. 9,725,399, issued Aug. 8, 2017, claiming the priority of Argentinian patent application No. 20140104761, filed Dec. 18, 2014; and (ii) U.S. application Ser. No. 16/220,695, filed Dec. 14, 2018, now U.S. Pat. No. 10,800, 729, issued Oct. 13, 2020, which is a continuation of U.S. application Ser. No. 15/406,099, filed Jan. 13, 2017, now U.S. Pat. No. 10,190,073, issued Jan. 29, 2019, which is a divisional of U.S. application Ser. No. 14/575,756, filed Dec. 18, 2014, now U.S. Pat. No. 9,725,399, issued Aug. 8, 2017, claiming priority of Australian Patent Applications Nos. 2014902471, filed Jun. 27, 2014 and 2013905033, filed Dec. 18, 2013, the contents of each of which are hereby incorporated by reference in their entirety.

REFERENCE TO A SEQUENCE LISTING

This application incorporates-by-reference nucleotide and/or amino acid sequences which are present in the file named "230614 87180 DA Se quence Listing AD .xml", which is 133 kilobytes in size, and which was created Jun. 14, 2023 in the IBM-PC machine format, having an operating system compatibility with MS-Windows, which is contained in the xml file filed Jun. 14, 2023 as part of this application.

FIELD OF THE INVENTION

The present invention relates to lipid comprising docosapentaenoic acid and/or docosahexaenoic acid obtained from plant cells or microbial cells, which may be preferentially esterified at the sn-2 position of triacylglycerol, and processes for producing and using the lipid.

BACKGROUND OF THE INVENTION

Omega-3 long-chain polyunsaturated fatty acids (LC-PUFA) are now widely recognized as important compounds for human and animal health. These fatty acids may be obtained from dietary sources or by conversion of linoleic (LA, 18:2ω6) or α-linolenic (ALA, 18:3ω3) fatty acids, both of which are regarded as essential fatty acids in the human diet. While humans and many other vertebrate animals are able to convert LA or ALA, obtained from plant sources to C22 they carry out this conversion at a very low rate. Moreover, most modern societies have imbalanced diets in which at least 90% of polyunsaturated fatty acids (PUFA)

are of the ω6 fatty acids, instead of the 4:1 ratio or less for ω6:ω3 fatty acids that is regarded as ideal (Trautwein, 2001). The immediate dietary source of LC-PUFAs such as eicosapentaenoic acid (EPA, 20:5ω3), docosapentaenoic acid (DPA) and docosahexaenoic acid (DHA, 22:6ω3) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula, for example. However, due to a decline in global and national fisheries, alternative sources of these beneficial health-enhancing oils are needed.

Flowering plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain ω3 fatty acids such as EPA, docosapentaenoic acid (DPA, 22:5ω3) and DHA that are derived from ALA. An important goal in plant biotechnology is therefore the engineering of crop plants which produce substantial quantities of LC-PUFA, thus providing an alternative source of these compounds.

LC-PUFA Biosynthesis Pathways

Biosynthesis of LC-PUFAs in organisms such as microalgae, mosses and fungi usually occurs as a series of oxygen-dependent desaturation and elongation reactions (FIG. 1). The most common pathway that produces EPA in these organisms includes a Δ6-desaturation, Δ6-elongation and Δ5-desaturation (termed the Δ6-desaturation pathway) whilst a less common pathway uses a Δ9-elongation, Δ8-desaturation and Δ5-desaturation (termed the Δ9-desaturation pathway). These consecutive desaturation and elongation reactions can begin with either the ω6 fatty acid substrate LA, shown schematically as the upper left part of FIG. 1 (ω6) or the ω3 substrate ALA through to EPA, shown as the lower right part of FIG. 1 (ω3). If the initial Δ6-desaturation is performed on the ω6 substrate LA, the LC-PUFA product of the series of three enzymes will be the ω6 fatty acid ARA. LC-PUFA synthesising organisms may convert ω6 fatty acids to ω3 fatty acids using an ω3-desaturase, shown as the Δ17-desaturase step in FIG. 1 for conversion of arachidonic acid (ARA, 20:4ω6) to EPA. Some members of the ω3-desaturase family can act on a variety of substrates ranging from LA to ARA. Plant ω3-desaturases often specifically catalyse the Δ15-desaturation of LA to ALA, while fungal and yeast ω3-desaturases may be specific for the Δ17-desaturation of ARA to EPA (Pereira et al., 2004a; Zank et al., 2005). Some reports suggest that non-specific ω3-desaturases may exist which can convert a wide variety of 06 substrates to their corresponding ω3 products (Zhang et al., 2008).

The conversion of EPA to DHA in these organisms occurs by a Δ5-elongation of EPA to produce DPA, followed by a Δ4-desaturation to produce DHA (FIG. 1). In contrast, mammals use the so-called "Sprecher" pathway which converts DPA to DHA by three separate reactions that are independent of a Δ4-desaturase (Sprecher et al., 1995).

The front-end desaturases generally found in plants, mosses, microalgae, and lower animals such as *Caenorhabditis elegans* predominantly accept fatty acid substrates esterified to the sn-2 position of a phosphatidylcholine (PC) substrate. These desaturases are therefore known as acyl-PC, lipid-linked, front-end desaturases (Domergue et al., 2003). In contrast, higher animal front-end desaturases generally accept acyl-CoA substrates where the fatty acid substrate is linked to CoA rather than PC (Domergue et al., 2005). Some microalgal desaturases and one plant desaturase are known to use fatty acid substrates esterified to CoA (Table 2).

Each PUFA elongation reaction consists of four steps catalysed by a multi-component protein complex: first, a condensation reaction results in the addition of a 2C unit from malonyl-CoA to the fatty acid, resulting in the formation of a β-ketoacyl intermediate. This is then reduced by NADPH, followed by a dehydration to yield an enoyl intermediate. This intermediate is finally reduced a second time to produce the elongated fatty acid. It is generally thought that the condensation step of these four reactions is substrate specific whilst the other steps are not. In practice, this means that native plant elongation machinery is capable of elongating PUFA providing that the condensation enzyme (typically called an 'elongase') specific to the PUFA is introduced, although the efficiency of the native plant elongation machinery in elongating the non-native PUFA substrates may be low. In 2007 the identification and characterisation of the yeast elongation cycle dehydratase was published (Denic and Weissman, 2007).

PUFA desaturation in plants, mosses and microalgae naturally occurs to fatty acid substrates predominantly in the acyl-PC pool whilst elongation occurs to substrates in the acyl-CoA pool. Transfer of fatty acids from acyl-PC molecules to a CoA carrier is performed by phospholipases (PLAs) whilst the transfer of acyl-CoA fatty acids to a PC carrier is performed by lysophosphatidyl-choline acyltransferases (LPCATs) (FIG. 9) (Singh et al., 2005).

Engineered Production of LC-PUFA

Most LC-PUFA metabolic engineering has been performed using the aerobic Δ6-desaturation/elongation pathway. The biosynthesis of γ-linolenic acid (GLA, 18:3ω6) in tobacco was first reported in 1996 using a Δ6-desaturase from the cyanobacterium *Synechocystis* (Reddy and Thomas, 1996). More recently, GLA has been produced in crop plants such as safflower (73% GLA in seedoil, WO 2006/127789) and soybean (28% GLA; Sato et al., 2004). The production of LC-PUFA such as EPA and DHA involves more complicated engineering due to the increased number of desaturation and elongation steps involved. EPA production in a land plant was first reported by Qi et al. (2004) who introduced genes encoding a Δ9-elongase from *Isochrysis galbana*, a Δ8-desaturase from *Euglena gracilis* and a Δ5-desaturase from *Mortierella alpina* into *Arabidopsis* yielding up to 3% EPA. This work was followed by Abbadi et al. (2004) who reported the production of up to 0.8% EPA in flax seed using genes encoding a Δ6-desaturase and Δ6-elongase from *Physcomitrella patens* and a Δ5-desaturase from *Phaeodactylum tricornutum*.

The first report of DHA production was in WO 04/017467 where the production of 3% DHA in soybean embryos is described, but not seed, by introducing genes encoding the *Saprolegnia diclina* Δ6-desaturase, *Mortierella alpina* Δ6-desaturase, *Mortierella alpina* Δ5-desaturase, *Saprolegnia diclina* Δ4-desaturase, *Saprolegnia diclina* Δ17-desaturase, *Mortierella alpina* Δ6-elongase and *Pavlova lutheri* Δ5-elongase. The maximal EPA level in embryos also producing DHA was 19.6%, indicating that the efficiency of conversion of EPA to DHA was poor (WO 2004/071467). This finding was similar to that published by Robert et al. (2005), where the flux from EPA to DHA was low, with the production of 3% EPA and 0.5% DHA in *Arabidopsis* using the *Danio rerio* Δ5/6-desaturase, the *Caenorhabditis elegans* Δ6-elongase, and the *Pavlova salina* Δ5-elongase and Δ4-desaturase. Also in 2005, Wu et al. published the production of 25% ARA, 15% EPA, and 1.5% DHA in *Brassica juncea* using the *Pythium irregulare*

Δ6-desaturase, a Thraustochytrid Δ5-desaturase, the *Physcomitrella patens* Δ6-elongase, the *Calendula officianalis* Δ12-desaturase, a Thraustochytrid Δ5-elongase, the *Phytophthora infestans* Δ17-desaturase, the *Oncorhyncus mykiss* LC-PUFA elongase, a Thraustochytrid Δ4-desaturase and a Thraustochytrid LPCAT (Wu et al., 2005). Summaries of efforts to produce oil-seed crops which synthesize ω3 LC-PUFAs is provided in Venegas-Caleron et al. (2010) and Ruiz-Lopez et al. (2012). As indicated by Ruiz-Lopez et al. (2012), results obtained to date for the production of DHA in transgenic plants has been no where near the levels seen in fish oils. More recently, Petrie et al (2012) reported the production of about 15% DHA in *Arabidopsis thaliana* seeds, and WO2013/185184 reported the production of certain seedoils having between 7% and 20% DHA. However, there are no reports of production of plant oils having more than 20% DHA.

There are no reports of the production of DPA in recombinant cells to significant levels without concomitant production of DHA. Indeed, the present inventors are unaware of any published suggestion or motivation to produce DPA in recombinant cells without production of DHA.

There therefore remains a need for more efficient production of LC-PUFA in recombinant cells, in particular of DHA or DPA in seeds of oilseed plants.

Further, to date, recombinant cells, such as recombinant plant cells, producing LC-PUFA have a propensity to esterify the LC-PUFA at the sn-1 and/or sn-3 position of triacylglycerols (TAG) which limits the total amount of LC-PUFA which can be found as TAG in these cells.

There therefore remains a need for more efficient production of TAG where LC-PUFA is esterified at the sn-2 position in recombinant cells, in particular in seeds of oilseed plants.

SUMMARY OF THE INVENTION

The present inventors have identified methods and plants for producing lipid with high levels of DHA and/or DPA. As described in WO2013/185184, the present inventors have previously disclosed extracted plant lipid, and plants and plant parts for producing such lipid, comprising DHA in the total fatty acid content of the extracted lipid of between 7% and 20%. An upper limited of 20% was defined because at the time it was considered a maximal amount of DHA which could be produced in plants. However, as described herein, the inventors were surprised to find that levels of DHA in the total fatty acid content greater than 20% can be obtained. The inventors also found plant lipid, and plant parts and plants for producing lipid comprising DPA in the total fatty acid content of the extracted lipid of between 7% and 35%, particularly in the absence of DHA.

Accordingly, in a first aspect the present invention provides extracted plant lipid, comprising fatty acids in an esterified form, the fatty acids comprising oleic acid, palmitic acid, ω6 fatty acids which comprise linoleic acid (LA), (ω3 fatty acids which comprise α-linolenic acid (ALA) and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is between 20.1% and 30% or between 20.1% and 35%, preferably between 30% and 35%.

In another aspect, the present invention provides extracted plant lipid, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of palmitic acid in the total fatty acid content of the extracted lipid is between about 2% and 16%, and wherein the level of myristic acid (C14:0) in the total fatty acid content of the extracted lipid, if present, is less than 1%, and wherein the level of DHA in the total fatty acid content of the extracted lipid is between 20.1% and 30% or between 20.1% and 35%, preferably between 30% and 35%.

In another aspect, the invention provides extracted lipid, preferably extracted plant lipid or extracted microbial lipid, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosapentaenoic acid (DPA), and optionally one or more of stearidonic acid (SDA), eicosapentaenoic acid (EPA), and eicosatetraenoic acid (ETA), wherein the level of DPA in the total fatty acid content of the extracted lipid is between about 7% and 35%. In embodiments of this aspect, the level of DPA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%.

In an embodiment of the above aspect, DHA is present at a level of less than 0.5% of the total fatty acid content of the extracted lipid and more preferably is absent from the total fatty acid content of the lipid.

The present inventors have identified methods and plants for producing lipid with enhanced levels of docosapentaenoic acid and/or docosahexaenoic acid preferentially esterified at the sn-2 position of triacylglycerol.

Thus, in another aspect, the invention provides extracted lipid, preferably extracted plant lipid or extracted microbial lipid, comprising fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG.

In an embodiment, the lipid is extracted plant lipid comprising fatty acids in an esterified form, the fatty acids comprising palmitic acid and C22 polyunsaturated fatty acid which comprises DPA and/or DHA, and optionally myristic acid, wherein at least 35% of the DPA and/or DHA esterified in the form of triacylglycerol (TAG) is esterified at the sn-2 position of the TAG, wherein the level of palmitic acid in the total fatty acid content of the extracted lipid is between about 2% and 16%, and wherein the level of myristic acid (C14:0) in the total fatty acid content of the extracted lipid, if present, is less than 1%.

In an embodiment, the extracted lipid is further characterised by one or more or all of (i) it comprises fatty acids comprising oleic acid, palmitic acid, ω6 fatty acids which comprise linoleic acid (LA), ω3 fatty acids which comprise α-linolenic acid (ALA) and optionally one or more of stearidonic acid (SDA), eicosapentaenoic acid (EPA), and eicosatetraenoic acid (ETA), (ii) at least about 40%, at least about 45%, at least about 48%, between 35% and about 60%, or between 35% and about 50%, of the DPA and/or DHA esterified in the form of triacylglycerol (TAG) is esterified at the sn-2 position of the TAG, and (iii) the level of DPA and/or DHA in the total fatty acid content of the extracted lipid is between about 1% and 35%, or between about 7% and 35% or between about 20.1% and 35%. In embodiments of this aspect, the level of DPA and/or DHA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%. In preferred embodiments, the extracted lipid is characterised by (i) and (ii), (i) and (iii) or (ii) and (iii), more preferably all of (i), (ii) and (iii). Preferably, the extracted lipid is further characterised by a level of palmitic acid in the total fatty acid content of the extracted lipid which is between about 2% and 16%, and a level of myristic acid (C14:0) in the total fatty acid content of the extracted lipid, if present, is less than 1%.

Embodiments of each of the four above aspects are described in further detail below. As the skilled person would understand, any embodiments described which are broader than the corresponding feature in an above aspect do not apply to that aspect.

In an embodiment, the level of DPA and/or DHA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%.

In an embodiment, the extracted lipid has one or more of the following features i) the level of palmitic acid in the total fatty acid content of the extracted lipid is between about 2% and 18%, between about 2% and 16%, between about 2% and 15%, or between about 3% and about 10%, ii) the level of myristic acid (C14:0) in the total fatty acid content of the extracted lipid is less than 6%, less than 3%, less than 2%, less than 1%, or about 0.1%, iii) the level of oleic acid in the total fatty acid content of the extracted lipid is between about 1% and about 30%, between about 3% and about 30%, between about 6% and about 30%, between 1% and about 20%, between about 30% and about 60%, about 45% to about 60%, about 30%, or between about 15% and about 30%, iv) the level of linoleic acid (LA) in the total fatty acid content of the extracted lipid is between about 4% and about 35%, between about 4% and about 20%, between about 4% and about 17%, or between about 5% and about 10%, v) the level of α-linolenic acid (ALA) in the total fatty acid content of the extracted lipid is between about 4% and about 40%, between about 7% and about 40%, between about 10% and about 35%, between about 20% and about 35%, between about 4% and 16%, or between about 2% and 16%, vi) the level of γ-linolenic acid (GLA) in the total fatty acid content of the extracted lipid is less than 4%, less than about 3%, less than about 2%, less than about 1%, less than about 0.5%, between 0.05% and about 7%, between 0.05% and about 4%, between 0.05% and about 3%, or between 0.05% and about 2%, vii) the level of stearidonic acid (SDA) in the total fatty acid content of the extracted lipid is less than about 10%, less than about 8%, less than about 7%, less than about 6%, less than about 4%, less than about 3%, between about 0.05% and about 7%, between about 0.05% and about 6%, between about 0.05% and about 4%, between about 0.05% and about 3%, between about 0.05% and about 10%, or between 0.05% and about 2%, viii) the level of eicosatetraenoic acid (ETA) in the total fatty acid content of the extracted lipid is less than about 6%, less than about 5%, less than about 4%, less than about 1%, less than about 0.5%, between 0.05% and about 6%, between 0.05% and about 5%, between 0.05% and about 4%, between 0.05% and about 3%, or between 0.05% and about 2%, ix) the level of eicosatrienoic acid (ETrA) in the total fatty acid content of the extracted lipid is less than 4%, less than about 2%, less than about 1%, between 0.05% and 4%, between 0.05% and 3%, or between 0.05% and about 2%, or between 0.05% and about 1%, x) the level of eicosapentaenoic acid (EPA) in the total fatty acid content of the extracted lipid is between 4% and 15%, less than 4%, less than about 3%, less than about 2%, between 0.05% and 10%, between 0.05% and 5%, between 0.05% and about 3%, or between 0.05% and about 2%, xi) if the level of DHA in the total fatty acid content of the extracted lipid is between 20.1% and 35%, the level of docosapentaenoic acid (DPA) in the total fatty acid content of the extracted lipid is less than 4%, less than about 3%, less than about 2%, between 0.05% and 8%, between 0.05% and 5%, between 0.05% and about 3%, between 5% and 15%, between 5% and 10%, or between 0.05% and about 2%, xii) the level of DHA in the total fatty acid content of the extracted lipid is about 22%, about 24%, about 26%, about 28%, about 31%, between 20.10% and 29%, between 20.10% and 28%, between 20.1% and about 27%, between 20.1% and about 26%, between 20.1% and about 25%, between 20.1% and about 24%, between 21% and 35%, between 21% and 30%, between 21% and 28%, between 21% and about 26%, or between 21% and about 24%, xiii) the lipid comprises ω6-docosapentaenoic acid (22:5$^{\Delta4,7,10,13,16}$) in its fatty acid content, xiv) the lipid comprises less than 0.1% of ω6-docosapentaenoic acid (22:5$^{\Delta4,7,10,13,16}$) in its fatty acid content, xv) the lipid comprises less than 0.1% of one or more or all of SDA, EPA and ETA in its fatty acid content, xvi) the level of total saturated fatty acids in the total fatty acid content of the extracted lipid is between about 4% and about 25%, between about 4% and about 20%, between about 6% and about 20%, or between about 6% and about 12%, xvii) the level of total monounsaturated fatty acids in the total fatty acid content of the extracted lipid is between about 4% and about 40%, between about 4% and about 35%, between about 8% and about 25%, between 8% and about 22%, between about 15% and about 40% or between about 15% and about 35%, xviii) the level of total polyunsaturated fatty acids in the total fatty acid content of the extracted lipid is between about 20% and about 75%, between 30% and 75%, between about 50% and about 75%, about 60%, about 65%, about 70%, about 75%, or between about 60% and about 75%, xix) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%, xx) the level of new ω6 fatty acids in the total fatty acid content of the extracted lipid is less than about 10%, less than about 8%, less than about 6%, less than 4%, between about 1% and about 20%, between about 1% and about 10%, between 0.5% and about 8%, or between 0.5% and 4%, xxi) the level of total ω3 fatty acids in the total fatty acid content of the extracted lipid is between 36% and about 65%, between 36% and about 70%, between 40% and about 60%, between about 30% and about 60%, between about 35% and about 60%, between 40% and about 65%, between about 30% and about 65%, between about 35% and about 65%, about 35%, about 40%, about 45%, about 50%, about 55%, about 60%, about 65% or about 70%, xxii) the level of new ω3 fatty acids in the total fatty acid content of the extracted lipid is between 21% and about 45%, between 21% and about 35%, between about 23% and about 35%, between about 25% and about 35%, between about 27% and about 35%, about 23%, about 25%, about 27%, about 30%, about 35%, about 40% or about 45%, xxiii) the ratio of total ω6 fatty acids:total ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 1.0, about 0.1, about 0.10 to about 0.4, or about 0.2, xxiv) the ratio of new ω6 fatty acids:new ω3 fatty acids in the fatty acid content of the extracted lipid is between about 1.0 and about 3.0, between about 0.02 and about 0.1, between about 0.1 and about 1, between about 0.1 and about 0.5, less than about 0.50, less than about 0.40, less than about 0.30, less than about 0.20, less than about 0.15, about 0.02, about 0.05, about 0.1, about 0.2 or about 1.0, xxv) the fatty acid composition of the lipid is based on an efficiency of conversion of oleic acid to LA by Δ12-desaturase of at least about 60%, at least about 70%, at least about 80%, between about 60% and about 98%, between about 70% and about 95%, or between about 75% and about 90%, xxvi) the fatty acid composition of the lipid is based on an efficiency of conversion of ALA to SDA by Δ6-desaturase of at least about 30%, at least about 40%, at least about 50%, at least about 60%, at least about 70%, between about 30% and about 70%, between about 35% and about 60%, or between about 50% and about 70%, xxvii) the fatty acid composition of the lipid is based on an efficiency of conversion of SDA to ETA acid by Δ6-elongase of at least about 60%, at least about 70%, at least about 75%, between about 60% and about 95%, between about 70% and about 88%, or between about 75% and about 85%, xxviii) the fatty acid composition of the lipid is based on an efficiency of conversion of ETA to EPA by Δ5-desaturase of at least about 60%, at least about 70%, at least about 75%, between about 60% and about 99%, between about 70% and about 99%, or between about 75% and about 98%, xxix) the fatty acid composition of the lipid is based on an efficiency of conversion of EPA to DPA by Δ5-elongase of at least about 80%, at least about 85%, at least about 90%, between about 50% and about 99%, between about 85% and about 99%, between about 50% and about 95%, or between about 85% and about 95%, xxx) if the level of DHA in the total fatty acid content of the extracted lipid is between 20.1% and 30% or between 20.1% and 35%, the fatty acid composition of the lipid is based on an efficiency of conversion of DPA to DHA by Δ4-desaturase of at least about 80%, at least about 90%, at least about 93%, between about 50% and about 95%, between about 80% and about 95%, or between about 85% and about 95%, xxxi) the fatty acid composition of the lipid is based on an efficiency of conversion of oleic acid to DPA and/or DHA of at least about 10%, at least about 15%, at least about 20%, at least about 25%, about 20%, about 25%, about 30%, between about 10% and about 50%, between about 10% and about 30%, between about 10% and about 25% or between about 20% and about 30%, xxxii) the fatty acid composition of the lipid is based on an efficiency of conversion of LA to DPA and/or DHA of at least about 15%, at least about 20%, at least about 22%, at least about 25%, at least about 30%, at least about 40%, about 25%, about 30%, about 35%, about 40%, about 45%, about 50%, between about 15% and about 50%, between about 20% and about 40%, or between about 20% and about 30%, xxxiii) the fatty acid composition of the lipid is based on an efficiency of conversion of ALA to DPA and/or DHA of at least about 17%, at least about 22%, at least about 24%, at least about 30%, about 30%, about 35%, about 40%, about 45%, about 50%, about 55%, about 60%, between about 22% and about 70%, between about 17% and about 55%, between about 22% and about 40%, or between about 24% and about 40%, xxxiv) the total fatty acid in the extracted lipid has less than 1.5% C20:1, less than 1% C20:1 or about 1% C20:1, xxxv) the triacylglycerol (TAG) content of the lipid is at least about 70%, at least about 80%, at least about 90%, at least 95%, between about 70% and about 99%, or between about 90% and about 99%, xxxvi) the lipid comprises diacylglycerol (DAG), which DAG preferably comprises DPA and/or DHA, xxxvii) the lipid comprises less than about 10%, less than about 5%, less than about 1%, or between about 0.001% and about 5%, free (non-esterified) fatty acids and/or phospholipid, or is essentially free thereof, xxxviii) at least 70%, at least 72% or at least 80%, of the DHA and/or DPA esterified in the form of TAG is in the sn-1 or sn-3 position of the TAG, xxxix) the most abundant DPA and/or DHA-containing TAG species in the lipid is DPA/18:3/18:3 (TAG 58:12) and/or DHA/18:3/18:3 (TAG 58:12), and xl) the lipid comprises tri-DPA TAG (TAG 66:18) and/or tri-DHA TAG (TAG 66:18).

xli) the level of DPA in the total fatty acid content of the extracted lipid is about 7%, about 8%, about 9%, about 10%, about 12%, about 15%, about 18%, about 20%, about 22%, about 24%, about 26%, about 28%, about 31%, between about 7% and about 31%, between about 7% and about 28%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%, optionally wherein the level of DHA is less than 0.5% of the total fatty acid content of the extracted lipid.

In another embodiment, the extracted lipid has one or more of the following features i) the level of palmitic acid in the total fatty acid content of the extracted plant lipid is between 2% and 15%, ii) the level of myristic acid (C14:0) in the total fatty acid content of the extracted plant lipid is about 0.1%, iii) the level of oleic acid in the total fatty acid content of the extracted plant lipid is between 1% and 30%, iv) the level of linoleic acid (LA) in the total fatty acid content of the extracted plant lipid is between 4% and 20%, v) the level of α-linolenic acid (ALA) in the total fatty acid content of the extracted plant lipid is between 4% and 40%, vi) the level of γ-linolenic acid (GLA) in the total fatty acid content of the extracted plant lipid is between 0.05% and 7%, vii) the level of stearidonic acid (SDA) in the total fatty acid content of the extracted plant lipid is between 0.05% and 10%, viii) the level of eicosatetraenoic acid (ETA) in the total fatty acid content of the extracted plant lipid is less than 6%, ix) the level of eicosatrienoic acid (ETrA) in the total fatty acid content of the extracted plant lipid is less than 4%, x) the extracted plant lipid comprises less than 0.1% of ω6-docosapentaenoic acid $(22:5^{\Delta 4,7,10,13,16})$ in its fatty acid content, xi) the level of new ω6 fatty acids in the total fatty acid content of the extracted plant lipid is less than 10%, xii) the ratio of total ω6 fatty acids:total ω3 fatty acids in the fatty acid content of the extracted plant lipid is between 1.0 and 3.0, or between 0.1 and 1, xiii) the ratio of new ω6 fattyacids:new ω3 fatty acids in the fatty acid content of the extracted plant lipid is between 1.0 and 3.0, between 0.02 and 0.1, or between 0.1 and 1, xiv) the fatty acid composition of the extracted plant lipid is based on an efficiency of conversion of oleic acid to DPA and/or DHA of at least 10%, xv) the fatty acid composition of the extracted plant lipid is based on an efficiency of conversion of LA to DPA and/or DHA of at least 15%, xvi) the fatty acid composition of the extracted plant lipid is based on an efficiency of conversion of ALA to DPA and/or DHA of at least 17%, xvii) the total fatty acid in the extracted plant lipid has less than 1.5% C20:1, and xviii) the triacylglycerol (TAG) content of the extracted plant lipid is at least 70%, and may be characterised by one or more of the following features xix) the extracted plant lipid comprises diacylglycerol (DAG) which comprises DPA and/or DHA, xx) the extracted plant lipid comprises less than 10% free (non-esterified) fatty acids and/or phospholipid, or is essentially free thereof, xxi) at least 70% of the DHA esterified in the form of TAG is in the sn-1 or sn-3 position of the TAG, xxii) the most abundant DPA and/or DHA-containing TAG species in the extracted plant lipid is DPA/18:3/ 18:3 (TAG 58:12) and/or DHA/18:3/18:3 (TAG 58:12), and xxiii) the extracted plant lipid comprises tri-DPA TAG (TAG 66:18) and/or tri-DHA TAG (TAG 66:18).

In an embodiment, the level of eicosapentaenoic acid (EPA) in the total fatty acid content of the extracted plant lipid is between 0.05% and 10%.

In another embodiment, where DHA is present between 20.1% and 35%, the level of docosapentaenoic acid (DPA) in the total fatty acid content of the extracted plant lipid is less than about 4%.

In a further embodiment, the level of DHA in the total fatty acid content of the extracted plant lipid is between 20.1% and 30%.

In a further embodiment for high levels of DPA, the level of DHA in the total fatty acid content of the extracted plant lipid is less than 2%, preferably less than 1%, or between 0.1% and 2%, more preferably is not detected. Preferably, the plant, or part thereof such as seed, or microbial cell has no polynucleotide encoding a Δ4-desaturase, or has no Δ4-desaturase polypeptide.

In another embodiment, the extracted lipid is in the form of an oil, wherein at least about 90%, least about 95%, at least about 98%, or between about 95% and about 98%, by weight of the oil is the lipid.

In a preferred embodiment of the first two aspects above, the lipid or oil, preferably a seedoil, has the following features: in the total fatty acid content of the lipid or oil, the level of DHA is between about 20.1% and 30% or between 20.1% and 35%, the level of palmitic acid is between about 2% and about 16%, the level of myristic acid is less than about 6%, the level of oleic acid is between about 1% and about 30%, the level of LA is between about 4% and about 35%, ALA is present, the level of total saturated fatty acids in the total fatty acid content of the extracted lipid is between about 4% and about 25%, the ratio of total ω6 fatty acids: total ω3 fatty acids in the fatty acid content of the extracted lipid is between 0.05 and about 3.0, and the triacylglycerol (TAG) content of the lipid is at least about 70%, and optionally the lipid is essentially free of cholesterol and/or the lipid comprises tri-DHA TAG (TAG 66:18). More preferably, the lipid or oil, preferably a seedoil, additionally has one or more or all of the following features: at least 70% of the DHA is esterified at the sn-1 or sn-3 position of tria- cylglycerol (TAG), ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of DPA is between 0.05% and about 8%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fattyacids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of DPA to DHA by Δ4-desaturase of between about 50% and about 95%, an efficiency of conversion of oleic acid to DHA of at least about 10%. Most preferably, at least 81% of the DHA is esterified at the sn-1 or sn-3 position of triacylglycerol (TAG).

In a preferred embodiment of the third aspect above, the lipid or oil, preferably a seedoil, has the following features: in the total fatty acid content of the lipid or oil, the level of DPA is between about 7% and 30% or between about 7% and 35%, the level of palmitic acid is between about 2% and about 16%, the level of myristic acid is less than 10%, the level of oleic acid is between about 1% and about 30%, the level of LA is between about 4% and about 35%, ALA is present, the level of total saturated fatty acids in the total fatty acid content of the extracted lipid is between about 4% and about 25%, the ratio of total ω6 fattyacids:total ω3 fatty acids in the fatty acid content of the extracted lipid is between 0.05 and about 3.0, and the triacylglycerol (TAG) content of the lipid is at least about 70%, and optionally the lipid is essentially free of cholesterol and/or the lipid com- prises tri-DPA TAG (TAG 66:15). More preferably, the lipid or oil, preferably a seedoil, additionally has one or more or all of the following features: at least 70% of the DPA is esterified at the sn-1 or sn-3 position of triacylglycerol (TAG), ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fattyacids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of oleic acid to DPA of at least about 10%. Most preferably, at least 81% of the DPA is esterified at the sn-1 or sn-3 position of triacylglycerol (TAG).

Preferably, the extracted lipid is *Brassica* sp. seedoil lipid or *Camelina sativa* seedoil lipid.

In another preferred embodiment, which may be for example an embodiment of the fourth aspect above, the lipid or oil, preferably a seedoil, more preferably a *Brassica* sp. seedoil or *Camelina sativa* seedoil, comprising DPA and/or DHA has the following features: in the total fatty acid content of the lipid or oil, the level of palmitic acid is between about 2% and about 16%, the level of myristic acid is less than 1%, the level of oleic acid is between about 1% and about 30%, the level of LA is between about 4% and about 35%, ALA is present, the level of total saturated fatty acids in the total fatty acid content of the extracted lipid is between about 4% and about 25%, the ratio of total 06 fattyacids:total ω3 fatty acids in the fatty acid content of the extracted lipid is between 0.05 and about 3.0, the tria-cylglycerol (TAG) content of the lipid is at least about 70%, and optionally the lipid comprises tri-DHA TAG (TAG 66:18) and/or tri-DPA TAG (TAG 66:15), optionally wherein at least 35% of the DPA and/or DHA esterified in the form of triacylglycerol (TAG) is esterified at the sn-2 position of the TAG. More preferably, the lipid or oil, preferably a seedoil, additionally has one or more or all of the following features: ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monoun-saturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fattyacids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of DPA to DHA by Δ4-desaturase (if present) of between about 50% and about 95%, and an efficiency of conversion of oleic acid to DPA and/or DHA of at least about 10%.

In the context of the extracted lipid or oil of the invention, in an embodiment the level of DPA and/DHA in the extracted lipid or oil has not been increased, or is substantially the same as, the level of DPA and/or DHA in the lipid or oil of the plant part or microbe prior to extraction. In other words, no procedure has been performed to increase the level of DPA and/or DHA in the lipid or oil relative to other fatty acids post-extraction. In this context, the oil may have been treated to purify the oil such as by removal of phospholipids (degumming), decolorizing, deodorising or bleaching, as known in that art. The oil may have been treated to remove one or more of free fatty acids, MAG, DAG and phospholipids, thereby increasing the proportion of TAG in the extracted lipid on a weight basis. As would be apparent, the lipid or oil may subsequently be treated by fractionation or other procedures to alter the fatty acid composition. In a further preferred embodiment, the lipid or oil, preferably a seedoil, has the following features: in the total fatty acid content of the lipid or oil, the level of DHA is between about 20.10% and 30% or between about 20.1% and 35%, the level of palmitic acid is between about 2% and about 16%, the level of myristic acid is less than about 6% and preferably less than 1%, the level of oleic acid is between about 1% and about 30%, the level of LA is between about 4% and about 35%, ALA is present, GLA is present, the level of SDA is between about 0.05% and about 10%, the level of ETA is less than about 6%, the level of EPA is between about 0.05% and about 10%, the level of DPA is between about 0.05% and about 8%.

In another preferred embodiment, the lipid or oil, preferably a seedoil and more preferably a *Brassica* seedoil such as mustard oil or canola oil or *C. sativa* seedoil, has the following features: in the total fatty acid content of the lipid or oil, the level of DPA and/or DHA is between about 7% and 35%, the level of palmitic acid is between about 2% and about 16%, the level of myristic acid is less than about 6% and preferably less than 1%, the level of oleic acid is between about 1% and about 30%, the level of LA is between about 4% and about 35%, ALA is present, the level of SDA is between about 0.05% and about 10%, the level of ETA is less than about 6%, the level of EPA is between about 0.05% and about 10%. DHA is, or preferably is not, detectable in the lipid or oil. Preferably, DHA, if present, is present at a level of not more than 2% or not more than 0.5% of the total fatty acid content of the lipid or oil and more preferably is absent from the total fatty acid content of the lipid or oil. Optionally, the lipid is essentially free of cholesterol and/or the lipid comprises tri-DPA TAG (TAG 66:15) and/or tri-DHA TAG (TAG 66:15). More preferably, the lipid or oil, preferably a seedoil, additionally has one or more or all of the following features: at least 70% of the DPA is esterified at the sn-1 or sn-3 position of triacylglycerol (TAG), ALA is present at a level of between 4% and 40% of the total fatty acid content, GLA is present and/or the level of GLA is less than 4% of the total fatty acid content, the level of SDA is between 0.05% and about 10%, the level of ETA is less than about 4%, the level of EPA is between 0.05% and about 10%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of new ω6 fattyacids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of oleic acid to DPA and/or DHA of at least about 10%. In an embodiment, at least 81% of the DPA is esterified at the sn-1 or sn-3 position of triacylglycerol (TAG). Alternatively, at least 35% of the DPA esterified in the form of TAG is esterified at the sn-2 position of TAG.

In a further embodiment, the extracted lipid of the invention further comprises one or more sterols, preferably plant sterols.

In another embodiment, the extracted lipid is in the form of an oil, and comprises less than about 10 mg of sterols/g of oil, less than about 7 mg of sterols/g of oil, between about 1.5 mg and about 10 mg of sterols/g of oil, or between about 1.5 mg and about 7 mg of sterols/g of oil.

Examples of sterols which can be in the extracted lipid include, but are not necessarily limited to, one or more or all of campesterol/24-methylcholesterol, Δ5-stigmasterol, ebu-ricol, β-sitosterol/24-ethylcholesterol, Δ5-avenasterol/isofu-costerol, Δ7-stigmasterol/stigmast-7-en-3β-ol, and Δ7-ave-nasterol.

In an embodiment, the plant species is one listed in Table 14, such as canola, and the level of sterols are about the same as that listed in Table 14 for that particular plant species. The plant species may be *B. napus*, mustard (*B. juncea*) or *C. sativa* and comprise a level of sterols about that found in wild-type *B. napus*, mustard or *C. sativa* extracted oil, respectively.

In an embodiment, the extracted plant lipid comprises one or more or all of campesterol/24-methylcholesterol, Δ5-stigmasterol, eburicol, β-sitosterol/24-ethylcholesterol, Δ5-ave-nasterol/isofucosterol, Δ7-stigmasterol/stigmast-7-en-3β-ol, and Δ7-avenasterol, or which has a sterol content essentially the same as wild-type canola oil.

In an embodiment, the extracted lipid has a sterol content essentially the same as wild-type canola oil, mustard oil or *C. sativa* oil.

In an embodiment, the extracted lipid comprises less than about 0.5 mg of cholesterol/g of oil, less than about 0.25 mg of cholesterol/g of oil, between about 0 mg and about 0.5 mg of cholesterol/g of oil, or between about 0 mg and about 0.25 mg of cholesterol/g of oil, or which is essentially free of cholesterol.

In a further embodiment, the lipid is an oil, preferably oil from an oilseed. Examples of such oils include, but are not limited to, *Brassica* sp. oil such as for example canola oil or mustard oil, *Gossypium hirsutum* oil, *Linum usitatissimum* oil, *Helianthus* sp. oil, *Carthamus tinctorius* oil, *Glycine max* oil, *Zea mays* oil, *Arabidopsis thaliana* oil, *Sorghum bicolor* oil, *Sorghum vulgare* oil, *Avena sativa* oil, *Trifolium* sp. oil, *Elaesis guineenis* oil, *Nicotiana benthamiana* oil, *Hordeum vulgare* oil, *Lupinus angustifolius* oil, *Oryza sativa* oil, *Oryza glaberrima* oil, *Camelina sativa* oil, *Crambe abyssinica* oil, *Miscanthus* x *giganteus* oil, or *Miscanthus sinensis* oil. More preferably, the oil is a *Brassica* sp. oil, a *Camelina sativa* oil or a *Glycine max* (soybean) oil. In an embodiment the lipid comprises or is *Brassica* sp. oil such as *Brassica napus* oil or *Brassica juncea* oil, *Gossypium hirsutum* oil, *Linum usitatissimum* oil, *Helianthus* sp. oil, *Carthamus tinctorius* oil, *Glycine max* oil, *Zea mays* oil, *Elaesis guineenis* oil, *Nicotiana benthamiana* oil, *Lupinus angustifolius* oil, *Camelina sativa* oil, *Crambe abyssinica* oil, *Miscanthus* x *giganteus* oil, or *Miscanthus sinensis* oil. In a further embodiment, the oil is canola oil, mustard (*B. juncea*) oil, soybean (*Glycine max*) oil, *Camelina sativa* oil or *Arabidopsis thaliana* oil. In an alternative embodiment, the oil is a plant oil other than *A. thaliana* oil and/or other than *C. sativa* oil. In an embodiment, the plant oil is an oil other than *G. max* (soybean) oil. In an embodiment, the oil was obtained from a plant grown under standard conditions, for Example as described in Example 1, or from a plant grown in the field or in a glasshouse under standard conditions.

In another aspect, the present invention provides a process for producing extracted lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA) and γ-linolenic acid (GLA), ω3 fatty acids which comprise α-linolenic acid (ALA), stearidonic acid (SDA), docosapentaenoic acid (DPA) and docosahexaenoic acid (DHA), and optionally one or more of eicosapentaenoic acid (EPA) and eicosatetraenoic acid (ETA), wherein the level of DHA in the total fatty acid content of extractable lipid in the plant part is between 20.10% and 30% or between 20.1% and 35%, and ii) extracting lipid from the plant part, wherein the level of DHA in the total fatty acid content of the extracted lipid is between 20.1% and 30% or between 20.1% and 35%.

In a further aspect, the present invention provides a process for producing extracted plant lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA) and γ-linolenic acid (GLA), ω3 fatty acids which comprise α-linolenic acid (ALA), stearidonic acid (SDA), docosapentaenoic acid (DPA) and docosahexaenoic acid (DHA), and optionally one or more of eicosapentaenoic acid (EPA) and eicosatetraenoic acid (ETA), wherein the level of palmitic acid in the total fatty acid content of the extracted lipid is between about 2% and 16%, and wherein the level of myristic acid (C14:0) in the total fatty acid content of the extracted lipid, if present, is less than 1%, and wherein the level of DHA in the total fatty acid content of extractable lipid in the plant part is between 20.1% and 30% or between 20.1% and 35%, and ii) extracting lipid from the plant part, wherein the level of DHA in the total fatty acid content of the extracted lipid is between 20.1% and 30% or between 20.1% and 35%.

In another aspect, the present invention provides a process for producing extracted lipid, comprising the steps of i) obtaining cells, preferably a plant part, or a plurality of plant parts, comprising the cells or microbial cells, more preferably *Brassica* seed or *C. sativa* seed, comprising lipid, the lipid comprising fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG, and ii) extracting lipid from the cells, In an embodiment, at least 35% of the DPA and/or DHA esterified in the form of triacylglycerol (TAG) in the total fatty acid content of the extracted lipid is esterified at the sn-2 position of the TAG.

In an embodiment, step i) comprises obtaining a plant part, or a plurality of plant parts, comprising lipid, the lipid comprising fatty acids in an esterified form, the fatty acids comprising palmitic acid and C22 polyunsaturated fatty acid which comprises DPA and/or DHA, and optionally myristic acid, wherein at least 35% of the DPA and/or DHA esterified in the form of triacylglycerol (TAG) is esterified at the sn-2 position of the TAG, wherein the level of palmitic acid in the total fatty acid content of the extracted lipid is between about 2% and 16%, and wherein the level of myristic acid (C14:0) in the total fatty acid content of the extracted lipid, if present, is less than 1%.

In an embodiment, the lipid has one or more of the following features i) the fatty acids further comprise one or more or all of oleic acid, ω6 fatty acids which comprise linoleic acid (LA), ω3 fatty acids which comprise α-linolenic acid (ALA) and optionally one or more of stearidonic acid (SDA), eicosapentaenoic acid (EPA), and eicosatetraenoic acid (ETA), ii) at least about 40%, at least about 45%, at least about 48%, between 35% and about 60%, or between 35% and about 50%, of the DPA and/or DHA esterified in the form of triacylglycerol (TAG) is esterified at the sn-2 position of the TAG, iii) the triacylglycerol (TAG) content of the lipid is at least about 70%, at least about 80%, at least about 90%, at least 95%, between about 70% and about 99%, or between about 90% and about 99%, and iv) the level of DPA and/or DHA in the total fatty acid content of the extracted lipid is between about 1% and 35%, or between about 7% and 35% or between about 20.1% and 35%.

In a further aspect, the present invention provides a process for producing extracted plant lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), stearidonic acid (SDA), docosapentaenoic acid (DPA) and docosahexaenoic acid (DHA), and optionally one or more of eicosapentaenoic acid (EPA) and eicosatetraenoic acid (ETA), wherein the level of palmitic acid in the total fatty acid content of the extracted lipid is between about 2% and 16%, and wherein the level of myristic acid (C14:0) in the total fatty acid content of the extracted lipid, if present, is less than 1%, and wherein the level of DHA in the total fatty acid content of extractable lipid in the plant part is between 20.1% and 30% or between 20.1% and 35%, and ii) extracting lipid from the plant part, wherein the level of DHA in the total fatty acid content of the extracted lipid is between 20.1% and 30% or between 20.1% and 35%.

In an embodiment of the three above aspect, the invention provides a process for producing extracted plant lipid, comprising the steps of i) obtaining a plant part comprising lipid, the lipid comprising fatty acids in an esterified form, wherein the lipid has a fatty acid composition comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is between 20.1% and 30% or between 20.1% and 35%, preferably between 30% and 35%, (ii) the level of palmitic acid in the total fatty acid content of the extracted lipid is between 2% and 16%, (iii) the level of myristic acid (C14:0) in the total fatty acid content of the extracted lipid is less than 1%, (iv) the level of oleic acid in the total fatty acid content of the extracted lipid is between 1% and 30%, (v) the level of linoleic acid (LA) in the total fatty acid content of the extracted lipid is between 4% and 35%. (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fattyacids:total ω3 fatty acids in the fatty acid content of the extracted lipid is between 0.05 and 1, (x) the triacylglycerol (TAG) content of the lipid is at least 70%, and (xi) at least 70% of the DHA esterified in the form of TAG is in the sn-1 or sn-3 position of the TAG, and ii) extracting lipid from the plant part, wherein the level of DHA in the total fatty acid content of the extracted lipid is between about 20.1% and 30% or between 20.1% and 35%, preferably between 30% and 35%. Preferably, at least 81% or at least 90% of the DHA esterified in the form of TAG is in the sn-1 or sn-3 position of the TAG.

In a further aspect, the invention provides a process for producing extracted plant lipid or microbial lipid, comprising the steps of i) obtaining a plant part or microbial cells comprising lipid, the lipid comprising fatty acids in an esterified form, the fatty acids comprising oleic acid, palmitic acid, 06 fatty acids which comprise linoleic acid (LA), ω3 fatty acids which comprise α-linolenic acid (ALA)

and docosapentaenoic acid (DPA), and optionally one or more of stearidonic acid (SDA), eicosapentaenoic acid (EPA), and eicosatetraenoic acid (ETA), wherein the level of DPA in the total fatty acid content of the lipid of the plant part or microbial cells between about 7% and 35%, and ii) extracting lipid from the plant part or microbial cells, wherein the level of DPA in the total fatty acid content of the extracted lipid is between about 7% and 35%. In an embodiment, the level of DPA in the total fatty acid content of the extracted lipid is between about 7% and 20%, or between 20.1% and 35%.

In an embodiment of the above aspect, the invention provides a process for producing extracted plant lipid or microbial lipid, comprising the steps of i) obtaining a plant part or microbial cells comprising lipid, the lipid comprising fatty acids in an esterified form, wherein the lipid has a fatty acid composition comprising oleic acid, palmitic acid, ω6 fatty acids which comprise linoleic acid (LA), ω3 fatty acids which comprise α-linolenic acid (ALA) and docosahexaenoic acid (DPA), and one or more of stearidonic acid (SDA), eicosapentaenoic acid (EPA), and eicosatetraenoic acid (ETA), wherein (i) the level of DPA in the total fatty acid content of the extracted lipid is between 7% and 30% or between 7% and 35%, preferably between 30% and 35%, (ii) the level of palmitic acid in the total fatty acid content of the extracted lipid is between 2% and 16%, (iii) the level of myristic acid (C14:0) in the total fatty acid content of the extracted lipid is less than 6%, preferably less than 1%, (iv) the level of oleic acid in the total fatty acid content of the extracted lipid is between 1% and 30%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fattyacids:total ω3 fatty acids in the fatty acid content of the extracted lipid is between 0.05 and 1, (x) the triacylglycerol (TAG) content of the lipid is at least 70%, and (xi) at least 70% of the DPA esterified in the form of TAG is in the sn-1 or sn-3 position of the TAG and ii) extracting lipid from the plant part, wherein the level of DPA in the total fatty acid content of the extracted lipid is between about 7% and 30% or between 7% and 35%, preferably between 30% and 35%. Preferably, at least 81% or at least 90% of the DPA esterified in the form of TAG is in the sn-1 or sn-3 position of the TAG.

In another aspect, the present invention provides a process for producing extracted lipid, comprising the steps of i) obtaining cells, preferably a plant part comprising the cells or microbial cells, comprising lipid, the lipid comprising fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG, and ii) extracting lipid from the cells, wherein at least 35% of the DPA and/or DHA esterified in the form of triacylglycerol (TAG) in the total fatty acid content of the extracted lipid is esterified at the sn-2 position of the TAG.

In an embodiment, the level of DPA and/or DHA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%.

In an embodiment, the plant part has one or more or all of the following features i) the efficiency of conversion of oleic acid to DPA and/or DHA in the plant part is at least about 10%, at least about 15%, at least about 20%, at least about 25%, about 20%, about 25%, about 30%, between about 10% and about 50%, between about 10% and about 30%, between about 10% and about 25%, or between about 20% and about 30%, ii) the efficiency of conversion of LA to DPA and/or DHA in the plant part is at least about 15%, at least about 20%, at least about 22%, at least about 25%, at least about 30%, about 25%, about 30%, about 35%, between about 15% and about 50%, between about 20% and about 40%, or between about 20% and about 30%, and iii) the efficiency of conversion of ALA to DPA and/or DHA in the plant part is at least about 17%, at least about 22%, at least about 24%, at least about 30%, about 30%, about 35%, about 40%, between about 17% and about 55%, between about 22% and about 35%, or between about 24% and about 35%.

In an embodiment, the total oil content of the plant part is at least about 40%, at least about 50%, at least about 60%, at least about 70%, between about 50% and about 80%, or between about 80% and about 100% of the total oil content of a corresponding wild-type plant part.

In an embodiment, the extracted lipid produced by the process is further characterised by one or more or all of (i) it comprises fatty acids comprising oleic acid, palmitic acid, ω6 fatty acids which comprise linoleic acid (LA), ω3 fatty acids which comprise α-linolenic acid (ALA) and optionally one or more of stearidonic acid (SDA), eicosapentaenoic acid (EPA), and eicosatetraenoic acid (ETA), (ii) at least about 40%, at least about 45%, at least about 48%, between 35% and about 60%, or between 35% and about 50%, of the DPA and/or DHA esterified in the form of triacylglycerol (TAG) is esterified at the sn-2 position of the TAG, and (iii) the level of DPA and/or DHA in the total fatty acid content of the extracted lipid is between about 1% and about 35%, or between about 7% and 35% or between about 20.1% and 35%. In embodiments of this aspect, the level of DPA and/or DHA in the total fatty acid content of the extracted lipid is about 7%, about 8%, about 9%, about 10%, about 12%, about 15%, about 18%, about 20%, about 22%, about 24%, about 26%, about 28%, about 30%, between about 7% and about 28%, between about 7% and about 25%, between about 10% and 35%, between about 10% and about 30%, between about 10% and about 25%, between about 10% and about 22%, between about 14% and 35%, between about 16% and 35%, between about 16% and about 30%, between about 16% and about 25%, or between about 16% and about 22%. In preferred embodiments, the extracted lipid is characterised by (i) and (ii), (i) and (iii) or (ii) and (iii), more preferably all of (i), (ii) and (iii). Preferably, the extracted lipid is further characterised by a level of palmitic acid in the total fatty acid content of the extracted lipid which is between about 2% and 16%, and a level of myristic acid (C14:0) in the total fatty acid content of the extracted lipid, if present, is less than 1%.

In an embodiment of the above aspect, the invention provides a process for producing extracted lipid, comprising the steps of i) obtaining cells, preferably a plant part or a plurality of plant parts comprising the cells or microbial cells, more preferably *Brassica* seed or *C. sativa* seed, comprising lipid, the lipid comprising fatty acids in an esterified form, the fatty acids comprising docosapentaenoic acid (DPA) and/or docosahexaenoic acid (DHA), and further comprising oleic acid, palmitic acid, ω6 fatty acids which comprise linoleic acid (LA), ω3 fatty acids which comprise α-linolenic acid (ALA), and one or more of stearidonic acid (SDA), eicosapentaenoic acid (EPA), and eicosatetraenoic acid (ETA), wherein (i) the level of palmitic acid in the total fatty acid content of the extracted lipid is between 2% and 16%, (ii) the level of myristic acid (C14:0) in the total fatty acid content of the extracted lipid is less than 1%, (iii) the level of oleic acid in the total fatty acid content of the extracted lipid is between 1% and 30%, (iv) the level of linoleic acid (LA) in the total fatty acid content of the extracted lipid is between 4% and 35%, (v) the level of α-linolenic acid (ALA) in the total fatty acid content of the extracted lipid is between 4% and 40%, (vi) the level of eicosatrienoic acid (ETrA) in the total fatty acid content of the extracted lipid is less than 4%, (vii) the level of total saturated fatty acids in the total fatty acid content of the extracted lipid is between 4% and 25%, (viii) the ratio of total ω6 fatty acids:total ω3 fatty acids in the fatty acid content of the extracted lipid is between 0.05 and 1, (ix) the triacylglycerol (TAG) content of the lipid is at least 70%, and (x) at least 35% of the DPA and/or DHA esterified in the form of triacylglycerol (TAG) is esterified at the sn-2 position of the TAG, and ii) extracting lipid from the cells, preferably a plant part or a plurality of plant parts comprising the cells or microbial cells, more preferably *Brassica* seed or *C. sativa* seed, wherein at least 35% of the DPA and/or DHA esterified in the form of triacylglycerol (TAG) in the total fatty acid content of the extracted lipid is esterified at the sn-2 position of the TAG.

The step of obtaining the plant part, plurality of plant parts or microbial cells may comprise harvesting plant parts, preferably seed, from plants that produce the plant parts, recovery of the microbial cells from cultures of such cells, or obtaining the plant parts or microbial cells by purchase from a producer or supplier, or by importation. The process may comprise a step of determining the fatty acid composition of the lipid in a sample of the plant parts or microbial cells, or of the extracted lipid.

In a preferred embodiment, the extracted lipid obtained by a process of the invention has, where relevant, one or more of the features defined herein, for example as defined above in relation to the first two, or alternatively four, aspects.

Embodiments of the above aspects of the invention are described in further detail below. As the skilled person would understand, any features described of embodiments which are broader than the corresponding feature in an above aspect do not apply to that aspect.

In an embodiment, the plant part is a seed, preferably an oilseed. Examples of such seeds include, but are not limited to, *Brassica* sp., *Gossypium hirsutum, Linum usitatissimum, Helianthus* sp., *Carthamus tinctorius, Glycine max, Zea mays, Arabidopsis thaliana, Sorghum bicolor, Sorghum vulgare, Avena sativa, Trifolium* sp., *Elaesis guineenis, Nicotiana benthamiana, Hordeum vulgare, Lupinus angustifolius, Oryza sativa, Oryza glaberrima, Camelina sativa*, or *Crambe abyssinica*, preferably a *Brassica* sp. seed, a *C. sativa* seed or a *G. max* (soybean) seed, more preferably a *Brassica napus, B. juncea* or *C. sativa* seed. In an embodiment, the plant part is a seed, preferably an oilseed such as *Brassica* sp. such as *Brassica napus* or *Brassica juncea, Gossypium hirsutum, Linum usitatissimum, Helianthus* sp., *Carthamus tinctorius, Glycine max, Zea mays, Elaesis guineenis, Nicotiana benthamiana, Lupinus angustifolius, Camelina sativa*, or *Crambe abyssinica*, preferably a *Brassica napus, B juncea* or *C. sativa* seed. In an embodiment, the seed is canola seed, mustard seed, soybean seed, *Camelina sativa* seed or *Arabidopsis thaliana* seed. In an alternate embodiment, the seed is a seed other than *A. thaliana* seed and/or other than *C. sativa* seed. In an embodiment, the seed is a seed other than soybean seed. In an embodiment, the plant part is *Brassica* sp. seed. The plant part is preferably *Brassica* sp. seed or *Camelina sativa* seed. In an embodiment, the seed was obtained from a plant grown under standard conditions, for Example as described in Example 1, or from a plant grown in the field or in a glasshouse under standard conditions.

In another embodiment, the seed comprises at least about 18 mg, at least about 22 mg, at least about 26 mg, between about 18 mg and about 100 mg, between about 22 mg and about 70 mg, about 80 mg, between about 30 mg and about 80 mg, or between about 24 mg and about 50 mg, of DPA and/or DHA per gram of seed.

In a further embodiment, the plant part such as a seed comprises exogenous polynucleotides encoding one of the following sets of enzymes;

i) an ω3-desaturase, a Δ6-desaturase, a Δ5-desaturase, a Δ6-elongase and a Δ5-elongase, ii) a Δ15-desaturase, a Δ6-desaturase, a Δ5-desaturase, a Δ6-elongase and a Δ5-elongase, iii) a Δ12-desaturase, a Δ6-desaturase, a Δ5-desaturase, a Δ6-elongase and an Δ5-elongase, iv) a Δ12-desaturase, a ω3-desaturase and/or a Δ15-desaturase, a Δ6-desaturase, a Δ5-desaturase, a Δ6-elongase and an Δ5-elongase, v) an ω3-desaturase, a Δ8-desaturase, a Δ5-desaturase, a Δ9-elongase and an Δ5-elongase, vi) a Δ15-desaturase, a Δ8-desaturase, a Δ5-desaturase, a Δ9-elongase and a Δ5-elongase, vii) a Δ12-desaturase, a Δ8-desaturase, a Δ5-desaturase, a Δ9-elongase and an Δ5-elongase, viii) a Δ12-desaturase, a ω3-desaturase and/or a Δ15-desaturase, a Δ8-desaturase, a Δ5-desaturase, a Δ9-elongase and an Δ5-elongase, and wherein each polynucleotide is operably linked to one or more promoters that are capable of directing expression of said polynucleotides in a cell of the plant part. In an embodiment, for the production of DHA the plant part such as a seed further comprises an exogenous polynucleotide encoding a Δ4 desaturase.

In a further embodiment, the plant part such as a seed or recombinant cells such as microbial cells comprise exogenous polynucleotides encoding one of the following sets of enzymes;

i) an ω3-desaturase and/or a Δ15-desaturase, a Δ6-desaturase, a Δ5-desaturase, a Δ6-elongase and a Δ5-elongase, ii) a Δ12-desaturase, a Δ6-desaturase, a Δ5-desaturase, a Δ6-elongase and an Δ5-elongase, iii) a Δ12-desaturase, a ω3-desaturase and/or a Δ15-desaturase, a Δ6-desaturase, a Δ5-desaturase, a Δ6-elongase and an Δ5-elongase, iv) an ω3-desaturase and/or a Δ15-desaturase, a Δ8-desaturase, a Δ5-desaturase, a Δ9-elongase and a Δ5-elongase, v) a Δ12-desaturase, a Δ8-desaturase, a Δ5-desaturase, a Δ9-elongase and an Δ5-elongase, vi) a Δ12-desaturase, a ω3-desaturase and/or a Δ15-desaturase, a Δ8-desaturase, a Δ5-desaturase, a Δ9-elongase and an Δ5-elongase, and wherein each polynucleotide is operably linked to one or more promoters that are capable of directing expression of said polynucleotides in a cell of the plant part or the cells. In an embodiment, for the production of DHA the plant part such as a seed or recombinant cells such as microbial cells further comprises an exogenous polynucleotide encoding a Δ4 desaturase.

In an embodiment, if the plant part or cells comprise lipid comprising fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG, the plant part such as a seed or recombinant cells such as microbial cells comprise an exogenous polynucleotide encoding an 1-acyl-glycerol-3-phosphate acyltransferase (LPAAT), wherein the polynucleotide is operably linked to one or more promoters that are capable of directing expression of the polynucleotide in a cell of the plant part or the cells. In a further embodiment, the cell comprises exogenous polynucleotides encoding one of the following sets of enzymes;

i) an 1-acyl-glycerol-3-phosphate acyltransferase (LPAAT), an ω3-desaturase, a Δ6-desaturase, a Δ5-desaturase, a Δ6-elongase and a Δ5-elongase, ii) an 1-acyl-glycerol-3-phosphate acyltransferase (LPAAT), a Δ15-desaturase, a Δ6-desaturase, a Δ5-desaturase, a Δ6-elongase, and a Δ5-elongase, iii) an 1-acyl-glycerol-3-phosphate acyltransferase (LPAAT), a Δ12-desaturase, a Δ6-desaturase, a Δ5-desaturase, a Δ6-elongase and a Δ5-elongase, iv) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase, v) an 1-acyl-glycerol-3-phosphate acyltransferase (LPAAT), an ω3-desaturase, a Δ8-desaturase, a Δ5-desaturase, a Δ9-elongase and a Δ5-elongase, vi) an 1-acyl-glycerol-3-phosphate acyltransferase (LPAAT), a Δ15-desaturase, a Δ8-desaturase, a Δ5-desaturase, a Δ9-elongase, and a Δ5-elongase, vii) an 1-acyl-glycerol-3-phosphate acyltransferase (LPAAT), a Δ12-desaturase, a Δ8-desaturase, a Δ5-desaturase, a Δ9-elongase and a Δ5-elongase, viii) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase, and a Δ5-elongase, wherein each polynucleotide is operably linked to one or more promoters that are capable of directing expression of said polynucleotides in the cell. In an embodiment, for the production of DHA the cell further comprises an exogenous polynucleotide encoding a Δ4 desaturase. Preferably, the LPAAT can use a C22 polyunsaturated fatty acyl-CoA substrate such as DPA-CoA and/or DHA-CoA.

For the production of high levels of DPA, preferably, the plant, or part thereof such as seed, or microbial cell has no polynucleotide encoding a Δ4-desaturase, or has no Δ4-desaturase polypeptide.

In an embodiment, the Δ12-desaturase also has ω3-desaturase and/or Δ15-desaturase activity, i.e. the activities are conferred by a single polypeptide. Alternatively, the Δ12-desaturase does not have ω3-desaturase activity and does not have Δ15-desaturase activity i.e. the Δ12-desaturase is a separate polypeptide to the polypeptide having ω3-desaturase activity and/or Δ15-desaturase.

In yet a further embodiment, the plant part such as a seed or recombinant cells such as microbial cells have one or more or all of the following features:

i) the Δ12-desaturase converts oleic acid to linoleic acid in one or more cells of the plant part or in the recombinant cells with an efficiency of at least about 60%, at least about 70%, at least about 80%, between about 60% and about 95%, between about 70% and about 90%, or between about 75% and about 85%, ii) the ω3-desaturase converts ω6 fatty acids to ω3 fatty acids in one or more cells of the plant part or in the recombinant cells with an efficiency of at least about 65%, at least about 75%, at least about 85%, between about 65% and about 95%, between about 75% and about 91%, or between about 80% and about 91%, iii) the Δ6-desaturase converts ALA to SDA in one or more cells of the plant part or in the recombinant cells with an efficiency of at least about 20%, at least about 30%, at least about 40%, at least about 50%, at least about 60%, at least about 70%, between about 30% and about 70%, between about 35% and about 60%, or between about 50% and about 70%, iv) the Δ6-desaturase converts linoleic acid to γ-linolenic acid in one or more cells of the plant part or in the recombinant cells with an efficiency of less than about 5%, less than about 2.5%, less than about 1%, between about 0.1% and about 5%, between about 0.5% and about 2.5%, or between about 0.5% and about 1%, v) the Δ6-elongase converts SDA to ETA in one or more cells of the plant part or in the recombinant cells with an efficiency of at least about 60%, at least about 70%, at least about 75%, between about 60% and about 95%, between about 70% and about 80%, or between about 75% and about 80%, vi) the Δ5-desaturase converts ETA to EPA in one or more cells of the plant part or in the recombinant cells with an efficiency of at least about 60%, at least about 70%, at least about 75%, at least about 80%, at least about 90%, between about 60% and about 95%, between about 70% and about 95%, or between about 75% and about 95%, vii) the Δ5-elongase converts EPA to DPA in one or more cells of the plant part or in the recombinant cells with an efficiency of at least about 80%, at least about 85%, at least about 90%, between about 50% and about 90%, or between about 85% and about 95%, viii) the Δ4-desaturase converts DPA to DHA in one or more cells of the plant part or in the recombinant cells with an efficiency of at least about 80%, at least about 90%, at least about 93%, between about 50% and about 95%, between about 80% and about 95%, or between about 85% and about 95%, ix) the efficiency of conversion of oleic acid to DPA and/or DHA in one or more cells of the plant part or in the recombinant cells is at least about 10%, at least about 15%, at least about 20%, at least about 25%, about 20%, about 25%, about 30%, between about 10% and about 50%, between about 10% and about 30%, between about 10% and about 25%, or between about 20% and about 30%, x) the efficiency of conversion of LA to DPA and/or DHA in one or more cells of the plant part or in the recombinant cells is at least about 15%, at least about 20%, at least about 22%, at least about 25%, at least about 30%, about 25%, about 30%, about 35%, between about 15% and about 50%, between about 20% and about 40%, or between about 20% and about 30%, xi) the efficiency of conversion of ALA to DPA and/or DHA in one or more cells of the plant part or in the recombinant cells is at least about 17%, at least about 22%, at least about 24%, at least about 30%, about 30%, about 35%, about 40%, between about 17% and about 55%, between about 22% and about 35%, or between about 24% and about 35%, xii) one or more cells of the plant part or the recombinant cells comprise at least about 25%, at least about 30%, between about 25% and about 40%, or between about 27.5% and about 37.5%, more ω3 fatty acids than corresponding cells lacking the exogenous polynucleotides, xiii) the Δ6-desaturase preferentially desaturates α-linolenic acid (ALA) relative to linoleic acid (LA), xiv) the Δ6-elongase also has Δ9-elongase activity, xv) the Δ12-desaturase also has Δ15-desaturase activity, xvi) the Δ6-desaturase also has Δ8-desaturase activity, xvii) the Δ8-desaturase also has Δ6-desaturase activity or does not have Δ6-desaturase activity, xviii) the Δ15-desaturase also has ω3-desaturase activity on GLA, xix) the ω3-desaturase also has Δ15-desaturase activity on LA, xx) the ω3-desaturase desaturates both LA and/or GLA, xxi) the ω3-desaturase preferentially desaturates GLA relative to LA, xxii) one or more or all of the desaturases, preferably the Δ6-desaturase and/or the Δ5-desaturase, have greater activity on an acyl-CoA substrate than a corresponding acyl-PC substrate, xxiii) the Δ6-desaturase has greater Δ6-desaturase activity on ALA than LA as fatty acid substrate, xxiv) the Δ6-desaturase has greater Δ6-desaturase activity on ALA-CoA as fatty acid substrate than on ALA joined to the sn-2 position of PC as fatty acid substrate, xxv) the Δ6-desaturase has at least about a 2-fold greater Δ6-desaturase activity, at least 3-fold greater activity, at least 4-fold greater activity, or at least 5-fold greater activity, on ALA as a substrate compared to LA, xxvi) the Δ6-desaturase has greater activity on ALA-CoA as fatty acid substrate than on ALA joined to the sn-2 position of PC as fatty acid substrate, xxvii) the Δ6-desaturase has at least about a 5-fold greater Δ6-desaturase activity or at least 10-fold greater activity, on ALA-CoA as fatty acid substrate than on ALA joined to the sn-2 position of PC as fatty acid substrate, xxviii) the desaturase is a front-end desaturase, and xxix) the Δ6-desaturase has no detectable Δ5-desaturase activity on ETA.

In yet a further embodiment, the plant part such as a seed, preferably a *Brassica* seed or a *C. sativa* seed, or the recombinant cell such as microbial cells has one or more or all of the following features i) the Δ12-desaturase comprises amino acids having a sequence as provided in SEQ ID NO:4, a biologically active fragment thereof, or an amino acid sequence which is at least 50% identical to SEQ ID NO:4, ii) the ω3-desaturase comprises amino acids having a sequence as provided in SEQ ID NO:6, a biologically active fragment thereof, or an amino acid sequence which is at least 50% identical to SEQ ID NO:6, iii) the Δ6-desaturase comprises amino acids having a sequence as provided in SEQ ID NO:9, a biologically active fragment thereof, or an amino acid sequence which is at least 50% identical to SEQ ID NO:9, iv) the Δ6-elongase comprises amino acids having a sequence as provided in SEQ ID NO:16, a biologically active fragment thereof such as SEQ ID NO:17, or an amino acid sequence which is at least 50% identical to SEQ ID NO:16 and/or SEQ ID NO:17, v) the Δ5-desaturase comprises amino acids having a sequence as provided in SEQ ID NO:20, a biologically active fragment thereof, or an amino acid sequence which is at least 50% identical to SEQ ID NO:20, vi) the Δ5-elongase comprises amino acids having a sequence as provided in SEQ ID NO:25, a biologically active fragment thereof, or an amino acid sequence which is at least 50% identical to SEQ ID NO:25, and vii) the Δ4-desaturase comprises amino acids having a sequence as provided in SEQ ID NO:28, a biologically active fragment thereof, or an amino acid sequence which is at least 50% identical to SEQ ID NO:28.

In an embodiment, the plant part such as a seed or the recombinant cells such as microbial cells further comprise(s) an exogenous polynucleotide encoding a diacylglycerol acyltransferase (DGAT), monoacylglycerol acyltransferase (MGAT), glycerol-3-phosphate acyltransferase (GPAT), 1-acyl-glycerol-3-phosphate acyltransferase (LPAAT) preferably an LPAAT which can use a C22 polyunsaturated fatty acyl-CoA substrate such as DHA-CoA and/or DPA-CoA, acyl-CoA:lysophosphatidylcholine acyltransferase (LPCAT), phospholipase A$_2$ (PLA$_2$), phospholipase C (PLC), phospholipase D (PLD), CDP-choline diacylglycerol choline phosphotransferase (CPT), phoshatidylcholine diacylglycerol acyltransferase (PDAT), phosphatidylcholine:diacylglycerol choline phosphotransferase (PDCT), acyl-CoA synthase (ACS), or a combination of two or more thereof.

In another embodiment, the plant part such as a seed or the recombinant cells such as microbial cells further comprise(s) an introduced mutation or an exogenous polynucleotide which down regulates the production and/or activity of an endogenous enzyme in a cell of the plant part selected from FAE1, DGAT, MGAT, GPAT, LPCAT, PLA$_2$, PLC, PLD, CPT, PDAT, a thioesterase such as FATB, or a Δ12-desaturase, or a combination of two or more thereof.

In a further embodiment, at least one, or preferably all, of the promoters are seed specific promoters. In an embodiment, at least one, or all, of the promoters have been obtained from an oil biosynthesis or accumulation gene such as a gene encoding oleosin, or from a seed storage protein genes such as a gene encoding conlinin.

In another embodiment, the promoter(s) directing expression of the exogenous polynucleotides encoding the Δ5-elongase and/or the Δ4-desaturase initiate expression of the polynucleotides in developing seed of the plant or the recombinant cells such as the microbial cells before, or reach peak expression before, the promoter(s) directing expression of the exogenous polynucleotides encoding the Δ12-desaturase and the ω3-desaturase.

In a further embodiment, the exogenous polynucleotides are covalently linked in a DNA molecule, preferably a T-DNA molecule, integrated into the genome of cells of the plant part or the recombinant cells such as the microbial cells and preferably where the number of such DNA molecules integrated into the genome of the cells of the plant part or the recombinant cells is not more than one, two or three, or is two or three.

In yet another embodiment, the plant part comprises at least two different, exogenous polynucleotides each encoding a Δ6-desaturase which have the same or different amino acid sequences.

In a further embodiment, the total oil content of the plant part comprising the exogenous polynucleotides is at least about 40%, at least about 50%, at least about 60%, at least about 70%, between about 50% and about 80%, or between about 80% and about 100% of the total oil content of a corresponding plant part lacking the exogenous polynucleotides. In a further embodiment, the seed comprising the exogenous polynucleotides has a seed weight at least about 40%, at least about 50%, at least about 60%, at least about 70%, between about 50% and about 80%, or between about 80% and about 100% of the weight of a corresponding seed lacking the exogenous polynucleotides.

In another embodiment, the lipid is in the form of an oil, preferably a seedoil from an oilseed, and wherein at least about 90%, or about least 95%, at least about 98%, or between about 95% and about 98%, by weight of the lipid is triacylglycerols.

In a further embodiment, the process further comprises treating the lipid to increase the level of DPA and/or DHA as a percentage of the total fatty acid content. In an embodiment, the the treatment comprises one or more of fractionation, distillation or transesterification. In an embodiment, the treatment produces methyl- or ethyl-esters of DPA and/or DHA. In an example, the treatment comprises hydrolysis of the esterified fatty acids to produce free fatty acids, or transesterification. For example, the lipid such as canola oil may be treated to convert the fatty acids in the oil to alkyl esters such as methyl or ethyl esters, which may then be fractionated to enrich the lipid or oil for the DPA and/or DHA. In embodiments, the fatty acid composition of the lipid after such treatment comprises at least 40%, at least 50%, at least 60%, at least 70%, at least 80% or at least 90% DPA and/or DHA. The ratio of DHA:DPA in the lipid after treatment is preferably greater than 2:1, or alternatively less than 0.5:1. Alternatively, the level of DHA in the total fatty acid content of the lipid after treatment is less than 2.0% or less than 0.5%, preferably is absent from the lipid and/or not detected in the lipid. The process may also comprise removal of phospholipids (degumming), decolorizing, deodorising or bleaching, as known in that art. The oil may be treated to remove one or more of free fatty acids, MAG, DAG and phospholipids, thereby increasing the proportion of TAG in the extracted lipid on a weight basis.

Also provided is lipid, or oil comprising the lipid, such as free fatty acids or alkyl esters, produced using a process of the invention.

In a further aspect, the present invention provides a method of treating a lipid to increase the level of DPA and/or DHA as a percentage of the total fatty acid content, the method comprising one or more of fractionating, distillating or transesterifiying lipid, preferably extracted plant lipid or extracted microbial lipid, comprising fatty acids in an esterified form, the fatty acids comprising DPA and/or DHA, wherein at least 35% of the DPA and/or DHA esterified in the form of triacylglycerol (TAG) is esterified at the sn-2 position of the TAG.

In an embodiment of the above aspect, the lipid is plant lipid comprising fatty acids in an esterified form, the fatty acids comprising palmitic acid and C22 polyunsaturated fatty acid which comprises DPA and/or DHA, and optionally myristic acid, wherein at least 35% of the DPA and/or DHA esterified in the form of triacylglycerol (TAG) is esterified at the sn-2 position of the TAG, wherein the level of palmitic acid in the total fatty acid content of the extracted lipid is between about 2% and 16%, and wherein the level of myristic acid (C14:0) in the total fatty acid content of the extracted lipid, if present, is less than 1%.

In another aspect, the present invention provides a process for producing methyl or ethyl esters of polyunsaturated fatty acids, the process comprising reacting triacylglycerols in extracted plant lipid, or during the process of extraction, with methanol or ethanol, respectively, wherein the extracted plant lipid comprises fatty acids esterified in the form of TAG, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is between about 20.1% and 30%, or between 20.1% and 35%, preferably between 30% and 35%, thereby producing the methyl or ethyl esters of polyunsaturated fatty acids.

In another aspect, the present invention provides a process for producing methyl or ethyl esters of polyunsaturated fatty acids, the process comprising reacting triacylglycerols in extracted plant lipid, or during the process of extraction, with methanol or ethanol, respectively, wherein the extracted plant lipid comprises fatty acids esterified in the form of TAG, the fatty acids comprising oleic acid, palmitic acid, ω6 fatty acids which comprise linoleic acid (LA), ω3 fatty acids which comprise α-linolenic acid (ALA), and docosapentaenoic acid (DPA), and optionally one or more of stearidonic acid (SDA), eicosapentaenoic acid (EPA), and eicosatetraenoic acid (ETA), wherein the level of DPA in the total fatty acid content of the extracted lipid is between about 7% and 35%, preferably between 20.1% and 30% or between 20.1% and 35%, thereby producing the methyl or ethyl esters of polyunsaturated fatty acids. In an embodiment, the method comprises the production of methyl- or ethyl-esters of DPA and/or DHA.

In another aspect, the present invention provides a process for producing methyl or ethyl esters of docosapentaenoic acid (DPA) and/or docosahexaenoic acid (DHA), the process comprising reacting triacylglycerols (TAG) in extracted plant lipid, or during the process of extraction, with methanol or ethanol, respectively, wherein the extracted plant lipid comprises fatty acids in an esterified form, the fatty acids comprising docosapentaenoic acid (DPA) and/or docosahexaenoic acid (DHA), wherein at least 35% of the DPA and/or DHA esterified in the form of TAG is esterified at the sn-2 position of the TAG, thereby producing the methyl or ethyl esters of polyunsaturated fatty acids.

In a preferred embodiment, the lipid which is used in the process of the above aspects has one or more of the features defined herein in the context of the extracted lipid or oil of the invention.

In another aspect, the present invention provides an oilseed plant or part thereof such as a seed comprising
  a) lipid in its seed, the lipid comprising fatty acids in an esterified form, and
  b) exogenous polynucleotides encoding one of the following sets of enzymes;
    i) a Δ12-desaturase, a ω3-desaturase and/or Δ15-desaturase, a Δ6-desaturase, a Δ5-desaturase, a Δ4-desaturase, a Δ6-elongase and an Δ5-elongase, or
    ii) a Δ12-desaturase, a ω3-desaturase and/or Δ15-desaturase, a Δ8-desaturase, a Δ5-desaturase, a Δ4-desaturase, a Δ9-elongase and an Δ5-elongase,
  wherein each polynucleotide is operably linked to one or more seed-specific promoters that are capable of directing expression of said polynucleotides in developing seed of the plant, wherein the fatty acids comprise oleic acid, palmitic acid, 06 fatty acids which comprise linoleic acid (LA) and γ-linolenic acid (GLA), ω3 fatty acids which comprise α-linolenic acid (ALA), stearidonic acid (SDA), docosapentaenoic acid (DPA) and docosahexaenoic acid (DHA), and optionally eicosapentaenoic acid (EPA) and/or eicosatetraenoic acid (ETA), and wherein the level of DHA in the total fatty acid content of the lipid of the seed is between 20.1% and 30%, or between 20.1% and 35%, preferably between 30% and 35%.

In another aspect, the present invention provides an oilseed plant or part thereof such as a seed comprising
  a) lipid in its seed, the lipid comprising fatty acids in an esterified form, and
  b) exogenous polynucleotides encoding one of the following sets of enzymes;
    i) a Δ12-desaturase, a ω3-desaturase and/or Δ15-desaturase, a Δ6-desaturase, a Δ5-desaturase, a Δ4-desaturase, a Δ6-elongase and an Δ5-elongase, or
    ii) a Δ12-desaturase, a ω3-desaturase and/or Δ15-desaturase, a Δ8-desaturase, a Δ5-desaturase, a Δ4-desaturase, a Δ9-elongase and an Δ5-elongase,
  wherein each polynucleotide is operably linked to one or more seed-specific promoters that are capable of directing expression of said polynucleotides in developing seed of the plant, wherein the fatty acids comprise oleic acid, palmitic acid, ω6 fatty acids which comprise linoleic acid (LA), ω3 fatty acids which comprise α-linolenic acid (ALA), stearidonic acid (SDA), docosapentaenoic acid (DPA) and docosahexaenoic acid (DHA), and optionally eicosapentaenoic acid (EPA) and/or eicosatetraenoic acid (ETA), and wherein the level of DHA in the total fatty acid content of the lipid of the seed is between 20.1% and 30%, or between 20.1% and 35%, preferably between 30% and 35%.

In another aspect, the present invention provides an oilseed plant or part thereof such as a seed comprising
  a) lipid in its seed, the lipid comprising fatty acids in an esterified form, and
  b) exogenous polynucleotides encoding one of the following sets of enzymes;
    i) a Δ12-desaturase, a ω3-desaturase and/or Δ15-desaturase, a Δ6-desaturase, a Δ5-desaturase, a Δ4-desaturase, a Δ6-elongase and an Δ5-elongase, or
    ii) a Δ12-desaturase, a ω3-desaturase and/or Δ15-desaturase, a Δ8-desaturase, a Δ5-desaturase, a Δ4-desaturase, a Δ9-elongase and an Δ5-elongase, wherein each polynucleotide is operably linked to one or more seed-specific promoters that are capable of directing expression of said polynucleotides in developing seed of the plant, wherein the fatty acids comprise oleic acid, palmitic acid, ω6 fatty acids which comprise linoleic acid (LA) and γ-linolenic acid (GLA), ω3 fatty acids which comprise α-linolenic acid (ALA), stearidonic acid (SDA), docosapentaenoic acid (DPA) and docosahexaenoic acid (DHA), and optionally eicosapentaenoic acid (EPA) and/or eicosatetraenoic acid (ETA), and wherein the level of DHA in the total fatty acid content of the lipid of the seed is between 20.1% and 30%, or between 20.1% and 35%, and wherein the level of palmitic acid in the total fatty acid content of the lipid is between about 2% and 16%, and wherein the level of myristic acid (C14:0) in the total fatty acid content of the lipid, if present, is less than 1%.

In another aspect, the present invention provides an oilseed plant or part thereof such as a seed comprising lipid in its seed, or a microbial cell, comprising a) lipid comprising fatty acids in an esterified form, and b) exogenous polynucleotides encoding one of the following sets of enzymes;

i) a Δ12-desaturase, a ω3-desaturase and/or Δ15-desaturase, a Δ6-desaturase, a Δ5-desaturase, a Δ6-elongase and an Δ5-elongase, ii) a Δ12-desaturase, a ω3-desaturase and/or Δ15-desaturase, a Δ8-desaturase, a Δ5-desaturase, a Δ9-elongase and an Δ5-elongase, iii) a ω3-desaturase and/or Δ15-desaturase, a Δ6-desaturase, a Δ5-desaturase, a Δ6-elongase and an Δ5-elongase, or iv) a ω3-desaturase and/or Δ15-desaturase, a Δ8-desaturase, a Δ5-desaturase, a Δ9-elongase and an Δ5-elongase, wherein each polynucleotide is operably linked to one or more seed-specific promoters that are capable of directing expression of said polynucleotides in developing seed of the plant, or one or more promoters that are capable of directing expression of said polynucleotides in the microbial cell, wherein the fatty acids comprise oleic acid, palmitic acid, ω6 fatty acids which comprise linoleic acid (LA) and optionally γ-linolenic acid (GLA), ω3 fatty acids which comprise α-linolenic acid (ALA), stearidonic acid (SDA), and docosapentaenoic acid (DPA), and optionally docosahexaenoic acid (DHA), eicosapentaenoic acid (EPA) and/or eicosatetraenoic acid (ETA), and wherein the level of DPA in the total fatty acid content of the lipid of the seed or microbial cell is between 7% and 35%. In a preferred embodiment of this aspect, DHA is present at a level of less than 0.5% of the total fatty acid content of the lipid of the seed and of the extracted lipid and more preferably is absent from the total fatty acid content of the lipids.

In another aspect, the present invention provides a cell, preferably a cell in or from a plant such as an oilseed plant or part thereof such as a seed, or an oilseed plant or part thereof, or a microbial cell, comprising a) fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG, and b) exogenous polynucleotides encoding one of the following sets of enzymes;

i) an 1-acyl-glycerol-3-phosphate acyltransferase (LPAAT), an ω3-desaturase, a Δ6-desaturase, a Δ5-desaturase, a Δ6-elongase, a Δ5-elongase and optionally a Δ4-desaturase, ii) an 1-acyl-glycerol-3-phosphate acyltransferase (LPAAT), a Δ15-desaturase, a Δ6-desaturase, a Δ5-desaturase, a Δ6-elongase, a Δ5-elongase and optionally a Δ4-desaturase, iii) an 1-acyl-glycerol-3-phosphate acyltransferase (LPAAT), a Δ12-desaturase, a Δ6-desaturase, a Δ5-desaturase, a Δ6-elongase, an Δ5-elongase and optionally a Δ4-desaturase, iv) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase and optionally a Δ4-desaturase, v) an 1-acyl-glycerol-3-phosphate acyltransferase (LPAAT), an ω3-desaturase, a Δ8-desaturase, a Δ5-desaturase, a Δ9-elongase, an Δ5-elongase and optionally a Δ4-desaturase, vi) an 1-acyl-glycerol-3-phosphate acyltransferase (LPAAT), a Δ15-desaturase, a Δ8-desaturase, a Δ5-desaturase, a Δ9-elongase, a Δ5-elongase and optionally a Δ4-desaturase, vii) an 1-acyl-glycerol-3-phosphate acyltransferase (LPAAT), a Δ12-desaturase, a Δ8-desaturase, a Δ5-desaturase, a Δ9-elongase, an Δ5-elongase and optionally a Δ4-desaturase, viii) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase, an Δ5-elongase and optionally a Δ4-desaturase, wherein each polynucleotide is operably linked to one or more promoters that are capable of directing expression of said polynucleotides in the cell.

In another aspect, the present invention provides a cell, preferably a cell in or from a plant such as an oilseed plant or part or plurality of plant parts thereof such as a seed, or an oilseed plant or part thereof, preferably a *Brassica* plant or a *C. sativa* plant, or a microbial cell, comprising a) fatty acids in an esterified form, the fatty acids comprising docosapentaenoic acid (DPA) and/or docosahexaenoic acid (DHA), wherein at least 35% of the DPA and/or DHA esterified in the form of triacylglycerol (TAG) is esterified at the sn-2 position of the TAG, and b) exogenous polynucleotides encoding one of the following sets of enzymes;

i) an 1-acyl-glycerol-3-phosphate acyltransferase (LPAAT), an ω3-desaturase, a Δ6-desaturase, a Δ5-desaturase, a Δ6-elongase and a Δ5-elongase, ii) an 1-acyl-glycerol-3-phosphate acyltransferase (LPAAT), a Δ15-desaturase, a Δ6-desaturase, a Δ5-desaturase, a Δ6-elongase and a Δ5-elongase, iii) an 1-acyl-glycerol-3-phosphate acyltransferase (LPAAT), a Δ12-desaturase, a Δ6-desaturase, a Δ5-desaturase, a Δ6-elongase and a Δ5-elongase, iv) an 1-acyl-glycerol-3-phosphate acyltransferase (LPAAT), a Δ12-desaturase, a ω3-desaturase and/or a Δ15-desaturase, a Δ6-desaturase, a Δ5-desaturase, a Δ6-elongase and an Δ5-elongase, v) an 1-acyl-glycerol-3-phosphate acyltransferase (LPAAT), an ω3-desaturase, a Δ8-desaturase, a Δ5-desaturase, a Δ9-elongase, and a Δ5-elongase, vi) an 1-acyl-glycerol-3-phosphate acyltransferase (LPAAT), a Δ15-desaturase, a Δ8-desaturase, a Δ5-desaturase, a Δ9-elongase and a Δ5-elongase, vii) an 1-acyl-glycerol-3-phosphate acyltransferase (LPAAT), a Δ12-desaturase, a Δ8-desaturase, a Δ5-desaturase, a Δ9-elongase and a Δ5-elongase, viii) an 1-acyl-glycerol-3-phosphate acyltransferase (LPAAT), a Δ12-desaturase, a ω3-desaturase and/or a Δ15-desaturase, a Δ8-desaturase, a Δ5-desaturase, a Δ9-elongase and a Δ5-elongase, wherein each polynucleotide is operably linked to one or more promoters that are capable of directing expression of said polynucleotides in the cell. In an embodiment, for the production of DHA the cell further comprises an exogenous polynucleotide encoding a Δ4 desaturase.

Preferably, the LPAAT can use a C22 polyunsaturated fatty acyl-CoA substrate such as DPA-CoA and/or DHA-CoA and the level of DPA and/or DHA in the total fatty acid content of the extracted lipid is between about 1% and 35%, or between about 7% and 35% or between about 20.1% and 35%. In embodiments, at least about 40%, at least about 45%, at least about 48%, between 35% and about 60%, or between 35% and about 50%, of the DPA and/or DHA esterified in the form of triacylglycerol (TAG) is esterified at the sn-2 position of the TAG.

In preferred embodiments of each of the above aspects, the Δ15-desaturase is a fungal Δ15-desaturase and the ω3-desaturase is a fungal ω3-desaturase.

In a preferred embodiment, the oilseed plant, microbial cell or cell of the invention has, where relevant, one or more of the features defined herein, for example as defined above in relation to extracted plant lipid, extracted microbial lipid or a process for the production thereof.

Examples of oilseed plants include, but are not limited to, *Brassica* sp., *Gossypium hirsutum*, *Linum usitatissimum*, *Helianthus* sp., *Carthamus tinctorius*, *Glycine max*, *Zea mays*, *Arabidopsis thaliana*, *Sorghum bicolor*, *Sorghum vulgare*, *Avena sativa*, *Trifolium* sp., *Elaesis guineenis*, *Nicotiana benthamiana*, *Hordeum vulgare*, *Lupinus angustifolius*, *Oryza sativa*, *Oryza glaberrima*, *Camelina sativa*, or *Crambe abyssinica*. In an embodiment, the plant is a *Brassica* sp. plant, a *C. sativa* plant or a *G. max* (soybean) plant. In an embodiment, the oilseed plant is a canola, *B. juncea*, *Glycine max*, *Camelina sativa* or *Arabidopsis thaliana* plant. In an alternate embodiment, the oilseed plant is other than *A. thaliana* and/or other than *C. sativa*. In an embodiment, the oilseed plant is a plant other than *G. max* (soybean). The plant is preferably *Brassica* sp. or *Camelina sativa*. In an embodiment, the oilseed plant is in the field, or was grown in the field, or was grown in a glasshouse under standard conditions, for example as described in Example 1.

In an embodiment, one or more of the desaturases used in a process of the invention or present in a cell, or plant or part or plurality of plant parts thereof of the invention, is capable of using an acyl-CoA substrate. In a preferred embodiment, one or more of the Δ6-desaturase, Δ5-desaturase, Δ4-desaturase and Δ8-desaturase, if present, is capable of using an acyl-CoA substrate, preferably each of the i) Δ6-desaturase, Δ5-desaturase and Δ4-desaturase or ii) Δ5-desaturase, Δ4-desaturase and Δ8-desaturase is capable of using an acyl-CoA substrate. In an embodiment, a Δ12-desaturase and/or an ω3-desaturase is capable of using an acyl-CoA substrate. The acyl-CoA substrate is preferably an ALA-CoA for Δ6-desaturase, ETA-CoA for Δ5-desaturase, DPA-CoA for Δ4-desaturase, and ETrA-CoA for Δ8-desaturase, oleoyl-CoA for the Δ12-desaturase, or one or more of LA-CoA, GLA-CoA, and ARA-CoA for ω3-desaturase.

In an embodiment, mature, harvested seed of the plant has a DHA and/or DPA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In a further aspect, the present invention provides a *Brassica napus*, *B. juncea* or *Camelina sativa* plant which is capable of producing seed comprising DHA and/or DPA, wherein mature, harvested seed of the plant has a DHA and/or DPA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In another aspect, the present invention provides a plant cell of a plant of the invention comprising the exogenous polynucleotides defined herein.

Also provided is a plant part, preferably a seed, or recombinant cells such as microbial cells which has one or more of the following features i) is from a plant of the invention, ii) comprises lipid as defined herein, or iii) can be used in a process of the invention.

In yet another aspect, the present invention provides mature, harvested *Brassica napus*, *B. juncea* or *Camelina sativa* seed comprising DHA and/or DPA and a moisture content of between about 4% and about 15% by weight, preferably between about 6% and about 8% by weight or between about 4% and about 8% by weight, more preferably between about 4% and about 6% by weight, wherein the DHA and/or DPA content of the seed is at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed, about 80 mg per gram seed, or between about 30 mg and about 80 mg per gram seed.

In an embodiment, the cell of the invention, the oilseed plant of the invention, the *Brassica napus*, *B. juncea* or *Camelina sativa* plant of the invention, the plant part of the invention, or the seed of the invention, can be used to produce extracted lipid comprising one or more or all of the features defined herein.

In yet a further aspect, the present invention provides a method of producing a plant or cell which can be used to produce extracted lipid of the invention, the method comprising a) assaying the level of DPA and/or DHA in lipid produced by one or more plant parts such as seeds or recombinant cells such as microbial cells from a plurality of plants or recombinant cells such as microbial cells, each plant or recombinant cell such as a microbial cell comprising one or more exogenous polynucleotides encoding one of the following sets of enzymes;

i) an LPAAT, an ω3-desaturase, a Δ6-desaturase, a Δ5-desaturase, a Δ6-elongase and a Δ5-elongase, ii) an LPAAT, a Δ15-desaturase, a Δ6-desaturase, a Δ5-desaturase, a Δ6-elongase and a Δ5-elongase, iii) an LPAAT, a Δ12-desaturase, a Δ6-desaturase, a Δ5-desaturase, a Δ6-elongase and an Δ5-elongase, iv) an LPAAT, a Δ12-desaturase, a ω3-desaturase or a Δ15-desaturase, a Δ6-desaturase, a Δ5-desaturase, a Δ6-elongase and an Δ5-elongase, v) an LPAAT, an ω3-desaturase, a Δ8-desaturase, a Δ5-desaturase, a Δ9-elongase and an Δ5-elongase, vi) an LPAAT, a Δ15-desaturase, a Δ8-desaturase, a Δ5-desaturase, a Δ9-elongase and a Δ5-elongase, vii) an LPAAT, a Δ12-desaturase, a Δ8-desaturase, a Δ5-desaturase, a Δ9-elongase and an Δ5-elongase, viii) an LPAAT, a Δ12-desaturase, a ω3-desaturase or a Δ15-desaturase, a Δ8-desaturase, a Δ5-desaturase, a Δ9-elongase and an Δ5-elongase, ix) an LPAAT, an ω3-desaturase, a Δ6-desaturase, a Δ5-desaturase, a Δ6-elongase and a Δ5-elongase, x) an LPAAT, a Δ15-desaturase, a Δ6-desaturase, a Δ5-desaturase, a Δ6-elongase and a Δ5-elongase, xi) an LPAAT, a Δ12-desaturase, a Δ6-desaturase, a Δ5-desaturase, a Δ6-elongase and an Δ5-elongase, xii) a Δ12-desaturase, a ω3-desaturase or a Δ15-desaturase, a Δ6-desaturase, a Δ5-desaturase, a Δ6-elongase and an Δ5-elongase, or xiii) a Δ12-desaturase, a ω3-desaturase or a Δ15-desaturase, a Δ8-desaturase, a Δ5-desaturase, a Δ9-elongase and an Δ5-elongase, wherein each polynucleotide is operably linked to one or more promoters that are capable of directing expression of said polynucleotides in a cell of a plant part or recombinant cell, and b) identifying a plant or recombinant cell, from the plurality of plants or recombinant cells, which can be used to produce extracted plant lipid or cell lipid of the invention in one or more of its parts, and c) optionally, producing progeny plants or recombinant cells from the identified plant or recombinant cell, or seed therefrom. In an embodiment, for the production of DHA the cells further comprises an exogenous polynucleotide encoding a Δ4 desaturase. In an embodiment, the plant or recombinant cell does not comprise an exogenous polynucleotide encoding an LPAAT as defined herein.

Preferably, the progeny plant is at least a second or third generation removed from the identified plant, and is preferably homozygous for the one or more polynucleotides. More preferably, the one or more polynucleotides are present in the progeny plant at only a single insertion locus. That is, the invention provides such a method which can be used as a screening method to identify a plant or seed therefrom from a plurality of transformed candidate plants or seeds, wherein the identified plant or its progeny plant produces lipid of the invention, preferably in its seed. Such a plant or progeny plant or its seed is selected if it produces lipid of the invention, in particular having the specified DPA and/or DHA level, or is not selected if it does not produce lipid of the invention.

In an embodiment, the exogenous polynucleotide(s) present in a cell such as a microbial cell, or plant or part thereof as defined herein, become stably integrated into the genome of the cell, plant or the plant part such as seed. Preferably, the exogenous polynucleotide(s) become stably integrated into the genome of the cell, plant or plant part such as seed at a single locus in the genome, and is preferably homozygous for the insertion. More preferably, the plant, plant part or seed is further characterised in that it is lacking exogenous polynucleotides other than one or more T-DNA molecules. That is, no exogenous vector sequences are integrated into the genome other than the T-DNA sequences.

In an embodiment, before step a) the method includes introducing the one or more exogenous polynucleotides into one or more cells of the plant.

Also provided is a plant produced using a method of the invention, and seeds of such plants.

In an embodiment, the plant of the invention is both male and female fertile, preferably has levels of both male and female fertility that are at least 70% relative to, or preferably are about the same as, a corresponding wild-type plant. In an embodiment, the pollen produced by the plant of the invention or the plant produced from the seed of the invention is 90-100% viable as determined by staining with a viability stain. For example, the pollen viability may be assessed as described in Example 1.

In another aspect, the present invention provides a method of producing seed, the method comprising, a) growing a plant of the invention, or a plant which produces a part of the invention, preferably in a field as part of a population of at least 1000 or 2000 or 3000 such plants or in an area of at least 1 hectare or 2 hectares or 3 hectares planted at a standard planting density, alternatively in a glasshouse under standard conditions, b) harvesting seed from the plant or plants, and c) optionally, extracting lipid from the seed, preferably to produce oil with a total DPA and/or DHA yield of at least 60 kg or 70 kg or 80 kg DPA and/or DHA/hectare.

In an embodiment, the plant, plant cell, plant part or seed, or recombinant cell, of the invention has one or more of the following features i) its oil is as defined herein, or ii) the plant part or seed or recombinant cell is capable of being used in a process of the invention.

For example, the seed can be used to produce a plant of the invention. The plant may be grown in the field or in a glasshouse under standard conditions, for example as described in Example 1.

In a further aspect, the present invention provides lipid, or oil, produced by, or obtained from, using the process of the invention, the cell of the invention, the oilseed plant of the invention, the *Brassica* sp., *Brassica napus, B. juncea, G. max* or *Camelina sativa* plant of the invention, the plant part of the invention, the seed of the invention, or the plant, plant cell, plant part or seed of the invention. Preferably, the lipid or oil is purified to remove contaminants such as nucleic acid (DNA and/or RNA), protein and/or carbohydrate, or pigments such as chlorophyll. The lipid or oil may also be purified to enrich the proportion of TAG, for example by removal of free fatty acids (FFA) or phospholipid.

In an embodiment, the lipid or oil is obtained by extraction of oil from an oilseed. Examples of oil from oilseeds include, but are not limited to, canola oil (*Brassica napus, Brassica rapa* ssp.), mustard oil (*Brassica juncea*), other *Brassica* oil, sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil, cottonseed oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*) or *Arabidopsis* seed oil (*Arabidopsis thaliana*).

In an embodiment, a cell (recombinant cell) of, or used in, the invention is a microbial cell such as a cell suitable for fermentation, preferably an oleaginous microbial cell which is capable of accumulating triacylglycerols to a level of at least 25% on a weight basis. Preferred fermentation processes are anaerobic fermentation processes, as are well known in the art. Suitable fermenting cells, typically microorganisms are able to ferment, i.e., convert, sugars, such as glucose or maltose, directly or indirectly into the desired fatty acids. Examples of fermenting microorganisms include fungal organisms, such as yeast. As used herein, "yeast" includes *Saccharomyces* spp., *Saccharomyces cerevisiae, Saccharomyces carlbergensis, Candida* spp., *Kluveromyces* spp., *Pichia* spp., *Hansenula* spp., *Trichoderma* spp., *Lipomyces starkey*, and preferably *Yarrowia lipolytica*.

In a further aspect, the present invention provides fatty acid produced by, or obtained from, using the process of the invention, the cell of the invention, the oilseed plant of the invention, the *Brassica* sp., *Brassica napus, B. juncea, G. max* or *Camelina sativa* plant of the invention, the plant part of the invention, the seed of the invention, or the plant, plant cell, plant part or seed of the invention. Preferably the fatty acid is DPA and/or DHA. The fatty acid may be in a mixture of fatty acids having a fatty acid composition as described herein, or may be enriched so that the fatty acid, preferably DPA and/or DHA, comprises at least 40% or at least 90% of the fatty acid content of the mixture. In an embodiment, the fatty acid is non-esterified. Alternatively, the fatty acid is esterified such as, for example, to a methyl, ethyl, propyl or butyl group.

Also provided is seedmeal obtained from seed of the invention or obtained from a plant of the invention. Preferred seedmeal includes, but not necessarily limited to, *Brassica* sp., *Brassica napus, B. juncea, Camelina sativa* or *Glycine max* seedmeal. In an embodiment, the seedmeal comprises an exogenous polynucleotide(s) and/or genetic constructs as defined herein. In a preferred embodiment, the seedmeal retains some of the lipid or oil produced in the seed from which the seedmeal is obtained, but at a low level (for example, less than 2% by weight) after extraction of most of the lipid or oil. The seedmeal may be used as an animal feed or as an ingredient in food production.

In another aspect, the present invention provides a composition comprising one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, or the seedmeal of the invention. In embodiments, the composition comprises a carrier suitable for pharmaceutical, food or agricultural use, a seed treatment compound, a fertiliser, another food or feed ingredient, or added protein or vitamins.

Also provided is feedstuffs, cosmetics or chemicals comprising one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, or the composition of the invention. A preferred feedstuff is infant formula comprising the lipid or oil of the invention.

In another aspect, the present invention provides a method of producing a feedstuff, preferably infant formula, the method comprising mixing one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, or the composition of the invention, with at least one other food ingredient. The method may comprise steps of blending, cooking, baking, extruding, emulsifying or otherwise formulating the feedstuff, or packaging the feedstuff, or of analysing the amount of lipid or oil in the feedstuff.

In another aspect, the present invention provides a method of treating or preventing a condition which would benefit from a PUFA, preferably DPA and/or DHA, the method comprising administering to a subject one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, the composition of the invention, or the feedstuff of the invention. In a preferred embodiment, the PUFA is administered in the form of a pharmaceutical composition comprising an ethyl ester of the PUFA. The subject may be a human or an animal other than a human.

Examples of conditions which would benefit from a PUFA include, but are not limited to, elevated serum triglyceride levels, elevated serum cholesterol levels such as elevated LDL cholesterol levels, cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

Also provided is the use of one or more of the lipid or oil of the invention, the fatty acid of the invention, the cell according of the invention, the oilseed plant of the invention, the *Brassica* sp., *Brassica napus, B. juncea, Glycine max* or *Camelina sativa* plant of the invention, the plant part of the invention, the seed of the invention, the seedmeal of the invention, the composition of the invention, or the feedstuff of the invention for the manufacture of a medicament for treating or preventing a condition which would benefit from a PUFA preferably DPA and/or DHA.

The production of the medicament may comprise mixing the oil of the invention with a pharmaceutically acceptable carrier, for treatment of a condition as described herein. The method may comprise firstly purifying the oil and/or transesterification, and/or fractionation of the oil to increase the level of DPA and/or DHA. In a particular embodiment, the method comprises treating the lipid or oil such as canola oil to convert the fatty acids in the oil to alkyl esters such as methyl or ethyl esters. Further treatment such as fractionation or distillation may be applied to enrich the lipid or oil for the DPA and/or DHA. In a preferred embodiment, the medicament comprises ethyl esters of DPA and/or DHA. In an even more preferred embodiment, the level of ethyl esters of DPA and/or DHA in the medicament is between 30% and 50%, or at least 80% or at least about 85% or at least 90% or at least about 95%. The medicament may further comprise ethyl esters of EPA, such as between 30% and 50%, or at least 90%, of the total fatty acid content in the medicament. Such medicaments are suitable for administration to human or animal subjects for treatment of medical conditions as described herein.

In another aspect, the present invention provides a method of trading seed, comprising obtaining seed of the invention, and trading the obtained seed for pecuniary gain.

In an embodiment, obtaining the seed comprises cultivating plants of the invention and/or harvesting the seed from the plants.

In another embodiment, obtaining the seed further comprises placing the seed in a container and/or storing the seed.

In a further embodiment, obtaining the seed further comprises transporting the seed to a different location.

In yet another embodiment, the method further comprises transporting the seed to a different location after the seed is traded.

In a further embodiment, the trading is conducted using electronic means such as a computer.

In yet a further aspect, the present invention provides a process of producing bins of seed comprising:

a) swathing, windrowing and/or reaping above-ground parts of plants comprising seed of the invention, b) threshing and/or winnowing the parts of the plants to separate the seed from the remainder of the plant parts, and c) sifting and/or sorting the seed separated in step b), and loading the sifted and/or sorted seed into bins, thereby producing bins of seed.

In an embodiment, where relevant, the lipid or oil, preferably seedoil, of, or useful for, the invention has fatty levels about those provided in a Table in the Examples section, such as seed CT136-27-18-2 or CT136-27-18-19 of Table 10, or the seedoil of Tables 12, 20, 22, 23 or 24.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Aerobic DPA and/or DHA biosynthesis pathways.

Figure 2:
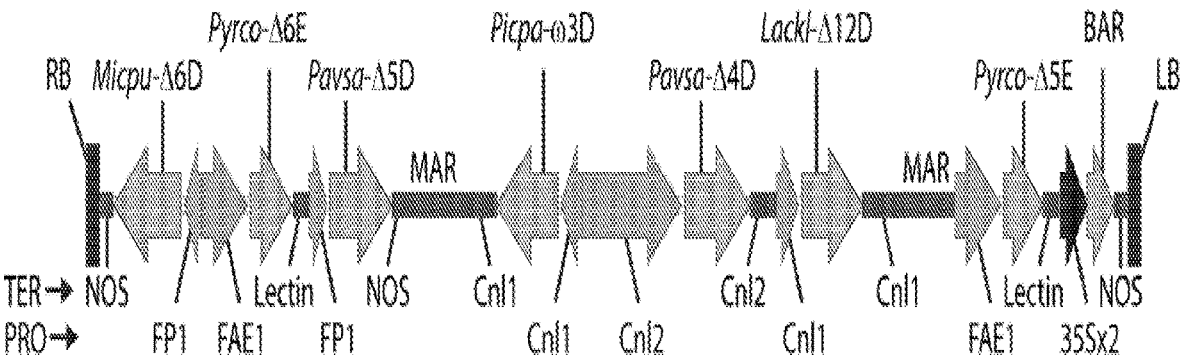

FIG. 2. Map of the T-DNA insertion region between left and right borders of pJP3416-GA7. RB denotes right border; LB, left border; TER, transcription terminator/polyadenylation region; PRO, promoter; Coding regions are indicated above the arrows, promoters and terminators below the arrows. Micpu-Δ6D, *Micromonas pusilla* Δ6-desaturase; Pyrco-Δ6E, *Pyramimonas cordata* Δ6-elongase; Pavsa-Δ5D, *Pavlova salina* Δ5-desaturase; Picpa-ω3D, *Pichia pastoris* ω3-desaturase; Pavsa-Δ4D, *P. salina* Δ4-desaturase; Lackl-Δ12D, *Lachancea kluyveri* Δ12-desaturase; Pyrco-Δ5E, *Pyramimonas cordata* Δ5-elongase. NOS denotes the *Agrobacterium tumefaciens* nopaline synthase transcription terminator/polyadenylation region; FP1, *Brassica napus* truncated napin promoter; FAE1, *Arabidopsis thaliana* FAE1 promoter; Lectin, *Glycine max* lectin transcription terminator/polyadenylation region; Cnl1 and Cnl2 denotes the *Linum usitatissimum* conlinin1 or conlinin2 promoter or terminator. MAR denotes the Rb7 matrix attachment region from *Nicotiana tabacum*.

Figure 3:
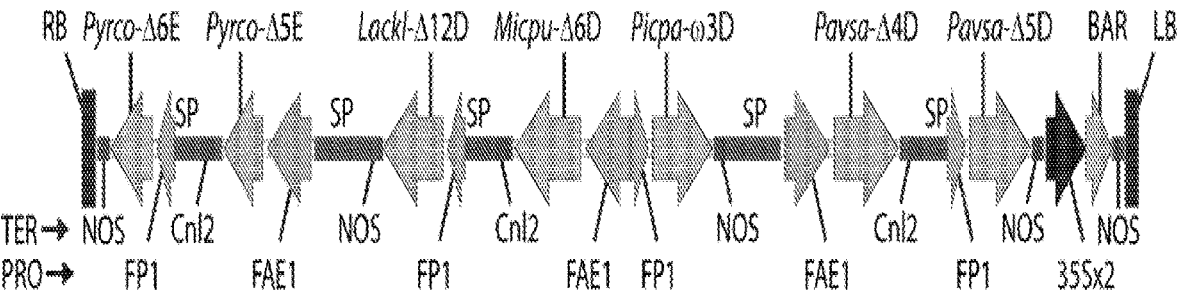

FIG. 3. Map of the T-DNA insertion region between the left and right borders of pJP3404. Labels are as in FIG. 2.

Figure 4:
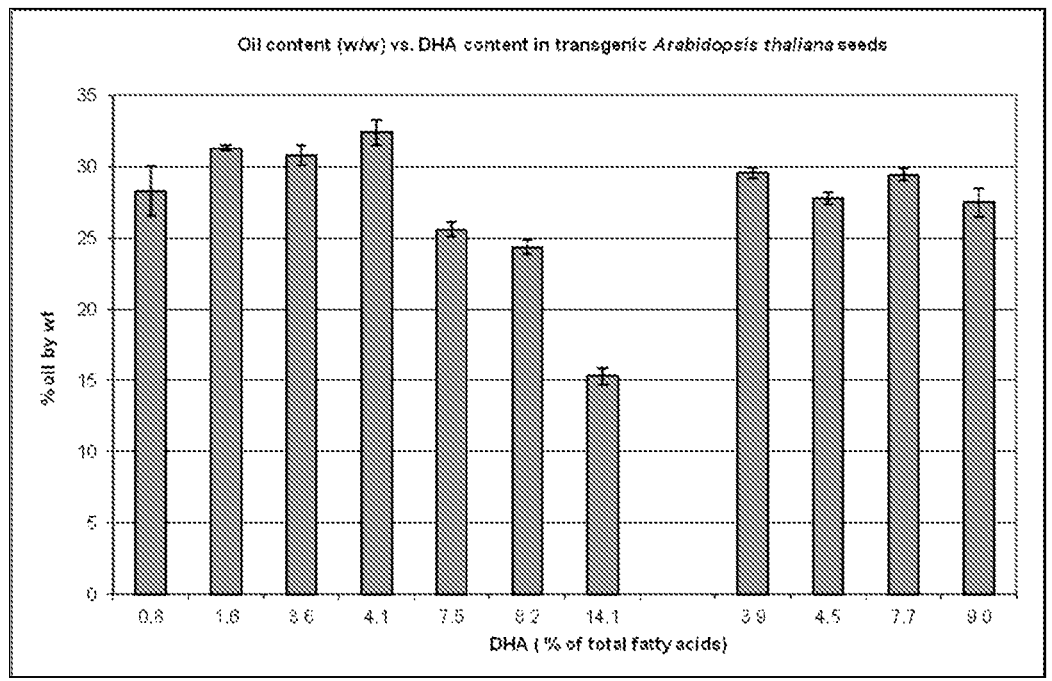

FIG. 4. Oil content (w/w) vs. DHA content, as a percentage of total fatty acid content of lipid from transgenic *Arabidopsis thaliana* seeds.

Figure 5:
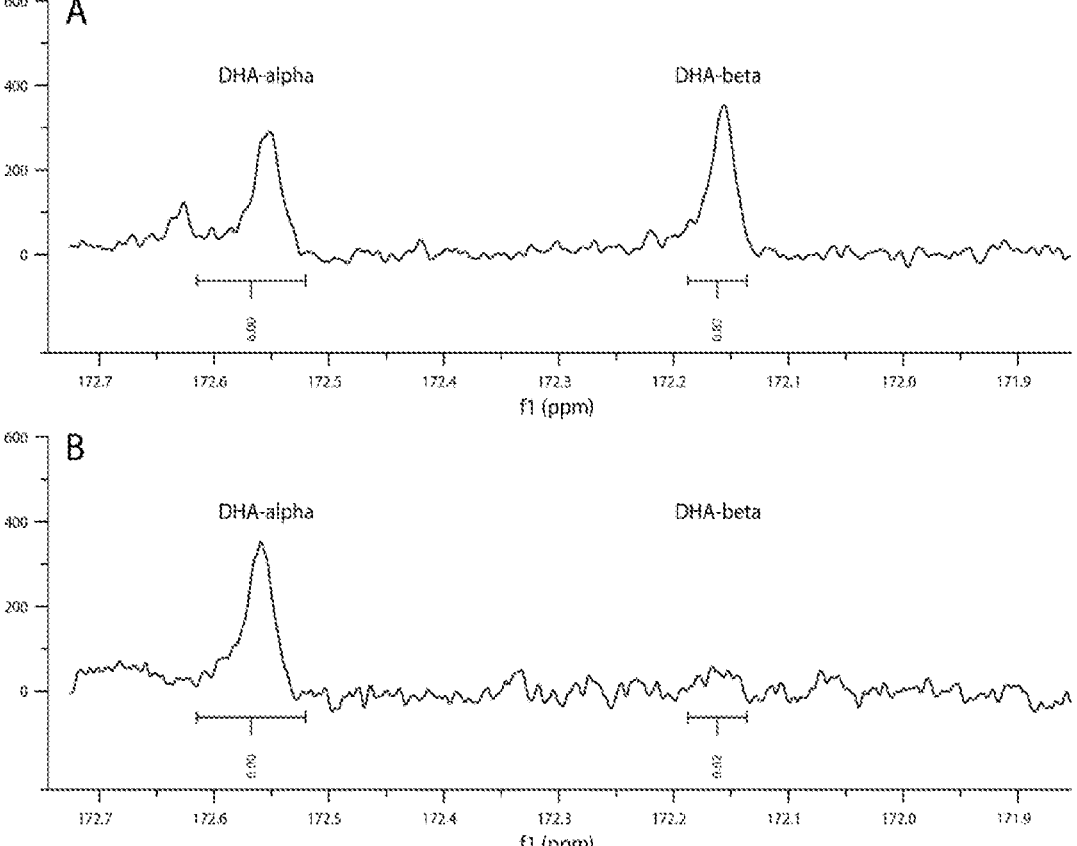

FIG. 5. Positional distribution analysis by NMR on A) Tuna oil and, B) transgenic DHA *Arabidopsis* seed oil. The peaks labelled 'DHA-alpha' represent the amount of DHA present at the sn-1 and sn-3 positions of TAG (with no positional preference this would equal 66% of total DHA) whilst the peaks labelled 'DHA-beta' represent the amount of DHA present at the sn-2 position of TAG (with no preference this would equal 33% of DHA).

Figure 6:
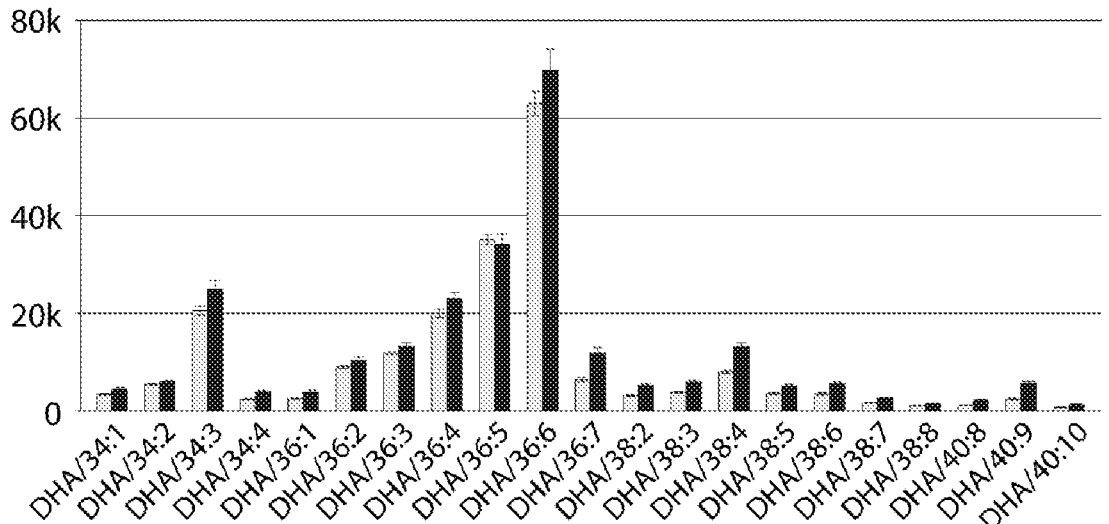

FIG. 6. LC-MS analysis of major DHA-containing triacylglycerol species in transgenic *A. thaliana* developing (grey) and mature (black) seeds. The number following the DHA denotes the total number of carbon atoms and total number of double bonds in the other two fatty acids. Therefore DHA/34:1 can also be designated TAG 56:7, etc.

Figure 7:
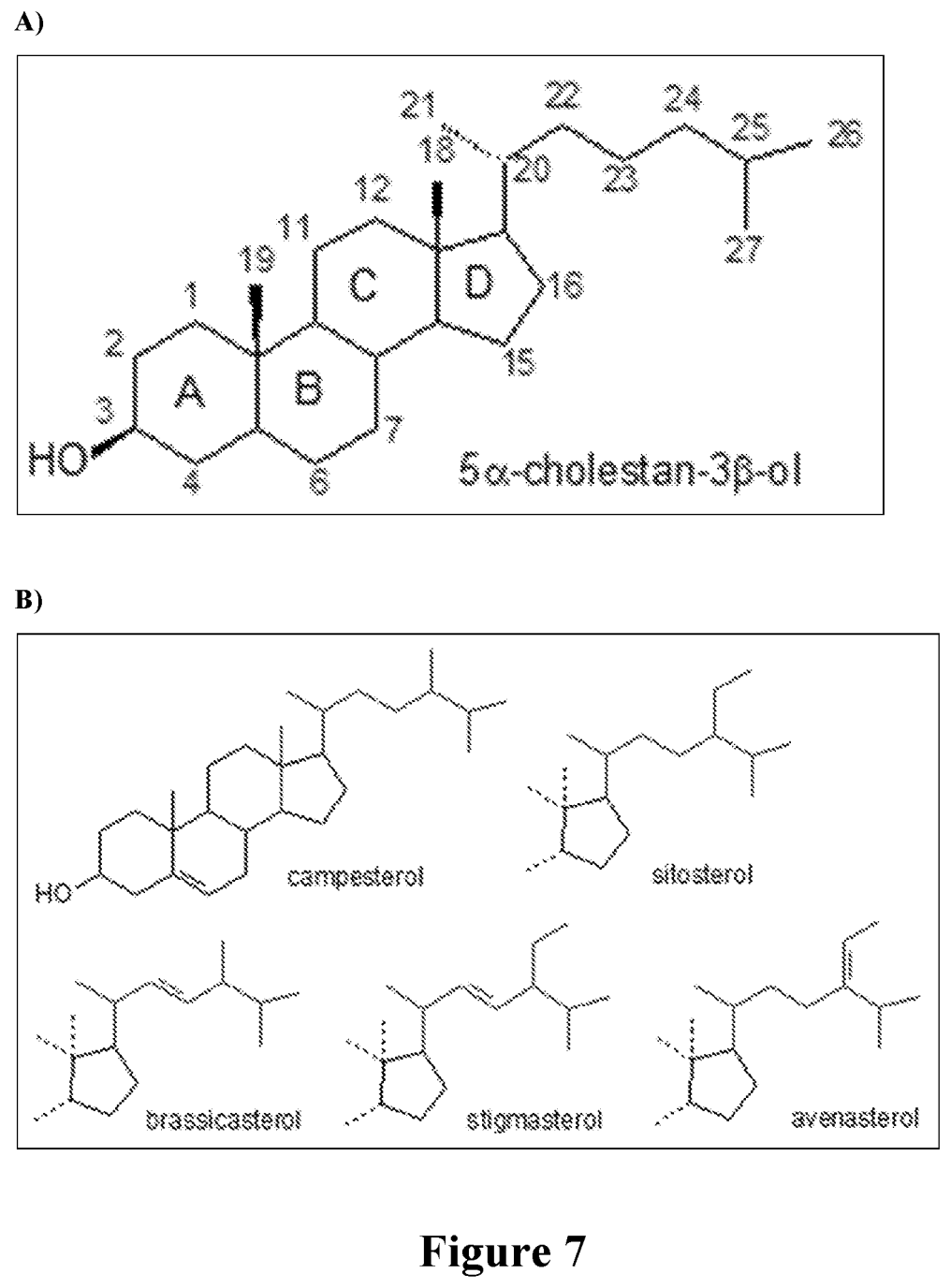

FIG. 7. (A) Basic phytosterol structure with ring and side chain numbering. (B) Chemical structures of some of the phytosterols.

Figure 8:
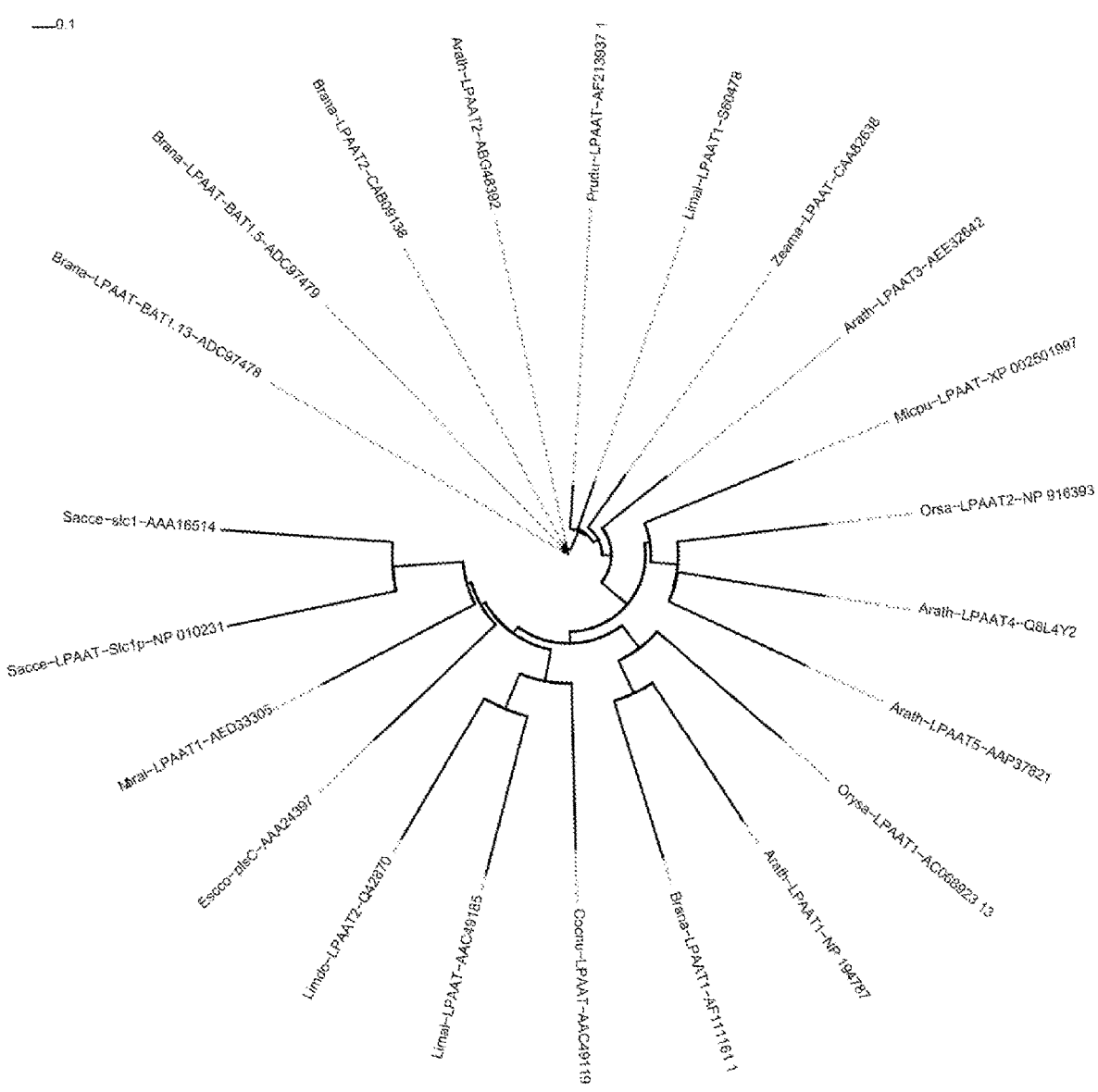

FIG. 8. Phylogenetic tree of known LPAATs.

Figure 9:
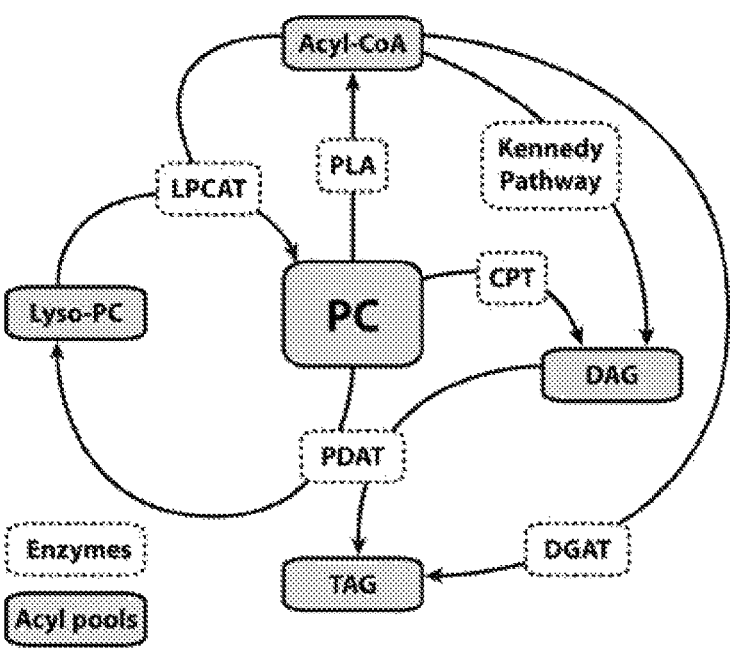

FIG. 9. The various acyl exchange enzymes which transfer fatty acids between PC, CoA pools, and TAG pools. Adapted from Singh et al. (2005).

Figure 10:
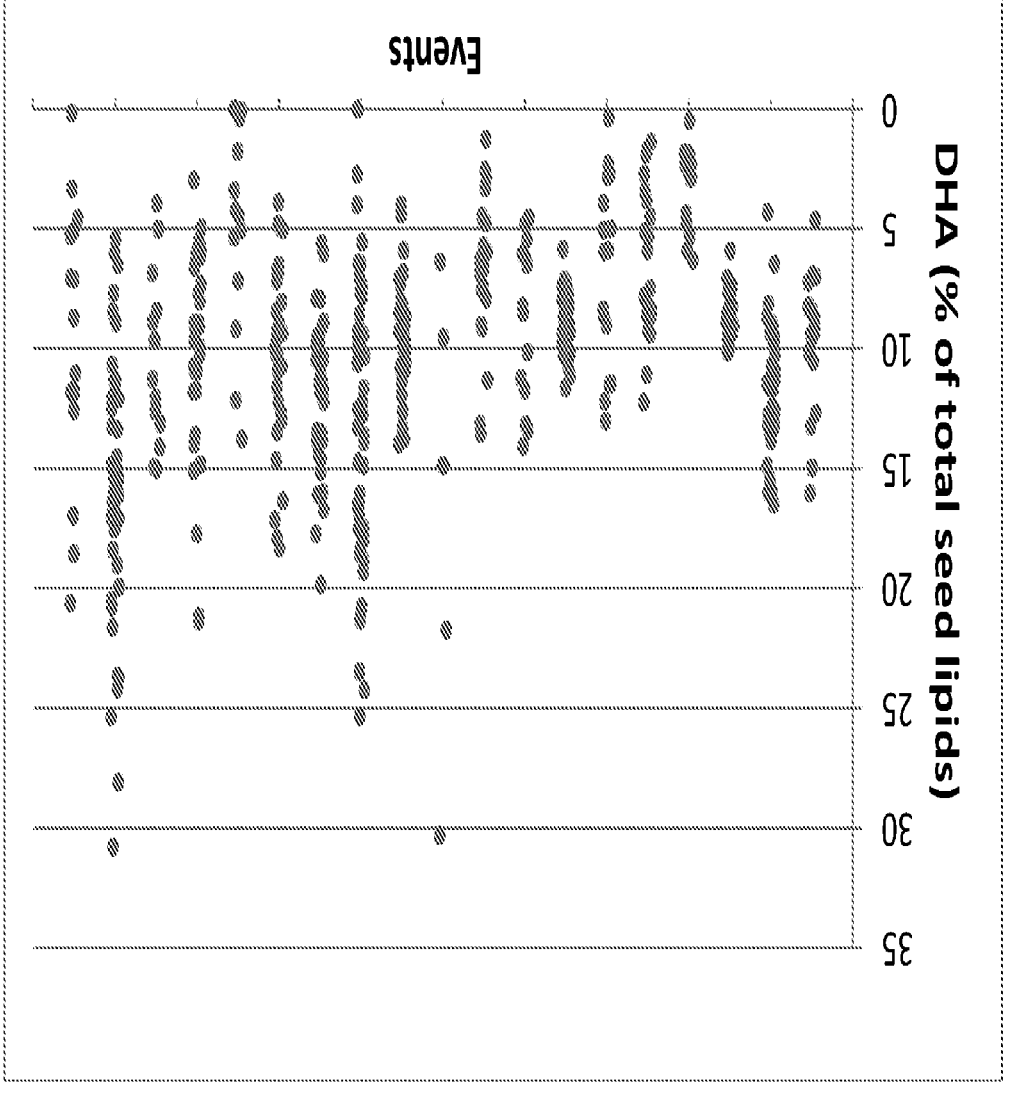

FIG. 10. DHA levels in the total fatty acid content of seedoil obtained from individual T2 seeds from *B. napus* seeds transformed with the T-DNA from the GA7-modB construct. Each dot shows the DHA level in an individual seed, with each column of dots representing T2 seeds from an individual T1 plant.

KEY TO THE SEQUENCE LISTING

SEQ ID NO:1—pJP3416-GA7 nucleotide sequence.

SEQ ID NO:2—pGA7-mod_B nucleotide sequence.

SEQ ID NO:3—Codon-optimized open reading frame for expression of *Lachancea kluyveri* Δ12 desaturase in plants.

SEQ ID NO:4—*Lachancea kluyveri* Δ12-desaturase.

SEQ ID NO:5—Codon-optimized open reading frame for expression of *Pichia pastoris* ω3 desaturase in plants.

SEQ ID NO:6—*Pichia pastoris* ω3 desaturase.

SEQ ID NO:7—Open reading frame encoding *Micromonas pusilla* Δ6-desaturase.

SEQ ID NO:8—Codon-optimized open reading frame for expression of *Micromonas pusilla* Δ6-desaturase in plants.

SEQ ID NO:9—*Micromonas pusilla* Δ6-desaturase.

SEQ ID NO: 10—Open reading frame encoding *Ostreococcus lucimarinus* Δ6-desaturase.

SEQ ID NO:11—Codon-optimized open reading frame for expression of *Ostreococcus lucimarinus* Δ6-desaturase in plants.

SEQ ID NO:12—*Ostreococcus lucimarinus* Δ6-desaturase.

SEQ ID NO:13—*Ostreococcus tauri* Δ6-desaturase.

SEQ ID NO:14—Open reading frame encoding *Pyramimonas cordata* Δ6-elongase.

SEQ ID NO: 15—Codon-optimized open reading frame for expression of *Pyramimonas cordata* Δ6-elongase in plants (truncated at 3' end and encoding functional elongase).

SEQ ID NO:16—*Pyramimonas cordata* Δ6-elongase.

SEQ ID NO:17—Truncated *Pyramimonas cordata* Δ6-elongase.

SEQ ID NO:18—Open reading frame encoding *Pavlova salina* Δ5-desaturase.

SEQ ID NO:19—Codon-optimized open reading frame for expression of *Pavlova salina* Δ5-desaturase in plants.

SEQ ID NO:20—*Pavlova salina* Δ5-desaturase.

SEQ ID NO:21—Open reading frame encoding *Pyramimonas cordata* Δ5-desaturase.

SEQ ID NO:22—*Pyramimonas cordata* Δ5-desaturase.

SEQ ID NO:23—Open reading frame encoding *Pyramimonas cordata* Δ5-elongase.

SEQ ID NO:24—Codon-optimized open reading frame for expression of *Pyramimonas cordata* Δ5-elongase in plants.

SEQ ID NO:25—*Pyramimonas cordata* Δ5-elongase.

SEQ ID NO:26—Open reading frame encoding *Pavlova salina* Δ4-desaturase.

SEQ ID NO:27—Codon-optimized open reading frame for expression of *Pavlova salina* Δ4-desaturase in plants.

SEQ ID NO:28—*Pavlova salina* Δ4-desaturase.

SEQ ID NO:29—*Isochrysis galbana* Δ9-elongase.

SEQ ID NO:30—Codon-optimized open reading frame for expression of *Emiliania huxleyi* Δ9-elongase in plants.

SEQ ID NO:31—*Emiliania huxleyi* CCMP1516Δ9-elongase.

SEQ ID NO:32—Open reading frame encoding *Pavlova pinguis* Δ9-elongase.

SEQ ID NO:33—*Pavlova pinguis* Δ9-elongase.

SEQ ID NO:34—Open reading frame encoding *Pavlova salina* Δ9-elongase.

SEQ ID NO:35—*Pavlova salina* Δ9-elongase.

SEQ ID NO:36—Open reading frame encoding *Pavlova salina* Δ8-desaturase.

SEQ ID NO:37—*Pavlova salina* Δ8-desaturase.

SEQ ID NO:38—V2 viral suppressor.

SEQ ID NO:39—Open reading frame encoding V2 viral suppressor.

SEQ ID NO: 40—*Arabidopsis thaliana* LPAAT2.

SEQ ID NO: 41—*Limnanthes alba* LPAAT.

SEQ ID NO: 42—*Saccharomyces cerevisiae* LPAAT.

SEQ ID NO: 43—*Micromonas pusilla* LPAAT.

SEQ ID NO: 44—*Mortierella alpina* LPAAT.

SEQ ID NO: 45—*Braccisa napus* LPAAT.

SEQ ID NO: 46—*Brassica napus* LPAAT.

SEQ ID NO: 47—*Phytophthora infestans* ω3 desaturase.

SEQ ID NO: 48—*Thalassiosira pseudonana* ω3 desaturase.

SEQ ID NO: 49—*Pythium irregulare* ω3 desaturase.

SEQ ID NO's: 50 to 58—Oligonucleotide primers/probes.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, fatty acid synthesis, transgenic plants, recombinant cells, protein chemistry, and biochemistry).

Unless otherwise indicated, the protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors), Antibodies: A Laboratory Manual, Cold Spring Harbour Laboratory, (1988), and J. E. Coligan et al. (editors), Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about" unless stated to the contrary, refers to +/−10%, more preferably +/−5%, more preferably +/−1% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, the terms "extracted plant lipid" and "isolated plant lipid" refer to a lipid composition which has been extracted from, for example by crushing, a plant or part thereof such as seed. The extracted lipid can be a relatively crude composition obtained by, for example, crushing a plant seed, or a more purified composition where most, if not all, of one or more or each of the water, nucleic acids, proteins and carbohydrates derived from the plant material have been removed. Examples of purification methods are described below. In an embodiment, the extracted or isolated plant lipid comprises at least about 60%, at least about 70%, at least about 80%, at least about 90%, or at least about 95% (w/w) lipid by weight of the composition. The lipid may be solid or liquid at room temperature, when liquid it is considered to be an oil. In an embodiment, extracted lipid of the invention has not been blended with another lipid such as DHA and/or DPA produced by another source (for example, DHA and DPA from fish oil). In an embodiment, following extraction the ratio of one or more or all of, oleic acid to DHA and/or DPA, palmitic acid to DHA and/or DPA, linoleic acid to DHA and/or DPA, and total ω6 fattyacids: total ω3 fatty acids, has not been significantly altered (for example, no greater than a 10% or 5% alteration) when compared to the ratio in the intact seed or cell. In an another embodiment, the extracted plant lipid has not been exposed to a procedure, such as hydrogenation or fractionation, which may alter the ratio of one or more or all of, oleic acid to DHA and/or DPA, palmitic acid to DHA and/or DPA, linoleic acid to DHA and/or DPA, and total ω6 fattyacids: total ω3 fatty acids, when compared to the ratio in the intact seed or cell. When the extracted plant lipid of the invention is comprised in an oil, the oil may further comprise non-fatty acid molecules such as sterols.

As used herein, the terms "extracted plant oil" and "isolated plant oil" refer to a substance or composition comprising extracted plant lipid or isolated plant lipid and which is a liquid at room temperature. The oil is obtained from a plant or part thereof such as seed. The extracted or isolated oil can be a relatively crude composition obtained by, for example, crushing a plant seed, or a more purified composition where most, if not all, of one or more or each of the water, nucleic acids, proteins and carbohydrates derived from the plant material have been removed. The composition may comprise other components which may be lipid or non-lipid. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil such as DHA and/or DPA produced by another source (for example, DHA and/or DPA from fish oil). In an embodiment, following extraction, the ratio of one or more or all of, oleic acid to DHA and/or DPA, palmitic acid to DHA and/or DPA, linoleic acid to DHA and/or DPA, and total 06 fatty acids: total ω3 fatty acids, has not been significantly altered (for example, no greater than a 10% or 5% alteration) when compared to the ratio in the intact seed or cell. In an another embodiment, the extracted plant oil has not been exposed to a procedure, such as hydrogenation or fractionation, which may alter the ratio of one or more or all of, oleic acid to DHA and/or DPA, palmitic acid to DHA and/or DPA, linoleic acid to DHA and/or DPA, and total ω6 fattyacids:total ω3 fatty acids, when compared to the ratio in the intact seed or cell. Extracted plant oil of the invention may comprise non-fatty acid molecules such as sterols.

As used herein, terms such as "extracted microbial lipid" or "extracted microbial oil" have analogous meanings as the corresponding terms "extracted plant lipid" and "extracted plant oil" respectively, with the main difference being the source of the lipid or oil.

As used herein, an "oil" is a composition comprising predominantly lipid and which is a liquid at room temperature. For instance, oil of the invention preferably comprises at least 75%, at least 80%, at least 85% or at least 90% lipid by weight. Typically, a purified oil comprises at least 90% triacylglycerols (TAG) by weight of the lipid in the oil. Minor components of an oil such as diacylglycerols (DAG), free fatty acids (FFA), phospholipid and sterols may be present as described herein.

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Preferred fatty acids of the invention have carbon chains of 18-22 carbon atoms (C18, C20, C22 fatty acids), more preferably 20-22 carbon atoms (C20, C22) and most preferably 22 carbon atoms (C22). Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms. In an embodiment, the fatty acid is esterified to a methyl or ethyl group, such as, for example, a methyl or ethyl ester of a C20 or C22 PUFA. Preferred fatty acids are the methyl or ethyl esters of EPA, DPA or DHA, or the mixtures EPA and DHA, or EPA, DPA and DHA, or EPA and DPA.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (—CH3—) and each carbon within the chain contains 2 hydrogens (—CH2—).

"Unsaturated fatty acids" are of similar form to saturated fatty acids, except that one or more alkene functional groups exist along the chain, with each alkene substituting a singly-bonded "—CH2-CH2—" part of the chain with a doubly-bonded "—CH=CH—" portion (that is, a carbon double bonded to another carbon). The two next carbon atoms in the chain that are bound to either side of the double bond can occur in a cis or trans configuration, preferably in the cis configuration. In an embodiment, the lipid or oil or the invention has a fatty acid composition which comprises less than 1% fatty acids having a carbon-carbon double bond in the trans configuration (trans fatty acids).

As used herein, the term "monounsaturated fatty acid" refers to a fatty acid which comprises at least 12 carbon atoms in its carbon chain and only one alkene group (carbon-carbon double bond) in the chain. As used herein, the terms "polyunsaturated fatty acid" or "PUFA" refer to a fatty acid which comprises at least 12 carbon atoms in its carbon chain and at least two alkene groups (carbon-carbon double bonds).

As used herein, the terms "long-chain polyunsaturated fatty acid" and "LC-PUFA" refer to a fatty acid which comprises at least 20 carbon atoms in its carbon chain and at least two carbon-carbon double bonds, and hence include VLC-PUFAs. As used herein, the terms "very long-chain polyunsaturated fatty acid" and "VLC-PUFA" refer to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of; arachidonic acid (ARA, 20:4Δ5,8,11,14; ω6), eicosatetraenoic acid (ETA, 20:4Δ8,11,14,17, ω3), eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acids are at least DHA and/or DPA, preferably, DPA and DHA, or EPA, DPA and DHA, or EPA and DPA. In an embodiment, as extracted from the plant, DHA is present in the lipid or oil at a level of 20.1-30% or between 20.1% and 35%, preferably between 30% to 35% of the total fatty acid composition. For example, DHA can be present at a level of between 30.1% and 35% of the total fatty acid composition. In an embodiment, the level of DHA is greater than the level of DPA, more preferably greater than the level of each of EPA and DPA, most preferably greater than the combined level of EPA and DPA. In an alternative embodiment, DPA is present at a level of between about 7% and 30% or 35% and DHA is either absent or, if present, is present at a level of less than 2.0%, preferably less than 1.0%, more preferably less than 0.5% of the total fatty acid composition and most preferably absent or undetectable. This may be accomplished by the absence of a Δ4-desaturase activity in the cell. In an embodiment, the level of DPA is greater than the level of EPA, more preferably greater than the level of each of EPA and DHA, most preferably greater than the combined level of EPA and DHA. In this embodiment, DHA may be absent or, if present, is present at a level of less than 0.5% of the total fatty acid composition.

Furthermore, as used herein the terms "long-chain polyunsaturated fatty acid" (LC-PUFA) and "very long-chain polyunsaturated fatty acid" (VLC-PUFA) refer to the fatty acid being in a free state (non-esterified) or in an esterified form such as part of a triglyceride (triacylglycerol), diacylglyceride, monoacylglyceride, acyl-CoA bound or other bound form. In the triglyceride, the LC-PUFA or VLC-PUFA such as DHA or DPA may be esterified at the sn-1/3 or sn-2 positions, or the triglyceride may comprise two or three acyl groups selected from LC-PUFA and VLC-PUFA acyl groups. For example, the triglyceride may comprise DHA or DPA at both of the sn-1, sn-2 and sn-3 positions. The fatty acid may be esterified as a phospholipid such as a phosphatidylcholine (PC), phosphatidylethanolamine, phosphatidylserine, phosphatidylglycerol, phosphatidylinositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or at least 85% triacylglycerols, with the remainder present as other forms of lipid such as those mentioned, with at least said triacylglycerols comprising the LC-PUFA. The oil may subsequently be further purified or treated, for example by hydrolysis with a strong base to release the free fatty acids, or by transesterification, distillation or the like.

As used herein, "total ω6 fatty acids" or "total ω6 fatty acid content" or the like refers to the sum of all the ω6 fatty acids, esterified and non-esterified, in the extracted lipid, oil, recombinant cell, plant part or seed, as the context determines, expressed as a percentage of the total fatty acid content. These ω6 fatty acids include (if present) LA, GLA, DGLA, ARA, EDA and ω6-DPA, and exclude any ω3 fatty acids and monounsaturated fatty acids. The ω6 fatty acids present in the plants, seeds, lipid or oils of the invention are all included in the class of polyunsaturated fatty acids (PUFA).

As used herein, "new ω6 fatty acids" or "new ω6 fatty acid content" or the like refers to the sum of all the ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts and seeds of the invention by the expression of the genetic constructs (exogenous polynucleotides) introduced into the cells, and include (if present) GLA, DGLA, ARA, EDA and ω6-DPA, but exclude LA and any ω3 fatty acids and monounsaturated fatty acids. Exemplary total ω6 fatty acid contents and new ω6 fatty acid contents are determined by conversion of fatty acids in a sample to FAME and analysis by GC, as described in Example 1.

As used herein, "total ω3 fatty acids" or "total ω3 fatty acid content" or the like refers to the sum of all the ω3 fatty acids, esterified and non-esterified, in the extracted lipid, oil, recombinant cell, plant part or seed, as the context determines, expressed as a percentage of the total fatty acid content. These ω3 fatty acids include (if present) ALA, SDA, ETrA, ETA, EPA, DPA and DHA, and exclude any ω6 fatty acids and monounsaturated fatty acids. The ω3 fatty acids present in the plants, seeds, lipid or oils of the invention are all included in the class of polyunsaturated fatty acids (PUFA).

As used herein, "new ω3 fatty acids" or "new ω3 fatty acid content" or the like refers to the sum of all the ω3 fatty acids excluding ALA, esterified and non-esterified, in the extracted lipid, oil, recombinant cell, plant part or seed, as the context determines, expressed as a percentage of the total fatty acid content. These new ω3 fatty acids are the ω3 fatty acids that are produced in the cells, plants, plant parts and seeds of the invention by the expression of the genetic constructs (exogenous polynucleotides) introduced into the cells, and include (if present) SDA, ETrA, ETA, EPA, DPA and DHA, but exclude ALA and any ω6 fatty acids and monounsaturated fatty acids. Exemplary total (ω3 fatty acid contents and new ω3 fatty acid contents are determined by conversion of fatty acids in a sample to FAME and analysis by GC, as described in Example 1.

As the skilled person would appreciate, the term "obtaining a plant part" as a step in the process of the invention can include obtaining one or more plant parts for use in the process. Obtaining the plant part includes harvesting the plant part from a plant such as with a mechanical harvester, or purchasing the plant part, or receiving the plant part from a supplier. In another example, obtaining a plant part may be acquiring the plant from someone else who has harvested the plant part.

The desaturase, elongase and acyl transferase proteins and genes encoding them that may be used in the invention are any of those known in the art or homologues or derivatives thereof. Examples of such genes and encoded protein sizes are listed in Table 1. The desaturase enzymes that have been shown to participate in LC-PUFA biosynthesis all belong to the group of so-called "front-end" desaturases. Preferred proteins, or combinations of proteins, are those encoded by the genetic constructs provided herein as SEQ ID NOs: 1 and 2.

TABLE 1

Cloned genes involved in LC-PUFA biosynthesis

| Enzyme | Type of organism | Species | Accession Nos. | Protein size (aa's) | References |
|---|---|---|---|---|---|
| Δ6-desaturase | Protist | *Euglena gracilis* | AY278558 | 541 | Meyer et al., 2003 |
| | Algae | *Pavlova lutherii* | AY332747 | 445 | Tonon et al., 2003 |
| | | *Isochrysis galbana* | AAV33631 | 433 | Pereira et al., 2004b |
| | | *Pavlova salina* | AAY15136 | 447 | Zhou et al., 2007 |
| | Thraustochytrid | *Thraustochytrium aureum* | AAN75707 AAN75708 AAN75709 AAN75710 | 515 | N/A |
| | | *Thraustochytrium* sp. ATCC21685 | AAM09688 | 519 | Qiu et al. 2001 |
| Δ5-desaturase | Mammals | *Homo sapiens* | AF199596 | 444 | Cho et al., 1999b Leonard et al., 2000b |
| | Nematode | *Caenorhabditis elegans* | AF11440 NM 069350 | 447 | Michaelson et al., 1998b; Watts and Browse, 1999b |
| | Fungi | *Mortierella alpina* | AF067654 | 446 | Michaelson et al., 1998a; Knutzon et al., 1998 |
| | | *Pythium irregulare* | AF419297 | 456 | Hong et al., 2002a |
| | | *Dictyostelium discoideum* | AB022097 | 467 | Saito et al., 2000 |
| | | *Saprolegnia diclina* | | 470 | WO02081668 |
| | Diatom | *Phaeodactylum tricornutum* | AY082392 | 469 | Domergue et al., 2002 |
| | Algae | *Thraustochytrium sp* | AF489588 | 439 | Qiu et al., 2001 |
| | | *Thraustochytrium aureum* | | 439 | WO02081668 |
| | | *Isochrysis galbana* | | 442 | WO02081668 |
| | Moss | *Marchantia polymorpha* | AY583465 | 484 | Kajikawa et al., 2004 |
| Δ6-desaturase | Mammals | *Homo sapiens* | NM 013402 | 444 | Cho et al., 1999a; Leonard et al., 2000 |
| | | *Mus musculus* | NM 019699 | 444 | Cho et al., 1999a |
| | Nematode | *Caenorhabditis elegans* | Z70271 | 443 | Napier et al., 1998 |
| | Plants | *Borago officinales* | U79010 | 448 | Sayanova et al., 1997 |
| | | *Echium* | AY055117 AY055118 | | Garcia-Maroto et al., 2002 |
| | | *Primula vialii* | AY234127 | 453 | Sayanova et al., 2003 |
| | | *Anemone leveillei* | AF536525 | 446 | Whitney et al., 2003 |
| | Mosses | *Ceratodon purpureus* | AJ250735 | 520 | Sperling et al., 2000 |
| | | *Mar chantia polymorpha* | AY583463 | 481 | Kajikawa et al., 2004 |
| | | *Physcomitrella patens* | CAA11033 | 525 | Girke et al., 1998 |
| | Fungi | *Mortierella alpina* | AF110510 AB020032 | 457 | Huang et al., 1999; Sakuradani et al., 1999 |
| | | *Pythium irregulare* | AF419296 | 459 | Hong et al., 2002a |
| | | *Mucor circinelloides* | AB052086 | 467 | NCBI* |
| | | *Rhizopus* sp. | AY320288 | 458 | Zhang et al., 2004 |
| | | *Saprolegnia diclina* | | 453 | WO02081668 |
| | Diatom | *Phaeodactylum tricornutum* | AY082393 | 477 | Domergue et al., 2002 |
| | Bacteria | *Synechocystis* | L11421 | 359 | Reddy et al., 1993 |
| | Algae | *Thraustochytrium aureum* | | 456 | WO02081668 |
| Bifunctional Δ5/Δ6-desaturase | Fish | *Danio rerio* | AF309556 | 444 | Hastings et al., 2001 |
| C20 Δ8-desaturase | Algae | *Euglena gracilis* | AF139720 | 419 | Wallis and Browse, 1999 |
| | Plants | *Borago officinales* | AAG43277 | 446 | Sperling et al., 2001 |
| Δ6-elongase | Nematode | *Caenorhabditis elegans* | NM 069288 | 288 | Beaudoin et al., 2000 |
| | Mosses | *Physcomitrella patens* | AF428243 | 290 | Zank et al., 2002 |
| | | *Marchantia polymorpha* | AY583464 | 290 | Kajikawa et al., 2004 |
| | Fungi | *Mortierella alpina* | AF206662 | 318 | Parker-Barnes et al., 2000 |
| | Algae | *Pavlova lutheri*** | | 501 | WO 03078639 |
| | | *Thraustochytrium* | AX951565 | 271 | WO 03093482 |
| | | *Thraustochytrium* sp** | AX214454 | 271 | WO 0159128 |
| PUFA-elongase | Mammals | *Homo sapiens* | AF231981 | 299 | Leonard et al., 2000b; Leonard et al., 2002 |
| | | *Rattus norvegicus* | AB071985 | 299 | Inagaki et al., 2002 |
| | | *Rattus norvegicus*** | AB071986 | 267 | Inagaki et al., 2002 |
| | | *Mus musculus* | AF170907 | 279 | Tvrdik et al., 2000 |
| | | *Mus musculus* | AF170908 | 292 | Tvrdik et al., 2000 |
| | Fish | *Danio rerio* | AF532782 | 291 (282) | Agaba et al., 2004 |
| | | *Danio rerio*** | NM 199532 | 266 | Lo et al., 2003 |
| | Worm | *Caenorhabditis elegans* | Z68749 | 309 | Abbott et al., 1998 Beaudoin et al., 2000 |
| | Algae | *Thraustochytrium aureum*** | AX464802 | 272 | WO 0208401-A2 |
| | | *Pavlova lutheri*** | | 320 | WO 03078639 |
| Δ9-elongase | Algae | *Isochrysis galbana* | AF390174 | 263 | Qi et al., 2002 |
| | | *Euglena gracilis* | | 258 | WO 08/128241 |

TABLE 1-continued

Cloned genes involved in LC-PUFA biosynthesis

| Enzyme | Type of organism | Species | Accession Nos. | Protein size (aa's) | References |
|---|---|---|---|---|---|
| Δ5-elongase | Algae | Ostreococcus tauri | AAV67798 | 300 | Meyer et al., 2004 |
| | | Pyramimonas cordata | | 268 | WO 2010/057246 |
| | | Pavlova sp. CCMP 459 | AAV33630 | 277 | Pereira et al., 2004b |
| | | Pavlova salina | AAY15135 | 302 | Robert et al., 2009 |
| | Diatom | Thalassiosira pseudonana | AAV67800 | 358 | Meyer et al., 2004 |
| | Fish | Oncorhynchus mykiss | CAM55862 | 295 | WO 06/008099 |
| | Moss | Marchantia polymorpha | BAE71129 | 348 | Kajikawa et al., 2006 |

*http://www.ncbi.nlm.nih.gov/
**Function not proven/not demonstrated

As used herein, the term "front-end desaturase" refers to a member of a class of enzymes that introduce a double bond between the carboxyl group and a pre-existing unsaturated part of the acyl chain of lipids, which are characterized structurally by the presence of an N-terminal cytochrome b5 domain, along with a typical fatty acid desaturase domain that includes three highly conserved histidine boxes (Napier et al., 1997).

Activity of any of the elongases or desaturases for use in the invention may be tested by expressing a gene encoding the enzyme in a cell such as, for example, a plant cell or preferably in somatic embryos or transgenic plants, and determining whether the cell, embryo or plant has an increased capacity to produce LC-PUFA compared to a comparable cell, embryo or plant in which the enzyme is not expressed.

In one embodiment one or more of the desaturases and/or elongases for use in the invention can purified from a microalga, i.e. is identical in amino acid sequence to a polypeptide which can be purified from a microalga.

Whilst certain enzymes are specifically described herein as "bifunctional", the absence of such a term does not necessarily imply that a particular enzyme does not possess an activity other than that specifically defined.

Desaturases

As used herein, the term "desaturase" refers to an enzyme which is capable of introducing a carbon-carbon double bond into the acyl group of a fatty acid substrate which is typically in an esterified form such as, for example, acyl-CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, a "Δ4-desaturase" refers to a protein which performs a desaturase reaction that introduces a carbon-carbon double bond at the $4^{th}$ carbon-carbon bond from the carboxyl end of a fatty acid substrate. The "Δ4-desaturase" is at least capable of converting DPA to DHA. Preferably, the "Δ4-desaturase" is capable of converting DPA-CoA to DHA-CoA, i.e. it is an acyl-CoA desaturase. In an embodiment, the "Δ4-desaturase" is capable of converting DPA esterified at the sn-2 position of PC to DHA-PC. Preferably the Δ4-desaturase has greater activity on DPA-CoA than on DPA-PC. The desaturation step to produce DHA from DPA is catalysed by a Δ4-desaturase in organisms other than mammals, and a gene encoding this enzyme has been isolated from the freshwater protist species Euglena gracilis and the marine species Thraustochytrium sp. (Qiu et al., 2001; Meyer et al., 2003). In one embodiment, the Δ4-desaturase comprises amino acids having a sequence as provided in SEQ ID NO:28, or a Thraustochytrium sp. Δ4-desaturase, a biologically active fragment thereof, or an amino acid sequence which is at least 80% identical to SEQ ID NO:28. In an embodiment, a plant, plant part (such as seed) or cell of, or used in, the invention which produces high levels of DPA, such as 5% to 35% of the total extractable fatty acid content is DPA, does not comprise a gene encoding a functional Δ4-desaturase.

As used herein, a "Δ5-desaturase" refers to a protein which performs a desaturase reaction that introduces a carbon-carbon double bond at the $5^{th}$ carbon-carbon bond from the carboxyl end of a fatty acid substrate. In an embodiment, the fatty acid substrate is ETA and the enzyme produces EPA. Preferably, the "Δ5-desaturase" is capable of converting ETA-CoA to EPA-CoA, i.e. it is an acyl-CoA desaturase. In an embodiment, the "Δ5-desaturase" is capable of converting ETA esterified at the sn-2 position of PC. Preferably the Δ5-desaturase has greater activity on ETA-CoA than on ETA-PC. Examples of Δ5-desaturases are listed in Ruiz-Lopez et al. (2012) and Petrie et al. (2010a) and in Table 1 herein. In one embodiment, the Δ5-desaturase comprises amino acids having a sequence as provided in SEQ ID NO:20, a biologically active fragment thereof, or an amino acid sequence which is at least 80% identical to SEQ ID NO:20. In another embodiment, the Δ5-desaturase comprises amino acids having a sequence as provided in SEQ ID NO:22, a biologically active fragment thereof, or an amino acid sequence which is at least 53% identical to SEQ ID NO:22. In another embodiment, the Δ5-desaturase is from Thraustochytrium sp or Emiliania huxleyi.

As used herein, a "Δ6-desaturase" refers to a protein which performs a desaturase reaction that introduces a carbon-carbon double bond at the $6^{th}$ carbon-carbon bond from the carboxyl end of a fatty acid substrate. In an embodiment, the fatty acid substrate is ALA and the enzyme produces SDA. Preferably, the "Δ6-desaturase" is capable of converting ALA-CoA to SDA-CoA, i.e. it is an acyl-CoA desaturase. In an embodiment, the "Δ6-desaturase" is capable of converting ALA esterified at the sn-2 position of PC. Preferably the Δ6-desaturase has greater activity on ALA-CoA than on ALA-PC. The Δ6-desaturase may also have activity as a Δ5-desaturase, being termed a Δ5/Δ6 bifunctional desaturase, so long as it has greater Δ6-desaturase activity on ALA than Δ5-desaturase activity on ETA. Examples of Δ6-desaturases are listed in Ruiz-Lopez et al. (2012) and Petrie et al. (2010a) and in Table 1 herein. Preferred Δ6-desaturases are from Micromonas pusilla, Pythium irregulare or Ostreococcus taurii.

In an embodiment, the Δ6-desaturase is further characterised by having at least two, preferably all three and preferably in a plant cell, of the following: i) greater Δ6-desaturase activity on α-linolenic acid (ALA, 18:3Δ9, 12,15, ω3) than linoleic acid (LA, 18:2Δ9,12, ω6) as fatty acid substrate; ii) greater Δ6-desaturase activity on ALA-CoA as fatty acid substrate than on ALA joined to the sn-2 position of PC as fatty acid substrate; and iii) Δ8-desaturase activity on ETrA. Examples of such Δ6-desaturases are provided in Table 2.

Preferably, the Δ8-desaturase is capable of converting ETrA-CoA to ETA-CoA, i.e. it is an acyl-CoA desaturase. In an embodiment, the Δ8-desaturase is capable of converting ETrA esterified at the sn-2 position of PC. Preferably the Δ8-desaturase has greater activity on ETrA-CoA than on ETrA-PC. The Δ8-desaturase may also have activity as a Δ6-desaturase, being termed a Δ6/Δ8 bifunctional desaturase, so long as it has greater Δ8-desaturase activity on ETrA

TABLE 2

| | | | | Protein size | |
|---|---|---|---|---|---|
| Enzyme | Type of organism | Species | Accession Nos. | (aa's) | References |
| Δ6-desaturase | Algae | *Mantoniella squamata* | CAQ30479 | 449 | Hoffmann et al., 2008 |
| | | *Ostreococcus tauri* | AAW70159 | 456 | Domergue et al., 2005 |
| | | *Micromonas pusilla* | EEH58637 | | Petrie et al., 2010a (SEQ ID NO: 7) |
| Δ5-desaturase | Algae | *Mantoniella squamata* | CAQ30478 | 482 | Hoffmann et al., 2008 |
| | Plant | *Anemone leveillei* | N/A | | Sayanova et al., 2007 |
| ω3-desaturase | Fungi | *Pythium aphanidermatum* | FW362186.1 | 359 | Xue et al., 2012; WO2008/054565 |
| | Fungi (oomycete) | *Phytophthora sojae* | FW362214.1 | 363 | Xue et al., 2012; WO2008/054565 |
| | Fungi (oomycete) | *Phytophthora ramorum* | FW362213.1 | 361 | Xue et al., 2012; WO2008/054565 |

Desaturases demonstrated to have activity on an acyl-CoA substrate

In an embodiment the Δ6-desaturase has greater activity on an ω3 substrate than the corresponding ω6 substrate and has activity on ALA to produce octadecatetraenoic acid (stearidonic acid, SDA, 18:4Δ6,9,12, 15, ω3) with an efficiency of at least 30%, more preferably at least 40%, or most preferably at least 50% when expressed from an exogenous polynucleotide in a recombinant cell such as a plant cell, or at least 35% when expressed in a yeast cell. In one embodiment, the Δ6-desaturase has greater activity, for example, at least about a 2-fold greater Δ6-desaturase activity, on ALA than LA as fatty acid substrate. In another embodiment, the Δ6-desaturase has greater activity, for example, at least about 5 fold greater Δ6-desaturase activity or at least 10-fold greater activity, on ALA-CoA as fatty acid substrate than on ALA joined to the sn-2 position of PC as fatty acid substrate. In a further embodiment, the Δ6-desaturase has activity on both fatty acid substrates ALA-CoA and on ALA joined to the sn-2 position of PC.

In one embodiment, the Δ6-desaturase has no detectable Δ5-desaturase activity on ETA. In another embodiment, the Δ6-desaturase comprises amino acids having a sequence as provided in SEQ ID NO:9, SEQ ID NO:12 or SEQ ID NO: 13, a biologically active fragment thereof, or an amino acid sequence which is at least 77% identical to SEQ ID NO:9, SEQ ID NO:12 or SEQ ID NO:13. In another embodiment, the Δ6-desaturase comprises amino acids having a sequence as provided in SEQ ID NO:12 or SEQ ID NO:13, a biologically active fragment thereof, or an amino acid sequence which is at least 67% identical to one or both of SEQ ID NO:12 or SEQ ID NO:13. The Δ6-desaturase may also have Δ8-desaturase activity.

As used herein, a "Δ8-desaturase" refers to a protein which performs a desaturase reaction that introduces a carbon-carbon double bond at the 8th carbon-carbon bond from the carboxyl end of a fatty acid substrate. The Δ8-desaturase is at least capable of converting ETrA to ETA.

than Δ6-desaturase activity on ALA. Examples of Δ8-desaturases are listed in Table 1. In one embodiment, the Δ8-desaturase comprises amino acids having a sequence as provided in SEQ ID NO:37, a biologically active fragment thereof, or an amino acid sequence which is at least 80% identical to SEQ ID NO:37.

As used herein, an "ω3-desaturase" refers to a protein which performs a desaturase reaction that introduces a carbon-carbon double bond at the 3rd carbon-carbon bond from the methyl end of a fatty acid substrate. A ω3-desaturase therefore may convert LA to ALA and GLA to SDA (all C18 fatty acids), or DGLA to ETA and/or ARA to EPA (C20 fatty acids). Some ω3-desaturases (group I) have activity only on C18 substrates, such as plant and cyanobacterial ω3-desaturases. Such ω3-desaturases are also Δ15-desaturases. Other ω3-desaturases have activity on C20 substrates with no activity (group II) or some activity (group III) on C18 substrates. Such ω3-desaturases are also Δ17-desaturases. Preferred ω3-desaturases are group III type which convert LA to ALA, GLA to SDA, DGLA to ETA and ARA to EPA, such as the *Pichia pastoris* ω3-desaturase (SEQ ID NO: 6). Examples of ω3-desaturases include those described by Pereira et al. (2004a) (*Saprolegnia diclina* ω3-desaturase, group TT), Horiguchi et al. (1998), Berberich et al. (1998) and Spychalla et al. (1997) (*C. elegans* ω3-desaturase, group III). In a preferred embodiment, the ω3-desaturase is a fungal ω3-desaturase. As used herein, a "fungal ω3-desaturase" refers to an ω3-desaturase which is from a fungal source, including an oomycete source, or a variant thereof whose amino acid sequence is at least 95% identical thereto. Genes encoding numerous ω3-desaturases have been isolated from fungal sources such as, for example, from *Phytophthora infestans* (Accession No. CAJ30870, WO2005083053; SEQ ID NO: 47), *Saprolegnia diclina* (Accession No. AAR20444, Pereira et al., 2004a & U.S. Pat. No. 7,211,656), *Pythium irregulare* (WO2008022963, Group II; SEQ ID NO: 49), *Mortierella alpina* (Sakuradani et al., 2005; Accession No. BAD91495; WO2006019192), *Thalassiosira pseudonana* (Armbrust et al., 2004; Accession No. XP_002291057; WO2005012316, SEQ ID NO: 48), *Lachancea kluyveri* (also known as *Saccharomyces kluyveri*; Oura et al., 2004; Accession No. AB118663). Xue et al. (2012) describes ω3-desaturases from the oomycetes *Pythium aphanidermatum, Phytophthora sojae,* and *Phytophthora ramorum* which were able to efficiently convert ω6 fatty acid substrates to the corresponding ω3 fatty acids, with a preference for C20 substrates, i.e. they had stronger Δ17-desaturase activity than Δ15-desaturase activity. These enzymes lacked Δ12-desaturase activity, but could use fatty acids in both acyl-CoA and phospholipid fraction as substrates.

In a more preferred embodiment, the fungal ω3-desaturase is the *Pichia pastoris* (also known as Komagataella *pastoris*) ω3-desaturase/Δ15-desaturase (Zhang et al., 2008; Accession No. EF116884; SEQ ID NO: 6), or a polypeptide which is at least 95% identical thereto.

In an embodiment, the ω3-desaturase is at least capable of converting one of ARA to EPA, DGLA to ETA, GLA to SDA, both ARA to EPA and DGLA to ETA, both ARA to EPA and GLA to SDA, or all three of these.

In one embodiment, the ω3-desaturase has Δ17-desaturase activity on a C20 fatty acid which has at least three carbon-carbon double bonds, preferably ARA. In another embodiment, the ω3-desaturase has Δ15-desaturase activity on a C18 fatty acid which has three carbon-carbon double bonds, preferably GLA. Preferably, both activities are present.

As used herein, a "Δ12-desaturase" refers to a protein which performs a desaturase reaction that introduces a carbon-carbon double bond at the 12$^{th}$ carbon-carbon bond from the carboxyl end of a fatty acid substrate. Δ12-desaturases typically convert either oleoyl-phosphatidylcholine or oleoyl-CoA to linoleoyl-phosphatidylcholine (18:1-PC) or linoleoyl-CoA (18:1-CoA), respectively. The subclass using the PC linked substrate are referred to as phospholipid-dependent Δ12-desaturases, the latter subclass as acyl-CoA dependent Δ12-desaturases. Plant and fungal Δ12-desaturases are generally of the former subclass, whereas animal Δ12-desaturases are of the latter subclass, for example the Δ12-desaturases encoded by genes cloned from insects by Zhou et al. (2008). Many other Δ12-desaturase sequences can be easily identified by searching sequence databases.

As used herein, a "Δ15-desaturase" refers to a protein which performs a desaturase reaction that introduces a carbon-carbon double bond at the 15$^{th}$ carbon-carbon bond from the carboxyl end of a fatty acid substrate. Numerous genes encoding Δ15-desaturases have been cloned from plant and fungal species. For example, U.S. Pat. No. 5,952,544 describes nucleic acids encoding plant Δ15-desaturases (FAD3). These enzymes comprise amino acid motifs that were characteristic of plant Δ15-desaturases. WO200114538 describes a gene encoding soybean FAD3. Many other Δ15-desaturase sequences can be easily identified by searching sequence databases.

As used herein, a "Δ17-desaturase" refers to a protein which performs a desaturase reaction that introduces a carbon-carbon double bond at the 17$^{th}$ carbon-carbon bond from the carboxyl end of a fatty acid substrate. A Δ17-desaturase is also regarded as an ω3-desaturase if it acts on a C20 substrate to introduce a desaturation at the ω3 bond.

In a preferred embodiment, the Δ12-desaturase and/or Δ15-desaturase is a fungal Δ12-desaturase or fungal Δ15- desaturase. As used herein, a "fungal Δ12-desaturase" or "a fungal Δ15-desaturase" refers to a Δ12-desaturase or Δ15-desaturase which is from a fungal source, including an oomycete source, or a variant thereof whose amino acid sequence is at least 95% identical thereto. Genes encoding numerous desaturases have been isolated from fungal sources. U.S. Pat. No. 7,211,656 describes a Δ12 desaturase from *Saprolegnia diclina*. WO2009016202 describes fungal desaturases from *Helobdella robusta, Laccaria bicolor, Lottia gigantea, Microcoleus chthonoplastes, Monosiga brevicollis, Mycosphaerella fijiensis, Mycospaerella graminicola, Naegleria gruben, Nectria haematococca, Nematostella vectensis, Phycomyces blakesleeanus, Trichoderma resii, Physcomitrella patens, Postia placenta, Selaginella moellendorffii* and *Microdochium nivale*. WO2005/012316 describes a Δ12-desaturase from *Thalassiosira pseudonana* and other fungi. WO2003/099216 describes genes encoding fungal Δ12-desaturases and Δ15-desaturases isolated from *Neurospora crassa, Aspergillus nidulans, Botrytis cinerea* and *Mortierella alpina*. WO2007133425 describes fungal Δ15 desaturases isolated from: *Saccharomyces kluyveri, Mortierella alpina, Aspergillus nidulans, Neurospora crassa, Fusarium graminearum, Fusarium moniliforme* and *Magnaporthe grisea*. A preferred Δ12 desaturase is from *Phytophthora sojae* (Ruiz-Lopez et al., 2012).

A distinct subclass of fungal Δ12-desaturases, and of fungal Δ15-desaturases, are the bifunctional fungal Δ12/Δ15-desaturases. Genes encoding these have been cloned from *Fusarium monoliforme* (Accession No. DQ272516, Damude et al., 2006), *Acanthamoeba castellanii* (Accession No. EF017656, Sayanova et al., 2006), *Perkinsus marinus* (WO2007042510), *Claviceps purpurea* (Accession No. EF536898, Meesapyodsuk et al., 2007) and *Coprinus cinereus* (Accession No. AF269266, Zhang et al., 2007).

In another embodiment, the ω3-desaturase has at least some activity on, preferably greater activity on, an acyl-CoA substrate than a corresponding acyl-PC substrate. As used herein, a "corresponding acyl-PC substrate" refers to the fatty acid esterified at the sn-2 position of phosphatidylcholine (PC) where the fatty acid is the same fatty acid as in the acyl-CoA substrate. For example, the acyl-CoA substrate may be ARA-CoA and the corresponding acyl-PC substrate is sn-2 ARA-PC. In an embodiment, the activity is at least two-fold greater. Preferably, the ω3-desaturase has at least some activity on both an acyl-CoA substrate and its corresponding acyl-PC substrate and has activity on both C18 and C20 substrates. Examples of such ω3-desaturases are known amongst the cloned fungal desaturases listed above.

In a further embodiment, the ω3-desaturase comprises amino acids having a sequence as provided in SEQ ID NO:6, a biologically active fragment thereof, or an amino acid sequence which is at least 60% identical to SEQ ID NO:6, preferably at least 90% or at least 95% identical to SEQ ID NO:6.

In yet a further embodiment, a desaturase for use in the present invention has greater activity on an acyl-CoA substrate than a corresponding acyl-PC substrate. In another embodiment, a desaturase for use in the present invention has greater activity on an acyl-PC substrate than a corresponding acyl-CoA substrate, but has some activity on both substrates. As outlined above, a "corresponding acyl-PC substrate" refers to the fatty acid esterified at the sn-2 position of phosphatidylcholine (PC) where the fatty acid is the same fatty acid as in the acyl-CoA substrate. In an embodiment, the greater activity is at least two-fold greater. In an embodiment, the desaturase is a Δ5 or Δ6-desaturase, or an ω3-desaturase, examples of which are provided, but not limited to, those listed in Table 2. To test which substrate a desaturase acts on, namely an acyl-CoA or an acyl-PC substrate, assays can be carried out in yeast cells as described in Domergue et al. (2003 and 2005). Acyl-CoA substrate capability for a desaturase can also be inferred when an elongase, when expressed together with the desaturase, has an enzymatic conversion efficiency in plant cells of at least about 90% where the elongase catalyses the elongation of the product of the desaturase. On this basis, the Δ5-desaturase and Δ4-desaturases expressed from the GA7 construct (Examples 2 and 3) and variants thereof (Example 4) are capable of desaturating their respective acyl-CoA substrates, ETA-CoA and DPA-CoA.

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus, the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

As used herein, a "Δ5-elongase" is at least capable of converting EPA to DPA. Examples of Δ5-elongases include those disclosed in WO2005/103253. In one embodiment, the Δ5-elongase has activity on EPA to produce DPA with an efficiency of at least 60%, more preferably at least 65%, more preferably at least 70% or most preferably at least 80% or 90%. In a further embodiment, the Δ5-elongase comprises an amino acid sequence as provided in SEQ ID NO:25, a biologically active fragment thereof, or an amino acid sequence which is at least 47% identical to SEQ ID NO:25. In a further embodiment, the Δ6-elongase is from *Ostreococcus taurii* or *Ostreococcus lucimarinus* (US2010/088776).

As used herein, a "Δ6-elongase" is at least capable of converting SDA to ETA. Examples of Δ6-elongases include those listed in Table 1. In one embodiment, the elongase comprises amino acids having a sequence as provided in SEQ ID NO:16, a biologically active fragment thereof (such as the fragment provided as SEQ ID NO:17), or an amino acid sequence which is at least 55% identical to one or both of SEQ ID NO:16 or SEQ ID NO:17. In an embodiment, the Δ6-elongase is from *Physcomitrella patens* (Zank et al., 2002; Accession No. AF428243) or *Thalassiosira pseudonana* (Ruiz-Lopez et al., 2012).

As used herein, a "Δ9-elongase" is at least capable of converting ALA to ETrA. Examples of Δ9-elongases include those listed in Table 1. In one embodiment, the Δ9-elongase comprises amino acids having a sequence as provided in SEQ ID NO:29, a biologically active fragment thereof, or an amino acid sequence which is at least 80% identical to SEQ ID NO:29. In another embodiment, the Δ9-elongase comprises amino acids having a sequence as provided in SEQ ID NO:31, a biologically active fragment thereof, or an amino acid sequence which is at least 81% identical to SEQ ID NO:31. In another embodiment, the Δ9-elongase comprises amino acids having a sequence as provided in SEQ ID NO:33, a biologically active fragment thereof, or an amino acid sequence which is at least 50% identical to SEQ ID NO:33. In another embodiment, the Δ9-elongase comprises amino acids having a sequence as provided in SEQ ID NO:35, a biologically active fragment thereof, or an amino acid sequence which is at least 50% identical to SEQ ID NO:35. In a further embodiment, the Δ9-elongase has greater activity on an ω6 substrate than the corresponding ω3 substrate, or the converse.

As used herein, the term "has greater activity on an ω6 substrate than the corresponding ω3 substrate" refers to the relative activity of the enzyme on substrates that differ by the action of an ω3 desaturase. Preferably, the ω6 substrate is LA and the ω3 substrate is ALA.

An elongase with Δ6-elongase and Δ9-elongase activity is at least capable of (i) converting SDA to ETA and (ii) converting ALA to ETrA and has greater Δ6-elongase activity than Δ9-elongase activity. In one embodiment, the elongase has an efficiency of conversion on SDA to produce ETA which is at least 50%, more preferably at least 60%, and/or an efficiency of conversion on ALA to produce ETrA which is at least 6% or more preferably at least 9%. In another embodiment, the elongase has at least about 6.5 fold greater Δ6-elongase activity than Δ9-elongase activity. In a further embodiment, the elongase has no detectable Δ5-elongase activity.

LPAATs

The transgenes introduced into the recombinant cell such as a microbial cell, or transgenic plant or part thereof may encode an LPAAT. As used herein, the term "1-acyl-glycerol-3-phosphate acyltransferase" (LPAAT), also termed lysophosphatidic acid-acyltransferase or acylCoA-lysophosphatidate-acyltransferase, refers to a protein which acylates sn-1-acyl-glycerol-3-phosphate (sn-1 G-3-P) at the sn-2 position to form phosphatidic acid (PA). Thus, the term "1-acyl-glycerol-3-phosphate acyltransferase activity" refers to the acylation of (sn-1 G-3-P) at the sn-2 position to produce PA (EC 2.3.1.51). Preferred LPAATs are those that can use a polyunsaturated C22 acyl-CoA as substrate to transfer the polyunsaturated C22 acyl group to the sn-2 position of LPA, forming PA. In an embodiment, the polyunsaturated C22 acyl-CoA is DHA-CoA and/or DPA-CoA. Such LPAATs are exemplified in Example 7 and can be tested as described therein. In an embodiment, an LPAAT useful for the invention comprises amino acids having a sequence as provided in any one of SEQ ID NOs: 40 to 46, a biologically active fragment thereof, or an amino acid sequence which is at least 40% identical to any one or more of SEQ ID NOs: 40 to 46. In another embodiment, the LPAAT does not have amino acids having a sequence as provided in any one of SEQ ID NO: 44. In a preferred embodiment, an LPAAT useful for the invention which can use a C22 polyunsaturated fatty acyl-CoA substrate, preferably DHA-CoA and/or DPA-CoA, comprises amino acids having a sequence as provided in any one of SEQ ID NOs: 41, 42 and 44, a biologically active fragment thereof, or an amino acid sequence which is at least 40% identical to any one or more of SEQ ID NOs: 41, 42 and 44. In a preferred embodiment, an LPAAT useful for the invention which can use a C22 polyunsaturated fatty acyl-CoA substrate, preferably DHA-CoA and/or DPA-CoA, comprises amino acids having a sequence as provided in any one of SEQ ID NOs: 41 or 42, a biologically active fragment thereof, or an amino acid sequence which is at least 40% identical to any one or both of SEQ ID NOs: 41 and 42. In an embodiment in which the genetic construct expresses a Δ4-desaturase in the transgenic cell and/or the transgenic cell produces DHA, the LPAAT is preferably an LPAAT other the *Mortierella alpina* LPAAT whose amino acid sequence is set forth as SEQ ID NO: 44. Alternatively, if the genetic construct does not express a Δ4-desaturase in the transgenic cell and/or the transgenic cell produces DPA but not DHA, the LPAAT is preferably the *Mortierella alpina* LPAAT whose amino acid sequence is set forth as SEQ ID NO: 44 or another LPAAT which is capable of using DPA-CoA as a substrate to transfer the DPA to LPA, forming DAG having DPA at the sn-2 position.

Other Enzymes

The transgenes introduced into the recombinant cell, transgenic plant or part thereof may also encode a DGAT. As used herein, the term "diacylglycerol acyltransferase" (EC 2.3.1.20; DGAT) refers to a protein which transfers a fatty acyl group from acyl-CoA to a diacylglycerol substrate to produce a triacylglycerol. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. DGAT1 polypeptides typically have 10 transmembrane domains, DGAT2 typically have 2 transmembrane domains, whilst DGAT3 is typically soluble. Examples of DGAT1 polypeptides include polypeptides encoded by DGAT1 genes from *Aspergillus fumigatus* (Accession No. XP_755172), *Arabidopsis thaliana* (CAB44774), *Ricinus communis* (AAR11479), *Vernicia fordii* (ABC94472), *Vernonia galamensis* (ABV21945, ABV21946), *Euonymus alatus* (AAV31083), *Caenorhabditis elegans* (AAF82410), *Rattus norvegicus* (NP 445889), *Homo sapiens* (NP_036211), as well as variants and/or mutants thereof. Examples of DGAT2 polypeptides include polypeptides encoded by DGAT2 genes from *Arabidopsis thaliana* (Accession No. NP_566952), *Ricinus communis* (AAY16324), *Vernicia fordii* (ABC94474), *Mortierella ramanniana* (AAK84179), *Homo sapiens* (Q96PD7, Q58HT5), *Bos taurus* (Q70VD8), *Mus musculus* (AAK84175), *Micromonas* CCMP1545, as well as variants and/or mutants thereof. Examples of DGAT3 polypeptides include polypeptides encoded by DGAT3 genes from peanut (*Arachis hypogaea*, Saha, et al., 2006), as well as variants and/or mutants thereof.

Polypeptides/Peptides

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10%, at least 50%, at least 75% or at least 90%, of the activity of the reference polypeptide.

As used herein a "biologically active" fragment is a portion of a polypeptide defined herein which maintains a defined activity of a full-length reference polypeptide, for example possessing desaturase and/or elongase activity or other enzyme activity. Biologically active fragments as used herein exclude the full-length polypeptide. Biologically active fragments can be any size portion as long as they maintain the defined activity. Preferably, the biologically active fragment maintains at least 10%, at least 50%, at least 75% or at least 90%, of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired enzyme activity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, desaturase or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites which are not conserved amongst naturally occurring desaturases or elongases. These sites are preferably substituted in a relatively conservative manner in order to maintain enzyme activity. Such conservative substitutions are shown in Table 3 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

Polynucleotides

The invention also provides for the use of polynucleotides which may be, for example, a gene, an isolated polynucleotide, a chimeric genetic construct such as a T-DNA molecule, or a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule".

In an embodiment, the polynucleotide is non-naturally occurring. Examples of non-naturally occurring polynucleotides include, but are not limited to, those that have been mutated (such as by using methods described herein), and polynucleotides where an open reading frame encoding a protein is operably linked to a promoter to which it is not naturally associated (such as in the constructs described herein).

TABLE 3

| Exemplary substitutions. | |
| --- | --- |
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA). Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins described herein and a complementary nucleotide sequence to any one of the above.

As used herein, a "chimeric DNA" or "chimeric genetic construct" or similar refers to any DNA molecule that is not a native DNA molecule in its native location, also referred to herein as a "DNA construct". Typically, a chimeric DNA or chimeric gene comprises regulatory and transcribed or protein coding sequences that are not found operably linked together in nature i.e. that are heterologous with respect to each other. Accordingly, a chimeric DNA or chimeric gene may comprise regulatory sequences and coding sequences that are derived from different sources, or regulatory sequences and coding sequences derived from the same source, but arranged in a manner different than that found in nature.

An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. Foreign or exogenous genes may be genes that are inserted into a non-native organism, native genes introduced into a new location within the native host, or chimeric genes. A "transgene" is a gene that has been introduced into the genome by a transformation procedure. The terms "genetically modified", "transgenic" and variations thereof include introducing genes into cells by transformation or transduction, mutating genes in cells and altering or modulating the regulation of a gene in a cell or organisms to which these acts have been done or their progeny. A "genomic region" as used herein refers to a position within the genome where a transgene, or group of transgenes (also referred to herein as a cluster), have been inserted into a cell, or an ancestor thereof. Such regions only comprise nucleotides that have been incorporated by the intervention of man such as by methods described herein.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides can be either from a naturally occurring source or recombinant. Preferred polynucleotides are those which have coding regions that are codon-optimised for translation in plant cells, as is known in the art.

Recombinant Vectors

Recombinant expression can be used to produce recombinant cells, or plants or plant parts of the invention. Recombinant vectors contain heterologous polynucleotide sequences, that is, polynucleotide sequences that are not naturally found adjacent to polynucleotide molecules defined herein that preferably are derived from a species other than the species from which the polynucleotide molecule(s) are derived. The vector can be either RNA or DNA and typically is a plasmid. Plasmid vectors typically include additional nucleic acid sequences that provide for easy selection, amplification, and transformation of the expression cassette in prokaryotic cells, e.g., pUC-derived vectors, pSK-derived vectors, pGEM-derived vectors, pSP-derived vectors, pBS-derived vectors, or preferably binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells. The recombinant vector may comprise more than one polynucleotide defined herein, for example three, four, five or six polynucleotides defined herein in combination, preferably a chimeric genetic construct described herein, each polynucleotide being operably linked to expression control sequences that are operable in the cell of interest. Preferably the expression control sequences include, or are all, heterologous promoters i.e. are heterologous with respect to the coding regions they control. More than one polynucleotide defined herein, for example 3, 4, 5 or 6 polynucleotides, preferably 7 or 8 polynucleotides each encoding a different polypeptide, are preferably covalently joined together in a single recombinant vector, preferably within a single T-DNA molecule, which may then be introduced as a single molecule into a cell to form a recombinant cell according to the invention, and preferably integrated into the genome of the recombinant cell, for example in a transgenic plant. The integration into the genome may be into the nuclear genome or into a plastid genome in the transgenic plant. Thereby, the polynucleotides which are so joined will be inherited together as a single genetic locus in progeny of the recombinant cell or plant. The recombinant vector or plant may comprise two or more such recombinant vectors, each containing multiple polynucleotides, for example wherein each recombinant vector comprises 3, 4, 5 or 6 polynucleotides.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

When there are multiple promoters present, each promoter may independently be the same or different. Preferably, at least 3 and up to a maximum of 6 different promoter sequences are used in the recombinant vector to control expression of the exogenous polynucleotides.

Recombinant molecules such as the chimeric DNAs or genetic constructs may also contain (a) one or more secretory signals which encode signal peptide sequences, to enable an expressed polypeptide defined herein to be secreted from the cell that produces the polypeptide or which provide for localisation of the expressed polypeptide, for example for retention of the polypeptide in the endoplasmic reticulum (ER) in the cell or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Recombinant molecules may also include intervening and/or untranslated sequences surrounding and/or within the nucleic acid sequences of nucleic acid molecules defined herein.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice such as a plant cell.

Examples of selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), or preferably a bar gene conferring resistance against bialaphos as, for example, described in WO91/02071.

Preferably, the nucleic acid construct is stably incorporated into the genome of the cell, such as the plant cell. Accordingly, the nucleic acid may comprise appropriate elements which allow the molecule to be incorporated into the genome, preferably the right and left border sequences of a T-DNA molecule, or the construct is placed in an appropriate vector which can be incorporated into a chromosome of the cell.

Expression

As used herein, an expression vector is a DNA vector that is capable of transforming a host cell and of effecting expression of one or more specified polynucleotide molecule(s). Expression vectors of the present invention can direct gene expression in plant cells or in recombinant cells such as microbial cells. Expression vectors useful for the invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, and the light-inducible promoter from the small subunit of the ribulose-1,5-bis-phosphate carboxylase.

For the purpose of expression in source tissues of the plant, such as the leaf, seed, root or stem, it is preferred that the promoters utilized in the present invention have relatively high expression in these specific tissues. Many examples are well known in the art. A variety of plant gene promoters that are regulated in response to environmental, hormonal, chemical, and/or developmental signals, also can be used for expression of genes in plant cells, or it may also be advantageous to employ organ-specific promoters.

As used herein, the term "seed specific promoter" or variations thereof refer to a promoter that preferentially, when compared to other plant tissues, directs gene transcription in a developing seed of a plant, preferably a *Brassica* sp., *Camelina sativa* or *G. max* plant. In an embodiment, the seed specific promoter is expressed at least 5-fold more strongly in the developing seed of the plant relative to the leaves and/or stems of the plant, and is preferably expressed more strongly in the embryo of the developing seed compared to other plant tissues. Preferably, the promoter only directs expression of a gene of interest in the developing seed, and/or expression of the gene of interest in other parts of the plant such as leaves is not detectable by Northern blot analysis and/or RT-PCR. Typically, the promoter drives expression of genes during growth and development of the seed, in particular during the phase of synthesis and accumulation of storage compounds in the seed. Such promoters may drive gene expression in the entire plant storage organ or only part thereof such as the seedcoat, or cotyledon(s), preferably in the embryos, in seeds of dicotyledonous plants or the endosperm or aleurone layer of a seeds of monocotyledonous plants.

Preferred promoters for seed-specific expression include i) promoters from genes encoding enzymes involved in fatty acid biosynthesis and accumulation in seeds, such as fatty acid desaturases and elongases, ii) promoters from genes encoding seed storage proteins, and iii) promoters from genes encoding enzymes involved in carbohydrate biosynthesis and accumulation in seeds. Seed specific promoters which are suitable are the oilseed rape napin gene promoter (U.S. Pat. No. 5,608,152), the *Vicia faba* USP promoter (Baumlein et al., 1991), the *Arabidopsis* oleosin promoter (WO98/45461), the *Phaseolus vulgaris* phaseolin promoter (U.S. Pat. No. 5,504,200), the *Brassica* Bce4 promoter (WO91/13980) or the legumin LeB4 promoter from *Vicia faba* (Baumlein et al., 1992), and promoters which lead to the seed-specific expression in monocots such as maize, barley, wheat, rye, rice and the like. Notable promoters which are suitable are the barley lpt2 or lpt1 gene promoter (WO95/15389 and WO95/23230) or the promoters described in WO99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the *sorghum* kasirin gene, the rye secalin gene). Other promoters include those described by Broun et al. (1998), Potenza et al. (2004), US20070192902 and US20030159173. In an embodiment, the seed specific promoter is preferentially expressed in defined parts of the seed such as the embryo, cotyledon(s) or the endosperm. Examples of such specific promoters include, but are not limited to, the FP1 promoter (Ellerstrom et al., 1996), the pea legumin promoter (Perrin et al., 2000), the bean phytohemagglutnin promoter (Perrin et al., 2000), the conlinin 1 and conlinin 2 promoters for the genes encoding the flax 2S storage proteins (Cheng et al., 2010), the promoter of the FAE1 gene from *Arabidopsis thaliana*, the BnGLP promoter of the globulin-like protein gene of *Brassica napus*, the LPXR promoter of the peroxiredoxin gene from *Linum usitatissimum*.

The 5' non-translated leader sequence can be derived from the promoter selected to express the heterologous gene sequence of the polynucleotide of the present invention, or preferably is heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene or a flax conlinin gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, integration of the polynucleotide molecule into one or more host cell chromosomes, addition of stability sequences to mRNAs, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Transgenic Plants

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same, as long as the plant part synthesizes lipid according to the invention.

A "transgenic plant", "genetically modified plant" or variations thereof refers to a plant that contains a gene construct ("transgene") not found in a wild-type plant of the same species, variety or cultivar. Transgenic plants as defined in the context of the present invention include plants and their progeny which have been genetically modified using recombinant techniques to cause production of the lipid or at least one polypeptide defined herein in the desired plant or plant organ. Transgenic plant cells and transgenic plant parts have corresponding meanings. A "transgene" as referred to herein has the normal meaning in the art of biotechnology and includes a genetic sequence which has been produced or altered by recombinant DNA or RNA technology and which has been introduced into a plant cell. The transgene may include genetic sequences derived from a plant cell which may be of the same species, variety or cultivar as the plant cell into which the transgene is introduced or of a different species, variety or cultivar, or from a cell other than a plant cell. Typically, the transgene has been introduced into the cell, such as a plant, by human manipulation such as, for example, by transformation but any method can be used as one of skill in the art recognizes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain or seed commonly has a moisture content of less than about 18-20%, preferably less than 10%. *Brassica* seed such as canola seed typically has a moisture content of about 4-8% or 6-8% when mature, preferably between about 4% to about 6%. "Developing seed" as used herein refers to a seed prior to maturity, typically found in the reproductive structures of the plant after fertilisation or anthesis, but can also refer to such seeds prior to maturity which are isolated from a plant.

As used herein, the term "obtaining a plant part" or "obtaining a seed" refers to any means of obtaining a plant part or seed, respectively, including harvesting of the plant parts or seed from plants in the field or in containment such as a glasshouse or growth chamber, or by purchase or receipt from a supplier of the plant parts or seed. Standard growth conditions in a glasshouse include 22-24° C. daytime temperature and 16-18° C. night-time temperature, with natural sunlight. The seed may be suitable for planting i.e. able to germinate and produce progeny plants, or alternatively has been processed in such a way that it is no longer able to germinate, e.g. cracked, polished or milled seed which is useful for food or feed applications, or for extraction of lipid of the invention.

As used herein, the term "plurality of plant parts" refers to 2 or more plant parts which may be the same or different parts of a plant. In an embodiment, the plurality of plant parts comprises at least 100, at least 1,000, at least 10,000 or more plant parts such as seeds. The plurality of plant parts may be from the same plant or two or more plants.

As used herein, the term "plant storage organ" refers to a part of a plant specialized to storage energy in the form of, for example, proteins, carbohydrates, fatty acids and/or oils. Examples of plant storage organs are seed, fruit, tuberous roots, and tubers. A preferred plant storage organ is seed.

The plants or plant parts of the invention or used in the invention are preferably phenotypically normal. As used herein, the term "phenotypically normal" refers to a genetically modified plant or plant organ, particularly a storage organ such as a seed, tuber or fruit not having a significantly reduced ability to grow and reproduce when compared to an unmodified plant or plant organ. In an embodiment, the genetically modified plant or plant organ which is phenotypically normal has an ability to grow or reproduce which is essentially the same as an isogenic plant or organ not comprising the exogenous polynucleotide(s). Preferably, the biomass, growth rate, germination rate, storage organ size, pollen viability, male and female fertility, seed size and/or the number of viable seeds produced is not less than 90% of that of a plant lacking said exogenous polynucleotide when grown under identical conditions. Preferably the pollen viability of the plant of the invention, or plants produced from seed of the invention, is about 100% relative to the pollen viability of a corresponding wild-type plant. This term does not encompass features of the plant which may be different to the wild-type plant but which do not affect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, *sorghum*, millet, cassava, barley, or pea), or other legumes. The plants may be grown for production of edible roots, tubers, leaves, stems, flowers or fruit. The plants may be vegetables or ornamental plants. The plants of, or useful for, the invention may be: corn (*Zea mays*), canola (*Brassica napus, Brassica rapa* ssp.), mustard (*Brassica juncea*), flax (*Linum usitatissimum*), alfalfa (*Medicago sativa*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis*

*hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley.

In a preferred embodiment, the plant is an angiosperm.

In an embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, *sorghum*, flax (linseed) or sugar beet. Furthermore, the oilseed plant may be other Brassicas, cotton, peanut, poppy, mustard, castor bean, sesame, sunflower, safflower, *Camelina, Crambe* or nut producing plants. The plant may produce high levels of oil in its fruit, such as olive, oil palm or coconut. Horticultural plants to which the present invention may be applied are lettuce, endive, or vegetable brassicas including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has i) less than 20%, less than 10% or less than 5% 18:2 fatty acids and/or ii) less than 10% or less than 5% 18:3 fatty acids.

In a preferred embodiment, the transgenic plant or part thereof is homozygous for each and every gene (exogenous polynucleotide) that has been introduced (transgene) so that its progeny do not segregate for the desired phenotype. The transgenic plant may also be heterozygous for the introduced transgene(s), preferably uniformly heterozygous for the transgene, such as for example in F1 progeny which have been grown from hybrid seed. Such plants may provide advantages such as hybrid vigour, well known in the art, or may be used in plant breeding or backcrossing.

Where relevant, the transgenic plant or part thereof may also comprise additional transgenes encoding enzymes involved in the production of LC-PUFAs such as, but not limited to, a Δ6-desaturase, a Δ9-elongase, a Δ8-desaturase, a Δ6-elongase, a Δ5-desaturase, an ω3-desaturase, a Δ4-desaturase, a Δ5-elongase, diacylglycerol acyltransferase, LPAAT, a Δ17-desaturase, a Δ15-desaturase and/or a Δ12 desaturase. Examples of such enzymes with one of more of these activities are known in the art and include those described herein. In specific examples, the transgenic plant at least comprises a set of exogenous polynucleotides encoding;

a) a Δ4-desaturase, a Δ5-desaturase, a Δ6-desaturase, a Δ5-elongase and a Δ6-elongase, b) a Δ4-desaturase, a Δ5-desaturase, a Δ8-desaturase, a Δ5-elongase and a Δ9-elongase, c) a Δ4-desaturase, a Δ5-desaturase, a Δ6-desaturase, a Δ5-elongase, a Δ6-elongase, and a Δ15-desaturase, d) a Δ4-desaturase, a Δ5-desaturase, a Δ8-desaturase, a Δ5-elongase, a Δ9-elongase, and a Δ15-desaturase, e) a Δ4-desaturase, a Δ5-desaturase, a Δ6-desaturase, a Δ5-elongase, a Δ6-elongase, and a Δ17-desaturase, f) a Δ4-desaturase, a Δ5-desaturase, a Δ8-desaturase, a Δ5-elongase, a Δ9-elongase, and a Δ17-desaturase, g) an ω3-desaturase or a Δ15-desaturase, a Δ6-desaturase, a Δ5-desaturase, a Δ6-elongase and a Δ5-elongase,

67

68 h) an $\omega$3-desaturase or a $\Delta$15-desaturase, a $\Delta$8-desaturase, a $\Delta$5-desaturase, a $\Delta$9-elongase and a $\Delta$5-elongase, i) a $\Delta$12-desaturase, a $\omega$3-desaturase or a $\Delta$15-desaturase, a $\Delta$6-desaturase, a $\Delta$5-desaturase, a $\Delta$6-elongase and an $\Delta$5-elongase, j) a $\Delta$12-desaturase, a $\omega$3-desaturase or a $\Delta$15-desaturase, a $\Delta$8-desaturase, a $\Delta$5-desaturase, a $\Delta$9-elongase and an $\Delta$5-elongase, k) an 1-acyl-glycerol-3-phosphate acyltransferase (LPAAT), an $\omega$3-desaturase, a $\Delta$6-desaturase, a $\Delta$5-desaturase, a $\Delta$6-elongase, a $\Delta$5-elongase and optionally a $\Delta$4-desaturase, l) an 1-acyl-glycerol-3-phosphate acyltransferase (LPAAT), a $\Delta$15-desaturase, a $\Delta$6-desaturase, a $\Delta$5-desaturase, a $\Delta$6-elongase, a $\Delta$5-elongase and optionally a $\Delta$4-desaturase, m) an 1-acyl-glycerol-3-phosphate acyltransferase (LPAAT), a $\Delta$12-desaturase, a $\Delta$6-desaturase, a $\Delta$5-desaturase, a $\Delta$6-elongase, an $\Delta$5-elongase and optionally a $\Delta$4-desaturase, n) an 1-acyl-glycerol-3-phosphate acyltransferase (LPAAT), a $\Delta$12-desaturase, a $\omega$3-desaturase and/or a $\Delta$15-desaturase, a $\Delta$6-desaturase, a $\Delta$5-desaturase, a $\Delta$6-elongase and an $\Delta$5-elongase and optionally a $\Delta$4-desaturase, o) an 1-acyl-glycerol-3-phosphate acyltransferase (LPAAT), an $\omega$3-desaturase, a $\Delta$8-desaturase, a $\Delta$5-desaturase, a $\Delta$9-elongase, an $\Delta$5-elongase and optionally a $\Delta$4-desaturase, p) an 1-acyl-glycerol-3-phosphate acyltransferase (LPAAT), a $\Delta$15-desaturase, a $\Delta$8-desaturase, a $\Delta$5-desaturase, a $\Delta$9-elongase, a $\Delta$5-elongase and optionally a $\Delta$4-desaturase, q) an 1-acyl-glycerol-3-phosphate acyltransferase (LPAAT), a $\Delta$12-desaturase, a $\Delta$8-desaturase, a $\Delta$5-desaturase, a $\Delta$9-elongase, an $\Delta$5-elongase and optionally a $\Delta$4-desaturase, or r) an 1-acyl-glycerol-3-phosphate acyltransferase (LPAAT), a $\Delta$12-desaturase, a $\omega$3-desaturase and/or a $\Delta$15-desaturase, a $\Delta$8-desaturase, a $\Delta$5-desaturase, a $\Delta$9-elongase, an $\Delta$5-elongase and optionally a $\Delta$4-desaturase.

In an embodiment, the exogenous polynucleotides encode set of polypeptides which are a *Pythium irregulare* $\Delta$6-desaturase, a Thraustochytrid $\Delta$5-desaturase or an *Emiliana huxleyi* $\Delta$5-desaturase, a *Physcomitrella patens* $\Delta$6-elongase, a Thraustochytrid $\Delta$5-elongase or an *Ostreocccus taurii* $\Delta$5-elongase, a *Phytophthora infestans* $\omega$3-desaturase or a *Pythium irregulare* $\omega$3-desaturase, and a Thraustochytrid $\Delta$4-desaturase.

In an embodiment, for the production of DHA the exogenous polynucleotides encode set of polypeptides which are an LPAAT, preferably an LPAAT which can use a C22 polyunsaturated fatty acyl-CoA substrate such as DPA-CoA and/or DHA-CoA, a *Pythium irregulare* $\Delta$6-desaturase, a Thraustochytrid $\Delta$5-desaturase or an *Emiliana huxleyi* $\Delta$5-desaturase, a *Physcomitrella patens* $\Delta$6-elongase, a Thraustochytrid $\Delta$5-elongase or an *Ostreocccus taurii* $\Delta$5-elongase, a *Phytophthora infestans* $\omega$3-desaturase or a *Pythium irregulare* $\omega$3-desaturase, and a Thraustochytrid $\Delta$4-desaturase.

In an embodiment, for the production of DPA, the exogenous polynucleotides encode set of polypeptides which are an LPAAT, preferably an LPAAT which can use a C22 polyunsaturated fatty acyl-CoA substrate such as DPA-CoA and/or DHA-CoA, a *Pythium irregulare* $\Delta$6-desaturase, a Thraustochytrid $\Delta$5-desaturase or an *Emiliana huxleyi*

$\Delta$5-desaturase, a *Physcomitrella patens* $\Delta$6-elongase, a Thraustochytrid $\Delta$5-elongase or an *Ostreocccus taurii* $\Delta$5-elongase, and a *Phytophthora infestans* $\omega$3-desaturase or a *Pythium irregulare* $\omega$3-desaturase.

In an embodiment, plants of, or used for, the invention are grown in the field, preferably as a population of at least 1,000, 1,000,000 or 2,000,000 plants that are essentially the same, or in an area of at least 1 hectare or 2 hectares. Planting densities differ according to the plant species, plant variety, climate, soil conditions, fertiliser rates and other factors as known in the art. For example, canola is typically grown at a planting density of 1.2-1.5 million plants per hectare. Plants are harvested as is known in the art, which may comprise swathing, windrowing and/or reaping of plants, followed by threshing and/or winnowing of the plant material to separate the seed from the remainder of the plant parts often in the form of chaff. Alternatively, seed may be harvested from plants in the field in a single process, namely combining.

Transformation of Plants

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

As used herein, the terms "stably transforming", "stably transformed" and variations thereof refer to the integration of the exogenous nucleic acid molecules into the genome of the cell such that they are transferred to progeny cells during cell division without the need for positively selecting for their presence. Stable transformants, or progeny thereof, can be selected by any means known in the art such as Southern blots on chromosomal DNA or in situ hybridization of genomic DNA. Preferably, plant transformation is performed as described in the Examples herein.

*Agrobacterium*-mediated transfer is a widely applicable system for introducing genes into plant cells because DNA can be introduced into cells in whole plant tissues or plant organs or explants in tissue culture, for either transient expression or for stable integration of the DNA in the plant cell genome. The use of *Agrobacterium*-mediated plant integrating vectors to introduce DNA into plant cells is well known in the art (see, for example, U.S. Pat. Nos. 5,177,010, 5,104,310, 5,004,863 or U.S. Pat. No. 5,159,135) including floral dipping methods using *Agrobacterium* or other bacteria that can transfer DNA into plant cells. The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO99/05265).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s); i.e., a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Backcrossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Enhancing Exogenous RNA Levels and Stabilized Expression

Silencing Suppressors

In an embodiment, a plant cell, plant or plant part comprises an exogenous polynucleotide encoding a silencing suppressor protein.

Post-transcriptional gene silencing (PTGS) is a nucleotide sequence-specific defense mechanism that can target both cellular and viral mRNAs for degradation PTGS occurs in plants or fungi stably or transiently transformed with foreign (heterologous) or endogenous DNA and results in the reduced accumulation of RNA molecules with sequence similarity to the introduced nucleic acid.

It has widely been considered that co-expression of a silencing suppressor with a transgene of interest will increase the levels of RNA present in the cell transcribed from the transgene. Whilst this has proven true for cells in vitro, significant side-effects have been observed in many whole plant co-expression studies. More specifically, as described in Mallory et al. (2002), Chapman et al. (2004), Chen et al. (2004), Dunoyer et al. (2004), Zhang et al. (2006), Lewsey et al. (2007) and Meng et al. (2008) plants expressing silencing suppressors, generally under constitutive promoters, are often phenotypically abnormal to the extent that they are not useful for commercial production.

Recently, it has been found that RNA molecule levels can be increased, and/or RNA molecule levels stabilized over numerous generations, by limiting the expression of the silencing suppressor to a seed of a plant or part thereof (WO2010/057246). As used herein, a "silencing suppressor protein" or SSP is any polypeptide that can be expressed in a plant cell that enhances the level of expression product from a different transgene in the plant cell, particularly over repeated generations from the initially transformed plant. In an embodiment, the SSP is a viral silencing suppressor or mutant thereof. A large number of viral silencing suppressors are known in the art and include, but are not limited to P19, V2, P38, Pe-Po and RPV-PO. In an embodiment, the viral silencing suppressor comprises amino acids having a sequence as provided in SEQ ID NO:38, a biologically active fragment thereof, or an amino acid sequence which is at least 50% identical to SEQ ID NO:38 and which has activity as a silencing suppressor.

As used herein, the terms "stabilising expression", "stably expressed", "stabilised expression" and variations thereof refer to level of the RNA molecule being essentially the same or higher in progeny plants over repeated generations, for example at least three, at least five or at least 10 generations, when compared to isogenic plants lacking the exogenous polynucleotide encoding the silencing suppressor. However, this term(s) does not exclude the possibility that over repeated generations there is some loss of levels of the RNA molecule when compared to a previous generation, for example not less than a 10% loss per generation.

The suppressor can be selected from any source e.g. plant, viral, mammal etc. See WO2010/057246 for a list of viruses from which the suppressor can be obtained and the protein (eg B2, P14 etc) or coding region designation for the suppressor from each particular virus. Multiple copies of a suppressor may be used. Different suppressors may be used together (e.g., in tandem).

RNA Molecules

Essentially any RNA molecule which is desirable to be expressed in a plant seed can be co-expressed with the silencing suppressor. The encoded polypeptides may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc, preferably the biosynthesis or assembly of TAG.

In a particular example, the plants produced increased levels of enzymes for oil production in plants such as Brassicas, for example canola or sunflower, safflower, flax, cotton, soya bean, *Camelina* or maize.

Levels of LC-PUFA Produced

The levels of the LC-PUFA or combination of LC-PUFAs that are produced in the recombinant cell or plant part such as seed are of importance. The levels may be expressed as a composition (in percent) of the total fatty acid that is a particular LC-PUFA or group of related LC-PUFA, for example the ω3 LC-PUFA or the ω6 LC-PUFA, or the VLC-PUFA, or other which may be determined by methods known in the art. The level may also be expressed as a LC-PUFA content, such as for example the percentage of LC-PUFA in the dry weight of material comprising the recombinant cells, for example the percentage of the weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. In a preferred method, total lipid is extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG.

In one embodiment, the sum total of ARA, EPA, DPA and DHA in the fatty acids in the extracted lipid is between about 21% and about 40% of the total fatty acids in the cell. In a further embodiment, the total fatty acid in the cell has less than 10% C20:1. In preferred embodiments, the extractable TAG in the cell comprises the fatty acids at the levels referred to herein. Each possible combination of the features defining the lipid as described herein is also encompassed.

The level of production of LC-PUFA in the recombinant cell, plant or plant part such as seed may also be expressed as a conversion percentage of a specific substrate fatty acid to one or more product fatty acids, which is also referred to herein as a "conversion efficiency" or "enzymatic efficiency". This parameter is based on the fatty acid composition in the lipid extracted from the cell, plant, plant part or seed, i.e., the amount of the LC-PUFA formed (including other LC-PUFA derived therefrom) as a percentage of one or more substrate fatty acids (including all other fatty acids derived therefrom). The general formula for a conversion percentage is: 100×(the sum of percentages of the product LC-PUFA and all products derived therefrom)/(the sum of the percentages of the substrate fatty acid and all products derived therefrom). With regard to DHA, for example, this may be expressed as the ratio of the level of DHA (as a percentage in the total fatty acid content in the lipid) to the level of a substrate fatty acid (e.g. OA, LA, ALA, SDA, ETA or EPA) and all products including DHA derived from the substrate. The conversion percentage or efficiency of conversion can be expressed for a single enzymatic step in a pathway, or for part or the whole of a pathway.

Specific conversion efficiencies are calculated herein according to the formulae:

1. OA to DHA=100×(% DHA)/(sum % for OA, LA, GLA, DGLA, ARA, EDA, ALA, SDA, ETrA, ETA, EPA, DPA and DHA).
2. LA to DHA=100×(% DHA)/(sum % for LA, GLA, DGLA, ARA, EDA, ALA, SDA, ETrA, ETA, EPA, DPA and DHA).
3. ALA to DHA=100×(% DHA)/(sum % for ALA, SDA, ETrA, ETA, EPA, DPA and DHA).
4. EPA to DHA=100×(% DHA)/(sum % for EPA, DPA and DHA).
5. DPA to DHA (Δ4-desaturase efficiency)=100×(% DHA)/(sum % for DPA and DHA).
6. Δ12-desaturase efficiency=100×(sum % for LA, GLA, DGLA, ARA, EDA, ALA, SDA, ETrA, ETA, EPA, DPA and DHA)/(sum % for OA, LA, GLA, DGLA, ARA, EDA, ALA, SDA, ETrA, ETA, EPA, DPA and DHA).
7. ω3-desaturase efficiency=100×(sum % for ALA, SDA, ETrA, ETA, EPA, DPA and DHA)/(sum % for LA, GLA, DGLA, ARA, EDA, ALA, SDA, ETrA, ETA, EPA, DPA and DHA).
8. OA to ALA=100×(sum % for ALA, SDA, ETrA, ETA, EPA, DPA and DHA)/(sum % for OA, LA, GLA, DGLA, ARA, EDA, ALA, SDA, ETrA, ETA, EPA, DPA and DHA).
9. Δ6-desaturase efficiency (on ω3 substrate ALA)=100× (sum % for SDA, ETA, EPA, DPA and DHA)/(% ALA, SDA, ETrA, ETA, EPA, DPA and DHA).
10. Δ6-elongase efficiency (on ω3 substrate SDA)=100× (sum % for ETA, EPA, DPA and DHA)/(sum % for SDA, ETA, EPA, DPA and DHA).
11. Δ5-desaturase efficiency (on ω3 substrate ETA)=100× (sum % for EPA, DPA and DHA)/(sum % for ETA, EPA, DPA and DHA).
12. Δ5-elongase efficiency (on ω3 substrate EPA)=100× (sum % for DPA and DHA)/(sum % for EPA, DPA and DHA).

The fatty acid composition of the lipid, preferably seedoil, of the invention, is also characterised by the ratio of ω6 fatty acids:ω3 fatty acids in the total fatty acid content, for either total ω6 fatty acids:total ω3 fatty acids or for new ω6 fatty acids:new ω3 fatty acids. The terms total 06 fatty acids, total ω3 fatty acids, new ω6 fatty acids and new ω3 fatty acids have the meanings as defined herein. The ratios are calculated from the fatty acid composition in the lipid extracted from the cell, plant, plant part or seed, in the manner as exemplified herein. It is desirable to have a greater level of ω3 than ω6 fatty acids in the lipid, and therefore an ω6:ω3 ratio of less than 1.0 is preferred. A ratio of 0.0 indicates a complete absence of the defined ω6 fatty acids; a ratio of 0.03 was achieved. Such low ratios can be achieved through the combined use of a Δ6-desaturase which has an ω3 substrate preference together with an ω3-desaturase, particularly a fungal ω3-desaturase such as the *Pichia pastoris* ω3-desaturase as exemplified herein.

The yield of LC-PUFA per weight of seed may also be calculated based on the total oil content in the seed and the % DHA and/or DPA in the oil. For example, if the oil content of canola seed is about 40% (w/w) and about 12% of the total fatty acid content of the oil is DHA, the DHA content of the seed is about 4.8% or about 48 mg per gram of seed. As described in Example 2, the DHA content of *Arabidopsis* seed having about 9% DHA, which has a lower oil content than canola, was about 25 mg/g seed. At a DHA content of about 210%, canola seed or *Camelina sativa* seed has a DHA content of about 84 mg per gram of seed. The present invention therefore provides *Brassica napus, B. juncea* and *Camelina sativa* plants, and seed obtained therefrom, comprising at least about 80 mg or at least about 84 mg DHA per gram seed. The seed has a moisture content as is standard for harvested mature seed after drying down (4-15% moisture). The invention also provides a process for obtaining oil, comprising obtaining the seed and extracting the oil from the seed, and uses of the oil and methods of obtaining the seed comprising harvesting the seeds from the plants according to the invention.

The amount of DHA and/or DPA produced per hectare can also be calculated if the seed yield per hectare is known or can be estimated. For example, canola in Australia typically yields about 2.5 tonnes seed per hectare, which at 40% oil content yields about 1000 kg of oil. At 20.1% DHA and/or DPA in the total oil, this provides about 200 kg of DHA and/or DPA per hectare. If the oil content is reduced by 50%, this still provides about 100 kg DHA and/or DPA/ha.

Evidence to date suggests that some desaturases expressed heterologously in yeast or plants have relatively low activity in combination with some elongases. This may be alleviated by providing a desaturase with the capacity of to use an acyl-CoA form of the fatty acid as a substrate in LC-PUFA synthesis, and this is thought to be advantageous in recombinant cells particularly in plant cells. A particularly advantageous combination for efficient DHA and/or DPA synthesis is a fungal ω3-desaturase, for example such as the *Pichia pastoris* ω3-desaturase (SEQ ID NO: 6), with a Δ6-desaturase which has a preference for ω3 acyl substrates such as, for example, the *Micromonas pusilla* Δ6-desaturase (SEQ ID NO: 9), or variants thereof which have at least 95% amino acid sequence identity.

As used herein, the term "essentially free" means that the composition (for example lipid or oil) comprises little (for example, less than about 0.5%, less than about 0.25%, less than about 0.10%, or less than about 0.01%) or none of the defined component. In an embodiment, "essentially free" means that the component is undetectable using a routine analytical technique, for example a specific fatty acid (such as ω6-docosapentaenoic acid) cannot be detected using gas chromatography as outlined in Example 1.

In an embodiment, extracted lipid, extracted oil, a plant or part thereof such as a seed (of the invention or used in a process/method of the invention), a feedstuff, or a composition of the invention does not comprise all-cis-6,9,12,15,18-heneicosapentaenoic acid (n-3 HPA).

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

In an embodiment, the majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures. As used herein, the term "purified" when used in connection with lipid or oil of the invention typically means that that the extracted lipid or oil has been subjected to one or more processing steps of increase the purity of the lipid/oil component. For example, a purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to increase the DPA and/or DHA content as a percentage of the total fatty acid content. Expressed in other words, the fatty acid composition of the purified lipid or oil is essentially the same as that of the unpurified lipid or oil.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali Refining

Alkali refining is one of the refining processes for treating crude oil, sometimes also referred to as neutralization. It usually follows degumming and precedes bleaching. Following degumming, the seedoil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. This treatment improves the colour of the seedoil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

As used herein, "transesterification" means a process that exchanges the fatty acids within and between TAGs or transfers the fatty acids to another alcohol to form an ester. This may initially involve releasing fatty acids from the TAGs as free fatty acids or it may directly produce fatty acid esters, preferably fatty acid methyl esters or ethyl esters. In a transesterification reaction of the TAG with an alcohol such as methanol or ethanol, the alkyl group of the alcohol forms an ester linkage with the acyl groups (including the DHA and/or DPA) of the TAG. When combined with a fractionation process, transesterification can be used to modify the fatty acid composition of lipids (Marangoni et al., 1995). Transesterification can use either chemical (e.g. strong acid or base catalysed) or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction, counter current chromatography and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis under either acid or base catalysed reaction conditions, whereby one mol of TAG is reacted with at least 3 mol of alcohol (e.g. ethanol for ethyl esters or methanol for methyl esters) with excess alcohol used to enable separation of the formed alkyl esters and the glycerol that is also formed, or by lipases. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Feedstuffs

The present invention includes compositions which can be used as feedstuffs. For purposes of the present invention, "feedstuffs" include any food or preparation for human or animal consumption which when taken into the body (a) serve to nourish or build up tissues or supply energy; and/or (b) maintain, restore or support adequate nutritional status or metabolic function. Feedstuffs of the invention include nutritional compositions for babies and/or young children such as, for example, infant formula, and seedmeal of the invention.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, protein, carbohydrate, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

Additionally, fatty acids produced in accordance with the present invention or host cells transformed to contain and express the subject genes may also be used as animal food supplements to alter an animal's tissue, egg or milk fatty acid composition to one more desirable for human or animal consumption. Examples of such animals include sheep, cattle, horses, poultry such as chickens and the like.

Furthermore, feedstuffs of the invention can be used in aquaculture to increase the levels of fatty acids in fish or crustaceans such as, for example, prawns for human or animal consumption. Preferred fish are salmon.

Preferred feedstuffs of the invention are the plants, seed and other plant parts such as leaves and stems which may be used directly as food or feed for humans or other animals. For example, animals may graze directly on such plants grown in the field or be fed more measured amounts in controlled feeding. The invention includes the use of such plants and plant parts as feed for increasing the LC-PUFA levels in humans and other animals.

In an embodiment, a feedstuff is infant formula comprising the lipid or oil of the invention. As used herein, "infant formula" means a non-naturally occurring composition that satisfies at least a portion of the nutrient requirements of an infant. An "infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. As used herein, "non-naturally occurring" means that the product is not found in nature but has been produced by human intervention. As used herein, the infant formula of the invention excludes pure human breast milk (Koletzko et al., 1988) and pure milk produced by non-human animals, although the infant formula of the invention may comprise components derived from milk such as milk proteins or carbohydrates, for example whey proteins or lactose. The infant formula of the invention excludes naturally occurring meats such as beef, seal meat, whale meat or fish, although the infant formula of the invention may comprise components such as proteins from these sources. The infant formula of the invention always comprises lipid comprising the DPA and/or DHA, preferably at a level of between 0.05% to about 0.5% by weight of the total fatty acid content. The DPA and/or DHA is at least present as TAG, but can also include phospholipid or as non-esterified fatty acid, or a mixture thereof.

Lipid or oil of the invention can be incorporated into infant formula using procedures known in the art. For example, the skilled person can readily produce infant formula of the invention generally using the procedures described in WO 2008/027991, US20150157048, US2015094382 and US20150148316, where the DPA and/or DHA is added in addition to, or instead of, one or more of the polyunsaturated fatty acids described therein.

In one example, the infant formula comprises DPA (ie omega-3 DPA as described herein) and/or DHA, optionally with prebiotics, especially polydextrose (PDX) and galacto-oligosaccharides (GOS), lactoferrin from a non-human source, and other long-chain polyunsaturated fatty acids (LC-PUFAs). In some embodiments, the nutritional composition further comprises SDA and/or gamma-linolenic acid (GLA). In certain embodiments, the infant formula comprises up to about 7 g/100 kcal of a fat or lipid source, more preferably about 3 g/100 kcal to about 7 g/100 kcal of a fat or lipid source, wherein the fat or lipid source comprises at least about 0.5 g/100 kcal, and more preferably from about 1.5 g/100 kcal to about 7 g/100 kcal; up to about 7 g/100 kcal of a protein or protein equivalent source, more preferably about 1 g/100 kcal to about 7 g/100 kcal of a protein source or protein equivalent source; and at least about 5 g/100 kcal of a carbohydrate, more preferably about 5 g to about 25 g/100 kcal of a carbohydrate. The infant formula may further comprise one or more or all of 1) at least about 10 mg/100 kcal of lactoferrin, more preferably from about 10 mg/100 kcal to about 200 mg/100 kcal of lactoferrin; 2) about 0.1 g/100 kcal to about 1 g/100 kcal of a prebiotic composition comprising PDX and GOS; and 3) at least about 5 mg/100 kcal of an additional LC-PUFA (i.e., an LC-PUFA other than DPA and/or and/or DHA) comprising DHA, more preferably from about 5 mg/100 kcal to about 75 mg/100 kcal of an additional LC-PUFA comprising DHA.

In an embodiment, the ratio of DPA:DHA in the total fatty acid content of the infant formula is between 1:3 and 2:1. EPA may also be present but is preferable absent. If present, the ratio of EPA:DPA In the total fatty acid content is preferably less than 1:2, more preferably less than 1:5. ARA may also be absent but is preferably present, preferably the ratio of ARA:DPA in the total fatty acid content is between 1:3 and 2:1. Most preferably, the levels of each LC-PUFA in the infant formula is about the same as found in any human breast milk, which naturally show variation based on a mother's age, genetic factors, dietary intake and nutritional status. For example, see Koletzko et al. (1988). In a preferred embodiment, the infant formula does not contain detectable levels of heneicosapentaenoic acid (HPA, 21:5ω3)

The infant formula may refer to, for example, liquids, powders, gels, pastes, solids, concentrates, suspensions, or ready-to-use forms of enteral formulas, oral formulas, formulas for infants.

Prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide and gentio-oligosaccharides.

Lactoferrin may also be also included in the nutritional composition of the present disclosure. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively.

The protein or protein equivalent source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

Suitable carbohydrate sources can be any used in the art, e.g., lactose, glucose, fructose, corn syrup solids, maltodextrins, sucrose, starch, rice syrup solids, and the like. The amount of the carbohydrate component in the nutritional composition is at least about 5 g/100 kcal and typically can vary from between about 5 g and about 25 g/100 kcal. In some embodiments, the amount of carbohydrate is between about 6 g and about 22 g/100 kcal. In other embodiments, the amount of carbohydrate is between about 12 g and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes. Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Preferably, one or more vitamins and/or minerals may also be added to the infant formula in amounts sufficient to supply the daily nutritional requirements of a subject. It is to be understood by one of ordinary skill in the art that vitamin and mineral requirements will vary, for example, based on the age of the child. The nutritional composition may optionally include, but is not limited to, one or more of the following vitamins or derivations thereof: vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin3, 1,25,-dihydroxyvitamin D), vitamin E (α-tocopherol, α-tocopherol acetate, α-tocopherol succinate, α-tocopherol nicotinate, α-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof. Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound. The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the infant formula of, or produced using the invention, does not comprise human or animal breast milk or an extract thereof comprising DPA and/or DHA.

In another embodiment, the level of omega-6 DPA and/or omega-6 DHA in the total fatty acid content of the infant formula is less than 2%, preferably less than 1%, or between 0.1% and 2%, more preferably is absent.

Compositions

The present invention also encompasses compositions, particularly pharmaceutical compositions, comprising one or more of the fatty acids and/or resulting oils produced using the methods of the invention, preferably in the form of ethyl esters of the fatty acids.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid(s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

EXAMPLES

Example 1. Materials and Methods

Expression of Genes in Plant Cells in a Transient Expression System

Exogenous genetic constructs were expressed in plant cells in a transient expression system essentially as described by Voinnet et al. (2003) and Wood et al. (2009).

Gas Chromatography (GC) Analysis of Fatty Acids

FAME were analysed by gas chromatography using an Agilent Technologies 7890A GC (Palo Alto, California, USA) equipped with a 30 m SGE-BPX70 column (70% cyanopropyl polysilphenylene-siloxane, 0.25 mm inner diameter, 0.25 mm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min then raised to 210° C. at 3° C. min$^{-1}$, again raised to 240° C. at 50° C. min$^{-1}$ and finally holding for 1.4 min at 240° C. Peaks were quantified with Agilent Technologies ChemStation software (Rev B.04.03 (16), Palo Alto, California, USA) based on the response of the known amount of the external standard GLC-411 (Nu-check) and C17:0-ME internal standard.

Liquid Chromatography-Mass Spectrometry (LC-MS) Analysis of Lipids

Total lipids were extracted from freeze-dried developing seeds, twelve days after flowering (daf), and mature seeds after adding a known amount of tri-C17:0-TAG as an internal quantitation standard. The extracted lipids were dissolved into 1 mL of 10 mM butylated hydroxytoluene in butanol:methanol (1:1 v/v) per 5 mg dry material and analysed using an Agilent 1200 series LC and 6410b electrospray ionisation triple quadrupole LC-MS. Lipids were chromatographically separated using an Ascentis Express RP-Amide column (50 mm×2.1 mm, 2.7 μm, Supelco) operating a binary gradient with a flow rate of 0.2 mL/min. The mobile phases were: A. 10 mM ammonium formate in H$_2$O:methanol: tetrahydrofuran (50:20:30 v/v/v); B. 10 mM ammonium formate in H$_2$O:methanol: tetrahydrofuran (5:20:75, v/v/v). Multiple reaction monitoring (MRM) lists were based on the following major fatty acids: 16:0, 18:0, 18:1, 18:2, 18:3, 18:4, 20:1, 20:2, 20:3, 20:4, 20:5, 22:4, 22:5, 22:6 using a collision energy of 30 V and fragmentor of 60 V. Individual MRM TAG was identified based on ammoniated precursor ion and product ion from neutral loss of 22:6. TAG was quantified using a 10 μM tristearin external standard.

Lipid Profiling with LC-MS

The extracted total lipids were analysed using an Agilent 1200 series LC coupled to an Agilent 6410B electrospray ionisation QQQ-MS (Agilent, Palo Alto, California, USA). A 5 μL injection of each total lipid extract was chromatographically separated with an Ascentis Express RP-Amide 50 mm×2.1 mm, 2.7 μm HPLC column (Sigma-Aldrich, Castle Hill, Australia) using a binary gradient with a flow rate of 0.2 mL/min. The mobile phases were: A. 10 mM ammonium formate in H$_2$O:methanol:tetrahydrofuran (50:20:30, v/v/v.); B. 10 mM ammonium formate in H$_2$O: methanol:tetrahydrofuran (5:20:75, v/v/v.). Selected neutral lipids (TAG and DAG) and phospholipids (PL, including PC, PE, PI, PS, PA, PG) were analysed by multiple reaction monitoring (MRM) using a collision energy of 30 V and fragmentation energy of 60 V. Neutral lipids were targeted on the following major fatty acids: 16:0 (palmitic acid), 18:0 (stearic acid), 18:1ω9 (oleic acid, OA), 18:2ω6 (linoleic acid, LA), 18:3ω3 (α-linolenic acid, ALA), 18:4ω3 (stearidonic acid, SDA), 20:1, 20:2, 20:3, 20:4ω3, 20:5ω3, 22:4ω3, 22:5ω3, 22:6ω3, while phospholipids were scanned containing C$_{16}$, C$_{18}$, C$_{20}$ and C$_{22}$ species with double bonds of 0-3, 0-4, 0-5, 4-6 respectively.

Individual MRM TAG was identified based on ammoniated precursor ion and product ion from neutral loss of 20:1, SDA, EPA and DHA. TAG and DAG were quantified using the 50 μM tristearin and distearin as external standards. PL were quantified with 10 uM of di-18:0-PC, di-17:0-PA, di-17:0-PE, 17:0-17:1-PG, di-18:1-PI and di-17:0-PS external standards (Avanti Polar Lipids, Alabaster, Alabama, USA). Selected TAG, DAG and PL species were further confirmed by Agilent 6520 Q-TOF MS/MS.

Determination of Seed Fatty Acid Profile and Oil Content

Where seed oil content was to be determined, seeds were dried in a desiccator for 24 h and approximately 4 mg of seed was transferred to a 2 ml glass vial containing Teflon-lined screw cap. 0.05 mg triheptadecanoin dissolved in 0.1 ml toluene was added to the vial as internal standard.

Seed FAME were prepared by adding 0.7 ml of 1N methanolic HCl (Supelco) to the vial containing seed material, vortexed briefly and incubated at 80° C. for 2 h. After cooling to room temperature, 0.3 ml of 0.9% NaCl (w/v) and 0.1 ml hexane was added to the vial and mixed well for 10 min in Heidolph Vibramax 110. The FAME was collected into 0.3 ml glass insert and analysed by GC with a flame ionization detector (FID) as mentioned earlier.

The peak area of individual FAME were first corrected on the basis of the peak area responses of known amount of the same FAMEs present in a commercial standard GLC-411

(NU-CHEK PREP, INC., USA). GLC-411 contains equal amounts of 31 fatty acids (% by wt), ranging from C8:0 to C22:6. In case of fatty acids, which were not present in the standard, the inventors took the peak area responses of the most similar FAME. For example, peak area response of FAMEs of 16:1d9 was used for 16:1d7 and FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAMES and dividing total moles of FAMEs by three. TAG was calculated as the sum of glycerol and fatty acyl moieties using a relation: % oil by weight=100×((41× total mol FAME/3)+(total g FAME- (15× total mol FAME)))/g seed, where 41 and 15 are molecular weights of glycerol moiety and methyl group, respectively.

Analysis of the Sterol Content of Oil Samples

Samples of approximately 10 mg of oil together with an added aliquot of C24:0 monol as an internal standard were saponified using 4 mL 5% KOH in 80% MeOH and heating for 2 h at 80° C. in a Teflon-lined screw-capped glass tube. After the reaction mixture was cooled, 2 mL of Milli-Q water were added and the sterols were extracted into 2 mL of hexane: dichloromethane (4:1 v/v) by shaking and vortexing. The mixture was centrifuged and the sterol extract was removed and washed with 2 mL of Milli-Q water. The sterol extract was then removed after shaking and centrifugation. The extract was evaporated using a stream of nitrogen gas and the sterols silylated using 200 mL of BSTFA and heating for 2 h at 80° C.

For GC/GC-MS analysis of the sterols, sterol-OTMSi derivatives were dried under a stream of nitrogen gas on a heat block at 40° C. and then re-dissolved in chloroform or hexane immediately prior to GC/GC-MS analysis. The sterol-OTMS derivatives were analysed by gas chromatography (GC) using an Agilent Technologies 6890A GC (Palo Alto, California, USA) fitted with an Supelco Equity™-1 fused silica capillary column (15 m×0.1 mm i.d., 0.1 μm film thickness), an FID, a split/splitless injector and an Agilent Technologies 7683B Series auto sampler and injector. Helium was the carrier gas. Samples were injected in splitless mode at an oven temperature of 120° C. After injection, the oven temperature was raised to 270° C. at 10° C. min$^{-1}$ and finally to 300° C. at 5° C. min$^{-1}$. Peaks were quantified with Agilent Technologies ChemStation software (Palo Alto, California, USA). GC results are subject to an error of ±5% of individual component areas.

GC-mass spectrometric (GC-MS) analyses were performed on a Finnigan Thermoquest GCQ GC-MS and a Finnigan Thermo Electron Corporation GC-MS; both systems were fitted with an on-column injector and Thermoquest Xcalibur software (Austin, Texas, USA). Each GC was fitted with a capillary column of similar polarity to that described above. Individual components were identified using mass spectral data and by comparing retention time data with those obtained for authentic and laboratory standards. A full procedural blank analysis was performed concurrent to the sample batch.

RT-PCR Conditions

Reverse transcription-PCR (RT-PCR) amplification was typically carried out using the Superscript III One-Step RT-PCR system (Invitrogen) in a volume of 25 μL using 10 pmol of the forward primer and 30 pmol of the reverse primer, MgSO$_4$ to a final concentration of 2.5 mM, 400 ng of total RNA with buffer and nucleotide components according to the manufacturer's instructions. Typical temperature regimes were: 1 cycle of 45° C. for 30 minutes for the reverse transcription to occur; then 1 cycle of 94° C. for 2 minutes followed by 40 cycles of 94° C. for 30 seconds, 52° C. for 30 seconds, 70° C. for 1 minute; then 1 cycle of 72° C. for 2 minutes before cooling the reaction mixtures to 5° C.

Determination of Copy-Number of Transgenes by Digital PCR

To determine the copy-number of transgenes in a transgenic plant, a digital PCR method was used as follows. This method could also be used to determine whether a plant was transgenic for the genetic constructs described herein. About a centimetre square of leaf tissue was harvested from each individual plant and placed in a collection microtube (Qiagen). The samples were then freeze dried for 24 to 48 hr. For breaking up the samples for DNA extraction, stainless steel ball bearings were added to each dried sample and the tubes shaken on a Qiagen Tissue lyser. 375 μL of extraction buffer (0.1M Tris-HCl pH8, 0.05M EDTA pH8 and 1.25% SDS) was added to each tube, the mixtures incubated at 65° C. for 1 hr, and then cooled before 187 μL of 6M ammonium acetate (4° C.) was added to each tube with thorough mixing. The samples were then centrifuged for 30 min at 3000 rpm. The supernatant from each tube was removed into new microtubes each containing 220 μL of isopropanol for precipitation of the DNA at room temperature for 5 min. DNA was collected by centrifuging the tubes at 3000 rpm for 30 min, the DNA pellets washed with 320 μL of 70% ethanol and dried before resuspension of the DNA in 225 μL of water. Non-dissolved material was pelleted by centrifugation at 3000 rpm for 20 min, and 150 μL of each supernatant transferred to 96-well plates for long term storage.

For efficient and quantitative digital PCR (ddPCR) the DNA was digested with restriction enzymes prior to amplification reactions, to ensure that multiple copies of the transgenes or multiple insertions were physically separated. Aliquots of the DNA preparations were therefore digested with EcoRI and BamHI, together, in 20 μL volumes using 10×EcoRI buffer, 5 μL of DNA and about 4 units of each enzyme per sample, incubated overnight at 37° C.

The primers used in these PCR reactions were designed using Primer3 software to confirm that primers for the reference and target genes were not predicted to interact, or such interaction would not be a problem under the conditions used. The reference gene used in the assay was the canola Hmg (high mobility group) gene, present at one gene per canola genome (Weng et al., 2004). Since canola is an allotetraploid, it was taken that there were 4 copies of the Hmg gene, i.e. 2 alleles of each of the two genes, in *Brassica napus*. The reference gene reactions used the pair of primers and a dual-labelled probe, as follows: Sense primer, Can11 GCGAAGCACATCGAGTCA (SEQ ID NO:50); Antisense primer, Can12 GGTTGAGGTGGTAGCTGAGG (SEQ ID NO:51); Probe, Hmg-P3 5'-Hex/TCTCTAC/zen/CCGTCT-CACATGACGC/3IABkFQ/-3' (SEQ ID NO:52). The amplification product size was 73 bp.

In one target gene amplification reaction which detected a region of the PPT selectable marker gene to screen all of the transgenic plants, the sense primer was Can17, ATA-CAAGCACGGTGGATGG (SEQ ID NO:53); the antisense primer, Can18 TGGTCTAACAGGTCTAGGAGGA (SEQ ID NO:54); the probe, PPT-P3 5'-/FAM/TGGCAAAGA/zen/GATTTCGAGCTTCCTGC/3IABkFQ/-3' (SEQ ID NO:55). The size of this target gene amplification product was 82 bp. On some occasions, a second target gene assay was performed in parallel to detect partial insertions of the T-DNA. This second assay detected a region of the Δ6-desaturase gene using a sense primer, Can23 CAAGCACCGTAGTAAGAGAGCA (SEQ ID NO:56), the antisense primer, Can24 CAGACAGCCTGAGGTTAGCA (SEQ ID NO:57); the probe, D6des-P3 5'-/FAM/TCCC-CACTT/zen/CTTAGCGAAAGGAACGA/3IABkFQ/-3' (SEQ ID NO:58). The size of this target gene amplification product was 89 bp. Reactions routinely used 2 μL of the digested DNA preparations. Reaction composition per sample: reference sense primer (10 pM), 1 μL; reference antisense primer (10 pM), 1 μL; reference gene probe (10 pM), 0.5 μL; target gene sense primer (10 pM), 1 μL; target gene antisense primer (10 pM), 1 μL; target gene probe (10 pM), 0.5 μL; ddPCR reagent mix, 12.5βL; water 5.5 μL in a total volume of 25 μL.

The mixtures were then placed into a QX100 droplet generator, which partitioned each sample into 20000 nanoliter-sized droplets. This was done in 8-well cartridges until all of the samples were processed and transferred to a 96-well PCR plate. This plate was then heat sealed with a pierceable foil using a plate sealer machine. The samples were then treated under the following reaction conditions: 95° C., 10 min, ramping at 2.5° C./s; then 39 cycles of 94° C., 30 s ramping at 2.5° C./s; 61° C., 1 min, ramping at 2.5° C./s; 98° C., 10 min, followed by cooling to 12° C. Following the amplification reactions of the DNA in the droplets, the plate was placed in a QX100 droplet reader which analysed each droplet individually using a two-color detection system (set to detect FAM or Hex). The droplet digital PCR data were viewed as either a 1-D plot with each droplet from a sample plotted on the graph of fluorescence intensity, or a 2-D plot in which fluorescence (FAM) was plotted against fluorescence (Hex) for each droplet. The software measured the number of positive and negatives droplets for each fluorophore (FAM or Hex) in each sample. The software then fitted the fraction of positive droplets to a Poisson algorithm to determine the concentration of the target DNA molecule in units of copies/μL input. The copy number variation was calculated using the formula: CNV= (A/B)*Nb, where A=concentration of target gene, B=concentration of reference gene, and Nb=4, the number of copies of the reference gene in the genome.

Assessment of Pollen Viability

Fluorescein diacetate (FDA) was dissolved in acetone at 2 mg/ml to provide a stock solution. FDA dilutions were prepared just before use by adding drops of the FDA stock solution to 2 ml of a sucrose solution (0.5 M) until saturation was reached as indicated by the appearance of persistent cloudiness.

Propidium iodide (PI) was dissolved in sterile distilled water at 1 mg/ml to provide a stock solution. Just before use, 100 μl of the stock solution was added to 10 ml of sterile distilled water to make a working solution. To check the ratio of viable and non-viable pollen, PI and FDA stock solutions were mixed in 2:3 ratio.

Transgenic and wild-type canola and mustard plants were grown under standard conditions in a glasshouse at 22±2° C. with a 16 hr photoperiod per day. Mature flower buds which were ready to open in the next day were labelled and collected on the following morning at 9-10 am. Pollen from opened flowers were stained with the FDA/PI mixture and visualized using a Leica MZFLIII fluorescence microscope. GFP-2, a 510 nm long pass emission filter (transmitting red and green light) with a 480/40 nm excitation filter was used to detect viable and non-viable pollen. Non-viable pollen which took up the PI stain appeared red under the fluorescence microscope whereas viable pollen appeared bright green when stained with PI and FDA.

Example 2. Stable Expression of Transgenic DHA Pathways in *Arabidopsis thaliana* Seeds Binary Vector Construction The binary vectors pJP3416-GA7 (also referred to herein as "GA7" described in WO 2013/185184) and pJP3404 each contained seven heterologous fatty acid biosynthesis genes, encoding 5 desaturases and 2 elongases, and a plant selectable marker between the left and right border repeats of the T-DNA present in each vector (FIGS. 2 and 3). SEQ ID NO:1 provides the nucleotide sequence of the T-DNA region of pJP3416-GA7 from the right to left border sequences. Both genetic constructs contained plant codon-optimised genes encoding a *Lachancea kluyveri* Δ12-desaturase (comprising nucleotides 14143-16648 of SEQ ID NO: 1), a *Pichia pastoris* ω3-desaturase (comprising nucleotides 7654-10156 of SEQ ID NO:1), a *Micromonas pusilla* Δ6-desaturase (comprising nucleotides 226-2309 of SEQ ID NO:1), *Pavlova salina* Δ5- and Δ4-desaturases (comprising nucleotides 4524-6485 and 10157-14142 of SEQ ID NO:1, respectively) and *Pyramimonas cordata* Δ6- and Δ5-elongases (comprising nucleotides 2310-4523 and 17825-19967 of SEQ ID NO:1, respectively).

The seven coding regions in the constructs were each under the control of a seed specific promoter—three different promoters were used, namely the truncated *Brassica napus* napin promoter (pBnFP1), the *Arabidopsis thaliana* FAE1 promoter (pAtFAE1) and the *Linum usitatissimum* conlinin 1 promoter (pLuCnl1). The seven fatty acid biosynthesis genes together coded for an entire DHA synthesis pathway that was designed to convert $18:1^{\Delta 9}$ (oleic acid) through to $22:6^{\Delta 4,10,13,16,19}$ (DHA). Both binary vectors contained a BAR plant selectable marker coding region operably linked to a Cauliflower Mosaic Virus (CaMV) 35S promoter with duplicated enhancer region and *A. tumefaciens* nos3' polyadenylation region-transcription terminator. The plant selectable marker was situated adjacent to the left border of the T-DNA region, therefore distally located on the T-DNA with respect to the orientation of T-DNA transfer into the plant cells. This increased the likelihood that partial transfer of the T-DNA, which would be likely to not include the selectable marker gene, would not be selected. pJP3416-GA7 and pJP3404 each contained an RiΔ4 origin of replication from *Agrobacterium rhizogenes* (Hamilton, 1997).

The GA7 construct also included two *Nicotiana tabacum* Rb7 matrix attachment region (MAR) sequences, as described by Hall et al. (1991). MAR sequences, sometimes termed nuclear attachment regions, are known to bind specifically to the nuclear matrix in vitro and may mediate binding of chromatin to the nuclear matrix in vivo. MARs are thought to function to reduce transgene silencing. In pJP3416-GA7 the MARs were also inserted and positioned within the T-DNA region in order to act as DNA spacers to insulate transgenic expression cassettes. The pJP3416 vector prior to insertion of the GA7 region contained only the plant selectable marker cassette between the borders.

A. *Thaliana* Transformation and Analysis of Fatty Acid Composition

The chimeric vectors were introduced into *A. tumefaciens* strain AGL1 and cells from cultures of the transformed *Agrobacterium* used to treat *A. thaliana* (ecotypes Columbia and a fad2 mutant) plants using the floral dip method for transformation (Clough and Bent, 1998). After maturation, the T₁ seeds from the treated plants were harvested and plated onto MS plates containing PPT for selection of plants containing the BAR selectable marker gene. Surviving, healthy $T_1$ seedlings were transferred to soil. After growth of the plants to maturity and allowing for self-fertilisation, $T_2$ seeds from these plants were harvested and the fatty acid composition of their seed lipid analysed by GC analysis as described in Example 1.

The pJP3416-GA7 construct resulted in the production of slightly higher levels of DHA, as a percentage of total fatty acid content, on average than the pJP3404 construct. The conversion efficiencies for each enzymatic step in the production of DHA from oleic acid were calculated as (% products×100)/(% remaining substrate+% products), thereby expressed as a percentage.

The highest observed level of DHA produced in the pJP3416-GA7 $T_2$ transformed lines was 6.2%, additionally with 0.5% EPA and 0.2% DPA (line #14). These $T_2$ seeds were still segregating for the transgene i.e. were not yet uniformly homozygous. The level of ω3 fatty acids produced as a result of the transgenes in these seeds (total new ω3 fatty acids, excluding the level of ALA which was produced endogenously in the Columbia background) was 10.7% while the level of ω6 fatty acids (total new ω6 fatty acids but excluding $18:2^{\Delta9,12}$) was 1.5%. This represents an extremely favourable ration of new ω3 fatty acids:new ω6 fatty acids, namely 7.3:1.

$T_2$ seeds of selected lines transformed with pJP3416-GA7, namely for lines designated 7, 10, 14, 22 and 34 in the Columbia background and for lines designated 18, 21 and 25 in the fad2 mutant background, were plated onto MS media containing PPT for selection of transgenic seedlings in vitro. Twenty PPT-resistant seedlings for each line were transferred to soil and grown to maturity after self-fertilisation. These plants were highly likely to be homozygous for the selectable marker gene, and therefore for at least one T-DNA insertion in the genome of the plants. $T_3$ seed from these plants were harvested and analysed for fatty acid composition in their seedoil by GC. This analysis revealed that the pJP3416-GA7 construct generated higher levels of the ω3 LC-PUFA DHA in $T_3$ seeds of the homozygous plants than in the segregating $T_2$ seed. Up to about 13.9% DHA was observed in the $T_3$ pJP3416-GA7 transformed line designated 22.2 in the Columbia background, increased from about 5.5% in the hemizygous $T_2$ seed, with a sum level of about 24.3% of new ω3 fatty acids as a percentage of the total fatty acids in the seed lipid content. New ω6 fatty acids were at a level of 1.10% of total fatty acids, representing a very favourable ratio of new ω3 fatty acids:new ω6 fatty acids, namely about 22:1. Similarly, transformants in the fad2 mutant background yielded 20.6% as a sum of new ω3 fatty acids, including 11.5% DHA, as a percentage of the total fatty acids in the seed lipid content.

Enzymatic conversion efficiencies for each enzyme step in the pathway for production of DHA from oleic acid are shown in Table 4 for the $T_3$ seeds with the higher DHA levels. The Δ12-desaturase conversion efficiency in seeds of line 22.2 was 81.6% and the ω3-desaturase efficiency was 89.1%, both of them remarkably high and indicating that these fungal (yeast) enzymes were able to function well in developing seeds. The activities of the other exogenous enzymes in the DHA pathway were similarly high for ω3 substrates with the Δ6-desaturase acting at 42.2% efficiency, Δ6-elongase at 76.8%, Δ5-desaturase at 95.0%, Δ5-elongase at 88.7% and Δ4-desaturase at 93.3% efficiency. The Δ6-desaturase activity on the ω6 substrate LA was much lower, with the Δ6-desaturase acting at only 0.7% conversion efficiency on LA. GLA was present at a level of only 0.4% and was the only new ω6 product aside from 20:206 detected in the $T_3$ seeds with the highest DHA content. Compiled data from the total seed lipid profiles from independent transgenic seed are shown in Table 5.

$T_3$ seeds from the pJP3416-GA7 line 22.2 in the Columbia background, which were progeny from $T_2$ line 22, were sown directly to soil and the fatty acid composition of mature seed from the resultant $T_3$ plants analysed by GC. The average DHA level of these seeds was 13.3%±1.6 (n=10) as a percentage of total fatty acids in the seed lipid. The line with the highest level of DHA contained 15.1% DHA in the total fatty acids of the seed lipid. The enzymatic conversion efficiencies are shown in Table 4 for each step in the production of DHA from oleic acid.

Southern blot hybridisation analysis was performed. The results showed that the high-accumulating DHA lines were either single- or double-copy for the T-DNA from the pJP3416-GA7 construct with the exception of transgenic line Columbia #22, which had three T-DNA insertions in the genome of the *Arabidopsis* plant. The T5 generation seed was also analysed and found to have up to 13.6% DHA in the total seed lipids. The GA7 construct was found to be stable across multiple generations in terms of DHA production capability.

TABLE 4

| | | Conversion efficiencies of the individual enzymatic steps for the production of DHA from oleic acid, observed in total seed lipid from transgenic $T_3$ *Arabidopsis* seeds. | | | | | | | | | |
|---|---|---|---|---|---|---|---|---|---|---|---|
| | | GA7_Col_7.2 | GA7_Col_34.2 | GA7_Col_10.13 | GA7_Col_22.2 | GA7_Col_14.19 | GA7_FAD2-25.10 | GA7_FAD2-21.2 | GA7_FAD2-18.14 | $T_4$ Col_22.2 (mean) | $T_4$ Col_22.2 best line |
| Omega-6 | d12-des | 75.4% | 73.1% | 75.7% | 81.6% | 73.4% | 66.6% | 78.5% | 63.1% | 67.6% | 82.7% |
| | d15-des | 85.3% | 84.4% | 86.2% | 89.1% | 70.2% | 87.5% | 82.2% | 87.6% | 81.0% | 90.9% |
| | d6-des | 0.3% | 0.3% | 0.3% | 0.7% | 0.3% | 0.6% | 1.0% | 0.2% | 1.3% | 0.7% |
| | (d9-elo) | 1.7% | 1.7% | 1.2% | 1.2% | 2.6% | 1.1% | 2.0% | 1.3% | 1.6% | 1.5% |
| | d6-elo | | | | | | | | | | |
| | d5-des | | | | | | | | | | |
| | d5-elo | | | | | | | | | | |
| | d4-des | | | | | | | | | | |
| Omega-3 | d6-des | 30.7% | 29.3% | 28.2% | 42.2% | 30.2% | 38.5% | 40.0% | 29.2% | 41.0% | 45.7% |
| | (d9-elo) | 2.7% | 2.7% | 2.3% | 2.4% | 3.0% | 2.3% | 2.7% | 2.9% | 2.8% | 3.1% |
| | d6-elo | 79.0% | 81.1% | 79.0% | 76.8% | 70.9% | 79.2% | 73.2% | 79.1% | 77.5% | 77.7% |
| | d5-des | 94.0% | 94.6% | 94.5% | 95.0% | 97.9% | 87.8% | 93.3% | 91.1% | 95.0% | 95.8% |
| | d5-elo | 91.9% | 91.7% | 93.6% | 88.7% | 89.5% | 89.9% | 92.2% | 91.6% | 90.8% | 90.2% |
| | d4-des | 93.2% | 93.7% | 94.4% | 93.3% | 93.7% | 92.5% | 95.0% | 93.9% | 92.2% | 90.9% |

TABLE 5

Compiled data from the total seed lipid profiles from independent transgenic seed.

| Parameter | GA7-Col_7.2 | GA7-Col_34.2 | GA7-Col_10.13 | GA7-Col_22.2 | GA7-Col_14.19 | GA7-FAD2-25.10 | GA7-FAD2-21.2 | GA7-FAD2-18.14 | $T_4$ Col_22.2 (mean ± SD) | $T_4$ Col_22.2 best line |
|---|---|---|---|---|---|---|---|---|---|---|
| total w3 (% of total FA) | 50.0 | 48.9 | 51.6 | 55.8 | 38.6 | 47.1 | 49.4 | 44.8 | 54.0 | 55.9 |
| total w6 (% of total FA) | 8.7 | 9.1 | 8.3 | 6.7 | 16.3 | 6.7 | 10.7 | 6.3 | 6.7 | 5.7 |
| w3/w6 ratio | 5.75 | 5.37 | 6.22 | 8.33 | 2.37 | 7.03 | 4.62 | 7.11 | 8.06 | 9.81 |
| w6/w3 ratio | 0.17 | 0.19 | 0.16 | 0.12 | 0.42 | 0.14 | 0.22 | 0.14 | 0.12 | 0.10 |
| total novel w3 (% of total FA) | 16.3 | 15.2 | 15.5 | 24.3 | 12.5 | 18.8 | 20.5 | 14.0 | 23.0 | 26.4 |
| total novel w6 (% of total FA) | 1.2 | 1.2 | 0.9 | 1.1 | 1.5 | 0.9 | 1.8 | 0.7 | 1.4 | 1.4 |
| novel w3/w6 ratio | 13.58 | 12.67 | 17.22 | 22.09 | 8.33 | 20.89 | 11.39 | 20.00 | 16.43 | 18.86 |
| novel w6/w3 ratio | 0.07 | 0.08 | 0.06 | 0.05 | 0.12 | 0.05 | 0.09 | 0.05 | 0.06 | 0.05 |
| OA to EPA efficiency | 14.1% | 13.3% | 13.4% | 21.8% | 10.2% | 15.0% | 16.8% | 11.2% | 20.4% | 24.5% |
| OA to DHA efficiency | 12.0% | 11.4% | 11.8% | 18.0% | 8.6% | 12.6% | 14.8% | 9.6% | 17.1% | 20.1% |
| LA to EPA efficiency | 18.9% | 18.4% | 17.9% | 26.9% | 14.2% | 22.9% | 21.8% | 18.0% | 26.2% | 29.9% |
| LA to DHA efficiency | 16.2% | 15.9% | 15.7% | 22.2% | 12.0% | 19.1% | 19.1% | 15.5% | 21.9% | 24.5% |
| ALA to EPA efficiency | 22.2% | 21.9% | 20.7% | 30.1% | 20.2% | 26.1% | 26.5% | 20.5% | 29.4% | 32.9% |
| ALA to DHA efficiency | 19.0% | 18.8% | 18.2% | 24.9% | 17.1% | 21.9% | 23.3% | 17.6% | 24.6% | 27.0% |
| total saturates | 16.0 | 14.7 | 15.4 | 16.0 | 16.2 | 13.4 | 16.5 | 12.9 | 16.0 | 17.8 |
| total monounsaturates | 23.7 | 25.8 | 23.4 | 19.2 | 26.5 | 30.9 | 21.3 | 34.3 | 21.1 | 18.1 |
| total polyunsaturates | 58.7 | 58.0 | 59.9 | 62.5 | 54.9 | 53.8 | 60.1 | 51.1 | 60.7 | 61.6 |
| total C20 | 19 | 19.8 | 16.8 | 15.9 | 19.1 | 21.5 | 18.2 | 23.3 | 18 | 16.6 |
| total C22 | 11.4 | 11 | 10.8 | 15.5 | 8.6 | 12.1 | 13.2 | 9.9 | 15.4 | 17.5 |
| C20/C22 ratio | 1.67 | 1.80 | 1.56 | 1.03 | 2.22 | 1.78 | 1.38 | 2.35 | 1.17 | 0.95 |

Determination of Oil Content in Transgenic *A. thaliana* DHA Lines

The oil content of transgenic *A. thaliana* seeds with various levels of DHA was determined by GC as described in Example 1. The data are shown in FIG. 4, graphing the oil content (% oil by weight of seed) against the DHA content (as a percentage of total fatty acids). Up to 26.5 mg of DHA per gram of seed was observed (Table 6). The oil content of the transgenic *Arabidopsis* seeds was found to be negatively correlated with DHA content. The amount of DHA per weight of seed was greater in the transformed seeds with a DHA level of about 9% relative to the seeds with about 14% DHA. Subsequent data from species other than *Arabidopsis* has shown that this negative correlation is more pronounced in *Arabidopsis* than in *C. sativa* or *Brassica* species (Example 8 below).

TABLE 6

Proportion and amount of DHA in GA7-transformed Arabidopsis seeds.

| | DHA content (% of TFA) | Oil content (% oil per g seeds) | DHA content per weight (mg/g seed) |
|---|---|---|---|
| GA7/col 22.2-1 | 14.2 | 14.89 | 20.2 |
| GA7/col 22.2-2 | 14.3 | 15.02 | 20.5 |
| GA7/col 22.2-3 | 14.0 | 15.92 | 21.2 |
| GA7/col 10.15-1 | 8.7 | 30.23 | 25.06 |
| GA7/col 10.15-2 | 8.6 | 31.25 | 25.77 |
| GA7/col 10.15-3 | 8.8 | 31.70 | 26.49 |

Example 3. Stable Expression of a Transgenic DHA Pathway in *Camelina sativa* Seeds The binary vector pJP3416-GA7 as described above was introduced into *A. tumefaciens* strain AGL1 and cells from a culture of the transformed *Agrobacterium* used to treat *C. sativa* flowering plants using a floral dip method for transformation (Lu and Kang, 2008). After growth and maturation of the plants, the $T_1$ seeds from the treated plants were harvested, sown onto soil and the resultant plants treated by spraying with the herbicide BASTA to select for plants which were transgenic for, and expressing, the bar selectable marker gene present on the T-DNA of pJP3416-GA7. Surviving $T_1$ plants which were tolerant to the herbicide were grown to maturity after allowing them to self-fertilise, and the resultant $T_2$ seed harvested. Five transgenic plants were obtained, only three of which contained the entire T-DNA.

Lipid was extracted from a pool of approximately twenty seeds from each of the three plants that contained the entire T-DNA. Two of the pooled samples contained very low, barely detectable levels of DHA, but the third pool contained about 4.7% DHA. Therefore, lipid was extracted from 10 individual $T_2$ seeds from this plant and the fatty acid composition analysed by GC. The fatty acid composition data of the individual seeds for this transformed line is also shown in Table 7. Compiled data from the total seed lipid profiles (Table 7) are shown in Table 8.

DHA was present in six of the 10 individual seeds. The four other seeds did not have DHA and were presumed to be null segregants which did not have the T-DNA, based on hemizygosity of the T-DNA insertion in the parental plant. Extracted lipid from the single seed with the highest level of DHA had 9.0% DHA while the sum of the percentages for EPA, DPA and DHA was 11.4%.

Homozygous seed from this line was obtained in the $T_4$ generation. Up to 10.3% DHA was produced in event FD5-46-18-110 with an average of 7.3% DHA observed across the entire T4 generation. A subsequent generation (T5) was established to further test the stability of PUFA production over multiple generations, particularly the DHA. The maximum DHA levels observed was found to be stable in the fifth generation, even though the pooled seed DHA content had not stabilised until the $T_4$ generation due to the presence of multiple transgenic loci. $T_5$ seed batches were also germinated on MS media in vitro alongside parental *C. sativa* seed with no obvious difference in germination efficiency or speed observed. Further generations of the transgenic line (T6, T7 generations etc) did not show any reduction in the seed DHA level. The transgenic plants were fully male and female fertile, and the pollen showed about 100% viability as for the wild-type plants. Analysis of the oil content of the seeds having different levels of DHA did not identify a correlation between DHA level and oil content, contrary to the correlation seen in *Arabidopsis thaliana*.

In several further transgenic lines, the DHA content of single seeds from independent events exceeded 12%. The transgenic:null ratio of these lines was found to be between approximately 3:1 and 15:1. Analysis of representative fatty acid profiles from the top DHA samples from each construct found only 1.2-1.4% GLA with no other new ω6 PUFA detected. In contrast, new ω3 PUFA (SDA) ω3 LC-PUFA (ETA, EPA, DPA, DHA) were found to accumulate to 18.5% with a DHA level of 9.6% of the total fatty acid content. Δ6-desaturation was 32% and EPA was 0.8% of the total fatty acid content. The Δ5-elongation efficiency was 93% and Δ6-elongation efficiency was 60%. DHA was detected in the polar seed lipid fraction of GA7 lines.

TABLE 7

Fatty acid composition of total seed lipids from transgenic T$_2$ *Camelina sativa* seeds transformed with the T-DNA from pJP3416-GA7. The fatty acid composition is shown for a pooled seed batch (FD5.46) and for 10 single seeds ranked (left to right) from highest to lowest DHA.

| Fatty acid | FD5.46 pooled | # 2 | # 4 | # 8 | # 7 | # 9 | # 1 | # 3 | # 5 | # 6 | # 10 |
|---|---|---|---|---|---|---|---|---|---|---|---|
| 14:0 | 0 | 0.2 | 0.2 | 0.1 | 0.2 | 0.2 | 0.2 | 0.2 | 0.1 | 0.2 | 0.2 |
| 16:0 | 11.6 | 12.1 | 12.3 | 12.1 | 13.2 | 12.3 | 12.8 | 11.9 | 11.4 | 11.5 | 11.7 |
| 16:1 | 0.2 | 0.0 | 0.1 | 0.1 | 0.0 | 0.2 | 0.0 | 0.2 | 0.2 | 0.2 | 0.2 |
| 16:3 | 0.3 | 0 | 0.0 | 0.0 | 0.0 | 0.0 | 0.0 | 0.0 | 0.0 | 0.0 | 0.0 |
| 18:0 | 3.7 | 3.3 | 3.2 | 3.2 | 3.0 | 3.1 | 3.2 | 3.3 | 3.1 | 3.2 | 3.2 |
| 18:1 | 10.8 | 8.0 | 8.0 | 8.6 | 8.5 | 9.4 | 11.0 | 10.2 | 8.3 | 9.4 | 8.6 |
| 18:1 Δ11 | 1.7 | 1.3 | 1.4 | 1.4 | 1.7 | 1.4 | 1.5 | 1.3 | 1.3 | 1.3 | 1.3 |
| 18:2 | 24.7 | 18.2 | 19.5 | 19.2 | 18.5 | 20.1 | 23.8 | 32.2 | 30.3 | 29.8 | 31.6 |
| 18:3ω3 | 27.4 | 26.7 | 26.6 | 27.3 | 28.9 | 28.2 | 27.4 | 28.3 | 29.2 | 29.5 | 28.2 |
| 18:3ω6 | 0.2 | 1.4 | 0.3 | 0.3 | 0.4 | 0.2 | 0.5 | 0.0 | 0.5 | 0.4 | 0.6 |
| 20:0 | 1.6 | 1.4 | 1.3 | 1.4 | 1.2 | 1.4 | 1.4 | 1.8 | 2.1 | 1.9 | 2.0 |
| 18:4ω3 | 2.2 | 6.8 | 6.4 | 5.7 | 7.2 | 5.7 | 4.1 | 0.0 | 0.0 | 0.0 | 0.0 |
| 20:1 Δ11 | 5.3 | 4.4 | 4.6 | 4.8 | 3.3 | 4.1 | 3.5 | 4.4 | 6.1 | 5.8 | 5.5 |
| 20:1iso | 0.4 | 0.3 | 0.3 | 0.3 | 0.3 | 0.3 | 0.0 | 0.5 | 0.6 | 0.5 | 0.5 |
| 20:2ω6 | 0.8 | 0.8 | 0.9 | 0.8 | 0.6 | 0.8 | 0.7 | 1.3 | 1.5 | 1.4 | 1.4 |
| 20:3ω3 | 0.6 | 0.8 | 0.8 | 0.8 | 0.7 | 0.8 | 0.7 | 0.6 | 0.7 | 0.7 | 0.6 |
| 22:0 | 0.4 | 0.5 | 0.5 | 0.5 | 0.4 | 0.5 | 0.5 | 0.6 | 0.6 | 0.6 | 0.6 |
| 20:4ω3 | 0.2 | 0.3 | 0.3 | 0.3 | 0.4 | 0.4 | 0.5 | 0.0 | 0.0 | 0.0 | 0.0 |
| 22:1 | 1.1 | 1.1 | 1.2 | 1.1 | 0.5 | 0.9 | 0.8 | 1.6 | 2.2 | 1.9 | 2.0 |
| 20:5ω3 | 0.7 | 1.3 | 1.6 | 1.5 | 1.6 | 1.1 | 1.7 | 0.0 | 0.0 | 0.0 | 0.1 |
| 22:2ω6 | 0.1 | 0.0 | 0.0 | 0.0 | 0.0 | 0.0 | 0.0 | 0.2 | 0.3 | 0.2 | 0.2 |
| 22:4ω6 + 22:3ω3 | 0.3 | 0.2 | 0.3 | 0.3 | 0.0 | 0.3 | 0.0 | 0.4 | 0.6 | 0.5 | 0.5 |
| 24:0 | 0.3 | 0.3 | 0.3 | 0.3 | 0.0 | 0.3 | 0.0 | 0.4 | 0.4 | 0.4 | 0.4 |
| 24:1 | 0.3 | 0.4 | 0.4 | 0.3 | 0.0 | 0.3 | 0.0 | 0.5 | 0.6 | 0.5 | 0.5 |
| 22:5ω3 | 0.3 | 1.1 | 1.2 | 1.1 | 1.1 | 0.9 | 0.8 | 0.0 | 0.0 | 0.0 | 0.0 |
| 22:6ω3 | 4.7 | 9.0 | 8.5 | 8.3 | 8.3 | 7.1 | 4.9 | 0.0 | 0.0 | 0.0 | 0.0 |

TABLE 8

Compiled data from the total seed lipid profiles from transgenic seed as shown in Table 7. Calculations do not include the 'minor fatty acids' in Table 7.

| Parameter | FD5.46 pooled | # 2 | # 4 | # 8 | # 7 | # 9 | # 1 | # 3 | # 5 | # 6 | # 10 |
|---|---|---|---|---|---|---|---|---|---|---|---|
| total ω3 (% of total FA) | 36.1 | 46 | 45.4 | 45 | 48.2 | 44.2 | 40.1 | 28.9 | 29.9 | 30.2 | 28.9 |
| total ω6 (% of total FA) | 25.8 | 20.4 | 20.7 | 20.3 | 19.5 | 21.1 | 25 | 33.7 | 32.6 | 31.8 | 33.8 |
| ω3/ω6 ratio | 1.40 | 2.25 | 2.19 | 2.22 | 2.47 | 2.09 | 1.60 | 0.86 | 0.92 | 0.95 | 0.86 |
| ω6/ω3 ratio | 0.71 | 0.44 | 0.46 | 0.45 | 0.40 | 0.48 | 0.62 | 1.17 | 1.09 | 1.05 | 1.17 |
| total novel ω3 (% of total FA) | 8.1 | 18.5 | 18 | 16.9 | 18.6 | 15.2 | 12 | 0 | 0 | 0 | 0.1 |
| total novel ω6 (% of total FA) | 1.1 | 2.2 | 1.2 | 1.1 | 1 | 1 | 1.2 | 1.5 | 2.3 | 2 | 2.2 |
| novel ω3/ω6 ratio | 7.36 | 8.41 | 15.00 | 15.36 | 18.60 | 15.20 | 10.00 | | | | 0.05 |
| novel ω6/ω3 ratio | 0.14 | 0.12 | 0.07 | 0.07 | 0.05 | 0.07 | 0.10 | | | | 22.00 |
| OA to EPA efficiency | 8.2% | 15.6% | 15.5% | 15.1% | 15.1% | 12.8% | 10.5% | 0.0% | 0.0% | 0.0% | 0.1% |
| OA to DHA efficiency | 6.7% | 12.3% | 11.6% | 11.5% | 11.4% | 10.0% | 7.0% | 0.0% | 0.0% | 0.0% | 0.0% |
| LA to EPA efficiency | 9.2% | 17.2% | 17.1% | 16.7% | 16.2% | 13.9% | 11.4% | 0.0% | 0.0% | 0.0% | 0.2% |
| LA to DHA efficiency | 7.6% | 13.6% | 12.9% | 12.7% | 12.3% | 10.9% | 7.5% | 0.0% | 0.0% | 0.0% | 0.0% |
| ALA to EPA efficiency | 15.8% | 24.8% | 24.9% | 24.2% | 22.8% | 20.6% | 18.5% | 0.0% | 0.0% | 0.0% | 0.3% |
| ALA to DHA efficiency | 13.0% | 19.6% | 18.7% | 18.4% | 17.2% | 16.1% | 12.2% | 0.0% | 0.0% | 0.0% | 0.0% |
| total saturates | 17.6 | 17.8 | 17.8 | 17.6 | 18 | 17.8 | 18.1 | 18.2 | 17.7 | 17.8 | 18.1 |
| total monounsaturates | 19.8 | 15.5 | 16 | 16 | 14.3 | 16.6 | 16.8 | 18.7 | 19.3 | 19.6 | 18.6 |
| total polyunsaturates | 62.5 | 66.6 | 66.4 | 65.6 | 67.7 | 65.6 | 65.1 | 63 | 63.1 | 62.5 | 63.2 |
| total C20 | 9.6 | 9.3 | 9.8 | 9.9 | 8.1 | 8.9 | 8.5 | 8.6 | 11 | 10.3 | 10.1 |
| total C22 | 5.4 | 10.3 | 10 | 9.7 | 9.4 | 8.3 | 5.7 | 0.6 | 0.9 | 0.7 | 0.7 |
| C20/C22 ratio | 1.78 | 0.90 | 0.98 | 1.02 | 0.86 | 1.07 | 1.49 | 14.33 | 12.22 | 14.71 | 14.43 |

It was noted that the segregation ratios observed (~3:1 to ~15:1) indicated that one or, at most, two transgenic loci were required to produce fish oil-like levels of DHA in *C. sativa*. This had important implications for the ease with which the transgenic trait can be bred as well as for transgene stability.

Homozygous seed was planted out across several glass-houses to generate a total of over 600 individual plants. Oil was extracted from the seed using a variety of methods including soxhlet, acetone and hexane extractions.

$^{13}$C NMR regiospecificity analysis was performed on the transgenic *C. sativa* seed oil to determine the positional distribution of the ω3 LC-PUFA on TAG. An event with approximately equal EPA and DHA was selected to maximise response for these fatty acids and the ratio of sn-1,3 to sn-2 was found to be 0.75:0.25 for EPA and 0.86:0.14 for DHA where an unbiased distribution would be 0.66:0.33. That is, 75% of the EPA and 86% of the DHA were located at the sn-1,3 position of TAG. This indicated that both fatty acids were preferentially located on the sn-1,3 positions in *C. sativa* TAG although the preference for EPA was weaker than for DHA. The finding that DHA was predominantly found on sn-1,3 was similar to results previously reported in *A. thaliana* seed (Petrie et al., 2012).

Since only a small number of independent transgenic lines were obtained in the transformation experiment described above, further *C. sativa* transformations were performed using the GA7-modB construct (Example 4). More transformants were obtained and homozygous lines producing in excess of 20.1% DHA are identified.

Example 4. Modifications to T-DNAs Encoding DHA Pathways in Plant Seeds

In order to improve the DHA production level in *B. napus* beyond the levels described in WO2013/185184, the binary vectors pJP3416-GA7-modA, pJP3416-GA7-modB, pJP3416-GA7-modC, pJP3416-GA7-modD, pJP3416-GA7-modE and pJP3416-GA7-modF were constructed as described in WO2013/185184 and tested in transgenic plants. These binary vectors were variants of the pJP3416-GA7 construct described in Example 2 and were designed to further increase the synthesis of DHA in plant seeds, particularly by improving Δ6-desaturase and Δ6-elongase functions. SDA had been observed to accumulate in some seed transformed with the GA7 construct due to a relatively low Δ6 elongation efficiency compared to the Δ5-elongase, so amongst other modifications, the two elongase gene positions were switched in the T-DNA.

The two elongase coding sequences in pJP3416-GA7 were switched in their positions on the T-DNA to yield pJP3416-GA7-modA by first cloning a new *P. cordata* Δ6-elongase cassette between the Sb/f sites of pJP3416-GA7 to replace the *P. cordata* Δ5-elongase cassette. This construct was further modified by exchanging the FP1 promoter driving the *M. pusilla* Δ6-desaturase with a conlinin Cnl2 promoter (pLuCnl2) to yield pJP3416-GA7-modB. This modification was made in an attempt to increase the Δ6-desaturase expression and thereby enzyme efficiency. It was thought that the Cnl2 promoter might yield higher expression of the transgene in *B. napus* than the truncated napin promoter.

Eight transgenic pJP3416-GA7-modB *A. thaliana* events and 15 transgenic pJP3416-GA7-modG *A. thaliana* events were generated. Between 3.4% and 7.2% DHA in pooled pJP3416-GA7-modB seed was observed and between 0.6 and 4.1% DHA in pooled T2 pJP3416-GA7-modG seed was observed. Several of the highest pJP3416-GA7-modB events were sown out on selectable media and surviving seedlings taken to the next generation. Seed is being analysed for DHA content. Since the pooled T1 seeds represented populations that were segregating for the transgenes and included any null segregants, it is expected that the homozygous seeds from progeny plants would have increased levels of DHA, up to 30% of the total fatty acid content in the seed oil. The other modified constructs were used to transform *A. thaliana*. Although only a small number of transformed lines were obtained, none yielded higher levels of DHA than the modB construct.

The pJP3416-GA7-modB construct was also used to generate transformed *B. napus* plants of cultivar Oscar and of a series of breeding lines designated NX002, NX003, NX005, NX050, NX052 and NX054. A total of 1558 transformed plants were obtained including 77 independent transformed plants (TO) for the Oscar transformation, and 1480 independent plants for the breeding lines including 189 for NX005 which is a line having a high oleic acid content in its seedoil by virtue of mutations in FAD2 genes. The other breeding lines had higher levels of LA and ALA. Transgenic plants which exhibited more than 4 copies of the T-DNA as determined by a digital PCR method (Example 1) were discarded; about 25% of the TO plants were discarded by this criterion. About 53% of the TO transgenic plants had 1 or 2 copies of the T-DNA as determined by the digital PCR method, 12% had about 3 copies and 24% 4 or more copies. Seed (T1 seed) was harvested from about 450 of the transgenic lines after self-fertilisation, achieved by bagging the plants during flowering to avoid out-crossing. T1 seed are harvested from the remainder of the transgenic plants when mature. About 1-2% of the plant lines were either male or female sterile and produced no viable seeds, these TO plants were discarded.

Pools of seed (20 T1 seeds in each pool) were tested for levels of DHA in the pooled seed oil, and lines which showed the highest levels were selected. In particular, lines having a DHA content of at least 2% of the total fatty content in the pooled T1 seeds were selected. About 15% of the transgenic lines were selected in this way; the other 85% were discarded. Some of these were designated lines CT132-5 (in cultivar Oscar), CT133-15, -24, -63, -77, -103, -129 and -130 (in NX005). Selected lines in NX050 included CT136-4, -8, -12, -17, -19, -25, -27, -49 and -51. Twenty seeds from selected lines including CT132.5 and 11 seeds from CT133.15 were imbibed and, after two days, oil was extracted from a half cotyledon from each of the individual seeds. The other half cotyledons with embryonic axes were kept and cultured on media to maintain the specific progeny lines. The fatty acid composition in the oil was determined; the data is shown in Table 9 for CT132.5. The DHA level in ten of the 20 seeds analysed was in the range of 7-20% of the total fatty acid content as determined by the GC analysis. Other seeds had less than 7% DHA and may have contained a partial (incomplete) copy of the T-DNA from pJP3416-GA7-modB. The transgenic line appeared to contain multiple transgene insertions that were genetically unlinked. The seeds of transgenic line CT133.15 exhibited DHA levels in the range 0-5%. Seeds with no DHA were likely to be null segregants. These data confirmed that the modB construct performed well for DHA production in canola seed.

Twenty or 40 individual seeds (T2 seeds) obtained from each of multiple T1 plants, after self-fertilisation, from the selected transformed lines were tested individually for fatty acid composition. Seeds comprising DHA at levels greater than 20% were identified (Table 10). Two representative samples, CT136-27-18-2 and CT136-27-18-19 had 21.2% and 22.7% DHA, respectively. The total ω3 fatty acid content in these seeds was about 60% as a percentage of the total fatty acid content, and the ω6 content was less than 10%. Further sets of 20 or 40 T2 seeds from each of the T1 plants were tested for fatty acid composition. Representative data for DHA levels in the total fatty acid content of seedoil from individual T2 seeds is shown in FIG. 10. Seeds comprising up to 34.3% DHA were identified, for example in seed CT136-27-47-25 (Table 12). The fatty acid composition for seedoil obtained from CT136-27-47-25 is shown in Table 12. The fatty acid composition included 34.3% DHA together with about 1.5% DPA, 0.6% EPA and 0.5% ETA. The SDA level was about 7.5%, ALA about 21.9% and LA about 6.9%. The new ω6 PUFA exhibited 1.1% GLA but no detectable ω6-C20 or -C22 LC-PUFA. Total saturated fatty acids: 9.6%; monounsaturated fatty acids, 12.5%; total PUFA, 75.2%; total ω6-PUFA (including LA), 7.2%; total ω3-PUFA, 66.9%; the ratio of total ω6:ω3 fatty acids, 9.3:1; new ω6:new ω3 fatty acids, 37:1. The efficiencies of each of the enzymatic steps from oleic acid to DHA were as follows: Δ12-desaturase, 90%; Δ15/ω3-desaturase, 89%; Δ6-desaturase, 67%; Δ6-elongase, 83%; Δ5-desaturase, 99%; Δ5-elongase, 98%; Δ4-desaturase, 96%. The overall efficiency of conversion of oleic acid to DHA was about 50%. It was therefore clear that seeds producing DHA in the range of 20.1-35% of the total fatty acid content of the seedoil could be identified and selected, including seeds having between 20.1% and 30% DHA or between 30% and 35% DHA in the total fatty acid content.

The oil content in some seeds was decreased from about 44% in wild-type seeds to about 31-39% in some of the DHA producing seeds, but was was similar to wild-type levels in other DHA producing seeds.

Various transformed plant lines which were producing DHA at levels of at least 10% in T2 seed are crossed and the F1 progeny selfed in order to produce F2 progeny which are homozygous for multiple T-DNA insertions. Seedoil from homozygous seed is analysed and up to 30% or 35% of the total fatty acid content in the seed oil is DHA.

The TAG in the oil obtained from CT136-27-18-2 and CT136-27-18-19 was analysed by $^{13}$C NMR regiospecificity assay for positional distribution of the DHA on the glycerol backbone of the TAG molecules. The DHA was preferentially linked at the sn-1,3 position. More than 70%, indeed more than 90% of the DHA was in the sn-1,3 position.

In several further transgenic lines, the DHA content of single seeds from independent events exceeded 12%. The transgenic:null ratio of these lines was found to be approximately 3:1, corresponding to a single transgenic locus, or 15:1, corresponding to two transgenic loci. Analysis of representative fatty acid profiles from the samples from each construct with the highest levels of DHA found only 1.2-1.4% GLA with no other new ω6 PUFA detected. In contrast, new ω3 PUFA (SDA) and ω3 LC-PUFA (ETA, EPA, DPA, DHA) accumulated to a sum of 25.8% for the modF construct and 21.9% for the modG construct compared to 18.5% for the GA7-transformed seed. The DHA levels in the oil from these seeds were 9.6%, 12.4% and 11.5%, respectively. Δ6-desaturation was found to be lower in the GA7-transformed seeds than the modF- and modG-transformed seeds (32% vs 47% and 43%) and this resulted in a reduction of ALA in the modF and modG seeds relative to GA7. Another noteworthy difference was the accumulation of EPA in the modF seed (30.3% vs 0.8% in the other two transgenic seeds) and this was reflected in the reduced Δ5-elongation observed in modF (80%) seed relative to GA7 and modG seeds (93% and 94%). There was a slight increase in Δ6-elongation in these seeds (66% vs 60% and 61%) although the amount of SDA actually increased due to the slightly more active Δ6-desaturation. DHA was detected in the polar seed lipid fraction of GA7 lines.

The fatty acid composition was analysed of the lipid in the T1 seed of 70 independent transgenic plants of the *B. napus* breeding line NX54 transformed with the T-DNA of the modB construct. It was observed that one of these transgenic plants produced seed having DPA but no DHA in the seedoil. The T1 seed of this line (CT-137-2) produced about 4% DPA without any detectable DHA in the T1 pooled seed. The inventors concluded that this was caused by inactivation of the Δ4-desaturase gene in that particular inserted T-DNA, perhaps through a spontaneous mutation. PCR analysis and DNA sequencing showed the presence of a deletion, which was defined as having deleted nucleotides 12988-15317 of the T-DNA of GA7-modB (SEQ ID NO: 2). The deleted nucleotides correspond to a portion of the Linus Cnl2 promoter driving expression of the Δ4-desaturase coding region as well as the Δ4-desaturase coding region itself, explaining why the seeds transformed with the T-DNA comprising the deletion did not produce DHA.

Around 50 T1 seeds from this transgenic line were germinated and one emerged cotyledon from each analysed for fatty acid composition in the remaining oil. Selected seedlings exhibiting more than 5% DPA were then grown to maturity and T2 seed harvested. Pooled seed fatty acid compositions are shown in Table 11, more than 7% DPA was observed in these lines. T4 seed was produced from the *B. napus* DPA line CT-137-2 and analysed for fatty acid profile. Up to 13% DPA was observed in pooled mature seed samples.

Oil from seeds having about 10% DPA was treated with mild alkali to hydrolyse the fatty acids.

Another transgenic line designated B0003-514 exhibited about 10-16% DPA in T2 seed. Seed containing 15.8% DPA, 0.2-0.9% DHA and 0.1-2.5% EPA was selected. The T2 seed population showed a 1:2:1 segregation ration for high: medium:no DPA, indicating the presence of a single genetic locus for DPA production in that transgenic line.

Oil was extracted by a screw press from seed samples producing LC-PUFA, thereby producing seedmeal.

Construct Design

Whilst the focus of this experiment was the demonstration of DHA and DPA production in an oilseed crop species, the results noted above were also interesting from a construct design perspective. First, switching the Δ6- and Δ5-elongase coding region locations in the modF construct resulted in the intended profile change with more EPA accumulated due to lower Δ5-elongation. A concomitant increase in Δ6-elongation was observed but this did not result in lower SDA levels. This was due to an increase in Δ6-desaturation in the modF transformed seed, caused by adding an extra M *pusilla* Δ6-desaturase expression cassette as well as by replacing the truncated napin promoter (FP1) with a more highly active flax conlinin2 promoter. The somewhat lower increase in Δ6-desaturation observed with the modG construct was caused by capitalising on the highly expressed Δ5-elongase cassette in GA7. Switching the positions of the Δ6-desaturase and Δ5-elongase coding regions resulted in greater Δ6-desaturation. Δ5-elongase activity was not reduced in this instance due to the replacement of the FP1 promoter with the Cnl2 promoter.

These data confirmed that the modB, modF and modG constructs performed well for DHA production in *Camelina* seed, as for *Arabidopsis* and canola.

The inventors considered that, in general, the efficiency of rate-limiting enzyme activities in the DHA pathway can be greater in multicopy T-DNA transformants compared to single-copy T-DNA transformants, or can be increased by inserting into the T-DNA multiple genes encoding the enzyme which might be limiting in the pathway. Evidence for the possible importance of multi-copy transformants was seen in the *Arabidopsis* seeds transformed with the GA7 construct (Example 2), where the highest yielding DHA event had three T-DNAs inserted into the host genome. The multiple genes can be identical, or preferably are different variants that encode the same polypeptide, or are under the control of different promoters which have overlapping expression patterns. For example, increased expression could be achieved by expression of multiple Δ6-desaturase coding regions, even where the same protein is produced. In pJP3416-GA7-modF and pJP3416-GA7-modC, for instance, two versions of the *M. pusilla* Δ6-desaturase were present and expressed by different promoters. The coding sequences had different codon usage and therefore different nucleotide sequences, to reduce potential silencing or co-suppression effects but resulting in the production of the same protein.

TABLE 9

Fatty acid profiles of half cotyledons of germinating T1 transgenic *B. napus* seeds containing the modB construct. Up to 18.1% DHA was observed with numerous samples containing greater than 10% DHA.

| Seed | 14:0 | 16:0 | 16:1d3? | 16:1 | 16:3 | 18:0 | 18:1 | 18:1d11 | 18:2 | 18:3n6 | 18:3n3 | 20:0 | 18:4n3 |
|---|---|---|---|---|---|---|---|---|---|---|---|---|---|
| 1 | 0.1 | 4.2 | 0.1 | 0.1 | 0.2 | 1.8 | 29.9 | 2.5 | 9.9 | 0.1 | 38.4 | 0.5 | 0.8 |
| 2 | 0.1 | 4.7 | 0.1 | 0.1 | 0.2 | 4.0 | 23.0 | 2.3 | 7.4 | 0.3 | 29.3 | 1.0 | 4.3 |
| 3 | 0.1 | 3.7 | 0.2 | 0.1 | 0.2 | 1.8 | 55.1 | 1.9 | 4.7 | 0.2 | 15.2 | 0.8 | 1.8 |
| 4 | 0.1 | 4.6 | 0.2 | 0.2 | 0.2 | 2.9 | 22.1 | 1.8 | 6.6 | 0.4 | 26.5 | 1.0 | 7.2 |
| 5 | 0.1 | 4.0 | 0.1 | 0.1 | 0.2 | 1.7 | 27.4 | 2.1 | 8.1 | 0.3 | 26.4 | 0.6 | 2.8 |
| 6 | 0.1 | 3.5 | 0.1 | 0.1 | 0.2 | 1.6 | 59.8 | 2.0 | 4.3 | 0.1 | 18.5 | 0.6 | 0.5 |
| 7 | 0.1 | 6.0 | 0.3 | 0.3 | 0.3 | 1.7 | 16.6 | 2.6 | 23.9 | 1.0 | 23.2 | 0.6 | 5.4 |
| 8 | 0.1 | 4.9 | 0.1 | 0.1 | 0.2 | 2.7 | 12.9 | 1.4 | 11.7 | 0.3 | 34.3 | 0.9 | 5.0 |
| 9 | 0.1 | 3.9 | 0.1 | 0.1 | 0.1 | 2.4 | 41.6 | 1.7 | 21.5 | 0.0 | 23.4 | 0.7 | 0.0 |
| 10 | 0.1 | 3.7 | 0.2 | 0.1 | 0.1 | 2.1 | 30.9 | 1.7 | 19.2 | 0.4 | 23.6 | 0.7 | 2.1 |
| 11 | 0.1 | 5.7 | 0.4 | 0.3 | 0.2 | 3.8 | 41.2 | 2.4 | 26.7 | 2.1 | 7.2 | 1.3 | 0.3 |
| 12 | 0.1 | 4.6 | 0.0 | 0.1 | 0.2 | 2.4 | 25.5 | 1.7 | 16.1 | 0.3 | 28.9 | 0.8 | 3.9 |
| 13 | 0.1 | 4.3 | 0.1 | 0.1 | 0.1 | 4.2 | 19.4 | 1.6 | 9.2 | 0.1 | 45.5 | 1.0 | 0.2 |
| 14 | 0.1 | 6.3 | 0.2 | 0.2 | 0.2 | 4.0 | 10.5 | 2.3 | 8.4 | 0.3 | 31.1 | 1.3 | 3.9 |
| 15 | 0.1 | 5.1 | 0.1 | 0.2 | 0.2 | 3.3 | 16.8 | 2.4 | 11.2 | 0.3 | 28.8 | 1.0 | 4.5 |
| 16 | 0.1 | 4.4 | 0.1 | 0.1 | 0.2 | 4.0 | 16.2 | 1.5 | 11.6 | 0.2 | 33.5 | 0.9 | 2.8 |
| 17 | 0.2 | 7.2 | 0.2 | 0.2 | 0.2 | 4.9 | 15.0 | 2.1 | 8.9 | 0.3 | 25.9 | 1.4 | 5.1 |
| 18 | 0.1 | 4.0 | 0.1 | 0.1 | 0.2 | 2.3 | 64.8 | 1.2 | 7.2 | 0.1 | 12.5 | 1.0 | 3.5 |
| 19 | 0.1 | 3.9 | 0.1 | 0.1 | 0.2 | 4.6 | 36.9 | 1.7 | 7.1 | 0.2 | 28.6 | 1.2 | 1.8 |
| 20 | 0.1 | 4.8 | 0.1 | 0.1 | 0.2 | 6.0 | 18.5 | 1.2 | 12.8 | 0.2 | 34.8 | 1.4 | 2.4 |

| Seed | C20:1d11 | 20:1d13 | C20:2n6 | C20:3n3 | C22:0 | 20:4n3 | 20:53 | 22:3n3 | C24:0 | C24:1 | 22:5n3 | C22:6n3 |
|---|---|---|---|---|---|---|---|---|---|---|---|---|
| 1 | 1.0 | 0.0 | 0.1 | 2.1 | 0.3 | 2.8 | 0.3 | 0.1 | 0.2 | 0.2 | 0.5 | 3.9 |
| 2 | 1.1 | 0.0 | 0.1 | 1.9 | 0.4 | 6.9 | 1.0 | 0.0 | 0.3 | 0.1 | 1.7 | 9.5 |
| 3 | 1.4 | 0.0 | 0.1 | 0.3 | 0.5 | 11.3 | 0.0 | 0.0 | 0.3 | 0.2 | 0.0 | 0.0 |
| 4 | 1.0 | 0.0 | 0.1 | 0.8 | 0.5 | 11.2 | 1.9 | 0.0 | 0.2 | 0.2 | 1.7 | 8.7 |
| 5 | 1.0 | 0.0 | 0.1 | 1.5 | 0.3 | 7.6 | 1.5 | 0.0 | 0.1 | 0.1 | 1.8 | 12.2 |
| 6 | 1.3 | 0.0 | 0.0 | 0.7 | 0.3 | 6.0 | 0.0 | 0.0 | 0.2 | 0.1 | 0.0 | 0.0 |
| 7 | 0.8 | 0.0 | 0.2 | 0.6 | 0.4 | 2.6 | 1.1 | 0.0 | 0.3 | 0.3 | 1.7 | 9.9 |
| 8 | 0.9 | 0.0 | 0.2 | 2.4 | 0.5 | 4.1 | 1.3 | 0.0 | 0.2 | 0.2 | 1.8 | 13.8 |
| 9 | 1.2 | 0.0 | 0.1 | 2.2 | 0.4 | 0.0 | 0.0 | 0.1 | 0.3 | 0.2 | 0.0 | 0.0 |
| 10 | 1.1 | 0.0 | 0.1 | 1.5 | 0.4 | 3.6 | 0.6 | 0.0 | 0.2 | 0.1 | 0.7 | 6.9 |
| 11 | 1.2 | 0.0 | 0.2 | 0.3 | 0.8 | 4.8 | 0.0 | 0.0 | 0.6 | 0.3 | 0.0 | 0.0 |
| 12 | 1.1 | 0.0 | 0.1 | 1.9 | 0.4 | 3.9 | 0.6 | 0.0 | 0.2 | 0.0 | 1.1 | 6.2 |
| 13 | 1.1 | 0.0 | 0.1 | 5.2 | 0.4 | 2.6 | 0.3 | 0.2 | 0.2 | 0.1 | 0.4 | 3.4 |
| 14 | 0.8 | 0.0 | 0.1 | 2.3 | 0.6 | 4.6 | 1.8 | 0.1 | 0.3 | 0.2 | 2.5 | 18.1 |
| 15 | 0.9 | 0.0 | 0.1 | 2.1 | 0.6 | 3.2 | 1.5 | 0.1 | 0.3 | 0.1 | 1.8 | 15.1 |
| 16 | 1.1 | 0.0 | 0.2 | 3.7 | 0.4 | 4.6 | 0.7 | 0.1 | 0.3 | 0.1 | 1.3 | 12.1 |
| 17 | 0.9 | 0.0 | 0.0 | 1.6 | 0.8 | 4.9 | 2.1 | 0.0 | 0.6 | 0.3 | 2.2 | 15.0 |
| 18 | 1.5 | 0.0 | 0.1 | 0.0 | 0.7 | 0.0 | 0.0 | 0.0 | 0.5 | 0.2 | 0.0 | 0.0 |
| 19 | 1.2 | 0.0 | 0.1 | 1.4 | 0.5 | 4.3 | 0.4 | 0.0 | 0.4 | 0.1 | 0.8 | 4.3 |
| 20 | 1.1 | 0.0 | 0.1 | 3.4 | 0.6 | 3.2 | 0.4 | 0.1 | 0.3 | 0.1 | 0.7 | 7.6 |

TABLE 10

Fatty acid composition of lipid in T2 transgenic *B. napus* seeds containing the T-DNA from the GA7-modB construct.

| Sample (T2 seed) | C14:0 | C16:0 | C18:0 | C18:1 | C18:1d11 | C18:2 | C18:3n6 | C18:3n3 | 18:4n3 | C20:1d11 |
|---|---|---|---|---|---|---|---|---|---|---|
| CT136-27-18-1 | 0.1 | 5.0 | 2.6 | 25.4 | 3.6 | 6.7 | 0.2 | 37.5 | 1.4 | 1.0 |
| CT136-27-18-2 | 0.2 | 7.1 | 2.8 | 16.9 | 4.3 | 5.5 | 0.4 | 29.1 | 5.4 | 0.8 |
| CT136-27-18-3 | 0.1 | 5.4 | 2.5 | 26.5 | 3.8 | 6.4 | 0.4 | 26.4 | 4.7 | 1.0 |

TABLE 10-continued

Fatty acid composition of lipid in T2 transgenic *B. napus* seeds
containing the T-DNA from the GA7-modB construct.

| | | | | | | | | | | |
|---|---|---|---|---|---|---|---|---|---|---|
| CT136-27-18-4 | 0.1 | 5.3 | 2.4 | 34.7 | 4.0 | 5.9 | 0.3 | 30.3 | 1.3 | 1.1 |
| CT136-27-18-5 | 0.1 | 4.8 | 2.7 | 34.5 | 3.8 | 5.6 | 0.3 | 23.5 | 3.9 | 1.2 |
| CT136-27-18-6 | 0.1 | 5.0 | 2.1 | 54.3 | 3.8 | 5.7 | 0.2 | 18.2 | 0.6 | 1.5 |
| CT136-27-18-7 | 0.1 | 5.3 | 2.1 | 43.8 | 4.2 | 5.6 | 0.4 | 18.3 | 2.2 | 1.3 |
| CT136-27-18-8 | 0.1 | 5.4 | 2.7 | 25.8 | 4.1 | 6.7 | 0.4 | 26.6 | 5.7 | 1.0 |
| CT136-27-18-9 | 0.1 | 4.6 | 1.6 | 53.8 | 3.7 | 17.5 | 0.5 | 9.2 | 0.5 | 1.6 |
| CT136-27-18-10 | 0.1 | 4.8 | 2.4 | 44.1 | 3.7 | 5.4 | 0.4 | 19.1 | 2.3 | 1.1 |
| CT136-27-18-11 | 0.1 | 5.1 | 2.2 | 48.3 | 4.1 | 10.9 | 0.7 | 12.5 | 1.2 | 1.3 |
| CT136-27-18-12 | 0.1 | 5.3 | 2.7 | 23.3 | 3.7 | 6.0 | 0.4 | 27.9 | 4.9 | 0.9 |
| CT136-27-18-13 | 0.1 | 5.5 | 3.4 | 30.7 | 5.6 | 5.1 | 0.4 | 23.1 | 3.5 | 1.1 |
| CT136-27-18-14 | 0.1 | 5.4 | 2.3 | 23.9 | 3.5 | 6.0 | 0.4 | 30.1 | 3.7 | 1.0 |
| CT136-27-18-15 | 0.1 | 5.0 | 2.3 | 45.4 | 4.0 | 5.3 | 0.4 | 16.2 | 2.3 | 1.2 |
| CT136-27-18-16 | 0.1 | 4.8 | 2.7 | 37.9 | 4.1 | 6.2 | 0.4 | 22.0 | 2.4 | 1.0 |
| CT136-27-18-17 | 0.1 | 4.5 | 2.3 | 38.8 | 3.3 | 7.6 | 0.3 | 26.8 | 0.9 | 1.4 |
| CT136-27-18-18 | 0.1 | 5.1 | 2.3 | 29.0 | 3.6 | 5.7 | 0.4 | 26.5 | 3.8 | 1.1 |
| CT136-27-18-19 | 0.1 | 5.8 | 2.3 | 19.7 | 4.2 | 6.7 | 0.7 | 23.7 | 7.7 | 0.9 |
| CT136-27-18-20 | 0.1 | 5.7 | 2.9 | 23.2 | 4.0 | 5.6 | 0.3 | 35.8 | 2.4 | 1.0 |

| Sample (T2 seed) | C20: 2n6 | C20: 3n3 | 20: 4n3 | 20: 5n3 | 22: 5n3 | C22: 6n3 | Total ω3 (%) | Total ω6 (%) | Ratio ω6 to ω3 | Total PUFA content (%) |
|---|---|---|---|---|---|---|---|---|---|---|
| CT136-27-18-1 | 0.1 | 2.1 | 0.8 | 0.4 | 0.9 | 10.2 | 53.4 | 7.1 | 0.13 | 60.5 |
| CT136-27-18-2 | 0.1 | 1.2 | 0.5 | 0.5 | 1.9 | 21.2 | 59.8 | 6.1 | 0.10 | 66.0 |
| CT136-27-18-3 | 0.1 | 0.7 | 1.1 | 0.6 | 1.2 | 17.3 | 52.0 | 6.9 | 0.13 | 58.9 |
| CT136-27-18-4 | 0.1 | 1.1 | 1.5 | 0.3 | 0.4 | 9.3 | 44.4 | 6.3 | 0.14 | 50.7 |
| CT136-27-18-5 | 0.1 | 0.7 | 1.1 | 0.5 | 1.1 | 14.2 | 45.1 | 6.0 | 0.13 | 51.1 |
| CT136-27-18-6 | 0.1 | 1.1 | 0.7 | 0.1 | 0.2 | 4.4 | 25.5 | 6.1 | 0.24 | 31.5 |
| CT136-27-18-7 | 0.2 | 0.6 | 1.5 | 0.4 | 0.5 | 11.6 | 35.2 | 6.2 | 0.18 | 41.4 |
| CT136-27-18-8 | 0.1 | 0.6 | 1.3 | 0.6 | 1.2 | 15.8 | 51.9 | 7.1 | 0.14 | 59.0 |
| CT136-27-18-9 | 0.3 | 0.6 | 0.4 | 0.1 | 0.1 | 3.7 | 14.5 | 18.3 | 1.26 | 32.8 |
| CT136-27-18-10 | 0.1 | 0.6 | 1.5 | 0.5 | 0.8 | 11.4 | 36.1 | 5.9 | 0.16 | 42.0 |
| CT136-27-18-11 | 0.2 | 0.5 | 1.5 | 0.3 | 0.3 | 9.1 | 25.3 | 11.8 | 0.47 | 37.1 |
| CT136-27-18-12 | 0.1 | 0.7 | 1.3 | 0.8 | 1.5 | 18.5 | 55.7 | 6.6 | 0.12 | 62.2 |
| CT136-27-18-13 | 0.1 | 1.2 | 1.1 | 0.6 | 1.2 | 14.9 | 45.8 | 5.5 | 0.12 | 51.3 |
| CT136-27-18-14 | 0.1 | 1.0 | 0.7 | 0.6 | 1.2 | 18.2 | 55.5 | 6.6 | 0.12 | 62.1 |
| CT136-27-18-15 | 0.1 | 0.5 | 1.9 | 0.6 | 0.7 | 12.3 | 34.4 | 5.8 | 0.17 | 40.3 |
| CT136-27-18-16 | 0.1 | 0.7 | 1.4 | 0.5 | 0.8 | 13.1 | 41.0 | 6.7 | 0.16 | 47.7 |
| CT136-27-18-17 | 0.2 | 1.6 | 0.9 | 0.2 | 0.7 | 8.6 | 39.9 | 8.0 | 0.20 | 47.9 |
| CT136-27-18-18 | 0.2 | 0.8 | 0.8 | 0.6 | 1.0 | 17.4 | 50.8 | 6.3 | 0.12 | 57.1 |
| CT136-27-18-19 | 0.1 | 0.4 | 0.7 | 0.6 | 1.7 | 22.7 | 57.6 | 7.5 | 0.13 | 65.1 |
| CT136-27-18-20 | 0.1 | 1.3 | 1.1 | 0.5 | 1.0 | 13.0 | 55.1 | 6.1 | 0.11 | 61.2 |

ARA (C20:4ω6) was not detected in any of the samples.
The samples also contained about 0.2% or 0.3% C16:1, about 0.1 to 0.3% C16:3, between about 0.7% and 1.0% C20:0, about 0.3% C22:0, and some samples contained trace levels (<0.1%) of C20:1Δ13, C22:3ω3, C24:0 and C24:1

TABLE 11

Fatty acid composition of the lipid in T2 transgenic *B. napus* seeds transformed with the T-DNA of the GA7-modB
construct, with a mutation in the Δ4-desaturase gene. The lipids also contained about 0.1% 14:0, 0.2% 16:3,
0.2-0.4% GLA, 0.1% 20:1Δ13, 0.3-0.4% 22:0, and ARA, DPAω6 (22:5ω6), 16:2 and 22:1 were not detected.

| | C16: 0 | C16: 1 | C18: 0 | C18: 1 | C18: 1Δ 11 | C18: 2 | C18: 3ω 3 | C20: 0 | C18: 4ω 3 | C20: 1Δ 11 | C20: 2ω 6 |
|---|---|---|---|---|---|---|---|---|---|---|---|
| CT-137-2-34 | 5.3 | 0.2 | 3.7 | 26.8 | 3.1 | 12.4 | 29.1 | 0.8 | 2.5 | 0.8 | 0.1 |
| CT-137-2-38 | 5.3 | 0.2 | 4.2 | 24.4 | 3.0 | 12.6 | 29.4 | 0.9 | 2.5 | 0.8 | 0.1 |
| CT-137-2-48 | 5.0 | 0.2 | 4.2 | 24.1 | 3.1 | 11.9 | 31.0 | 0.9 | 2.4 | 0.9 | 0.1 |
| CT-137-2-51 | 5.7 | 0.2 | 4.6 | 22.3 | 3.4 | 12.3 | 34.5 | 1.0 | 2.0 | 0.8 | 0.1 |
| CT-137-2-59 | 5.4 | 0.2 | 3.9 | 25.7 | 3.4 | 12.9 | 27.8 | 0.9 | 2.6 | 0.8 | 0.1 |

| | C20: 3ω 6 | C20: 3ω 3 | C20: 4ω 3 | C20: 5ω 3 | C22: 2ω 6 | C22: 3ω 3 | C24 0 | C24: 1 | C22: 5ω 3 | C22: 6ω 3 |
|---|---|---|---|---|---|---|---|---|---|---|
| CT-137-2-34 | 0.0 | 1.1 | 1.7 | 0.8 | 0.0 | 0.1 | 0.1 | 0.1 | 10.0 | 0.0 |
| CT-137-2-38 | 0.0 | 1.3 | 2.2 | 0.9 | 0.0 | 0.1 | 0.2 | 0.1 | 10.8 | 0.0 |
| CT-137-2-48 | 0.0 | 1.5 | 2.0 | 1.0 | 0.0 | 0.1 | 0.1 | 0.1 | 10.5 | 0.0 |
| CT-137-2-51 | 0.0 | 1.9 | 1.2 | 0.5 | 0.0 | 0.1 | 0.2 | 0.2 | 7.9 | 0.0 |
| CT-137-2-59 | 0.0 | 1.0 | 1.0 | 0.9 | 0.0 | 0.1 | 0.2 | 0.1 | 11.0 | 0.0 |

TABLE 12

Fatty acid composition of seedoil from T2 seed of *B. napus* transformed with the T-DNA from GA7-modB.

| C16: 0 | C18: 0 | C18: 1Δ 9 | C18: 1Δ 7 | C18: 2ω 6 | C18: 3ω 6 | C18: 3ω 3 | C20: 0 | C18: 4ω 3 | C20: 1ω 9c | C20: 2ω 6 + C21: 0 | C20: 3ω 3 | C20: 4ω 3 | C20: 5ω 3 | C22: 5ω 6 | C22: 5ω 3 | C22: 6ω 3 |
|---|---|---|---|---|---|---|---|---|---|---|---|---|---|---|---|---|
| 6.3 | 2.4 | 8.4 | 1 | 6.9 | 1.1 | 21.9 | 0.7 | 7.5 | 0.7 | 0.1 | 0.5 | 0.5 | 0.6 | 0.2 | 1.5 | 34.3 |

The seedoil samples also contained 0.1% C14:0, 0.2% C16:1, 0.1% C20:3ω6, no C22:1 and C22:2ω6, 0.1% C24:0 and 0.2% C24:1, 2.6% other fatty acids.

Example 5. Analysis of TAG from Transgenic *A. thaliana* Seeds Producing DHA The positional distribution of DHA on the TAG from the transformed *A. thaliana* seed was determined by NMR. Total lipid was extracted from approximately 200 mg of seed by first crushing them under hexane before transferring the crushed seed to a glass tube containing 10 mL hexane. The tube was warmed at approximately 55° C. in a water bath and then vortexed and centrifuged. The hexane solution was removed and the procedure repeated with a further 4×10 mL. The extracts were combined, concentrated by rotary evaporation and the TAG in the extracted lipid purified away from polar lipids by passage through a short silica column using 20 mL of 7% diethyl ether in hexane. Acyl group positional distributions on the purified TAG were determined quantitatively as previously described (Petrie et al., 2010a and b).

The analysis showed that the majority of the DHA in the total seed oil was located at the sn-1/3 positions of TAG with little found at the sn-2 position (FIG. 5). This was in contrast to TAG from ARA producing seeds which demonstrated that 50% of the ARA ($20:4^{\Delta 5,8,11,14}$) was located at the sn-2 position of transgenic canola oil whereas only 33% would be expected in a random distribution (Petrie et al., 2012).

The total lipid from transgenic *A. thaliana* seeds was also analysed by triple quadrupole LC-MS to determine the major DHA-containing triacylglycerol (TAG) species (FIG. 6). The most abundant DHA-containing TAG species was found to be DHA-18:3-18:3 (TAG 58:12; nomenclature not descriptive of positional distribution) with the second-most abundant being DHA-18:3-18:2 (TAG 58:11). Tri-DHA TAG (TAG 66:18) was observed in total seed oil, albeit at low but detectable levels. Other major DHA-containing TAG species included DHA-34:3 (TAG 56:9), DHA-36:3 (TAG 58:9), DHA-36:4 (TAG 58:10), DHA-36:7 (TAG 58:13) and DHA-38:4 (TAG 60:10). The identities of the two major DHA-containing TAG were further confirmed by Q-TOF MS/MS.

Example 6. Assaying Sterol Content and Composition in Oils

The phytosterols from 12 vegetable oil samples purchased from commercial sources in Australia were characterised by GC and GC-MS analysis as O-trimethylsilyl ether (OTMSi-ether) derivatives as described in Example 1. Sterols were identified by retention data, interpretation of mass spectra and comparison with literature and laboratory standard mass spectral data. The sterols were quantified by use of a 5β(H)-Cholan-24-ol internal standard. The basic phytosterol structure and the chemical structures of some of the identified sterols are shown in FIG. 7 and Table 13.

The vegetable oils analysed were from: sesame (*Sesamum indicum*), olive (*Olea europaea*), sunflower (*Helianthus annus*), castor (*Ricinus communis*), canola (*Brassica napus*), safflower (*Carthamus tinctorius*), peanut (*Arachis hypogaea*), flax (*Linum usitatissimum*) and soybean (*Glycine max*). In decreasing relative abundance, across all of the oil samples, the major phytosterols were: β-sitosterol (range 28-55% of total sterol content), Δ5-avenasterol (isofucosterol) (3-24%), campesterol (2-33%), Δ5-stigmasterol (0.7-18%), Δ7-stigmasterol (1-18%) and Δ7-avenasterol (0.1-5%). Several other minor sterols were identified, these were: cholesterol, brassicasterol, chalinasterol, campestanol and eburicol. Four C29:2 and two C30:2 sterols were also detected, but further research is required to complete identification of these minor components. In addition, several other unidentified sterols were present in some of the oils but due to their very low abundance, the mass spectra were not intense enough to enable identification of their structures.

TABLE 13

IUPAC/systematic names of identified sterols.

| Sterol No. | Common name(s) | IUPAC/Systematic name |
|---|---|---|
| 1 | cholesterol | cholest-5-en-3β-ol |
| 2 | brassicasterol | 24-methylcholesta-5,22E-dien-3β-ol |
| 3 | chalinasterol/24-methylene cholesterol | 24-methylcholesta-5,24(28)E-dien-3β-ol |
| 4 | campesterol/24-methylcholesterol | 24-methylcholest-5-en-3β-ol |
| 5 | campestanol/24-methylcholestanol | 24-methylcholestan-3β-ol |
| 7 | Δ5-stigmasterol | 24-ethylcholesta-5,22E-dien-3β-ol |
| 9 | ergost-7-en-3β-ol | 24-methylcholest-7-en-3β-ol |
| 11 | eburicol | 4,4,14-trimthylergosta-8,24(28)-dien-3β-ol |
| 12 | β-sitosterol/24-ethylcholesterol | 24-ethylcholest-5-en-3β-ol |
| 13 | D5-avenasterol/isofucosterol | 24-ethylcholesta-5,24(28)Z-dien-3β-ol |
| 19 | D7-stigmasterol/stigmast-7-en-3b-ol | 24-ethylcholest-7-en-3β-ol |
| 20 | D7-avenasterol | 24-ethylcholesta 7,24(28)-dien-3β-ol |

The sterol contents expressed as mg/g of oil in decreasing amount were: canola oil (6.8 mg/g), sesame oil (5.8 mg/g), flax oil (4.8-5.2 mg/g), sunflower oil (3.7-4.1 mg/g), peanut oil (3.2 mg/g), safflower oil (3.0 mg/g), soybean oil (3.0 mg/g), olive oil (2.4 mg/g), castor oil (1.9 mg/g). The % sterol compositions and total sterol content are presented in Table 14.

Among all the seed oil samples, the major phytosterol was generally β-sitosterol (range 30-57% of total sterol content). There was a wide range amongst the oils in the proportions of the other major sterols: campesterol (2-17%), Δ5-stigmasterol (0.7-18%), Δ5-avenasterol (4-23%), Δ7-stigmasterol (1-18%). Oils from different species had a different sterol profile with some having quite distinctive profiles. In the case of canola oil, it had the highest proportion of campesterol (33.6%), while the other species samples generally had lower levels, e.g. up to 17% in peanut oil. Safflower oil had a relatively high proportion of Δ7-stigmasterol (18%), while this sterol was usually low in the other species oils, up to 9% in sunflower oil. Because they were distinctive for each species, sterol profiles can therefore be used to help in the identification of specific vegetable or plant oils and to check their genuineness or adulteration with other oils.

Two samples each of sunflower and safflower were compared, in each case one was produced by cold pressing of seeds and unrefined, while the other was not cold-pressed and refined. Although some differences were observed, the two sources of oils had similar sterol compositions and total sterol contents, suggesting that processing and refining had little effect on these two parameters. The sterol content among the samples varied three-fold and ranged from 1.9 mg/g to 6.8 mg/g. Canola oil had the highest and castor oil the lowest sterol content.

Example 7. Increasing Accumulation of DHA at the sn-2 TAG Position

The present inventors considered that DHA and/or DPA accumulation at the sn-2 position in TAG could be increased by co-expressing an 1-acyl-glycerol-3-phosphate acyltransferase (LPAAT) together with the DHA or DPA biosynthesis pathway such as conferred by the GA7 construct or its variants. Preferred LPAATs are those which can act on polyunsaturated C22 fatty acyl-CoA as substrate, preferably DHA-CoA and/or DPA-CoA, resulting in increased insertion of the polyunsaturated C22 chain at the sn-2 position of LPA to form PA, relative to the endogenous LPAAT. Cytoplasmic LPAAT enzymes often display varied substrate preferences, particularly where the species synthesises and accumulates unusual fatty acids in TAG. A LPAAT2 from *Limnanthes douglasii* was shown to use erucoyl-CoA (C22: 1-CoA) as a substrate for PA synthesis, in contrast to an LPAAT1 from the same species that could not utilise the C22 substrate (Brown et al., 2002).

TABLE 14

Sterol content and composition of assayed plant oils.

| Sterol number* | Sterol common name | Sesame | Olive | Sun-flower | Sun-flower cold-pressed | Castor | Canola | Saf-flower | Saf-flower cold-pressed | Peanut | Flax (linseed) | Flax (linseed) | Soy bean |
|---|---|---|---|---|---|---|---|---|---|---|---|---|---|
| 1 | cholesterol | 0.2 | 0.8 | 0.2 | 0.0 | 0.1 | 0.3 | 0.2 | 0.1 | 0.2 | 0.4 | 0.4 | 0.2 |
| 2 | brassicasterol | 0.1 | 0.0 | 0.0 | 0.0 | 0.3 | 0.1 | 0.0 | 0.0 | 0.0 | 0.2 | 0.2 | 0.0 |
| 3 | chalinasterol/24-methylene cholesterol | 1.5 | 0.1 | 0.3 | 0.1 | 1.1 | 2.4 | 0.2 | 0.1 | 0.9 | 1.5 | 1.4 | 0.8 |
| 4 | campesterol/24-methylcholesterol | 16.2 | 2.4 | 7.4 | 7.9 | 8.4 | 33.6 | 12.1 | 8.5 | 17.4 | 15.7 | 14.4 | 16.9 |
| 5 | campestanol/24-methylcholestanol | 0.7 | 0.3 | 0.3 | 0.1 | 0.9 | 0.2 | 0.8 | 0.8 | 0.3 | 0.2 | 0.2 | 0.7 |
| 6 | C29:2* | 0.0 | 0.0 | 0.1 | 0.2 | 0.0 | 0.1 | 0.5 | 0.5 | 0.0 | 1.2 | 1.3 | 0.1 |
| 7 | Δ5-stigmasterol | 6.4 | 1.2 | 7.4 | 7.2 | 18.6 | 0.7 | 7.0 | 4.6 | 6.9 | 5.1 | 5.8 | 17.6 |
| 8 | unknown | 0.5 | 1.3 | 0.7 | 0.6 | 0.8 | 0.7 | 0.7 | 1.3 | 0.4 | 0.7 | 0.6 | 1.3 |
| 9 | ergost-7-en-3β-ol | 0.1 | 0.1 | 1.9 | 1.8 | 0.2 | 0.4 | 2.7 | 4.0 | 1.4 | 1.4 | 1.4 | 1.0 |
| 10 | unknown | 0.0 | 1.3 | 0.9 | 0.8 | 1.2 | 0.9 | 1.8 | 0.7 | 1.2 | 0.7 | 0.5 | 0.7 |
| 11 | eburicol | 1.6 | 1.8 | 4.1 | 4.4 | 1.5 | 1.0 | 1.9 | 2.9 | 1.2 | 3.5 | 3.3 | 0.9 |
| 12 | β-sitosterol/24-ethylcholesterol | 55.3 | 45.6 | 43.9 | 43.6 | 37.7 | 50.8 | 40.2 | 35.1 | 57.2 | 29.9 | 28.4 | 40.2 |
| 13 | Δ5-avenasterol/isofucosterol | 8.6 | 16.9 | 7.2 | 4.1 | 19.3 | 4.4 | 7.3 | 6.3 | 5.3 | 23.0 | 24.2 | 3.3 |
| 14 | triterpenoid alcohol | 0.0 | 2.4 | 0.9 | 1.1 | 0.0 | 0.0 | 1.6 | 1.9 | 0.0 | 0.0 | 0.0 | 0.9 |
| 15 | triterpenoid alcohol | 0.0 | 0.0 | 0.7 | 0.6 | 0.0 | 0.0 | 2.8 | 1.8 | 0.0 | 0.0 | 0.3 | 0.0 |
| 16 | C29:2* | 0.0 | 0.5 | 0.7 | 0.7 | 1.5 | 1.2 | 2.8 | 1.9 | 2.0 | 1.0 | 0.7 | 0.5 |
| 17 | C29:2* | 1.0 | 0.9 | 2.3 | 2.4 | 0.6 | 0.4 | 1.3 | 1.9 | 0.9 | 1.0 | 1.0 | 1.0 |
| 18 | C30:2* | 0.0 | 0.0 | 0.0 | 0.0 | 1.9 | 0.0 | 0.0 | 0.0 | 0.0 | 0.0 | 0.0 | 0.0 |
| 19 | Δ7-stigmasterol/stigmast-7-en-3β-ol | 2.2 | 7.1 | 9.3 | 10.9 | 2.3 | 0.9 | 10.5 | 18.3 | 1.1 | 7.9 | 8.7 | 5.6 |
| 20 | Δ7-avenasterol | 1.3 | 0.1 | 4.0 | 3.6 | 0.6 | 0.2 | 2.0 | 4.7 | 0.7 | 0.4 | 0.4 | 0.6 |
| 21 | unknown | 0.7 | 7.1 | 0.9 | 0.8 | 0.0 | 0.4 | 0.3 | 0.4 | 0.0 | 3.0 | 3.6 | 0.0 |
| 22 | unknown | 0.3 | 0.0 | 0.3 | 0.9 | 0.0 | 0.0 | 1.2 | 1.3 | 0.2 | 0.1 | 0.0 | 0.3 |
| 23 | unknown | 0.2 | 0.2 | 0.3 | 0.3 | 0.2 | 0.1 | 0.3 | 0.2 | 0.2 | 0.1 | 0.2 | 0.5 |
| 24 | unknown | 0.0 | 3.1 | 0.9 | 1.3 | 0.6 | 0.4 | 0.2 | 0.4 | 0.7 | 1.7 | 1.9 | 0.8 |
| 25 | unknown | 0.9 | 0.4 | 0.3 | 0.5 | 0.3 | 0.1 | 0.5 | 0.7 | 0.3 | 0.1 | 0.1 | 0.6 |
| 26 | C30:2 | 2.2 | 6.0 | 4.6 | 5.7 | 1.4 | 0.6 | 1.0 | 1.2 | 1.2 | 1.2 | 1.1 | 5.2 |
| 27 | unknown | 0.0 | 0.4 | 0.4 | 0.3 | 0.3 | 0.2 | 0.1 | 0.2 | 0.3 | 0.1 | 0.0 | 0.3 |
| | Sum | 100.0 | 100.0 | 100.0 | 100.0 | 100.0 | 100.0 | 100.0 | 100.0 | 100.0 | 100.0 | 100.0 | 100.0 |
| | Total sterol (mg/g oil) | 5.8 | 2.4 | 4.1 | 3.7 | 1.9 | 6.8 | 3.2 | 3.0 | 3.2 | 4.8 | 5.2 | 3.0 |

C29:2* and and C30:2* denotes a C29 sterol with two double bonds and a C30 sterol with two double bonds, respectively Known LPAATs were considered and a number were selected for testing, including some which were not expected to increase DHA incorporation at the sn-2 position, as controls. The known LPAATs included: *Arabidopsis thaliana* LPAAT2: (SEQ ID NO: 40, Accession No. ABG48392, Kim et al., 2005), *Limnanthes alba* LPAAT (SEQ ID NO: 41, Accession No. AAC49185, Lassner et al., 1995), *Saccharomyces cerevisiae* Slc1p (SEQ ID NO: 42, Accession No. NP_010231, Zou et al., 1997), *Mortierella alpina* LPAAT1 (SEQ ID NO: 44, Accession No. AED33305; U.S. Pat. No. 7,879,591) and *Brassica napus* LPAATs (SEQ ID NO: 45 and SEQ ID NO:46, Accession Nos ADC97479 and ADC97478 respectively).

The *Arabidopsis* LPAAT2 (also designated LPAT2) is an endoplasmic reticulum-localised enzyme shown to have activity on C16 and C18 substrates, however activity on C20 or C22 substrates was not tested (Kim et al., 2005). *Limnanthes alba* LPAAT2 was demonstrated to insert a C22:1 acyl chain into the sn-2 position of PA, although the ability to use DHA or DPA as a substrate was not tested (Lassner et al., 1995). The selected *S. cerevisiae* LPAAT Slc1p was shown to have activity using 22:1-CoA in addition to 18:1-CoA as substrates, indicating a broad substrate specificity with respect to chain length (Zou et al., 1997). Again, DHA-CoA, DPA-CoA and other LC-PUFAs were not tested as substrates. The *Mortierella* LPAAT had previously been shown to have activity on EPA and DHA fatty acid substrates in transgenic *Yarrowia lipolytica* (U.S. Pat. No. 7,879,591) but its activity in plant cells was unknown.

Additional LPAATs were identified by the inventors. *Micromonas pusilla* is a microalga that produces and accumulates DHA in its oil, although the positional distribution of the DHA on TAG in this species has not been confirmed. The *Micromonas pusilla* LPAAT (SEQ ID NO: 43, Accession No. XP_002501997) was identified by searching the *Micromonas pusilla* genomic sequence using the *Arabidopsis* LPAAT2 as a BLAST query sequence. Several candidate sequences emerged and the sequence XP_002501997 was synthesised for testing on C22 LC-PUFA. The *Ricinus communis* LPAAT was annotated as a putative LPAAT in the castor genome sequence (Chan et al., 2010). Four candidate LPAATs from the castor genome were synthesised and tested in crude leaf lysates of infiltrated *N. benthamiana* leaf tissue. The candidate sequence described here showed LPAAT activity.

A number of candidate LPAATs were aligned with known LPAATs on a phylogenetic tree (FIG. 8). It was noted that the putative *Micromonas* LPAAT did not cluster with the putative C22 LPAATs but was a divergent sequence.

As an initial test of various LPAATs for their ability to use DHA-CoA as substrate, chimeric genetic constructs were made for constitutive expression of exogenous LPAATs in *N. benthamiana* leaves, each under the control of the 35S promoter, as follows: 35S:Arath-LPAAT2 (*Arabidopsis* ER LPAAT); 35S:Limal-LPAAT (*Limnanthes alba* LPAAT); 35S:Sacce-Slc1p (*S. cerevisiae* LPAAT); 35S:Micpu-LPAAT (*Micromonas pusilla* LPAAT); 35S:Moral-LPAAT1 (*Mortierella alpina* LPAAT); 35S:Brana-LPAAT1.13 (*Brassica napus* LPAAT1.13); 35S:Brana-LPAAT1.5 (*Brassica napus* LPAAT1.5). A 35S:p19 construct lacking an exogenous LPAAT was used as a control in the experiment; it was included in each *N. benthamiana* inoculation. Each of these constructs was introduced via *Agrobacterium* into *N. benthamiana* leaves as described in Example 1, and 5 days after infiltration, the treated leaf zones were excised and ground to make leaf lysates. Each lysate included the exogenous LPAAT as well as the endogenous enzymes for synthesizing LPA. In vitro reactions were set up by separately adding $^{14}$C-labelled-OA and -DHA to the lysates. Reactions were incubated at 25° C. and the level of incorporation of the $^{14}$C labelled fatty acids into PA determined by TLC. The ability of each LPAAT to use DHA relative to ARA and the C18 fatty acids were assessed. The meadowfoam (*Limnanthes alba*), *Mortierella* and *Saccharomyces* LPAATs were found to have activity on DHA substrate, with radiolabelled PA appearing for these but not the other LPAATs. All LPAATs were confirmed active by the oleic acid control feed.

To test LPAAT activity in seeds, several of the protein coding sequences or LPAATs were inserted into a binary vector under the control of a conlinin (pLuCnl2) promoter. The resultant genetic constructs containing the chimeric genes, Cnl2:Arath-LPAAT (negative control), Cnl2:Limal-LPAAT, Cn2:Sacce-Slc1p, and Cnl2:Moral-LPAAT, respectively, are then used to transform *A. thaliana* plants producing DHA in their seed to generate stable transformants expressing the LPAATs and the transgenic DHA pathway in a seed-specific manner to test whether there would be an increased incorporation of DHA at the sn-2 position of TAG. The constructs are also used to transform *B. napus* and *C. sativa* plants that already contain the GA7 construct and variants thereof (Examples 2 to 4) to generate progeny carrying both the parental and LPAAT genetic constructs. Increased incorporation of DHA at the sn-2 position of TAG is tested relative to the incorporation in plants lacking the LPAAT encoding transgenes. Oil content is also improved in the seeds, particularly for seeds producing higher levels of DHA, counteracting the trend seen in *Arabidopsis* seed as described in Example 2.

The seed specific pCnl2:Moral-LPAAT1 construct was used to transform an already transgenic *Arabidopsis thaliana* line which was homozygous for the T-DNA from the GA7 construct and whose seed contained approximately 15% DHA in seed lipids (Petrie et al., 2012). For this, use was made of the kanamycin selectable marker gene in the pCnl2:Moral-LPAAT1 construct which was different to the bar selectable marker gene already present in the transgenic line. Transgenic seedlings were selected which were resistant to kanamycin and grown to maturity in a glasshouse. T2 seeds were harvested and the fatty acid composition of their total seed lipids analysed by GC (Table 15). Three phenotypes were observed amongst the 33 independently transformed lines. In a first group (6/33 lines), DPA increased significantly to a level substantially greater than the level of DHA, up to about 10.6% of total seed lipids. This came at the expense of DHA which was strongly decreased in this group of lines. In two of the lines in this first group, the sum of DPA+DHA was reduced, but not in the other 4 lines. In a second group (5/33), the levels of DPA and DHA were about equal, with the sum of DPA+DHA about the same as for the parental seed. In the third group, the levels of DPA and DHA were similar to those in the parental seeds. One possible explanation for the increased level of DPA in the first and second groups is that the LPAAT out-competes the Δ4-desaturase for DPA-CoA substrate and preferentially incorporates the DPA into PA and thence into TAG, relative to the Δ4-desaturation. A second possible explanation is that the Δ4-desaturation is partially inhibited.

Seed from the *Arabidopsis* plants transformed with the T-DNA of the GA7 construct which had been further transformed with the Cnl2::Moral-LPAAT vector were harvested and oil extracted from the seed. The TAG fraction was then isolated from the extracted oil by TLC methods and recovered from the TLC plate. These TAG samples and samples of the seedoil prior to the fractionation were analysed by digestion with *Rhizopus* lipase to determine the positional distribution of the DHA. The lipase is specific for acyl groups esterified at the sn-1 or sn-3 position of TAG. This was performed by emulsifying each lipid sample in 5% gum arabic using an ultrasonicator, adding the *Rhizopus* lipase solution in 0.1M Tris-HCl pH 7.7 containing 5 mM CaCl$_2$) and incubating the mixtures at 30° C. with continuous shaking. Each reaction was stopped by adding chloroform: methanol (2/1, v/v) and one volume of 0.1M KCl to each mixture. The lipid was extracted into the chloroform fraction and the relative amounts determined of the sn-2 MAG, sn-1/3 FFA, DAG and TAG components of the resulting lipid by separation on 2.3% boric acid impregnated TLC using hexane/diethylether/acetic acid (50/50/1, v/v). Lipid bands were visualized by spraying 0.01% primuline in acetone/water (80/20, v/v) onto the TLC plate and visualisation under UV light. Individual lipid bands were identified on the basis of lipid standard spots, resolved on the same TLC plate. TLC lipid bands were collected into glass vials and their fatty acid methyl esters were prepared using 1N methanolic-HCl (Supelco) and incubating at 80° C. for 2 h. Fatty acid composition of individual lipids were analysed by GC.

This assay demonstrated that the DHA in the parental seeds transformed with the GA7 (lines 22-2-1-1 and 22-2-38-7) was preferentially esterified at the sn-1 or sn-3 position of the TAG. In contrast, the DHA in the NY11 and NY15 seed transformed with both the GA7 constructs and the transgene encoding LPAAT was enriched at the sn-2 position, with 35% of the DHA in one of the lines and 48% of the DHA in the other line being esterified at the sn-2 position of TAG i.e. after lipase digestion the DHA was present as sn-2-MAG (Table 16). Analogous results are obtained for *B. napus* and *B. juncea* seeds transformed with both the T-DNA from the GA7-modB construct and the LPAAT-encoding gene and producing DHA, and with *B. napus* and *B. juncea* seeds producing DPA.

In order to determine whether the *Mortierella* LPAAT or another LPAAT had preference for either DPA-CoA or DHA-CoA, in vitro reactions are set up by separately adding $^{14}$C-labelled-DPA-CoA or -DHA-CoA to lysates of *N. benthamiana* leaves transiently expressing the candidate LPAAT under control of a constitutive promoter as described above. Reactions are incubated at 25° C. and the level of incorporation of the $^{14}$C labelled fatty acids into PA determined by TLC analysis of the lipids. The ability of each LPAAT to use DHA-CoA relative to DPA-CoA is assessed. Genes encoding LPAATs which are confirmed to have good DHA incorporating LPAAT activity are used to produced transformed DHA-producing canola plants and seed.

Genes encoding LPAATs which have strong activity using DPA-CoA are used to transform DPA-producing plants and seed, to increase the amount of DPA esterified at the sn-2 position of TAG.

TABLE 15

Fatty acid composition (% of total fatty acids) of transgenic *A. thaliana* seeds transformed with an LPAAT1 construct as well as the T-DNA from the GA7 construct for DHA production. C20:4ω6 was not detected in the seeds. The seeds also contained 0.3-0.9% C22:0 and 0.4-1.5% C22:1.

| | C16:0 | C18:0 | C18:1 | C18:1d11 | C18:2 | C18:3n6 | C18:3n3 | C20:0 | 18:4n3 | C20:1d11 | 20:1d13 | C20:2n6 | C20:4n6 | C20:3n3 | C22:0 | 20:4n3 | C22:1 | 20:5n3 | 22:5n3 | C22:6n3 |
|---|---|---|---|---|---|---|---|---|---|---|---|---|---|---|---|---|---|---|---|---|
| NY-1 | 9.3 | 3.2 | 9.1 | 6.8 | 9.4 | 0.5 | 23.8 | 1.6 | 4.1 | 7.9 | 5.1 | 0.6 | 0.0 | 0.9 | 0.4 | 0.6 | 0.6 | 1.2 | 7.9 | 4.5 |
| NY-2 | 10.7 | 3.3 | 6.5 | 4.4 | 7.6 | 0.3 | 28.1 | 1.9 | 4.3 | 8.5 | 3.7 | 0.7 | 0.0 | 1.1 | 0.5 | 1.1 | 0.8 | 1.4 | 1.1 | 11.6 |
| NY-3 | 9.3 | 2.8 | 6.3 | 3.4 | 10.3 | 0.2 | 32.8 | 2.2 | 2.7 | 6.2 | 3.6 | 1.1 | 0.0 | 1.9 | 0.5 | 1.4 | 0.9 | 0.7 | 1.0 | 10.7 |
| NY-4 | 11.4 | 3.5 | 4.5 | 3.1 | 7.0 | 0.3 | 32.5 | 2.1 | 4.7 | 5.5 | 2.3 | 1.0 | 0.0 | 1.9 | 0.6 | 0.8 | 0.6 | 1.1 | 0.9 | 14.3 |
| NY-5 | 14.6 | 4.5 | 7.0 | 7.7 | 6.7 | 0.3 | 20.7 | 2.2 | 5.7 | 5.4 | 1.8 | 0.4 | 0.0 | 0.9 | 0.9 | 0.8 | 0.4 | 1.2 | 1.0 | 11.7 |
| NY-6 | 7.8 | 2.7 | 12.5 | 2.2 | 18.0 | 0.1 | 24.9 | 1.8 | 0.7 | 15.5 | 3.1 | 1.4 | 0.0 | 1.2 | 0.3 | 0.5 | 1.5 | 0.3 | 3.0 | 0.8 |
| NY-7 | 9.3 | 2.9 | 6.7 | 3.8 | 9.2 | 0.2 | 31.5 | 2.1 | 3.2 | 7.5 | 3.7 | 0.9 | 0.0 | 1.6 | 0.5 | 1.3 | 0.8 | 0.8 | 1.1 | 10.9 |
| NY-8 | 8.8 | 3.2 | 8.2 | 5.5 | 11.0 | 0.3 | 25.3 | 1.9 | 3.0 | 8.3 | 5.4 | 1.0 | 0.0 | 1.2 | 0.5 | 0.8 | 0.8 | 0.8 | 6.1 | 6.0 |
| NY-9 | 12.3 | 3.7 | 5.0 | 4.6 | 7.1 | 0.2 | 28.3 | 2.3 | 4.2 | 5.6 | 3.8 | 0.8 | 0.0 | 1.6 | 0.7 | 0.7 | 0.6 | 1.1 | 1.2 | 13.8 |
| NY-10 | 8.6 | 3.2 | 8.5 | 3.1 | 9.7 | 0.3 | 31.5 | 1.6 | 3.4 | 8.7 | 2.8 | 1.0 | 0.0 | 1.3 | 0.3 | 0.9 | 0.6 | 1.1 | 10.6 | 1.0 |
| NY-11 | 11.5 | 3.2 | 4.5 | 2.5 | 7.1 | 0.3 | 33.3 | 2.1 | 3.9 | 5.7 | 1.9 | 0.9 | 0.0 | 2.0 | 0.5 | 0.7 | 0.7 | 0.8 | 1.0 | 15.6 |
| NY-12 | 8.7 | 3.2 | 7.5 | 5.1 | 8.5 | 0.2 | 26.8 | 2.0 | 3.7 | 8.7 | 5.1 | 0.9 | 0.0 | 1.2 | 0.5 | 1.1 | 0.8 | 1.2 | 10.0 | 2.6 |
| NY-13 | 11.5 | 3.4 | 5.2 | 3.4 | 8.3 | 0.3 | 30.0 | 2.2 | 5.0 | 6.2 | 3.2 | 0.9 | 0.0 | 1.7 | 0.6 | 1.5 | 0.8 | 1.1 | 1.0 | 11.6 |
| NY-14 | 9.2 | 2.9 | 6.6 | 2.0 | 10.3 | 0.2 | 34.7 | 1.9 | 3.3 | 7.7 | 1.6 | 1.2 | 0.0 | 1.8 | 0.4 | 1.2 | 0.8 | 0.9 | 0.8 | 11.1 |
| NY-15 | 10.9 | 3.3 | 4.6 | 2.7 | 7.0 | 0.3 | 34.1 | 1.9 | 5.1 | 5.5 | 2.0 | 0.9 | 0.0 | 1.8 | 0.5 | 0.8 | 0.5 | 1.0 | 1.0 | 14.7 |
| NY-16 | 10.5 | 3.4 | 6.0 | 4.6 | 7.8 | 0.3 | 30.3 | 1.8 | 4.4 | 5.4 | 2.9 | 0.7 | 0.0 | 1.5 | 0.5 | 0.9 | 0.5 | 1.1 | 1.3 | 14.2 |
| NY-17 | 9.1 | 2.4 | 5.9 | 2.5 | 10.4 | 0.2 | 35.4 | 1.6 | 3.6 | 6.4 | 2.1 | 1.1 | 0.0 | 1.9 | 0.4 | 1.2 | 0.7 | 1.0 | 0.9 | 11.7 |
| NY-18 | 9.7 | 3.6 | 8.8 | 6.2 | 12.1 | 0.3 | 21.0 | 1.9 | 4.0 | 8.3 | 5.9 | 0.8 | 0.0 | 0.9 | 0.5 | 0.6 | 0.9 | 1.0 | 5.7 | 5.1 |
| NY-19 | 8.4 | 3.1 | 12.0 | 3.1 | 14.6 | 0.2 | 28.8 | 1.7 | 1.6 | 11.3 | 3.2 | 1.0 | 0.0 | 1.4 | 0.4 | 0.6 | 1.0 | 0.6 | 3.9 | 1.2 |
| NY-20 | 10.1 | 3.2 | 5.4 | 3.3 | 8.9 | 0.3 | 32.8 | 2.1 | 4.1 | 5.5 | 2.8 | 1.0 | 0.0 | 1.9 | 0.5 | 1.1 | 0.7 | 0.9 | 1.1 | 12.1 |
| NY-21 | 10.5 | 3.6 | 5.6 | 3.8 | 8.2 | 0.3 | 31.9 | 2.0 | 4.6 | 5.9 | 2.8 | 0.9 | 0.0 | 1.7 | 0.5 | 0.8 | 0.6 | 1.0 | 0.9 | 12.5 |
| NY-22 | 8.4 | 3.3 | 7.4 | 2.3 | 9.4 | 0.2 | 33.5 | 1.8 | 3.4 | 8.8 | 2.2 | 1.2 | 0.0 | 1.7 | 0.4 | 1.3 | 0.7 | 1.0 | 5.5 | 6.1 |
| NY-23 | 8.3 | 2.8 | 7.0 | 1.9 | 11.0 | 0.2 | 34.6 | 1.9 | 2.6 | 9.3 | 1.7 | 1.4 | 0.0 | 2.0 | 0.4 | 1.2 | 1.0 | 0.7 | 0.7 | 9.9 |
| NY-24 | 9.0 | 3.3 | 7.0 | 4.3 | 9.9 | 0.2 | 30.0 | 1.8 | 3.2 | 7.7 | 4.3 | 1.0 | 0.0 | 1.6 | 0.4 | 0.6 | 0.8 | 0.8 | 3.4 | 8.8 |
| NY-25 | 9.4 | 3.3 | 6.0 | 3.6 | 8.2 | 0.2 | 32.6 | 1.8 | 4.0 | 6.8 | 3.6 | 1.0 | 0.0 | 1.7 | 0.4 | 0.6 | 0.7 | 0.9 | 4.8 | 8.7 |
| NY-26 | 10.4 | 4.2 | 8.0 | 3.8 | 16.0 | 0.4 | 18.7 | 2.5 | 2.5 | 10.1 | 4.0 | 1.0 | 0.0 | 0.8 | 0.8 | 1.9 | 1.0 | 1.4 | 1.4 | 8.4 |
| NY-27 | 9.4 | 3.2 | 7.5 | 5.3 | 11.4 | 0.2 | 28.6 | 2.0 | 2.3 | 7.5 | 5.5 | 1.0 | 0.0 | 1.8 | 0.5 | 0.6 | 0.9 | 0.6 | 1.5 | 7.6 |
| NY-28 | 9.4 | 3.4 | 6.5 | 3.6 | 8.8 | 0.3 | 32.4 | 1.8 | 3.9 | 6.7 | 3.3 | 0.9 | 0.0 | 1.6 | 0.4 | 0.7 | 0.6 | 1.0 | 10.1 | 2.7 |
| NY-29 | 10.2 | 3.7 | 7.6 | 4.3 | 8.0 | 0.4 | 28.8 | 1.7 | 4.8 | 7.6 | 2.9 | 0.7 | 0.0 | 1.1 | 0.4 | 0.7 | 0.5 | 1.4 | 1.9 | 11.6 |
| NY-30 | 11.1 | 3.5 | 5.4 | 4.1 | 7.3 | 0.3 | 30.2 | 2.0 | 4.7 | 6.0 | 3.0 | 0.8 | 0.0 | 1.7 | 0.5 | 0.7 | 0.7 | 1.1 | 1.0 | 13.7 |
| NY-31 | 9.6 | 3.0 | 5.6 | 2.1 | 8.5 | 0.2 | 35.4 | 2.0 | 3.9 | 7.1 | 1.7 | 1.2 | 0.0 | 2.1 | 0.4 | 0.9 | 0.8 | 0.8 | 0.8 | 12.3 |
| NY-32 | 8.5 | 3.1 | 8.0 | 1.9 | 9.5 | 0.3 | 31.7 | 1.5 | 3.3 | 12.9 | 1.4 | 1.0 | 0.0 | 1.1 | 0.3 | 1.2 | 0.8 | 1.2 | 0.8 | 9.8 |
| NY-33 | 10.3 | 3.8 | 7.7 | 6.3 | 8.1 | 0.3 | 24.4 | 2.0 | 4.4 | 7.5 | 4.8 | 0.7 | 0.0 | 1.1 | 0.5 | 0.6 | 0.6 | 1.1 | 2.8 | 10.7 |

TABLE 16

Presence of DHA at the sn-2 position of TAG or in the total oil from transgenic *A. thaliana* seeds transformed with the Cnl2::Moral-LPAAT gene as well as the T-DNA of the GA7 construct. showing the positional distribution of DHA in TAG. The TAG and sn-2 MAG fatty acid compositions also contained 0-0.4% each of 14:0. 16:1ω13t, 16:2, 16:3, 22:0, and 24:0. The seeds contained no detected C20:3ω6, C20:4ω6.

| Sample | C16:0 | 16:1d9 | C18:0 | C18:1 | C18:1d11 | C18:2 | C18:3n6 | C18:3n3 | C20:0 | 18:4 | C20:1d11 | 20:1d13 |
|---|---|---|---|---|---|---|---|---|---|---|---|---|
| 22-2-1-1 TAG | 12.2 | 0.4 | 4.4 | 6.4 | 3.9 | 7.2 | 0.8 | 28.8 | 1.6 | 4.3 | 9.7 | 2.3 |
| 2-MAG | 0.6 | 0.1 | 0.3 | 8.3 | 2.5 | 10.1 | 0.7 | 53.9 | 0.2 | 6.5 | 0.3 | 0.1 |
| 22-2-38-7 oil | 10.0 | 0.2 | 3.7 | 6.0 | 2.7 | 6.4 | 0.4 | 33.8 | 1.6 | 3.7 | 11.3 | 1.8 |
| 2-MAG | 0.5 | 0.1 | 0.3 | 9.7 | 2.4 | 11.1 | 0.6 | 60.0 | 0.1 | 3.6 | 0.3 | 0.1 |
| Transformation additionally with gene encoding *Mortierella alpina* LPAAT | | | | | | | | | | | | |
| NY11- TAG | 11.0 | 0.2 | 3.4 | 6.0 | 2.8 | 9.2 | 0.3 | 34.8 | 1.6 | 3.6 | 6.3 | 1.8 |
| 2-MAG | 0.7 | 0.1 | 0.2 | 6.7 | 1.1 | 11.8 | 0.3 | 49.8 | 0.2 | 3.7 | 0.5 | 1.5 |
| NY-15-oil | 11.0 | 0.0 | 3.3 | 4.6 | 2.8 | 6.9 | 0.3 | 33.6 | 2.0 | 5.1 | 5.5 | 2.1 |
| 2-MAG | 0.8 | 0.1 | 0.3 | 6.4 | 1.3 | 11.4 | 0.3 | 50.2 | 0.2 | 4.9 | 0.4 | 1.4 |

| Sample | C20:2n6 | C20:3n6 | C20:4n6 | C20:3n3 | 20:4n3 | C22:1 | 20:5n3 | C22:4n6 | 22:5n6 | 22:4n3 | 22:5n3 | C22:6n3 |
|---|---|---|---|---|---|---|---|---|---|---|---|---|
| 22-2-1-1 TAG | 0.7 | 0.1 | 0.1 | 1.3 | 1.0 | 0.6 | 2.1 | | | 0.0 | 0.7 | 10.1 |
| 2-MAG | 0.1 | 0.0 | 0.0 | 0.3 | 0.2 | 0.0 | 3.8 | | | 0.0 | 2.3 | 9.1 |
| | | | | | | | | | | | DHA at sn-2 = 30% | |
| 22-2-38-7 oil | 0.8 | | | 1.3 | 0.9 | 0.6 | 1.2 | 0.1 | | | 0.7 | 11.6 |
| 2-MAG | 0.1 | 0.0 | 0.0 | 0.4 | 0.2 | 0.0 | 2.1 | | | 0.1 | 1.3 | 6.7 |
| | | | | | | | | | | | DHA at sn-2 = 19% | |
| Transformation additionally with gene encoding *Mortierella alpina* LPAAT | | | | | | | | | | | | |
| NY11- TAG | 1.0 | 0.0 | 0.0 | 1.8 | 0.7 | 0.6 | 0.9 | | 0.0 | 0.1 | 0.6 | 12.2 |
| 2-MAG | 0.3 | 0.0 | 0.0 | 1.6 | 0.6 | 0.1 | 0.8 | | 0.1 | 0.2 | 1.6 | 17.8 |
| | | | | | | | | | | | DHA at sn-2 = 48% | |
| NY-15-oil | 0.9 | 0.0 | 0.0 | 1.9 | 0.7 | 0.6 | 0.9 | 0.1 | 0.4 | | 0.9 | 14.9 |
| 2-MAG | 0.2 | 0.0 | 0.0 | 1.5 | 0.6 | 0.1 | 0.9 | 0.0 | 0.0 | 0.2 | 1.6 | 16.7 |
| | | | | | | | | | | | DHA at sn-2 = 37% | |

Example 8. Further Analysis of Transgenic *Camelina sativa* Seeds Total Lipid Content

*C. sativa* seed which was homozygous for the T-DNA from the GA7 construct and containing DHA in its total fatty acid content was analysed for its total lipid content and composition as follows. Two consecutive solvent extraction steps were performed on the seeds, firstly using hexane and secondly using chloroform/methanol. No antioxidants were added during the extractions or analysis. The Soxhlet extraction method which is commonly used to extract seed lipids by prolonged heating and refluxing of the lipid/solvent mixture was not used here because of the potential for degradation or oxidation of the ω3 PUFA such as DHA.

Hexane was used as the solvent in the first extraction since it is the industry standard for oilseeds. Also, it preferentially extracts TAG-containing oil due to its solvating properties and its relatively poor solubilization of polar lipids, particularly at room temperature. Transformed and control *Camelina* seeds (130 g and 30 g, respectively) were wetted with hexane and crushed using an electric agate mortar and pestle (Retsch Muhle, Germany). The mixtures were transferred to separatory funnels and extracted four times using a total of 800 mL hexane, including an overnight static extraction for the third extraction. For each extraction, extracts were filtered to remove fines through a GFC glass fiber filter under vacuum, and then rotary evaporated at 40° C. under vacuum. The extracts were pooled and constituted the TAG-rich hexane extracts.

Following extraction with hexane, the remaining seed meals were further extracted using chloroform-methanol (CM, 1:1 v/v) using the procedure as for the hexane extraction. The meal was then removed by filtration and the combined extracts rotary evaporated. The pooled CM total crude lipid extracts were then dissolved using a one-phase methanol-chloroform-water mix (2:1:0.8 v/v/v). The phases were separated by the addition of chloroform-water (final solvent ratio, 1:1:0.9 v/v/v methanol-chloroform-water). The purified lipid in each extract was partitioned in the lower chloroform phase, concentrated using rotary evaporation and constituted the polar lipid-rich CM extracts. The lipid content in each of these extracts was determined gravimetrically.

For fatty acid compositional analysis, aliquots of the hexane and CM extracts were trans-methylated according to the method of Christie et al. (1982) to produce fatty acid methyl esters (FAME) using methanol-chloroform-conc. hydrochloric acid (3 mL, 10:1:1, 80° C., 2 h). FAME were extracted into hexane-chloroform (4:1, 3×1.8 mL). Samples of the remaining seed meal (1-2 g) after the hexane and CM extractions were also trans-methylated to measure any residual lipid as FAME by gravimetry. The total lipid content of the seeds was calculated by adding the lipid contents of the hexane and CM extracts and the FAME content of the transmethylated meal after solvent extraction.

The transgenic seeds contained slightly less total lipid at 36.2% of seed weight compared to the wild-type *Camelina sativa* seeds at 40.9% of seed weight. For seeds including oilseeds, the total lipid was determined as the sum of solvent extractable lipid obtained by consecutive extractions with hexane, then chloroform-methanol, plus the residual lipid released by transmethylation of the extracted meal after the solvent extractions, as exemplified herein. This total lipid consisted mainly of fatty acid containing lipids such as triacylglycerols and polar lipids and small amounts of non-fatty acid lipids e.g. phytosterols and fatty alcohols which may be present in the free unesterified form or esterified with fatty acids. In addition, any sterol esters or wax esters and hydrocarbons such as carotenoids, for example β-carotene, were also included in the solvent extractable lipid if present. These were included in the overall gravimetric determination and were indicated in the TLC-FID analysis (Table 17).

Of the total lipid, 31%-38% of lipid per seed weight was extracted by hexane for the transgenic and control seeds, respectively, which accounted for 86% and 92% of the total lipid in the seeds. The CM extraction recovered a further 4.8% and 2.4% (of seed weight) mostly polar lipid-rich extract from the transgenic and control seeds, respectively. The residual lipid released by transmethylation of the remaining solvent extracted oilseed meal was 0.3% and 0.4% of seed weight, respectively. That is, the first and second solvent extractions together extracted 99% of the total lipid content of the seeds (i.e. of the 36.2% or 40.9% of the seed weight, which was mostly fatty acid containing lipid such as triglycerides and polar lipids consisting of glyco- and phospholipids (see next section—Lipid class analysis)).

Lipid Class Analysis

Lipid classes in the hexane and CM extracts were analyzed by thin-layer chromatography with flame-ionization detection (TLC-FID; Iatroscan Mark V, Iatron Laboratories, Tokyo, Japan) using hexane/diethyl ether/glacial acetic acid (70:10:0.1, v/v/v) as the developing solvent system in combination with Chromarod S-III silica on quartz rods. Suitable calibration curves were prepared using representative standards obtained from Nu-Chek Prep, Inc. (Elysian, MN, USA). Data were processed using SIC-48011 software (SISC Version: 7.0-E). Phospholipid species were separated by applying the purified phospholipid fraction obtained from silica column chromatography and developing the rods in chloroform/methanol/glacial acetic acid/water (85:17:5:2, v/v/v) prior to FID detection.

To separate TAG, glycolipid and phospholipid fractions from the CM extracts, silica gel 60 (100-200 mesh) (0.3-1 g) in a short glass column or Pasteur pipette plugged with glass wool was used to purify 10 mg of the purified CM lipid extract. The residual TAG fraction in the CM extract was eluted using 20 mL of 10% diethyl ether in hexane, the glycolipids eluted with 20 mL of acetone and the phospholipids eluted in two steps, first 10 mL of methanol then 10 mL of methanol-chloroform-water (5:3:2). This second elution increased the recovery of phospholipids. The yield of each fraction was determined gravimetrically and the purity checked by TLC-FID. All extracts and fractions were stored in dichloromethane at −20° C. until further analysis by GC and GC-MS.

The TAG-rich hexane extracts from each of the transgenic and control seeds contained about 96% TAG. The CM extracts contained residual TAG amounting to 44% and 13% by weight of the CM extracts, respectively, for the transgenic and wild-type seeds. In contrast to the hexane extracts, the CM extracts were rich in polar lipids, namely phospholipids and glycolipids, amounting to 50% and 76% by weight of the CM extracts, respectively, for the transgenic and control seeds (Table 17). The main phospholipid was phosphatidyl choline (PC) and accounted for 70%-79% of the total phospholipids followed by phosphatidyl ethanolamine (PE, 7%-13%) with relatively low levels of phosphatidic acid (PA, 2%-5%) and phosphatidyl serine (PS, <2%).

Fatty Acid Composition

Generally for seeds producing DHA and/or DPA, the inventors observed that the fatty acid composition of the total lipids in the seeds as determined by direct transmethylation of all of the lipid in the seed was similar to that of the TAG fraction. This was because more than 90% of the total lipids present in the seed occurred in the form of TAG.

The fatty acid composition of the different lipid classes in the hexane and CM extracts was determined by gas chromatography (GC) and GC-MS analysis using an Agilent Technologies 6890A GC instrument (Palo Alto, CA, USA) fitted with a Supelco Equity™-1 fused silica capillary column (15 m×0.1 mm i.d., 0.1 μm film thickness, Bellefont, PA, USA), an FID, a split/splitless injector and an Agilent Technologies 7683B Series auto sampler and injector. Helium was the carrier gas. Samples were injected in split-less mode at an oven temperature of 120° C. After injection, the oven temperature was raised to 270° C. at 10° C. min$^{-1}$ and finally to 300° C. at 5° C. min$^{-1}$. Eluted compounds were quantified with Agilent Technologies ChemStation software (Palo Alto, CA, USA). GC results were subject to an error of not more than 55% of individual component areas.

TABLE 17

Lipid class composition (% of total lipid obtained for each extraction step) of hexane and CM extracts from transgenic and control Camelina sativa seeds. SE, WE and HC were not separated from each other.

| Lipid class | Transgenic seeds | | Control seeds | |
| --- | --- | --- | --- | --- |
| | Hexane | CM | Hexane | CM |
| SE/WE/HC* | 1.0 | 1.4 | 1.0 | 1.4 |
| TAG | 95.6 | 44.2 | 96.0 | 13.1 |
| FFA | 0.9 | 1.3 | 0.8 | 1.4 |
| UN** | 0.9 | 1.1 | 0.8 | 1.2 |
| ST | 0.5 | 0.7 | 0.4 | 0.4 |
| MAG | 0.7 | 1.1 | 0.8 | 6.2 |
| PL | 0.3 | 50.3 | 0.3 | 76.3 |
| Total | 100.0 | 100.0 | 100.0 | 100.0 |

Abbreviations:
sterol esters (SE), wax esters (WE). hydrocarbons (HC), triacylglycerols (TAG), free fatty acids (FFA), unknown (UN), sterols (ST), monoacylglycerols (MAG), polar lipids (PL) consisting of glycolipids and phospholipids;
*SE, WE and HC co-elute with this system; May contain fatty alcohols and diacylglycerols (DAG).

GC-mass spectrometric (GC-MS) analyses were performed on a Finnigan Trace ultra Quadrupole GC-MS (model: ThermoQuest Trace DSQ, Thermo Electron Corporation). Data were processed with ThermoQuest Xcalibur software (Austin, TX, USA). The GC was fitted with an on-column injector and a capillary HP-5 Ultra Agilent J & W column (50 m×0.32 mm i.d., 0.17 μm film thickness, Agilent Technologies, Santa Clara, CA, USA) of similar polarity to that described above. Individual components were identified using mass spectral data and by comparing retention time data with those obtained for authentic and laboratory standards. A full procedural blank analysis was performed concurrent to the sample batch.

The data for the fatty acid composition in the different lipid classes in the extracts are shown in Table 18. In the DHA-producing Camelina seed, the DHA was distributed in the major lipid fractions (TAG, phospholipids and glycolipids) at a proportion ranging between 1.6% and 6.8% with an inverse relationship between the proportions of DHA and ALA. The TAG-rich hexane extract from the transgenic seed contained 6.8% DHA and 41% ALA (Table 18). The polar lipid-rich CM extract contained 4.2% DHA and 50% ALA i.e. relatively less DHA and more ALA. Residual TAG from the polar lipid-rich CM extract contained 6% DHA and 40% ALA. The glycolipid fraction isolated from the CM extract contained 3% DHA and 39% ALA and the phospholipid fraction contained the lowest level of DHA (1.6%) and the highest levels of ALA (54%). The transgenic *Camelina* seed contained higher levels of ALA and lower levels of LA (linoleic acid, 18:2ω6) compared with the control seeds in the major lipid classes (TAG, glycolipids and phospholiporganic phase was washed with 2 mL of Milli-Q water by shaking and centrifugation. After taking off the top sterol-containing organic layer, the solvent was evaporated using a stream of nitrogen gas and the sterols and alcohols silylated using 200 μL of Bis(trimethylsilyl)-trifluoroacetamide (BSTFA, Sigma-Aldrich) by heating for 2 h at 80° C. in a sealed GC vial. By this method, free hydroxyl groups were converted to their trimethylsilyl ethers. The sterol- and alcohol-OTMSi derivatives were dried under a stream of nitrogen gas on a heating block (40° C.) and re-dissolved in dichloromethane (DCM) immediately prior to GC/GC-MS analysis as described above.

TABLE 18

Fatty acid composition (% of total fatty acids) of lipid extracts and fractions of transgenic and control *C. sativa* seeds.

| | Transgenic seeds | | | | | | Control seeds | | | | | |
| | Hexane | CM | | | Meal | Hexane | CM | | | Meal |
| Fatty acid | TAG | Total | TAG | GL | PL | Residue | TAG | Total | TAG | GL | PL | Residue |
| --- | --- | --- | --- | --- | --- | --- | --- | --- | --- | --- | --- | --- |
| 16:1ω7 | 0.1 | 0.2 | 0.1 | 0.2 | 0.1 | 0.2 | 0.1 | 0.2 | 0.2 | — | — | 0.3 |
| 16:0 | 6.2 | 12.8 | 6.8 | 21.3 | 19.4 | 10.4 | 6.7 | 12.8 | 7.8 | 29.6 | 13.7 | 10.3 |
| 18:4ω3 | 3.7 | 3.3 | 3.4 | 2.1 | 2.9 | 3.6 | — | — | — | — | — | — |
| 18:2ω6 | 7.1 | 3.9 | 8.8 | 7.2 | 3.7 | 8.8 | 22.2 | 28.4 | 29.4 | 20.8 | 29.3 | 27.9 |
| 18:3ω3 | 41.9 | 50.3 | 39.9 | 38.6 | 54.1 | 38.9 | 32.0 | 20.6 | 19.7 | 13.0 | 12.3 | 20.0 |
| 18:1ω9 | 11.1 | 4.7 | 9.6 | 7.2 | 2.8 | 8.1 | 14.0 | 25.4 | 13.3 | 14.7 | 35.7 | 14.3 |
| 18:1ω7 | 1.4 | 2.3 | 2.1 | 3.7 | 3.4 | 2.8 | 1.0 | 1.5 | 2.2 | 4.0 | 2.8 | 2.2 |
| 18:0 | 3.2 | 4.0 | 3.0 | 4.5 | 5.7 | 3.1 | 3.0 | 2.7 | 2.9 | 5.7 | 3.6 | 2.7 |
| 20:5ω3 | 0.4 | 0.2 | 0.3 | — | — | 0.3 | — | — | — | — | — | — |
| 20:4ω3 | 0.4 | 0.4 | 0.4 | — | 0.2 | 0.3 | — | — | — | — | — | — |
| 20:2ω6 | 0.7 | 0.7 | 0.8 | 0.6 | 0.4 | 0.7 | 1.8 | 0.8 | 2.1 | 1.2 | — | 1.8 |
| 20:3ω3 | 0.8 | 1.2 | 0.9 | 0.6 | 1.3 | 0.5 | 0.9 | 0.3 | — | — | — | 0.4 |
| 20:1ω9/11 | 11.6 | 6.1 | 10.9 | 5.1 | 1.3 | 8.4 | 12.5 | 3.0 | 11.1 | 4.2 | 1.7 | 9.4 |
| 20:1ω7 | 0.6 | 0.8 | 1.4 | 0.6 | 0.2 | 1.1 | 0.6 | 0.6 | 2.0 | 1.3 | — | 1.8 |
| 20:0 | 1.3 | 0.8 | 1.4 | 0.6 | 0.1 | 1.4 | 1.5 | 0.7 | 2.0 | 1.4 | — | 1.8 |
| 22:6ω3 | 6.8 | 4.2 | 6.1 | 3.0 | 1.6 | 5.4 | — | — | — | — | — | — |
| 22:5ω3 | 0.3 | 1.1 | 0.4 | 0.6 | 1.4 | 0.3 | — | — | — | — | — | — |
| 22:1ω9 | 1.3 | 1.0 | 1.8 | 0.6 | 0.1 | 1.5 | 2.7 | 0.7 | 3.6 | 0.9 | — | 2.9 |
| 22:0 | 0.3 | 0.2 | 0.3 | 0.6 | 0.1 | 0.7 | 0.3 | 0.2 | 0.7 | 0.8 | — | 0.8 |
| 24:1ω9 | 0.3 | 0.4 | 0.4 | 0.6 | 0.3 | 0.6 | 0.3 | 0.6 | 0.7 | 0.9 | 0.5 | 1.0 |
| 24:0 | 0.1 | 0.4 | 0.2 | 0.9 | 0.4 | 1.1 | 0.1 | 0.4 | 0.5 | 1.4 | 0.4 | 1.3 |
| others * | 0.4 | 1.0 | 1.0 | 1.4 | 0.5 | 1.8 | 0.3 | 1.1 | 0.9 | 0.1 | — | 1.1 |
| Total | 100 | 100 | 100 | 100 | 100 | 100 | 100 | 100 | 100 | 100 | 100 | 100 |

Abbreviations:
triacylglycerols (TAG),
glycolipids (GL),
phospholipids (PL);
Total: polar lipid-rich extract containing GL and PL from CM extraction;
TAG, GL and PL were separated by silica column chromatography of the CM extracts;
* Sum of minor fatty acids ids). The proportions of ALA and LA were: ALA 39%-54% and LA 4%-9% for transgenic seeds and ALA 12%-32% and LA 20%-29% for control seeds. The relative level of erucic acid (22:1ω9) was lower in all fractions in the transgenic seeds than in the control seeds, for example, in the hexane extracts 1.3% versus 2.7% (Table 18).

Sterol Composition in the Seeds

To determine the sterol content and composition in the extracted lipids, samples of approximately 10 mg total lipid from the TAG-rich hexane extract and the polar lipid-rich CM extract were saponified using 4 mL 5% KOH in 80% MeOH and heated for 2 h at 80° C. in a Teflon-lined screw-capped glass test tube. After the reaction mixtures were cooled, 2 mL of Milli-Q water was added and the sterols and alcohols were extracted three times into 2 mL of hexane:dichloromethane (4:1, v/v) by shaking and vortexing. The mixtures were centrifuged and each extract in the The major sterols in both the transgenic and control seeds were 24-ethylcholesterol (sitosterol, 43%-54% of the total sterols), 24-methylcholesterol (campesterol, 20%-26%) with lower levels of cholesterol (5%-8%), brassicasterol (2%-7%), isofucosterol (Δ5-avenasterol, 4%-6%), stigmasterol (0.5%-3%), cholest-7-en-3β-ol, (0.2%-0.5%), 24-methylcholestanol (campestanol, 0.4%-1%) and 24-dehydrocholesterol (0.5%-2%) (Table 19). These nine sterols accounted for 86%-95% of the total sterols, with the remaining components being sterols only partially identified for the numbers of carbons and double bonds. The overall sterol profiles were similar between the transgenic and control seeds for both the hexane and CM extracts.

Fatty Alcohol Analysis

Fatty alcohols in the seeds were derivatised and analysed as for the sterols. A series of fatty alcohols from $C_{16}$-$C_{22}$, with accompanying iso-branched fatty alcohols, were identified in both the hexane and CM extracts. Similar profiles were observed for the transgenic and control seeds, with some variation in the proportions of individual components observed. Phytol, derived from chlorophyll, was the major aliphatic alcohol and accounted for 47% and 37% of the total fatty alcohols in the hexane fractions in the transgenic and control seeds, respectively. The odd-chain alcohols were present at higher levels in the CM extract (37%-38% of the total fatty alcohol content) than in the hexane extract (16%-23%). Iso-17:0 (16%-38%) predominated over 17:0 (0.3%-5.7%). Another odd-chain alcohol present was 19:0 (4.5%-6.5%). Other alcohols detected included iso-16:0, 16:0, iso-18:0, 18:1, 18:0, with minor levels of iso-20:0, 20:1, 20:0, iso-22:0, 22:1 and 22:0 also present.

Discussion

The results indicated that crushing using a motorized mortar and pestle with multiple extractions with hexane at room temperature was effective in recovering most of the TAG-containing oil from the transgenic seeds. In addition to the oil from the transgenic seeds containing moderate levels of DHA, the transgenic seeds also had markedly higher levels of ALA in the major lipid classes (triacylglycerols, glycolipids and phospholipids) compared with the control seeds. This showed that the Δ15-desaturase activity was considerably enhanced in the transgenic seeds during seed development. Interestingly, there were some slight differences in the fatty acid composition and proportion of DHA in the various extracts and fractions with the DHA levels being higher in the TAG-rich hexane extract and TAG from CM extraction (6%-6.8%) and lower in the polar lipid fractions (3% in glycolipids and 1.6% in phospholipids). The level of 16:0 was higher in the polar lipid fractions of glycolipids and phospholipids in the CM extracts (19%-21%) compared with the TAG-rich hexane extract and TAG from CM extraction (6%-7%).

TABLE 19

Sterol composition (% of total sterols) of transgenic and control Camelina seeds.

| Sterols | Transgenic seeds | | Control seeds | |
|---|---|---|---|---|
| | Hexane | CM | Hexane | CM |
| 24-dehydrocholesterol | 0.8 | 1.8 | 0.5 | 1.4 |
| cholesterol | 5.7 | 7.6 | 4.7 | 7.2 |
| brassicasterol | 4.4 | 6.5 | 1.9 | 4.2 |
| cholest-7-en-3β-ol | 0.2 | 0.5 | 0.3 | 0.4 |
| campesterol | 24.5 | 20.8 | 25.7 | 21.7 |
| campestanol | 0.4 | 1.1 | 0.4 | 0.9 |
| stigmasterol | 1.0 | 2.6 | 0.5 | 1.6 |
| sitosterol | 54.3 | 43.7 | 53.8 | 42.9 |
| Δ5-avenasterol | 4.2 | 5.2 | 4.7 | 5.5 |
| Sum | 95.5 | 89.6 | 92.6 | 85.9 |
| Others | | | | |
| UN1 C28 1db | 0.6 | 1.2 | 0.7 | 1.2 |
| UN2 C29 1db | 1.2 | 2.0 | 1.2 | 2.4 |
| UN3 C29 2db | 0.9 | 1.8 | 1.3 | 2.4 |
| UN4 C28 1db | 0.3 | 0.9 | 0.6 | 1.1 |
| UN5 C30 2db | 1.2 | 1.8 | 1.4 | 1.8 |
| UN6 C29 1db + C30 2db | 0.3 | 2.7 | 2.2 | 5.2 |
| Sum of others | 4.5 | 10.4 | 7.4 | 14.1 |
| Total | 100 | 100 | 100 | 100 |

Abbreviations:
UN denotes unknown sterol, the number after C indicates the number of carbon atoms and db denotes number of double bonds The sterol composition of the transgenic seeds and control seeds were similar to that found in refined Camelina oil (Shukla et al., 2002) with the same major sterols present, indicating that the added genes did not affect sterol synthesis in the seeds. The level of cholesterol in Camelina oil was higher than occurred in most vegetable oils. Brassicasterol was present, which is a characteristic sterol found in the Brassicaceae family which includes Camelina sativa.

Example 9. Production of LC-PUFA in Brassica juncea Seeds

Transgenic Brassica juncea plants were produced using the GA7-modB construct (Example 4) for the production of DHA, as follows. B. juncea seeds of a long-daylength sensitive variety were sterilized using chlorine gas as described by Kereszt et al. (2007). Sterilized seeds were germinated on ½ strength MS media (Murashige and Skoog, 1962) solidified with 0.8% agar, adjusted to pH 5.8 and grown at 24° C. under fluorescent lighting (50 µE/m²s) with a 16/8 hour (light/dark) photoperiod for 6-7 days. Cotyledonary petioles with 2-4 mm stalk were isolated aseptically from these seedlings and used as explants. Agrobacterium tumefaciens strain AGL1 was transformed with the binary construct GA7. Agrobacterium culture was initiated and processed for infection as described by Belide et al. (2013). For all transformations, about 50 freshly-isolated cotyledonary petioles were infected with 10 ml of A. tumefaciens culture for 6 minutes. The infected petioles were blotted on sterile filter paper to remove excess A. tumefaciens and transferred to co-cultivation media (MS containing 1.5 mg/L BA, 0.01 mg/L NAA and 100 µM acetosyringone, also supplemented with L-cysteine (50 mg/L), ascorbic acid (15 mg/L) and MES (250 mg/L). All plates were sealed with micropore tape and incubated in the dark at 24° C. for 48 hours of co-cultivation. The explants were then transferred to pre-selection medium (MS-agar containing 1.5 mg/L BA, 0.01 mg/L NAA, 3 mg/L AgNO₃, 250 mg/L cefotaxime and 50 mg/L timentin) and cultured for 4-5 days at 24° C. with a 16/8 hour photoperiod before the explants were transferred to selection medium (MS-agar containing 1.5 mg/L BA, 0.01 mg/L NAA, 3 mg/L AgNO₃, 250 mg/L cefotaxime, 50 mg/L timentin and 5 mg/L PPT) and cultured for 4 weeks at 24° C. with 16/8 hour photoperiod. Explants with green callus were transferred to shoot regeneration medium (MS-agar containing 2.0 mg/L BA, 3 mg/L AgNO₃, 250 mg/L cefotaxime, 50 mg/L timentin and 5 mg/L PPT) and cultured for another 2 weeks. Small regenerating shoot buds were transferred to hormone free MS medium (MS-agar containing 3 mg/L AgNO₃, 250 mg/L cefotaxime, 50 mg/L timentin and 5 mg/L PPT) and cultured for another 2-3 weeks.

Potential transgenic shoots of at least 1.5 cm in size were isolated and transferred to root induction medium (MS-agar containing 0.5 mg/L NAA, 3 mg/L AgNO₃, 250 mg/L cefotaxime and 50 mg/L timentin) and cultured for 2-3 weeks. Transgenic shoots confirmed by PCR and having prolific roots were transferred to soil in a greenhouse and grown under a photoperiod of 16/8 h (light/dark) at 22° C. Three confirmed transgenic plants were obtained. The transformed plants were grown in the greenhouse, allowed to self-fertilise, and T1 seed harvested. The fatty acid composition was analysed of the lipid from pools of T1 seeds from each TO transformed plants, which showed the presence of 2.8% DPA and 7.2% DHA in one line designated JT1-4, whereas another line designated JT1-6 exhibited 2.6% DPA.

Seedoil from individual T1 seeds was analysed for fatty acid composition; some of the data is shown in Table 20. Several T1 seeds produced DHA at a level of 10% to about 21% of the total fatty acid content, including JT1-4-A-13, JT1-4-A-5, and JT1-4-B-13. Surprisingly and unexpectedly, some of the T1 seeds contained DPA at levels of 10% to about 18% of the total fatty acid content and no detectable DHA (<0.1%). The inventors concluded that the Δ4-desaturase gene in the T-DNA inserted in these plants was inactivated, through a spontaneous mutation, similar to that described in Example 3. T1 seeds were germinated and one emerged cotyledon from each analysed for fatty acid composition in the remaining oil. The remainder of each seedling was maintained and grown to maturity to provide T2 seed.

Transgenic plants which were homozygous for single T-DNA insertions were identified and selected. Plants of one selected line designated JT1-4-17 had a single T-DNA insertion and produced DHA with only low levels of DPA, whereas those of a second selected line designated JT1-4-34 also had a single T-DNA insertion but produced DPA without producing DHA. The inventors concluded that the original transformant contained two separate T-DNAs, one which conferred production of DHA and the other which conferred production of DPA without DHA. The *B. juncea* plants producing DHA in their seeds were crossed with the plants producing DPA in their seeds. The F1 progeny included plants which were heterozygous for both of the T-DNA insertions. Seed from these progeny plants were observed to produce about 20% DHA and about 6% DPA, for a total DHA+DPA content of 26%. The F1 plants are self-fertilised and progeny which are homozygous for both of the T-DNA insertions are expected to produce up to 35% DHA and DPA.

About 18% DPA was observed in the lipid of pooled seed of the T3 progeny designated JT1-4-34-11. Similarly about 17.5% DHA was observed in the lipid from pooled seed in the progeny of T3 JT1-4-17-20. Fatty acid compositions of JT1-4 T1 pooled seed, T1 single seed, T2 pooled seed, T2 single seed, and T3 pooled seed, T3 single seed are in Tables 21 to 24. JT1-4 T3 segregant JT-1-4-34-11, had a pooled T3 seed DPA content of 18% and the single seed from this particular segregant had a DPA content of about 26%, each as a percentage of the total fatty acid content.

The following parameters were calculated for oil from a seed having 17.9% DPA: total saturated fatty acids, 6.8%; total monounsaturated fatty acids, 36.7%; total polyunsaturated fatty acids, 56.6%; total ω6 fatty acids, 7.1%; new 06 fatty acids, 0.4% of which all was GLA; total ω3 fatty acids, 46.5%; new ω3 fatty acids, 24.0%; ratio of total 06:total ω3 fatty acids, 6.5; ratio of new ω6:new ω3 fatty acids, 60; the efficiency of conversion of oleic acid to LA by Δ12-desaturase, 61%; the efficiency of conversion of ALA to SDA by Δ6-desaturase, 51%; the efficiency of conversion of SDA to ETA acid by Δ6-elongase, 90%; the efficiency of conversion of ETA to EPA by Δ5-desaturase, 87%; the efficiency of conversion of EPA to DPA by Δ5-elongase, 98%.

In order to produce more transgenic plants in *B. juncea* with the modB construct, the transformation was repeated five times and 16 presumed transgenic shoots/seedlings were regenerated. T1 seed analysis is carried out to determine DPA and DHA content.

In order to produce further seed containing DPA and no DHA, a genetic construct which was a variant of the modB construct was made, lacking a Δ4-desaturase gene, as follows. Two DNA fragments, EPA-DPA fragment 1 and EPA-DPA fragment 2, were synthesised (Geneart, Germany) with appropriate restriction sites. An intermediate cloning vector, pJP3660, was generated by cloning the AatII-MluI fragment of EPA-DPA fragment 1 into the AscI-AatII sites in a vector designated 11ABHZHC_GA7-frag_d6D_pMS, a vector earlier used in the construction of GA7-modB which contained a Δ6 desaturase cassette. pJP3661 was then generated by cloning the PmeI-PspOMI fragment of pJP3660 into the PmeI-PspOMI sites of modB. The DPA vector, pJP3662 (FIG. 4), was then assembled by cloning the BsiWI-PspOMI fragment of EPA-DPA fragment 2 into the BsiWI-PspOMI sites of pJP3661. This vector contained the fatty acid biosynthesis genes coding for enzymes which converted oleic acid to DPAω3 and the corresponding ω6 fatty acid. The resultant construct used to transform *B. juncea* and *B. napus*. Progeny seed with up to 35% DPA in the total fatty acid content of the seed lipid are produced.

When the oil extracted from the seeds of a plant producing DHA was examined by NMR, at least 95% of the DHA was observed to be present at the sn-1,3 position of the TAG molecules.

TABLE 20

| | | | | | | | | | | | | | | | | | |
|---|---|---|---|---|---|---|---|---|---|---|---|---|---|---|---|---|---|
| Fatty acid composition of seedoil from T1 seeds of *B. juncea* transformed with the T-DNA from GA7. | | | | | | | | | | | | | | | | | |
| T1 seed No. | C16: 0 | 16: 1d9 | C18: 0 | C18: 1 | C18: 1d11 | C18: 2 | C18: 3n6 | C18: 3n3 | C20: 0 | 18: 4n3 | C20: 1d11 | C20: 2n6 | C20: 3n3 | 20: 4n3 | 20: 5n3 | 22: 5n3 | C22: 6n3 |
| JT1-4-A-1 | 5.0 | 0.2 | 2.7 | 23.5 | 3.4 | 17.0 | 0.7 | 24.8 | 0.7 | 2.0 | 1.1 | 0.2 | 0.8 | 4.0 | 0.6 | 2.4 | 9.9 |
| JT1-4-A-2 | 4.3 | 0.3 | 2.6 | 37.2 | 3.2 | 11.0 | 0.3 | 22.1 | 0.7 | 0.9 | 1.3 | 0.2 | 1.4 | 3.2 | 0.3 | 9.4 | 0.0 |
| JT1-4-A-3 | 5.6 | 0.3 | 2.7 | 20.8 | 3.7 | 16.0 | 0.6 | 24.4 | 0.7 | 2.0 | 0.9 | 0.2 | 1.1 | 4.5 | 0.7 | 3.1 | 11.4 |
| JT1-4-A-4 | 4.6 | 0.4 | 2.8 | 36.2 | 3.4 | 10.6 | 0.3 | 24.5 | 0.8 | 9.9 | 1.7 | 0.2 | 0.3 | 0.5 | 0.0 | 2.5 | 0.0 |
| JT1-4-A-5 | 5.0 | 0.2 | 3.2 | 20.3 | 3.6 | 13.7 | 0.7 | 25.9 | 0.7 | 2.0 | 0.9 | 0.2 | 1.3 | 4.4 | 1.5 | 1.6 | 13.5 |
| JT1-4-A-6 | 4.8 | 0.4 | 3.4 | 37.9 | 3.7 | 7.4 | 0.4 | 19.9 | 0.9 | 1.4 | 1.4 | 0.1 | 0.8 | 1.9 | 0.4 | 13.9 | 0.0 |
| JT1-4-A-7 | 5.6 | 0.3 | 3.0 | 26.2 | 4.0 | 8.9 | 0.3 | 26.6 | 0.6 | 1.8 | 1.0 | 0.1 | 1.8 | 3.7 | 1.3 | 2.2 | 11.3 |
| JT1-4-A-8 | 4.8 | 0.4 | 2.9 | 40.3 | 3.4 | 7.8 | 0.3 | 22.2 | 0.8 | 1.4 | 1.3 | 0.1 | 0.8 | 2.4 | 0.4 | 9.6 | 0.0 |
| JT1-4-A-9 | 7.1 | 0.3 | 3.6 | 17.7 | 4.3 | 17.9 | 0.7 | 23.1 | 1.0 | 2.1 | 0.8 | 0.2 | 1.5 | 3.6 | 0.8 | 2.0 | 11.9 |
| JT1-4-A-10 | 5.1 | 0.2 | 4.2 | 22.3 | 3.4 | 19.5 | 0.7 | 21.7 | 0.8 | 1.5 | 0.9 | 0.2 | 1.7 | 7.8 | 0.9 | 1.0 | 6.5 |
| JT1-4-A-11 | 5.0 | 0.5 | 2.8 | 37.6 | 4.0 | 7.1 | 0.4 | 19.2 | 0.7 | 1.9 | 1.4 | 0.2 | 0.5 | 1.6 | 0.3 | 15.5 | 0.0 |
| JT1-4-A-12 | 5.2 | 0.3 | 3.0 | 28.2 | 4.0 | 9.2 | 0.3 | 27.4 | 0.6 | 1.9 | 0.9 | 0.1 | 1.5 | 3.2 | 1. | 1.8 | 10.2 |
| JT1-4-A-13 | 5.4 | 0.2 | 3.0 | 16.7 | 4.1 | 9.9 | 0.6 | 29.9 | 0.7 | 2.2 | 1.0 | 0.2 | 1.7 | 2.0 | 1.1 | 2.0 | 17.9 |
| JT1-4-A-14 | 5.1 | 0.4 | 3.1 | 30.0 | 4.0 | 11.5 | 0.3 | 27.7 | 0.7 | 2.2 | 1.0 | 0.1 | 0.6 | 2.4 | 0.8 | 1.3 | 7.8 |
| JT1-4-A-15 | 5.1 | 0.4 | 2.5 | 34.2 | 3.6 | 6.9 | 0.6 | 20.4 | 0.7 | 1.6 | 1.1 | 0.2 | 0.6 | 4.7 | 0.9 | 15.2 | 0.0 |
| JT1-4-B-1 | 5.5 | 0.2 | 2.7 | 18.9 | 4.0 | 17.6 | 0.8 | 24.1 | 0.8 | 2.2 | 1.0 | 0.2 | 1.2 | 4.6 | 0.9 | 2.2 | 11.5 |
| JT1-4-B-2 | 5.5 | 0.2 | 2.7 | 20.2 | 4.0 | 14.3 | 0.5 | 25.5 | 0.7 | 1.7 | 0.9 | 0.2 | 1.6 | 8.7 | 1.3 | 2.2 | 8.5 |
| JT1-4-B-3 | 5.3 | 0.3 | 3.6 | 34.1 | 3.5 | 35.0 | 0.6 | 9.3 | 0.8 | 0.2 | 1.4 | 0.4 | 0.6 | 0.9 | 0.1 | 0.3 | 2.1 |
| JT1-4-B-4 | 5.3 | 0.3 | 3.1 | 25.2 | 3.6 | 17.0 | 0.7 | 24.1 | 0.7 | 1.9 | 1.0 | 0.2 | 0.8 | 4.3 | 0.5 | 2.3 | 7.8 |
| JT1-4-B-5 | 5.5 | 0.5 | 2.2 | 30.1 | 4.6 | 10.2 | 0.5 | 21.7 | 0.6 | 1.4 | 1.1 | 0.2 | 0.9 | 2.4 | 0.5 | 16.1 | 0.0 |
| JT1-4-B-6 | 5.6 | 0.3 | 2.5 | 19.5 | 3.8 | 15.2 | 0.5 | 27.7 | 0.6 | 2.1 | 0.9 | 0.2 | 1.1 | 3.7 | 0.6 | 3.3 | 11.1 |

TABLE 20-continued

Fatty acid composition of seedoil from T1 seeds of *B. juncea* transformed with the T-DNA from GA7.

| T1 seed No. | C16:0 | 16:1d9 | C18:0 | C18:1 | C18:1d11 | C18:2 | C18:3n6 | C18:3n3 | C20:0 | 18:4n3 | C20:1d11 | C20:2n6 | 20:3n3 | 20:4n3 | 20:5n3 | 22:5n3 | C22:6n3 |
|---|---|---|---|---|---|---|---|---|---|---|---|---|---|---|---|---|---|
| JT1-4-B-7 | 5.9 | 0.5 | 2.0 | 29.9 | 4.0 | 11.2 | 0.3 | 26.2 | 0.6 | 11.5 | 1.4 | 0.2 | 0.3 | 0.4 | 0.0 | 4.1 | 0.1 |
| JT1-4-B-8 | 6.2 | 0.5 | 1.9 | 33.1 | 4.0 | 30.0 | 0.5 | 12.7 | 0.6 | 0.3 | 1.3 | 0.4 | 1.4 | 0.9 | 0.1 | 4.4 | 0.0 |
| JT1-4-B-9 | 4.9 | 0.2 | 3.4 | 24.6 | 3.0 | 18.5 | 0.3 | 26.2 | 0.8 | 1.3 | 1.1 | 0.2 | 2.0 | 5.5 | 0.6 | 0.8 | 5.2 |
| JT1-4-B-10 | 5.2 | 0.3 | 2.7 | 19.0 | 4.0 | 12.0 | 0.6 | 30.5 | 0.7 | 1.6 | 1.0 | 0.2 | 1.7 | 4.9 | 1.1 | 3.0 | 10.2 |
| JT1-4-B-11 | 4.8 | 0.2 | 3.0 | 23.7 | 3.1 | 18.1 | 0.6 | 23.5 | 0.7 | 1.6 | 1.2 | 0.2 | 1.5 | 4.5 | 0.8 | 1.6 | 9.6 |
| JT1-4-B-12 | 5.0 | 0.2 | 2.6 | 19.6 | 3.4 | 12.5 | 0.6 | 26.9 | 0.8 | 3.1 | 1.1 | 0.2 | 0.9 | 5.6 | 0.9 | 3.5 | 11.7 |
| JT1-4-B-13 | 5.6 | 0.3 | 2.8 | 20.9 | 3.9 | 11.9 | 0.4 | 27.0 | 0.7 | 2.0 | 1.0 | 0.2 | 1.7 | 2.3 | 0.7 | 4.1 | 13.5 |
| JT1-4-B-14 | 5.1 | 0.3 | 3.1 | 25.5 | 3.3 | 16.7 | 0.7 | 23.9 | 0.8 | 1.8 | 1.2 | 0.2 | 0.9 | 2.6 | 0.4 | 2.9 | 9.2 |
| JT1-4-B-15 | 5.6 | 0.3 | 2.7 | 19.5 | 4.1 | 14.0 | 0.8 | 24.6 | 0.7 | 2.7 | 0.9 | 0.2 | 0.7 | 9.4 | 1.3 | 2.5 | 8.5 |

The seedoil samples also contained 0.1% C14:0; 0.1-0.2% C16:3; 0.0-0.1% of each of C20:1Δ13, C20:3ω6 and C20:4ω6; 0.3-0.4% C22:0; no C22:1 and C22:2ω6; 0.2% C24:0 and 0.2-0.4% C24:1.

TABLE 21

Fatty acid composition of lipid from T1 seeds (pooled) of *B. juncea* transformed with the T-DNA from GA7-modB. The lipids also contained about 0.1% of each of 14:0, 16:3, 20:1d13, and 16:2, 22:1 were not detected.

| Seed | C16:0 | C16:1 | C18:0 | C18:1 | C18:1Δ11 | C18:2 | C18:3ω6 | C18:3ω3 | C20:0 | C18:4ω3 | C20:1Δ11 | C20:2ω6 |
|---|---|---|---|---|---|---|---|---|---|---|---|---|
| JT1-2 | 4.2 | 0.3 | 2.5 | 42.4 | 3.2 | 27.7 | 0.1 | 16.4 | 0.6 | 0.0 | 1.2 | 0.1 |
| JT1-3 | 4.5 | 0.3 | 2.7 | 44.6 | 3.1 | 26.8 | 0.1 | 14.8 | 0.7 | 0.0 | 1.2 | 0.1 |
| JT1-4 | 5.1 | 0.3 | 3.2 | 26.8 | 3.5 | 17.4 | 0.5 | 22.8 | 0.7 | 2.5 | 1.1 | 0.2 |
| JT1-5 | 4.7 | 0.4 | 2.4 | 41.6 | 3.4 | 28.4 | 0.1 | 15.8 | 0.7 | 0.0 | 1.2 | 0.1 |
| JT1-6 | 4.8 | 0.4 | 2.3 | 37.3 | 3.3 | 30.2 | 0.4 | 13.2 | 0.7 | 0.2 | 1.4 | 0.3 |

| Seed | C20:3ω6 | C20:4ω6 | C20:3ω3 | C22:0 | C20:4ω3 | C20:5ω3 | C22:2ω6 | C22:3ω3 | C24:0 | C24:1 | C22:5ω3 | C22:6ω3 |
|---|---|---|---|---|---|---|---|---|---|---|---|---|
| JT1-2 | 0.0 | 0.0 | 0.0 | 0.3 | 0.0 | 0.0 | 0.0 | 0.0 | 0.2 | 0.4 | 0.0 | 0.0 |
| JT1-3 | 0.0 | 0.0 | 0.0 | 0.3 | 0.0 | 0.0 | 0.0 | 0.0 | 0.2 | 0.4 | 0.0 | 0.0 |
| JT1-4 | 0.0 | 0.0 | 1.2 | 0.3 | 2.9 | 0.7 | 0.0 | 0.1 | 0.2 | 0.3 | 2.8 | 7.2 |
| JT1-5 | 0.0 | 0.0 | 0.0 | 0.3 | 0.0 | 0.0 | 0.0 | 0.0 | 0.2 | 0.4 | 0.0 | 0.0 |
| JT1-6 | 0.0 | 0.0 | 0.7 | 0.3 | 0.6 | 0.1 | 0.0 | 0.3 | 0.2 | 0.5 | 2.6 | 0.0 |

TABLE 22

Fatty acid composition of seed oil from T1(single) seeds of *B. juncea* transformed with the T-DNA from GA7-modB.

| T1 seed No. | C16:0 | C16:1Δ9 | C18:0 | C18:1 | 18:1Δ11 | C18:2 | C18:3ω6 | C18:3ω3 | C20:0 | C18:4ω3 | 20:1Δ11 | C20:2ω6 | C20:3ω3 | C20:4ω3 | C20:5ω3 | C22:5ω3 | C22:6ω3 |
|---|---|---|---|---|---|---|---|---|---|---|---|---|---|---|---|---|---|
| JT1-4-A-1 | 5.0 | 0.2 | 2.7 | 23.5 | 3.4 | 17.0 | 0.7 | 24.8 | 0.7 | 2.0 | 1.1 | 0.2 | 0.8 | 4.0 | 0.6 | 2.4 | 9.9 |
| JT1-4-A-2 | 4.3 | 0.3 | 2.6 | 37.2 | 3.2 | 11.0 | 0.3 | 22.1 | 0.7 | 0.9 | 1.3 | 0.2 | 1.4 | 3.2 | 0.3 | 9.4 | 0.0 |
| JT1-4-A-3 | 5.6 | 0.3 | 2.7 | 20.8 | 3.7 | 16.0 | 0.6 | 24.4 | 0.7 | 2.0 | 0.9 | S | 1.1 | 4.5 | 0.7 | 3.1 | 11.4 |
| JT1-4-A-4 | 4.6 | 0.4 | 2.8 | 36.2 | 3.4 | 10.6 | 0.3 | 24.5 | 0.8 | 9.9 | 1.7 | 0.2 | 0.3 | 0.5 | 0.0 | 2.5 | 0.0 |
| JT1-4-A-5 | 5.0 | 0.2 | 3.2 | 20.3 | 3.6 | 13.7 | 0.7 | 25.9 | 0.7 | 2.0 | 0.9 | 0.2 | 1.3 | 4.4 | 1.5 | 1.6 | 13.5 |
| JT1-4-A-6 | 4.8 | 0.4 | 3.4 | 37.9 | 3.7 | 7.4 | 0.4 | 19.9 | 0.9 | 1.4 | 1.4 | 0.1 | 0.8 | 1.9 | 0.4 | 13.9 | 0.0 |
| JT1-4-A-7 | 5.6 | 0.3 | 3.0 | 26.2 | 4.0 | 8.9 | 0.3 | 26.6 | 0.6 | 1.8 | 1.0 | 0.1 | 1.8 | 3.7 | 1.3 | 2.2 | 11.3 |
| JT1-4-A-8 | 4.8 | 0.4 | 2.9 | 40.3 | 3.4 | 7.8 | 0.3 | 22.2 | 0.8 | 1.4 | 1.3 | 0.1 | 0.8 | 2.4 | 0.4 | 9.6 | 0.0 |
| JT1-4-A-9 | 7.1 | 0.3 | 3.6 | 17.7 | 4.3 | 17.9 | 0.7 | 23.1 | 1.0 | 2.1 | 0.8 | 0.2 | 1.5 | 3.6 | 0.8 | 2.0 | 11.9 |
| JT1-4-A-10 | 5.1 | 0.2 | 4.2 | 22.3 | 3.4 | 19.5 | 0.7 | 21.7 | 0.8 | 1.5 | 0.9 | 0.2 | 1.7 | 7.8 | 0.9 | 1.0 | 6.5 |
| JT1-4-A-11 | 5.0 | 0.5 | 2.8 | 37.6 | 4.0 | 7.1 | 0.4 | 19.2 | 0.7 | 1.9 | 1.4 | 0.2 | 0.5 | 1.6 | 0.3 | 15.5 | 0.0 |
| JT1-4-A-12 | 5.2 | 0.3 | 3.0 | 28.2 | 4.0 | 9.2 | 0.3 | 27.4 | 0.6 | 1.9 | 0.9 | 0.1 | 1.5 | 3.2 | 1.1 | 1.8 | 10.2 |
| JT1-4-A-13 | 5.4 | 0.2 | 3.0 | 16.7 | 4.1 | 9.9 | 0.6 | 29.9 | 0.7 | 2.2 | 1.0 | 0.2 | 1.7 | 2.0 | 1.1 | 2.0 | 17.9 |
| JT1-4-A-14 | 5.1 | 0.4 | 3.1 | 30.0 | 4.0 | 11.5 | 0.3 | 27.7 | 0.7 | 2.2 | 1.0 | 0.1 | 0.6 | 2.4 | 0.8 | 1.3 | 7.8 |
| JT1-4-A-15 | 5.1 | 0.4 | 2.5 | 34.2 | 3.6 | 6.9 | 0.4 | 20.4 | 0.7 | 1.6 | 1.1 | 0.2 | 0.6 | 4.7 | 0.9 | 15.2 | 0.0 |
| JT1-4-B-1 | 5.5 | 0.2 | 2.7 | 18.9 | 4.0 | 17.6 | 0.8 | 24.1 | 0.8 | 2.2 | 1.0 | 0.2 | 1.2 | 4.6 | 0.9 | 2.2 | 11.5 |
| JT1-4-B-2 | 5.5 | 0.2 | 2.7 | 20.2 | 4.0 | 14.3 | 0.5 | 25.5 | 0.7 | 1.7 | 0.9 | 0.2 | 1.6 | 8.7 | 1.3 | 2.2 | 8.5 |
| JT1-4-B-3 | 5.3 | 0.3 | 3.6 | 34.1 | 3.5 | 35.0 | 0.6 | 9.3 | 0.8 | 0.2 | 1.4 | 0.4 | 0.6 | 0.9 | 0.1 | 0.3 | 2.1 |
| JT1-4-B-4 | 5.3 | 0.3 | 3.1 | 25.2 | 3.6 | 17.0 | 0.7 | 24.1 | 0.7 | 1.9 | 1.0 | 0.2 | 0.8 | 4.3 | 0.5 | 2.3 | 7.8 |
| JT1-4-B-5 | 5.5 | 0.5 | 2.2 | 30.1 | 4.6 | 10.2 | 0.5 | 21.7 | 0.6 | 1.4 | 1.1 | 0.2 | 0.9 | 2.4 | 0.5 | 16.1 | 0.0 |
| JT1-4-B-6 | 5.6 | 0.3 | 2.5 | 19.5 | 3.8 | 15.2 | 0.5 | 27.7 | 0.6 | 2.1 | 0.9 | 0.2 | 1.1 | 3.7 | 0.6 | 3.3 | 11.1 |
| JT1-4-B-7 | 5.9 | 0.5 | 2.0 | 29.9 | 4.0 | 11.2 | 0.3 | 26.2 | 0.6 | 11.5 | 1.4 | 0.2 | 0.3 | 0.4 | 0.0 | 4.1 | 0.1 |
| JT1-4-B-8 | 6.2 | 0.5 | 1.9 | 33.1 | 4.0 | 30.0 | 0.5 | 12.7 | 0.6 | 0.3 | 1.3 | 0.4 | 1.4 | 0.9 | 0.1 | 4.4 | 0.0 |
| JT1-4-B-9 | 4.9 | 0.2 | 3.4 | 24.6 | 3.0 | 18.5 | 0.3 | 26.2 | 0.8 | 1.3 | 1.1 | 0.2 | 2.0 | 5.5 | 0.6 | 0.8 | 5.2 |
| JT1-4-B-10 | 5.2 | 0.3 | 2.7 | 19.0 | 4.0 | 12.0 | 0.6 | 30.5 | 0.7 | 1.6 | 1.0 | 0.2 | 1.7 | 4.9 | 1.1 | 3.0 | 10.2 |

TABLE 22-continued

Fatty acid composition of seed oil from T1(single) seeds of *B. juncea* transformed with the T-DNA from GA7-modB.

| T1 seed No. | C16: 0 | C16: 1Δ 9 | C18: 0 | C18: 1 | 18: 1Δ 11 | C18: 2 | C18: 3ω 6 | C18: 3ω 3 | C20: 0 | C18: 4ω 3 | 20:1A 11 | C20: 2ω 6 | C20: 3ω 3 | C20: 4ω 3 | C20: 5ω 3 | C22: 5ω 3 | C22: 6ω 3 |
|---|---|---|---|---|---|---|---|---|---|---|---|---|---|---|---|---|---|
| JT1-4-B-11 | 4.8 | 0.2 | 3.0 | 23.7 | 3.1 | 18.1 | 0.6 | 23.5 | 0.7 | 1.6 | 1.2 | 0.2 | 1.5 | 4.5 | 0.8 | 1.6 | 9.6 |
| JT1-4-B-12 | 5.0 | 0.2 | 2.6 | 19.6 | 3.4 | 12.5 | 0.6 | 26.9 | 0.8 | 3.1 | 1.1 | 0.2 | 0.9 | 5.6 | 0.9 | 3.5 | 11.7 |
| JT1-4-B-13 | 5.6 | 0.3 | 2.8 | 20.9 | 3.9 | 11.9 | 0.4 | 27.0 | 0.7 | 2.0 | 1.0 | 0.2 | 1.7 | 2.3 | 0.7 | 4.1 | 13.5 |
| JT1-4-B-14 | 5.1 | 0.3 | 3.1 | 25.5 | 3.3 | 16.7 | 0.7 | 23.9 | 0.8 | 1.8 | 1.2 | 0.2 | 0.9 | 2.6 | 0.4 | 2.9 | 9.2 |
| JT1-4-B-15 | 5.6 | 0.3 | 2.7 | 19.5 | 4.1 | 14.0 | 0.8 | 24.6 | 0.7 | 2.7 | 0.9 | 0.2 | 0.7 | 9.4 | 1.3 | 2.5 | 8.5 |

The seed oil samples also contained 0.1% C14:0; 0.1-0.2% C16:3; 0.0-0.1% of each of C20:1Δ13, C20:3ω6 and C20:4ω6; 0.3-0.4% C22:0; no C22:1 and C22:2ω6: 0.2% C24:0 and 0.2-0.4% C24:1.

TABLE 23

Fatty acid composition of seed oil from T2 single seeds of *B. juncea* transformed with the T-DNA from GA7-modB.

| Code | C16: 0 | 16: 1d9 | 16: 3 | C18: 0 | C18: 1 | C18: 1d11 | C18: 2 | C18: 3n6 | C18: 3n3 | C20: 0 | 18: 4 | C20: 1d11 | C20: 2n6 | C20: 3n6 |
|---|---|---|---|---|---|---|---|---|---|---|---|---|---|---|
| JT-1-4-19 | 4.4 | 0.3 | 0.2 | 1.7 | 36.3 | 2.9 | 8.3 | 0.5 | 22.0 | 0.5 | 1.4 | 1.2 | 0.1 | 0.0 |
| JT-1-4-19 | 5.6 | 0.4 | 0.1 | 1.9 | 39.1 | 3.1 | 8.4 | 0.4 | 18.9 | 0.6 | 1.2 | 1.3 | 0.1 | 0.0 |
| JT-1-4-19 | 5.5 | 0.4 | 0.2 | 1.8 | 42.3 | 3.2 | 9.9 | 0.3 | 24.0 | 0.6 | 5.9 | 1.5 | 0.2 | 0.0 |
| JT-1-4-19 | 4.7 | 0.3 | 0.1 | 2.3 | 42.1 | 2.8 | 10.0 | 0.2 | 27.1 | 0.6 | 4.1 | 1.6 | 0.2 | 0.0 |
| JT-1-4-19 | 5.6 | 0.4 | 0.1 | 1.5 | 36.8 | 3.7 | 9.4 | 0.3 | 19.6 | 0.5 | 0.6 | 1.4 | 0.2 | 0.0 |
| JT-1-4-19 | 4.6 | 0.3 | 0.1 | 1.7 | 36.3 | 2.7 | 7.2 | 0.3 | 22.6 | 0.5 | 1.0 | 1.5 | 0.1 | 0.0 |
| JT-1-4-19 | 4.9 | 0.3 | 0.1 | 1.8 | 38.3 | 3.1 | 7.4 | 0.3 | 20.2 | 0.5 | 0.8 | 1.3 | 0.1 | 0.0 |
| JT-1-4-19 | 4.7 | 0.3 | 0.1 | 1.7 | 36.2 | 3.0 | 8.2 | 0.4 | 20.9 | 0.5 | 0.7 | 1.3 | 0.2 | 0.0 |
| JT-1-4-19 | 4.8 | 0.3 | 0.1 | 2.2 | 41.0 | 3.0 | 9.8 | 0.2 | 27.0 | 0.5 | 4.2 | 1.8 | 0.2 | 0.0 |
| JT-1-4-19 | 5.8 | 0.5 | 0.1 | 1.7 | 36.6 | 3.7 | 9.1 | 0.3 | 21.3 | 0.6 | 0.9 | 1.4 | 0.2 | 0.0 |
| JT-1-4-19 | 4.8 | 0.4 | 0.1 | 2.1 | 47.1 | 2.9 | 7.4 | 0.2 | 23.9 | 0.6 | 4.8 | 1.7 | 0.1 | 0.0 |
| JT-1-4-19 | 5.1 | 0.4 | 0.1 | 1.7 | 37.4 | 3.3 | 7.7 | 0.3 | 20.7 | 0.6 | 0.9 | 1.4 | 0.1 | 0.0 |
| JT-1-4-19 | 4.7 | 0.3 | 0.1 | 1.8 | 37.3 | 2.7 | 7.9 | 0.4 | 20.6 | 0.5 | 1.1 | 1.3 | 0.1 | 0.0 |
| JT-1-4-19 | 4.9 | 0.3 | 0.2 | 2.0 | 37.9 | 3.0 | 7.1 | 0.4 | 20.1 | 0.5 | 1.1 | 1.3 | 0.1 | 0.0 |
| JT-1-4-19 | 4.7 | 0.3 | 0.1 | 1.6 | 35.7 | 3.2 | 6.9 | 0.3 | 22.4 | 0.5 | 0.7 | 1.4 | 0.1 | 0.0 |
| JT-1-4-34 | 4.7 | 0.4 | 0.1 | 1.8 | 37.6 | 3.4 | 7.8 | 0.3 | 23.7 | 0.5 | 0.6 | 1.5 | 0.2 | 0.0 |
| JT-1-4-34 | 5.3 | 0.4 | 0.1 | 1.6 | 35.3 | 3.5 | 8.1 | 0.5 | 21.1 | 0.5 | 0.8 | 1.2 | 0.1 | 0.0 |
| JT-1-4-34 | 4.9 | 0.3 | 0.1 | 1.7 | 39.4 | 3.3 | 7.7 | 0.3 | 21.1 | 0.5 | 0.7 | 1.4 | 0.2 | 0.0 |
| JT-1-4-34 | 5.0 | 0.3 | 0.1 | 1.8 | 38.5 | 3.1 | 7.8 | 0.4 | 20.5 | 0.5 | 0.8 | 1.3 | 0.2 | 0.0 |
| JT-1-4-34 | 5.1 | 0.3 | 0.1 | 1.8 | 39.5 | 2.9 | 9.0 | 0.2 | 22.2 | 0.6 | 0.6 | 1.5 | 0.2 | 0.0 |
| JT-1-4-34 | 4.8 | 0.3 | 0.1 | 1.8 | 38.2 | 3.2 | 7.8 | 0.4 | 21.1 | 0.5 | 0.7 | 1.4 | 0.2 | 0.0 |
| JT-1-4-34 | 5.0 | 0.3 | 0.1 | 2.0 | 39.7 | 2.9 | 7.9 | 0.4 | 20.2 | 0.5 | 0.7 | 1.3 | 0.1 | 0.0 |
| JT-1-4-34 | 4.7 | 0.3 | 0.1 | 1.6 | 36.0 | 3.3 | 8.3 | 0.3 | 23.7 | 0.5 | 0.6 | 1.5 | 0.2 | 0.0 |
| JT-1-4-34 | 6.2 | 0.5 | 0.2 | 2.1 | 32.0 | 4.4 | 7.2 | 0.6 | 19.4 | 0.6 | 1.2 | 1.2 | 0.2 | 0.0 |

| Code | C20: 4n6 | C20: 3n3 | C22: 0 | 20: 4n3 | 20: 5n3 | C22: 26 | C22: 3n3 | C24: 0 | 22: 5n6 | 22: 4n3? | C24: 1 | 22: 5n3 | C22: 6n3 |
|---|---|---|---|---|---|---|---|---|---|---|---|---|---|
| JT-1-4-19 | 0.0 | 0.4 | 0.3 | 4.2 | 0.6 | 0.0 | 0.1 | 0.1 | 0.0 | 1.8 | 0.3 | 12.1 | 0.0 |
| JT-1-4-19 | 0.0 | 0.5 | 0.3 | 2.5 | 0.4 | 0.0 | 0.1 | 0.2 | 0.0 | 1.5 | 0.4 | 12.6 | 0.0 |
| JT-1-4-19 | 0.0 | 0.2 | 0.4 | 0.5 | 0.0 | 0.0 | 0.0 | 0.2 | 0.0 | 0.4 | 0.4 | 1.5 | 0.0 |
| JT-1-4-19 | 0.0 | 0.2 | 0.3 | 0.5 | 0.0 | 0.0 | 0.1 | 0.2 | 0.0 | 0.6 | 0.3 | 1.4 | 0.0 |
| JT-1-4-19 | 0.0 | 1.4 | 0.3 | 1.9 | 0.3 | 0.0 | 0.2 | 0.2 | 0.0 | 1.6 | 0.4 | 13.1 | 0.0 |
| JT-1-4-19 | 0.0 | 0.7 | 0.3 | 2.1 | 0.3 | 0.0 | 0.1 | 0.2 | 0.0 | 2.2 | 0.3 | 14.4 | 0.0 |
| JT-1-4-19 | 0.0 | 0.8 | 0.3 | 2.7 | 0.5 | 0.0 | 0.2 | 0.2 | 0.0 | 1.7 | 0.3 | 13.7 | 0.0 |
| JT-1-4-19 | 0.0 | 0.9 | 0.3 | 2.9 | 0.5 | 0.0 | 0.2 | 0.2 | 0.0 | 2.0 | 0.3 | 14.2 | 0.0 |
| JT-1-4-19 | 0.0 | 0.3 | 0.3 | 0.5 | 0.0 | 0.0 | 0.1 | 0.2 | 0.0 | 0.7 | 0.3 | 2.2 | 0.0 |
| JT-1-4-19 | 0.0 | 0.8 | 0.3 | 1.5 | 0.3 | 0.0 | 0.1 | 0.2 | 0.0 | 1.2 | 0.4 | 12.7 | 0.0 |
| JT-1-4-19 | 0.0 | 0.2 | 0.3 | 0.5 | 0.0 | 0.0 | 0.0 | 0.2 | 0.0 | 0.5 | 0.3 | 1.5 | 0.0 |
| JT-1-4-19 | 0.0 | 0.8 | 0.3 | 2.5 | 0.4 | 0.0 | 0.1 | 0.2 | 0.0 | 1.6 | 0.4 | 13.6 | 0.0 |
| JT-1-4-19 | 0.0 | 0.5 | 0.3 | 4.3 | 0.6 | 0.0 | 0.1 | 0.1 | 0.0 | 2.2 | 0.3 | 12.3 | 0.0 |
| JT-1-4-19 | 0.0 | 0.6 | 0.3 | 4.1 | 0.5 | 0.0 | 0.1 | 0.1 | 0.0 | 2.1 | 0.3 | 12.6 | 0.0 |
| JT-1-4-19 | 0.0 | 1.3 | 0.3 | 3.0 | 0.5 | 0.0 | 0.2 | 0.1 | 0.0 | 1.9 | 0.3 | 14.0 | 0.0 |
| JT-1-4-34 | 0.0 | 1.2 | 0.2 | 1.7 | 0.3 | 0.0 | 0.2 | 0.1 | 0.0 | 1.8 | 0.3 | 11.4 | 0.0 |
| JT-1-4-34 | 0.0 | 0.7 | 0.3 | 3.1 | 0.5 | 0.0 | 0.2 | 0.1 | 0.0 | 1.9 | 0.3 | 13.9 | 0.0 |
| JT-1-4-34 | 0.0 | 0.8 | 0.3 | 2.0 | 0.3 | 0.0 | 0.2 | 0.1 | 0.0 | 1.7 | 0.3 | 12.3 | 0.0 |
| JT-1-4-34 | 0.0 | 0.8 | 0.2 | 2.3 | 0.3 | 0.0 | 0.2 | 0.1 | 0.0 | 2.0 | 0.3 | 13.1 | 0.0 |
| JT-1-4-34 | 0.0 | 1.0 | 0.3 | 1.7 | 0.2 | 0.0 | 0.1 | 0.2 | 0.0 | 1.6 | 0.3 | 10.2 | 0.0 |
| JT-1-4-34 | 0.0 | 0.7 | 0.3 | 2.1 | 0.4 | 0.0 | 0.2 | 0.1 | 0.0 | 1.7 | 0.3 | 13.3 | 0.0 |
| JT-1-4-34 | 0.0 | 0.7 | 0.3 | 2.3 | 0.3 | 0.0 | 0.2 | 0.1 | 0.0 | 1.9 | 0.3 | 12.2 | 0.0 |
| JT-1-4-34 | 0.0 | 1.2 | 0.3 | 1.7 | 0.3 | 0.0 | 0.2 | 0.1 | 0.0 | 1.8 | 0.3 | 12.7 | 0.0 |
| JT-1-4-34 | 0.0 | 0.6 | 0.4 | 2.2 | 0.5 | 0.0 | 0.3 | 0.2 | 0.0 | 1.6 | 0.4 | 17.6 | 0.0 |

TABLE 24

Fatty acid composition of seed oil from T3 single seeds of *B. juncea* transformed with the T-DNA from GA7-modB.

| | C16:0 | 16:1d9 | 16:3 | C18:0 | C18:1 | C18:1d11 | C18:2 | C18:3n6 | C18:3n3 | C20:0 | 18:4 | C20:1d11 | 20:1d13 | C20:2n6 |
|---|---|---|---|---|---|---|---|---|---|---|---|---|---|---|
| JT-1-4-34-11 | 4.8 | 0.4 | 0.1 | 2.8 | 38.4 | 3.7 | 5.7 | 0.4 | 18.0 | 0.7 | 1.0 | 1.5 | 0.1 | 0.1 |
| JT-1-4-34-11 | 4.3 | 0.4 | 0.1 | 3.0 | 43.3 | 3.6 | 5.2 | 0.2 | 18.5 | 0.7 | 0.8 | 1.7 | 0.1 | 0.1 |
| JT-1-4-34-11 | 4.6 | 0.4 | 0.1 | 2.8 | 33.1 | 4.1 | 5.1 | 0.4 | 18.5 | 0.7 | 1.2 | 1.4 | 0.1 | 0.1 |
| JT-1-4-34-11 | 4.5 | 0.4 | 0.1 | 2.9 | 39.5 | 3.3 | 6.3 | 0.4 | 18.5 | 0.8 | 1.2 | 1.5 | 0.1 | 0.1 |
| JT-1-4-34-11 | 4.9 | 0.5 | 0.2 | 2.8 | 32.2 | 3.9 | 4.7 | 0.3 | 20.7 | 0.8 | 1.2 | 1.4 | 0.1 | 0.2 |
| JT-1-4-34-11 | 4.3 | 0.3 | 0.1 | 3.0 | 38.1 | 3.2 | 5.8 | 0.3 | 19.4 | 0.7 | 1.1 | 1.5 | 0.1 | 0.1 |
| JT-1-4-34-11 | 5.4 | 0.5 | 0.2 | 3.2 | 29.3 | 4.0 | 4.6 | 0.4 | 18.6 | 0.9 | 1.7 | 1.3 | 0.1 | 0.1 |
| JT-1-4-34-11 | 5.2 | 0.5 | 0.2 | 3.7 | 34.5 | 4.1 | 4.5 | 0.3 | 17.2 | 1.0 | 1.4 | 1.4 | 0.1 | 0.1 |
| JT-1-4-34-11 | 5.3 | 0.5 | 0.1 | 3.4 | 334 | 3.7 | 4.6 | 0.3 | 17.6 | 0.9 | 1.7 | 1.2 | 0.1 | 0.1 |
| JT-1-4-34-11 | 4.6 | 0.4 | 0.1 | 3.0 | 39.5 | 3.5 | 5.1 | 0.3 | 17.8 | 0.8 | 0.8 | 1.6 | 0.1 | 0.1 |
| JT-1-4-34-11 | 4.3 | 0.4 | 0.1 | 3.1 | 41.7 | 3.5 | 5.6 | 0.2 | 19.0 | 0.7 | 0.9 | 1.6 | 0.1 | 0.1 |
| JT-1-4-34-11 | 4.8 | 0.5 | 0.2 | 2.8 | 33.8 | 4.0 | 5.3 | 0.4 | 18.2 | 0.7 | 1.4 | 1.3 | 0.1 | 0.1 |
| JT-1-4-34-11 | 4.4 | 0.4 | 0.1 | 3.5 | 40.3 | 3.5 | 5.2 | 0.2 | 19.1 | 0.7 | 1.0 | 1.5 | 0.1 | 0.1 |
| JT-1-4-34-11 | 4.8 | 0.4 | 0.1 | 3.2 | 36.1 | 3.7 | 5.9 | 0.3 | 19.9 | 0.7 | 1.4 | 1.3 | 0.1 | 0.1 |
| JT-1-4-34-11 | 4.0 | 0.3 | 0.1 | 2.8 | 37.2 | 3.2 | 4.9 | 0.3 | 19.6 | 0.8 | 0.9 | 1.6 | 0.1 | 0.1 |
| JT-1-4-34-11 | 4.5 | 0.4 | 0.1 | 3.8 | 36.7 | 3.2 | 4.5 | 0.2 | 19.0 | 0.9 | 1.1 | 1.4 | 0.1 | 0.1 |
| JT-1-4-34-11 | 5.2 | 0.4 | 0.2 | 2.8 | 27.8 | 3.7 | 5.3 | 0.5 | 18.3 | 0.8 | 1.7 | 1.3 | 0.1 | 0.1 |
| JT-1-4-34-11 | 5.4 | 0.6 | 0.2 | 2.8 | 31.7 | 4.1 | 4.6 | 0.3 | 18.5 | 0.8 | 1.3 | 1.3 | 0.1 | 0.1 |
| JT-1-4-34-11 | 6.4 | 0.6 | 0.1 | 2.7 | 30.3 | 3.5 | 4.1 | 0.4 | 16.1 | 0.8 | 2.1 | 1.1 | 0.1 | 0.1 |
| JT-1-4-34-11 | 4.3 | 0.3 | 0.1 | 3.2 | 39.2 | 3.3 | 5.7 | 0.2 | 20.1 | 0.7 | 0.9 | 1.6 | 0.1 | 0.1 |
| JT-1-4-34-21 | 4.2 | 0.4 | 0.1 | 2.3 | 39.9 | 3.9 | 5.9 | 0.3 | 20.2 | 0.6 | 0.9 | 1.6 | 0.1 | 0.1 |
| JT-1-4-34-21 | 4.4 | 0.4 | 0.1 | 2.7 | 38.8 | 3.9 | 5.7 | 0.4 | 18.5 | 0.6 | 1.3 | 1.3 | 0.1 | 0.1 |
| JT-1-4-34-21 | 4.2 | 0.4 | 0.1 | 2.0 | 42.4 | 3.6 | 6.0 | 0.4 | 19.1 | 0.5 | 1.0 | 1.6 | 0.1 | 0.1 |

| | C20:3n6 | C20:4n6 | C20:3n3 | C22:0 | 20:4n3 | 20:5n3 | C22:26 | C22:3n3 | 22:5n6 | 22:4n3 | C24:1 | 22:5n3 | C22:6n3 |
|---|---|---|---|---|---|---|---|---|---|---|---|---|---|
| JT-1-4-34-11 | 0.0 | 0.0 | 1.1 | 0.3 | 1.4 | 0.4 | 0.0 | 0.3 | 0.0 | 1.4 | 0.5 | 16.3 | 0.0 |
| JT-1-4-34-11 | 0.0 | 0.0 | 1.4 | 0.3 | 1.2 | 0.3 | 0.0 | 0.2 | 0.0 | 1.2 | 0.3 | 12.4 | 0.0 |
| JT-1-4-34-11 | 0.0 | 0.0 | 1.1 | 0.3 | 1.6 | 0.5 | 0.0 | 0.3 | 0.0 | 1.4 | 0.4 | 20.8 | 0.0 |
| JT-1-4-34-11 | 0.0 | 0.0 | 1.0 | 0.3 | 1.7 | 0.3 | 0.0 | 0.2 | 0.0 | 1.8 | 0.3 | 14.2 | 0.0 |
| JT-1-4-34-11 | 0.0 | 0.0 | 2.0 | 0.3 | 1.4 | 0.5 | 0.0 | 0.3 | 0.0 | 1.2 | 0.4 | 19.4 | 0.0 |
| JT-1-4-34-11 | 0.0 | 0.0 | 1.2 | 0.3 | 1.5 | 0.4 | 0.0 | 0.2 | 0.0 | 1.3 | 0.4 | 16.0 | 0.0 |
| JT-1-4-34-11 | 0.0 | 0.0 | 1.2 | 0.4 | 1.6 | 0.7 | 0.0 | 0.3 | 0.0 | 1.4 | 0.5 | 22.9 | 0.0 |
| JT-1-4-34-11 | 0.0 | 0.0 | 1.5 | 0.4 | 1.4 | 0.6 | 0.0 | 0.3 | 0.0 | 1.2 | 0.5 | 19.4 | 0.0 |
| JT-1-4-34-11 | 0.0 | 0.0 | 1.1 | 0.4 | 1.5 | 0.6 | 0.0 | 0.2 | 0.0 | 1.2 | 0.5 | 20.7 | 0.0 |
| JT-1-4-34-11 | 0.0 | 0.0 | 1.4 | 0.4 | 1.3 | 0.4 | 0.0 | 0.3 | 0.0 | 1.3 | 0.4 | 16.1 | 0.0 |
| JT-1-4-34-11 | 0.0 | 0.0 | 1.3 | 0.3 | 1.4 | 0.3 | 0.0 | 0.2 | 0.0 | 1.5 | 0.3 | 12.7 | 0.0 |
| JT-1-4-34-11 | 0.0 | 0.0 | 1.2 | 0.3 | 1.6 | 0.6 | 0.0 | 0.3 | 0.0 | 1.3 | 0.4 | 20.1 | 0.0 |
| JT-1-4-34-11 | 0.0 | 0.0 | 1.6 | 0.3 | 1.4 | 0.4 | 0.0 | 0.2 | 0.0 | 1.4 | 0.3 | 13.8 | 0.0 |
| JT-1-4-34-11 | 0.0 | 0.0 | 1.1 | 0.3 | 1.9 | 0.5 | 0.0 | 0.2 | 0.0 | 1.7 | 0.3 | 15.4 | 0.0 |
| JT-1-4-34-11 | 0.0 | 0.0 | 1.5 | 0.4 | 1.3 | 0.5 | 0.0 | 0.3 | 0.0 | 1.1 | 0.4 | 17.9 | 0.0 |
| JT-1-4-34-11 | 0.0 | 0.0 | 1.8 | 0.4 | 1.2 | 0.5 | 0.0 | 0.2 | 0.0 | 1.0 | 0.5 | 17.8 | 0.0 |
| JT-1-4-34-11 | 0.0 | 0.0 | 1.0 | 0.4 | 1.9 | 0.7 | 0.0 | 0.3 | 0.0 | 1.7 | 0.5 | 24.7 | 0.0 |
| JT-1-4-34-11 | 0.0 | 0.0 | 1.4 | 0.4 | 1.4 | 0.6 | 0.0 | 0.2 | 0.0 | 1.3 | 0.4 | 21.8 | 0.0 |
| JT-1-4-34-11 | 0.0 | 0.0 | 0.9 | 0.4 | 1.4 | 0.7 | 0.0 | 0.2 | 0.0 | 1.1 | 0.5 | 25.8 | 0.0 |
| JT-1-4-34-11 | 0.0 | 0.0 | 1.7 | 0.3 | 1.3 | 0.3 | 0.0 | 0.2 | 0.0 | 1.3 | 0.3 | 14.1 | 0.0 |
| JT-1-4-34-21 | 0.0 | 0.0 | 1.1 | 0.3 | 1.5 | 0.3 | 0.0 | 0.3 | 0.0 | 1.8 | 0.4 | 13.3 | 0.0 |
| JT-1-4-34-21 | 0.0 | 0.0 | 0.8 | 0.3 | 1.8 | 0.4 | 0.0 | 0.3 | 0.0 | 1.7 | 0.3 | 15.6 | 0.0 |
| JT-1-4-34-21 | 0.0 | 0.0 | 0.9 | 0.2 | 1.5 | 0.3 | 0.0 | 0.3 | 0.0 | 1.6 | 0.3 | 12.9 | 0.0 |

Example 10. Further Analysis of Transformed Plants and Field Trials

Southern blot hybridisation analysis was carried out on selected T2 *B. napus* plants transformed with the T-DNA from the GA7-modB construct. DNA extracted from samples of plant tissue were digested with several restriction enzymes for the Southern blot hybridisation analysis. A radioactive probe corresponding to part of the T-DNA was hybridised to the blots, which were washed under stringent conditions, and the blots exposed to film to detect hybridising bands. Some of the samples exhibited single hybridising bands for each of the restriction digests, corresponding to single T-DNA insertions in the plants, while others showed two bands and others again showed multiple T-DNA bands, corresponding to 4 to 6 insertions. The number of hybridising bands observed by Southern Blot analysis correlated well with the T-DNA copy number in the transgenic plants as determined by the digital PCR method, up to a copy number of about 3 or 4. At higher copy numbers than about 5, the digital PCR method was less reliable.

Some of the selected lines were used as pollen donors in crosses with a series of about 30 different *B. napus* varieties of different genetic backgrounds. Further back-crosses are carried out to demonstrate whether the multiple T-DNA insertions are genetic linked or not, and allowing segregation of genetically-unlinked transgenic loci. Thereby, lines containing single transgenic loci are selected.

Single-primer PCR reactions are carried out on the transgenic lines, using primers adjacent to the left- and right-borders of the T-DNA, and any lines that show the presence of inverted repeats of the T-DNAs are discarded.

Several of the transgenic lines showed delayed flowering, while others had reduced seed-set and therefore reduced seed yield per plant after growth in the glasshouse, consistent with a reduced male or female fertility. Flower morphology was examined in these plants and it was observed that in some cases, dehiscence and release of pollen from the anthers was delayed so that styles had elongated before dehiscence occurred, thereby distancing the anthers from the stigmas. Full fertility could be restored by artificial pollination. Furthermore, pollen viability at dehiscence was determined by staining with the vital stains FDA and PI (Example 1) and was shown to be reduced in some of the lines, whereas in most of the transgenic lines, pollen viability was about 100% as in the wild-type controls. As a further test for a possible cause of the reduced seed yield in some plants, the fatty acid content and composition of flower buds including the anthers and stigmas/styles of some T3 and T4 plants was tested. No DHA was detected in the extracted lipids, indicating that the genes in the genetic construct were not expressed in the flower buds during plant development, and ruling this out as a cause of the reduced seed yield.

The oil content was measured by NMR and the DHA level in the total fatty acid content was determined for T2 seeds. Transgenic lines having less than 6% DHA were discarded. T-DNA copy number in leaf samples from plants of the T1, T2 and T3 generations were determined by the digital PCR method (Example 1).

Selected T3 and T4 seed lots were sown in the field at two sites in Victoria, Australia, each in 10 m rows at a sowing density of about 10 seeds/m. The selected seed lots included a B003-5-14 derived line which showed pooled seed DHA levels of about 8-11% and individual T2 seed DHA levels of up to about 19%, with a TO plant T-DNA copy number of 3. The selected seed lots also included B0050-27 derived lines which had shown T2 seed DHA levels in excess of 20%, and a T2 plant T-DNA copy number of 1 or 2. Seeds sown in the field germinated and plantlets emerged at the same rate as the wild-type seeds. Plants grown from most, but not all, of the sown seed lots were phenotypically normal, for example had morphology, growth rate, plant height, male and female fertility, pollen viability (100%), seed set, silique size and morphology that was essentially the same as the wild-type control plants grown under the same conditions. Seed yield per plant was similar to that of wild-type controls grown under the same conditions. Other seed samples were sown in larger areas to bulk-up the selected transgenic lines. The total DHA content in harvested seeds was at least 30 mg/g seed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013905033 filed 18 Dec. 2013, AU 2014902471 filed 27 Jun. 2014, U.S. Ser. No. 14/743,531 filed 18 Jun. 2015, PCT/AU2015/050340 filed 18 Jun. 2015, U.S. Ser. No. 14/575,756 filed 18 Dec. 2014, PCT/AU2014/050433 filed 18 Dec. 2014 and AR 20140104761 filed 18 Dec. 2014, the entire contents of each of which are incorporated herein by reference. All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abbadi et al. (2004) Plant Cell 16: 2734-2748.
Abbott et al. (1998) Science 282:2012-2018.
Agaba et al. (2004) Marine Biotechnol. (NY) 6:251-261.
Alvarez et al. (2000) Theor Appl Genet 100:319-327.
Armbrust et al. (2004) Science 306:79-86.
Baumlein et al. (1991) Mol. Gen. Genet. 225:459-467.
Baumlein et al. (1992) Plant J. 2:233-239.
Beaudoin et al. (2000) Proc. Natl. Acad. Sci. U.S.A. 97:6421-6426.
Belide et al. (2013) Plant Cell Tiss Organ Cult. 113:543-553.
Berberich. et al. (1998) Plant Mol. Biol. 36:297-306.
Broun et al. (1998) Plant J. 13:201-210.
Brown et al. (2002) Biochem J. 364:795-805.
Chan et al. (2006) Nature Biotechnology 28:951-956.
Chapman et al. (2004) Gen. Dev. 18:1179-1186.
Chen et al. (2004) The Plant Cell 16:1302-1313.
Cheng et al. (1996) Plant Cell Rep. 15:653-657.
Cheng et al. (2010) Transgenic Res 19: 221-229.
Cho et al. (1999a) J. Biol. Chem. 274:471-477.
Cho et al. (1999b) J. Biol. Chem. 274:37335-37339.
Clough and Bent (1998) Plant J. 16:735-743.
Christie (1982) J. Lipid Res. 23:1072-1075.
Damude et al. (2006). Proc Natl Acad Sci USA 103: 9446-9451.
Denic and Weissman (2007) Cell 130:663-677.
Domergue et al. (2002) Eur. J. Biochem. 269:4105-4113.
Domergue et al. (2003) J. Biol. Chem. 278: 35115-35126.
Domergue et al. (2005) Biochem. J. 1 389: 483-490.
Dunoyer et al. (2004) The Plant Cell 16:1235-1250.
Ellerstrom et al. (1996) Plant Mol. Biol. 32:1019-1027.
Gamez et al. (2003) Food Res International 36: 721-727.
Garcia-Maroto et al. (2002) Lipids 37:417-426.
Girke et al. (1998) Plant J. 15:39-48.
Hall et al. (1991) Proc. Natl. Acad. Sci. USA 88:9320-9324
Hamilton et al. (1997) Gene 200:107-16.
Harayama (1998). Trends Biotechnol. 16: 76-82.
Hastings et al. (2001) Proc. Natl. Acad. Sci. U.S.A. 98:14304-14309.
Hinchee et al. (1988) Biotechnology 6:915-922.
Hoffmann et al. (2008) J Biol. Chem. 283:22352-22362.
Hong et al. (2002a) Lipids 37:863-868.
Horiguchi et al. (1998) Plant Cell Physiol. 39:540-544.
Huang et al. (1999) Lipids 34:649-659.
Inagaki et al. (2002) Biosci. Biotechnol. Biochem. 66:613-621.
Kajikawa et al. (2004) Plant Mol. Biol. 54:335-52.
Kajikawa et al. (2006) FEBS Lett 580:149-154.
Kereszt et al. (2007) Nature Protoc 2:948-952.
Kim et al. (2005) Plant Cell. 2005 1073-89.
Knutzon et al. (1998) J. Biol Chem. 273:29360-6.
Koletzko et al. (1988) Am. J. Clin. Nutr. 47:954-959.
Koziel et al. (1996) Plant Mol. Biol. 32:393-405.
Lassner (1995) Plant Physiol. 109:1389-94.
Leonard et al. (2000) Biochem. J. 347:719-724.
Leonard et al. (2000b) Biochem. J. 350:765-770.
Leonard et al. (2002) Lipids 37:733-740.
Lewsey et al. (2007) Plant J. 50:240-252.
Lo et al. (2003) Genome Res. 13:455-466.
Lu and Kang (2008) Plant Cell Rep. 27:273-8.
Mallory et al. (2002) Nat. Biotech. 20:622-625.
Marangoni et al. (1995) Trends in Food Sci. Technol. 6: 329-335.
Meesapyodsuk et al. (2007) J Biol Chem 282: 20191-20199.
Meng et al. (2008) J. Gen. Virol. 89:2349-2358.
Meyer et al. (2003) Biochem. 42:9779-9788.

Meyer et al. (2004) Lipid Res 45:1899-1909.
Michaelson et al. (1998a) J. Biol. Chem. 273:19055-19059.
Michaelson et al. (1998b) FEBS Lett. 439:215-218.
Murashige and Skoog (1962) Physiologia Plantarum 15:473-497.
Napier et al. (1998) Biochem. J. 330:611-614.
Needleman and Wunsch (1970) J. Mol. Biol. 48:443-453.
Parker-Barnes et al. (2000) Proc. Natl. Acad. Sci. USA 97:8284-8289.
Pereira et al. (2004a) Biochem. J. 378:665-671.
Pereira et al. (2004b) Biochem. J. 384:357-366.
Perrin et al. (2000) Mol Breed 6:345-352.
Petrie et al. (2010a) Metab. Eng. 12:233-240.
Petrie et al. (2010b) Plant Methods 11:6:8.
Petrie et al. (2012) Transgenic Res. 21:139-147.
Potenza et al. (2004) In Vitro Cell Dev Biol-Plant 40:1-22.
Qi et al. (2002) FEBS Lett. 510:159-165.
Qi et al. (2004) Nat. Biotech. 22: 739-745.
Qiu et al. (2001) J. Biol. Chem. 276:31561-31566.
Reddy and Thomas (1996) Nat. Biotech. 14:639-642.
Reddy et al. (1993) Plant Mol. Biol. 22:293-300.
Robert et al. (2005) Func. Plant Biol. 32:473-479.
Robert et al. (2009) Marine Biotech 11:410-418.
Ruiz-Lopez et al. (2012) Transgenic Res. 21:139-147.
Saha et al. (2006) Plant Physiol. 141:1533-1543.
Saito et al. (2000) Eur. J. Biochem. 267:1813-1818.
Sakuradani et al. (1999) Gene 238:445-453.
Sato et al. (2004) Crop Sci. 44: 646-652.
Sakuradani et al. (2005) Appl. Microbiol. Biotechnol. 66:648-654.
Sayanova et al. (2006) J Biol Chem 281: 36533-36541.
Sayanova et al. (1997) Proc. Natl. Acad. Sci. U.S.A. 94:4211-4216.
Sayanova et al. (2003) FEBS Lett. 542:100-104.
Sayanova et al. (2006) Planta 224:1269-1277.

Sayanova et al. (2007) Plant Physiol 144:455-467.
Shukla et al. (2002) J. Amer. Oil Chem. Soc. 79:965-969.
Singh et al. (2005) Curr. Opin. in Plant Biol. 8:197-203.
Speranza et al. (2012) Process Biochemistry (In Press).
Sperling et al. (2000) Eur. J. Biochem. 267:3801-3811.
Sperling et al. (2001) Arch. Biochm. Biophys. 388:293-8.
Sprecher et al. (1995) J. Lipid Res. 36:2471-2477.
Spychalla et al. (1997) Proc. Natl. Acad. Sci. U.S.A. 94:1142-1147.
Tonon et al. (2003) FEBS Lett. 553:440-444.
Trautwein (2001) European J. Lipid Sci. and Tech. 103:45-55.
Tvrdik (2000) J. Cell Biol. 149:707-718.
Venegas-Caleron et al. (2010) Prog. Lipid Res. 49:108-119.
Voinnet et al. (2003) Plant J. 33:949-956.
Wallis and Browse (1999) Arch. Biochem. Biophys. 365:307-316.
Watts and Browse (1999b) Arch. Biochem. Biophys. 362:175-182.
Weiss et al. (2003) Int. J. Med. Microbiol. 293:95:106.
Weng et al., (2004) Plant Molecular Biology Reporter 22:289-300.
Whitney et al. (2003) Planta 217:983-992.
Wood (2009) Plant Biotechnol J. 7:914-24.
Wu et al. (2005) Nat. Biotech. 23:1013-1017.
Yang et al. (2003) Planta 216:597-603.
Zank et al. (2002) Plant J. 31:255-268.
Zank et al. (2005) WO 2005/012316
Zhang et al. (2004) FEBS Lett. 556:81-85.
Zhang et al. (2006) 20:3255-3268.
Zhang et al. (2007) FEBS Letters 581: 315-319.
Zhang et al. (2008) Yeast 25: 21-27.
Zhou et al. (2007) Phytochem. 68:785-796.
Zhou et al. (2008) Insect Mol Biol 17: 667-676.
Zou et al. (1997) Plant Cell. 9:909-23.

The invention claimed is:

1. Extracted oilseed plant seedoil, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of palmitic acid in the total fatty acid content of the extracted oilseed plant seedoil is between 2% and 16% by weight, and wherein the total fatty acid content of the oilseed plant seedoil comprises less than 1% myristic acid (C14:0) by weight and wherein the level of DHA in the total fatty acid content of the extracted oilseed plant seedoil is between 20.1% and 35% by weight.

2. The extracted oilseed plant seedoil of claim 1 which has one or more of the following features i) the level of palmitic acid in the total fatty acid content of the extracted oilseed plant seedoil between 2% and 15%, ii) the level of myristic acid (C14:0) in the total fatty acid content of the extracted oilseed plant seedoil is 0.1%, iii) the level of oleic acid in the total fatty acid content of the extracted oilseed plant seedoil is between 1% and 60%, iv) the level of linoleic acid (LA) in the total fatty acid content of the extracted oilseed plant seedoil is between 4% and 35%, v) the level of α-linolenic acid (ALA) in the total fatty acid content of the extracted oilseed plant seedoil is between 4% and 40%, vi) the total fatty acid content of the extracted oilseed plant seedoil comprises γ-linolenic acid (GLA) at a level of less than 4%, vii) the level of stearidonic acid (SDA) in the total fatty acid content of the extracted oilseed plant seedoil is less than 10%, viii) the level of eicosatetraenoic acid (ETA) in the total fatty acid content of the extracted oilseed plant seedoil is less than 6%, ix) the total fatty acid content of the extracted oilseed plant seedoil comprises eicosatrienoic acid (ETrA) at a level of less than 4%, x) the level of eicosapentaenoic acid (EPA) in the total fatty acid content of the extracted oilseed plant seedoil is between 0.05% and 10%, xi) the level of docosapentaenoic acid (DPA) in the total fatty acid content of the extracted oilseed plant seedoil is less than 4%, xii) the level of DHA in the total fatty acid content of the extracted oilseed plant seedoil is between 20.1% and 29%, xiii) the extracted oilseed plant seedoil comprises ω6-docosapentaenoic acid ($22:5^{\Delta4,7,10,13,16}$) in its fatty acid content, xiv) the extracted oilseed plant seedoil comprises less than 0.1% of ω6-docosapentaenoic acid ($22:5^{\Delta4,7,10,13,16}$) in its fatty acid content, XV) the extracted oilseed plant seedoil comprises less than 0.1% of one or more or all of SDA, EPA and ETA in its fatty acid content, xvi) the level of total saturated fatty acids in the total fatty acid content of the extracted oilseed plant seedoil is between 4% and 25%, xvii) the level of total monounsaturated fatty acids in the total fatty acid content of the extracted oilseed plant seedoil is between 4% and 40%, xviii) the level of total polyunsaturated fatty acids in the total fatty acid content of the extracted oilseed plant seedoil is between 20% and 75%, xix) the level of total 06 fatty acids in the total fatty acid content of the extracted oilseed plant seedoil is between 6% and 20%, xx) the total fatty acid content of the extracted oilseed plant seedoil comprises new ω6 fatty acids at a level of less than 10%, xxi) the level of total ω3 fatty acids in the total fatty acid content of the extracted oilseed plant seedoil is between 36% and 70%, xxii) the total fatty acid content of the extracted oilseed plant seedoil comprises new ω3 fatty acids a level of between 21% and 45%, xxiii) the ratio of total ω6 fattyacids:total ω3 fatty acids in the fatty acid content of the extracted oilseed plant seedoil is between 0.1 and 1, xxiv) the ratio of new ω6 fattyacids:new ω3 fatty acids in the fatty acid content of the extracted oilseed plant seedoil is between 0.1 and 1, xxv) the fatty acid composition of the extracted oilseed plant seedoil is based on an efficiency of conversion of ALA to DHA of between 22% and 70%, xxvi) the total fatty acid in the extracted oilseed plant seedoil has less than 1.5% C20:1, xxvii) the triacylglycerol (TAG) content of the extracted oilseed plant seedoil is at least 70%, xxviii) the extracted oilseed plant seedoil comprises diacylglycerol (DAG), which DAG comprises DHA, xxix) the extracted oilseed plant seedoil comprises less than 10%, free (non-esterified) fatty acids and/or phospholipid, or is essentially free thereof, xxx) at least 70%, of the DHA esterified in the form of TAG is in the sn-1 or sn-3 position of the TAG, xxxi) the most abundant DHA-containing TAG species in the extracted oilseed plant seedoil is DHA/18:3/18:3 (TAG 58:12), and xxxii) the lipid comprises tri-DHA TAG (TAG 66:18) wherein all percentages are by weight.

3. The extracted oilseed plant seedoil of claim 1, wherein the level of DHA in the total fatty acid content of the extracted oilseed plant seedoil is between 20.1% and 30% by weight.

4. The extracted oilseed plant seedoil of claim 1, wherein the oilseed plant seedoil is a Brassicaceae plant seedoil.

5. The extracted oilseed plant seedoil of claim 1, wherein the oilseed plant seedoil is *Brassica napus* or *Camelina sativa* seedoil.

6. The extracted oilseed plant seedoil of claim 1, wherein the oilseed plant seedoil is *Brassica napus* seedoil.

7. A process for producing the extracted oilseed plant seedoil of claim 1, comprising the steps of i) obtaining an oilseed plant seed comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), stearidonic acid (SDA), docosapentaenoic acid (DPA) and docosahexaenoic acid (DHA), and optionally one or more of eicosapentaenoic acid (EPA) and eicosatetraenoic acid (ETA), wherein the level of palmitic acid in the total fatty acid content of the extracted lipid is between 2% and 16% by weight, and wherein the total fatty acid content of the oilseed plant seedoil comprises less than 1% myristic acid (C14:0) by weight and wherein the level of DHA in the total fatty acid content of extractable lipid in the oilseed plant seed is between 20.1% and 35% by weight, and ii) extracting lipid from the plant seed, wherein the level of DHA in the total fatty acid content of the extracted oilseed plant seedoil is between 20.1% and 35% by weight.

8. The process of claim 7, wherein the oilseed plant seed has one or more or all of the following features i) the efficiency of conversion of oleic acid to DHA in the plant part is at between 10% and 50%, ii) the efficiency of conversion of LA to DHA in the plant part is between 15% and 50%, and iii) the efficiency of conversion of ALA to DHA in the plant part is between 17% and 55%.

9. The process of claim 7, wherein the total oil content of the oilseed plant seed is at least 40% by weight.

\*   \*   \*   \*   \*

SEQUENCE LISTING

```
Sequence total quantity: 58
SEQ ID NO: 1              moltype = DNA  length = 21527
FEATURE                  Location/Qualifiers
misc_feature             1..21527
                         note = pJP3416-GA7 nucleotide sequence.
source                   1..21527
                         mol_type = other DNA
                         organism = synthetic construct
SEQUENCE: 1
tcctgtggtt ggcatgcaca tacaaatgga cgaacggata aaccttttca cgccctttta  60
aatatccgat tattctaata aacgctcttt tctcttaggt ttacccgcca atatatcctg  120
tcaaacactg atagtttaaa ctgaaggcgg gaaacgacaa tctgctagtg gatctcccag  180
tcacgacgtt gtaaaacggg cgccccgcgg aaagcttgcg gccgcccgat ctagtaacat  240
agatgacacc gcgcgcgata atttatccta gtttgcgcgc tatattttgt tttctatcgc  300
gtattaaatg tataattgcg ggactctaat cataaaaacc catctcataa ataacgtcat  360
gcattacatg ttaattatta cgtgcttaac gtaattcaac agaaattata tgataatcat  420
cgcaagaccg gcaacaggat tcaatcttaa gaaactttat tgccaaatgt ttgaacgatc  480
ggcgcgcctc attagtgagc cttctcagcc tttccgttaa cgtagtagtg ctgtcccacc  540
ttatcaaggt tagagaaagt agccttccaa gcaccgtagt aagagagcac cttgtagttg  600
agtccccact tcttagcgaa aggaacgaat cttctgctaa cctcaggctg tctgaattga  660
ggcatatcag ggaagaggtg gtggataacc tgacagttaa ggtatcccat aagccagttc  720
acgtatcctc tagaaggatc gatatcaacg gtgtgatcaa cagcgtagtt aacccaagaa  780
aggtgcttat cagatggaac aacagggagg tgagtatgag aagtagagaa gtgagcgaaa  840
aggtacatgt aagcgatcca gtttccgaaa gtgaaccacc agtaagcaac aggccaagag  900
tatccagtag caagcttgat aacagcggtt ctaacaacat gagaaacgag catccaagaa  960
gcctcttcgt agttcttctt acggagaact tgtctagggt ggagaacgta gatccagaaa  1020
gcttgaacaa gaagtccaga ggtaacagga acgaaagtcc aagcttgaag tctagcccaa  1080
gctctagaga atcctctagg tctgttatcc tcaacagcag tgttgaagaa agccacagca  1140
ggagtggtat caagatccat atcgtgtcta accttttgag gggtagcatg gtgcttgtta  1200
tgcatctggt tccacatctc accagaagta gaaagtccga atccacaagt catagcctga  1260
agtctcttgt ccacgtaaac agatccggta agagagttat gtccaccctc atgttgaacc  1320
catccacatc tagctccgaa gaaagcaccg taaacaacag aagcaatgat agggtatcca  1380
gcgtacataa gagcagttcc aagagcgaat gtagcaagaa gctcgagaag tctgtaagcc  1440
```

-continued

```
acatgggtga tagaaggctt gaagaatcca tctctctcaa gctcagcacg ccatctagcg   1500
aaatcctcaa gcataggagc atcctcagac tcagatctct tgatctcagc aggtctagaa   1560
ggcaaagctc taagcatctt ccaagccttg agagaacgca tgtggaattc tttgaaagcc   1620
tcagtagcat cagcaccagt gttagcaagc atgtagaaga tcacagatcc accagggtgc   1680
ttgaagttag tcacatcgta ctcaacgtcc tcaactctaa cccatctagt ctcgaaagta   1740
gcagcaagct catgaggctc aagagtctta agatcaacag gagcagtaga agcatcctta   1800
gcatcaagag cctcagcaga agatttagac ctggtaagtg gagatctagg agaagatctt   1860
ccatcagtct taggagggca catggtatgg taattgtaaa tgtaattgta atgttgtttg   1920
ttgtttgttg ttgttggtaa ttgttgtaaa agatcctcgt gtatgttttt aatcttgttt   1980
gtatcgatga gttttggttt gagtaaagag tgaagcggat gagttaattt ataggctata   2040
aaggagattt gcatggcgat cacgtgtaat aatgcatgca cgcatgtgat tgtatgtgtg   2100
tgctgtgaga gagaagctct taggtgtttg aagggagtga caagtggcga agaaaaacaa   2160
ttctccgcgg ctgcatgcta tgtgtaacgt gtagctaatg ttctggcatg gcatcttatg   2220
aacgattctt tttaaaaaca aggtaaaaac ttaacttcat aaaattaaaa aaaaaaacgt   2280
ttactaagtt ggtttaaaag gggatgagac tagtagattg gttggttggt ttccatgtac   2340
cagaaggctt accctattag ttgaaagttg aaactttgtt ccctactcaa ttcctagttg   2400
tgtaaatgta tgtatatgta atgtgtataa aacgtagtac ttaaatgact aggagtggtt   2460
cttgagaccg atgagagatg ggagcagaac taaagatgat gacataatta agaacgaatt   2520
tgaaaggctc ttaggtttga atcctattcg agaatgtttt tgtcaaagat agtggcgatt   2580
ttgaaccaaa gaaaacattt aaaaaatcag tatccggtta cgttcatgca aatagaaagt   2640
ggtctaggat ctgattgtaa ttttagactt aaagagtctc ttaagattca atcctggctg   2700
tgtacaaaac tacaaataat atattttaga ctatttgacc ttaactaaac ttccactcat   2760
tatttactga ggttagagaa tagacttgcg aataaacaca ttcccgagaa atactcatga   2820
tcccataatt agtcagaggg tatgccaatc agatctaaga acacacattc cctcaaattt   2880
taatgcacat gtaatcatag tttagcacaa ttcaaaaata atgtagtatt aaagacagaa   2940
atttgtagac tttttttggg cgttaaaaga agactaagtt tatacgtaca ttttatttta   3000
agtggaaaac cgaaattttc catcgaaata tatgaattta gtatatatat ttctgcaatg   3060
tactattttg ctattttggc aactttcagt ggactactac tttattacaa tgtgtatgga   3120
tgcatgagtt tgagtataca catgtctaaa tgcatgcttt gtaaaacgta acggaccaca   3180
aaagaggatc catacaaata catctcatag cttcctccat tattttccga cacaaacaga   3240
gcattttaca acaattacca acaacaacaa acaacaaaca acattacaat tacatttaca   3300
attaccatac catggaattc gcccagcctc ttgttgctat ggctcaagag caatacgctg   3360
ctatcgatgc tgttgttgct cctgctatct tctctgctac tgattctatc ggatggggac   3420
ttaagcctat ctcttctgct actaaggact tgcctcttgt tgagtctcct acacctctca   3480
tcctttcttt gcttgcttac ttcgctatcg ttggatctgg actcgtttac agaaaggttt   3540
tccctagaac cgtgaaggga caagatccat tccttttgaa ggctcttatg cttgctcaca   3600
acgtgttcct tatcggactt tctctttaca tgtgcctcaa gcttgtgtac gaggcttacg   3660
ttaacaagta ctctttctgg ggaaacgctt acaaccctgc tcaaactgag atggctaagg   3720
ttatctggat cttctacgtg agcaagatct acgagttcat ggataccttc atcatgctcc   3780
tcaagggaaa tgttaaccag gttagcttcc ttcacgttta ccatcacgga tctatctctg   3840
gaatctggtg gatgattact tacgctgctc ctggtggtga tgcttacttc tctgctgctc   3900
ttaactcttg ggttcacgtg tgtatgtaca cctactattt tatggctgcc gtgcttccta   3960
aggacgagaa aactaagaga aagtacctct ggtggggaag ataccttact caaatgcaga   4020
tgttccagtt cttcatgaac cttctccagg ctgtttacct tctctactct tcatctcctt   4080
accctaagtt tatcgctcag ctcctcgtgg tgtacatggt tactcttctc atgctttttcg   4140
gaaacttcta ctacatgaag caccacgcta gcaagtgatg aggcgcgccg ggccgccgcc   4200
atgtgacaga tcgaaggaag aaagtgtaat aagacgactc cactactcg atcgctagtg   4260
attgtcattg ttatatataa taatgttatc tttcacaact tatcgtaatg catgtgaaac   4320
tataacacat taatcctact tgtcatatga taacactctc cccatttaaa actcttgtca   4380
atttaaagat ataagattct ttaaatgatt aaaaaaaata tattataaat tcaatcactc   4440
ctactaataa attattaatt attatttatt gattaaaaaa atacttatac taatttagtc   4500
tgaatagaat aattagattc tagtctcatc cccttttaaa ccaacttagt aaacgttttt   4560
ttttttaatt ttatgaagtt aagttttttac cttgtttttta aaagaatcg ttcataagat   4620
gccatgccag aacattagct acacgttaca catagcatgc agccgcgag aattgttttt   4680
cttcgccact tgtcactccc ttcaaacacc taagagcttc tctctcacag cacacacata   4740
caatcacatg cgtgcatgca ttattacacg tgatcgccat gcaaatctcc tttatagcct   4800
ataaattaac tcatccgctt cactctttac tcaaaccaaa actcatcgat acaaacaaga   4860
ttaaaaacat acacgaggat cttttacaac aattaccaac aacaacaaac aacaaacaac   4920
attacaatta catttacaat taccatacca tgcctccaag ggactcttac tcttatgctg   4980
ctcctccttc tgctcaactt cacgaagttg atactcctca agagcacgac aagaaagagc   5040
ttgttatcgg agatagggct tacgatgtta ccaacttcgt taagagacac cctggtggaa   5100
agatcattgc ttaccaagtt ggaactgatg ctaccgatgc ttacaagcag ttccatgtta   5160
gatctgctaa ggctgacaag atgcttaagt ctcttccttc tcgtcctgtt cacaagggat   5220
actctccaag aagggctgat cttatcgctg atttccaaga gttcaccaag caacttgagg   5280
ctgagggaat gttcgagcct tctcttcctc atgttgctta cagacttgct gaggttatcg   5340
ctatggcatgt tgctggtgct gctctatct ggcatggata cactttcgct ggaatcgcta   5400
tgcttggagt tgttcaggga agatgtggat ggcttatgca tgagggtgga cattactctc   5460
tcactggaaa cattgctttc gacagagcta tccaagttgc ttgttacgga cttggatatg   5520
gaatgtctgg tgcttggtgg cgtaaccagc ataacaagca ccatgctact cctcaaaagc   5580
ttcagcacga tgttgatctt gatacccttc ctctcgttgc tttccatgag agaatcgctg   5640
ctaaggttaa gtctcctgct atgaaggctt ggctttctat gcaagctaag cttttcgctc   5700
ctgttaccac tcttcttgtt gctcttggat ggcagcttta ccttcatcct agacacatgc   5760
tcaggactaa gcactacgat gagcttgcta tgctcggaat cagatacgga cttgttggat   5820
accttgctgc taactacggt gctggatacg ttctcgcttc ttaccttctt tacgttcagc   5880
ttggagctat gtacatcctc tgcaacttcg ctgtttctca tactcacctc cctgttgttg   5940
agcctaacga gcatgctact tgggttgagt acgctgctaa ccacactact aactgttctc   6000
catcttggtg gtgtgattgg tggatgtctt accttaacta ccagatcgag caccacctttt   6060
accccttctat gcctcaattc agacacccta agatcgctcc tagagttaag cagcttttcg   6120
agaagcacgg acttcactac gatgttagag gatacttcga ggctatggct gatactttcg   6180
```

-continued

```
ctaaccttga taacgttgcc catgctcctg agaagaaaat gcagtaatga gatcgttcaa  6240
acatttggca ataaagtttc ttaagattga atcctgttgc cggtcttgcg atgattatca  6300
tataatttct gttgaattac gttaagcacg taataattaa catgtaatgc atgacgttat  6360
ttatgagatg ggttttatg attagagtcc cgcaattata catttaatac gcgatagaaa  6420
acaaaatata gcgcgcaaac taggataaat tatcgcgcgc ggtgtcatct atgttactag  6480
atcggtcgat taaaaatccc aattatattt ggtctaattt agtttggtat tgagtaaaac  6540
aaattcgaac caaaccaaaa tataaatata tagtttttat atatatgcct ttaagacttt  6600
ttatagaatt ttctttaaaa aatatctaga aatatttgcg actcttctgg catgtaatat  6660
ttcgttaaat atgaagtgct ccatttttat taactttaaa taattggttg tacgatcact  6720
ttcttatcaa gtgttactaa aatgcgtcaa tctctttgtt cttccatatt catatgtcaa  6780
aatctatcaa aattcttata tatctttttc gaatttgaag tgaaatttcg ataatttaaa  6840
attaaataga acatatcatt atttaggtat catattgatt tttatactta attactaaat  6900
ttggttaact ttgaaagtgt acatcaacga aaaattagtc aaacgactaa aataaataaa  6960
tatcatgtgt tattaagaaa attctcctat aagaatattt taatagatca tatgtttgta  7020
aaaaaaatta attttttacta acacatatat ttacttatca aaaatttgac aaagtaagat  7080
taaaataata ttcatctaac aaaaaaaaaa ccagaaaatg ctgaaaaccc ggcaaaaccg  7140
aaccaatcca aaccgatata gttggtttgg tttgattttg atataaaccg aaccaactcg  7200
gtccatttgc acccctaatc ataatagctt taatatttca agatattatt aagttaacgt  7260
tgtcaatatc ctggaaattt tgcaaaatga atcaagccta tatggctgta atatgaattt  7320
aaaagcagct cgatgtggtg gtaatatgta atttacttga ttctaaaaaa atatcccaag  7380
tattaataat ttctgctagg aagaaggtta gctacgattt acagcaaagc cagaatacaa  7440
agaaccataa agtgattgaa gctcgaaata tacgaaggaa caaatatttt taaaaaaata  7500
cgcaatgact tggaacaaaa gaaagtgata tatttttttgt tcttaaacaa gcatcccctc  7560
taaagaatgg cagttttcct ttgcatgtaa ctattatgct cccttcgtta caaaaatttt  7620
ggactactat tgggaacttc ttctgaaaat agtgatagaa cccacacgag catgtgcttt  7680
ccatttaatt ttaaaaacca agaaacatac atacataact ttccatcagc ctctctctct  7740
ttttattacg gttaatgact taaaacacat tcatctcatt attattatta ttatccatcc  7800
gtctttatac gatctcatcg atcaccactt caaaaccatg cagactgctg ctgcccctgg  7860
agctggcatc ggctaggctg ggtgccgcac tgtcccggaa ggtccctagc gacttgttta  7920
gattgatggg accacctctc aacttcctgc tgctgtccct ggctgctggat gtcctgcctc  7980
atctggccga ttgcacgctc cagtcccctg catgtgcact cgctcctcaa ttgcttaaga  8040
tcatcgcagc agctatcgaa gtgctggctc tgttgccctc ctccacggcc ttggttgtag  8100
tagtagctgc cgccgcccctt ctggactttt tcccacagga accgccgaat aattcgatag  8160
aaccacacga gcatgtgctt tcatttattt taaaaaccaa gaaacataca taacatttca  8220
tcagcctctc tctctctctc tctctctctc tctctctctc tctctctctc tctctcttta  8280
ttacagctgt tacactaact taaaacacat tcatctcatt attattatta ttatccatcc  8340
ttaacaccta gcagtgtctt tgtacgatct cataatcgat caccccttca tcaggtatcc  8400
ttaggcttca ctccaacgtt gttgcagtta cggaacatgt acacaccatc atggttctca  8460
acgaactggc aagatctcca agttttccaa aggctaaccc acatgttctc atcggtgtgt  8520
ctgtagtgct ctcccataac tttcttgatg cactcggtag cttctctagc atggtagaat  8580
gggatccttg aaacgtagtg atggagcaca tgagtctcga tgatgtcatg gaagatgatt  8640
ccgaggattc cgaactctct atcgatagta gcagcagcac ccttagcgaa agtccactct  8700
tgagcatcgt aatgaggcat agaagaatcg gtgtgctgaa ggaaggtaac gaaaacaagc  8760
cagtggttaa caaggatcca aggacagaac catgtgatga aagtaggcca gaatccgaaa  8820
accttgtaag cggtgtaaac agaagtgagg gtagcaagga ttccaagatc agaaagaacg  8880
atgtaccagt agtccttctt atcgaaaaca gggctagaaa gccagtagtg agacttgaag  8940
aacttagaaa caccagggta aggttgtcca gtagcgttag tagcaaggta aagagaaagt  9000
cctccaagct gttggaacaa gagagcgaaa acagagtaga taggagtttc ctcagcgata  9060
tcgtgaaggc tggtaacttg gtgcttctct ttgaattcct cggcggtgta aggaacgaaa  9120
accatatctc tggtcatgtg tccagtagcc ttatggtgct tagcatgaga gaacttccag  9180
ctgaagtaag gaaccataac aagagagtgg agaacccatc caacggtatc gttaacccat  9240
ccgtagttag agaaagcaga atgtccacac tcatgtccaa ggatccagat tccgaatccg  9300
aaacaagaga tagagaacac gtaagcagac caagcagcga atctaaggaa ttcgttaggg  9360
agaagaggga tgtaggtaag tccaacgtaa gcgatagcag agatagccac gatatctctc  9420
accacgtaag acatagactt cacgagagat ctctcgtaac agtgcttagg gatagcgtca  9480
aggatatcct tgatggtgta atctggcacc ttgaaaacgt ttccgaaggt atcgatagcg  9540
gtctttttgct gcttgaaaga tgcaacgttt ccagaacgcc taacggtctt agtagatccc  9600
tcaaggatct cagatccaga cacggtaacc ttagacatgg tatggtaatt gtaaatgtaa  9660
ttgtaatgtt gtttgttgtt tgttgttgtt ggtaattgtt gtaaaatttt tggtggtgat  9720
tggttcttta aggtgtgaga gtgagttgtg agttgtgttg tgggtttggt ggagttgggg  9780
atggtgggtt tatatagtgg agactgagga atggggtcgt gagtgttaac tttgcatggg  9840
ctacacgtgg gttctttttgg gcttacacgt agtattattc atgcaaatgc agccaataca  9900
tatacggtat tttaataatg tgtgggaata caatatgccg agtattttac taattttggc  9960
aatgacaagt gtacatttgg attatcttac ttggcctctc ttgctttaat ttggattatt 10020
tttattctct taccttggcc gttcatattc acatccctaa aggcaagaca gaattgaatg 10080
gtggccaaaa attaaaacga tggatatgac ctacatagtg taggatcaat taacgtcgaa 10140
ggaaaatact gattctctca agcatacgga caagggtaaa taacatagtc accagaacat 10200
aataaacaaa aagtgcagaa gcaagactaa aaaaattagc tatggacatt caggttcata 10260
ttggaaacat cattatccta gtcttgtgac catccttcct cctgctctag ttgagaggcc 10320
ttgggactaa cgagaggtca gttgggatag cagatcctta tcctggacta gcctttctgg 10380
tgtttcagag tcttcgtgcc gccgctcaca tctatctcca ttaggtctga agatgactct 10440
tcacaccaac gacgtttaag gtctctatcc tactcctagc ttgcaatacc tggcttgcaa 10500
tacctggagc atcgtgcacg atgattggat actgtggagg aggagtgttt gctgatttag 10560
agctcccggt tgggtgattt gacttcgatt tcagtttagg cttgttgaaa tttttcaggt 10620
tccattgtga agcctttaga gcttgagctt ccttccatgt taatgccttg atcgaatact 10680
cctagagaaa agggaagtcg atctctgagt attgaaatcg aagtgcacat ttttttttcaa 10740
cgtgtccaat caatccacaa acaaagcaga agacaggtaa tctttcatac ttatactgac 10800
aagtaatagt cttaccgtca tgcataataa cgtctcgttc cttcaagagg ggttttccga 10860
catccataac gacccgaagc ctcatgaaag cattagggaa gaacttttgg ttcttcttgt 10920
```

-continued

```
catggcctt ataggtgtca gccgagctcg ccaattcccg tccgactggc tccgcaaaat    10980
attcgaacgg caagttatgg acttgcaacc ataactccac ggtattgagc aggacctatt    11040
gtgaagactc atctcatgga gcttcagaat gtggttgtca gcaaaccaat gaccgaaatc    11100
catcacatga cggacgtcca gtgggtgagc gaaacgaaac aggaagcgcc tatctttcag    11160
agtcgtgagc tccacaccgg attccggcaa ctacgtgttg ggcaggcttc gccgtattag    11220
agatatgttg aggcagaccc atctgtgcca ctcgtacaat tacgagagtt gtttttttg     11280
tgattttcct agtttctcgt tgatggtgag ctcatattct acatcgtatg gtctctcaac    11340
gtcgtttcct gtcatctgat atcccgtcat ttgcatccac gtgcgccgcc tcccgtgcca    11400
agtccctagg tgtcatgcac gccaaattgg tggtggtgcg ggctgccctg tgcttcttac    11460
cgatgggtgg aggttgagtt tgggggtctc cgcggcgatg gtagtgggtt gacggtttgg    11520
tgtgggttga cggcattgat caatttactt cttgcttcaa attctttggc agaaaacaat    11580
tcattagatt agaactggaa accagagtga tgagacggat taagtcagat tccaacagag    11640
ttacatctct taagaaataa tgtaacccct ttagacttta tatatttgca attaaaaaaa    11700
taatttaact tttagacttt atatatagtt ttaataacta agtttaacca ctctattatt    11760
tatatcgaaa ctatttgtat gtctcccctc тaaataaaact tggtattgtg tttacagaac    11820
ctataatcaa ataatcaata ctcaactgaa gtttgtgcag ttaattgaag ggattaacgg    11880
ccaaaatgca ctagtattat caaccgaata gattcacact agatggccat ttccatcaat    11940
atcatcgccg ttcttcttct gtcccacatat cccctctgaa acttgagaga cacctgcact    12000
tcattgtcct tattacgtgt tacaaaatga aacccatgca tccatgcaaa ctgaagaatg    12060
gcgcaagaac ccttcccctc catttcttat gtggcgacca tccatttcac catctcccgc    12120
tataaaacac ccccatcact tcacctagaa catcatcact acttgcttat ccatccaaaa    12180
gatacccact tttacaacaa ttaccaacaa caacaaacaa caaacaacat tacaattaca    12240
tttacaatta ccataccatg ccacctagcg ctgctaagca aatgggagct tctactggtg    12300
ttcatgctgg tgttactgac tcttctgctt tcaccagaaa ggatgttgct gatagacctg    12360
atctcaccat cgttggagat tctgtttacg atgctaaggc tttcagatct gagcatcctg    12420
gtggtgctca tttcgtttct ttgttcggag gaagagatgc tactgaggct ttcatggaat    12480
accatagaag ggcttggcct aagtctagaa tgtctagatt ccacgttgga tctcttgctt    12540
ctactgagga acctgttgct gctgatgagg gataccttca actttgtgct aggatcgcta    12600
agatggtgcc ttctgtttct tctggattcg ctcctgcttc ttactgggtt aaggctggac    12660
ttatccttgg atctgctatc gctcttgagg cttacatgct ttacgctgga aagagacttc    12720
tcccttctat cgttcttgga tggcttttcg ctcttatcgg tcttaacatc cagcatgatg    12780
ctaaccatgg tgctttgtct aagtctgctt ctgttaacct tgctcttgga ctttgtcagg    12840
attggatcgg aggatctatg atcctttggc ttcaagagca tgttgttatg caccacctcc    12900
acactaacga tgttgataag gatcctgatc aaaaggctca cggtgctctt agactcaagc    12960
ctactgatgc ttggtcacct atgcattggc ttcagcatct ttaccttttg cctggtagga    13020
ctatgtacgc tttcaagctt ttgttcctcg acatctctga gcttgttatg tggcgttggg    13080
agggtgagcc tatctctaag cttgctggat acctctttat gccttctttg cttctcaagc    13140
ttaccttctg ggctagattc gttgctttgc ctctttacct tgctccttct gttcatactg    13200
ctgtgtgtat cgctgctact gttatgactg gatctttcta cctgcctttc ttcttcttca    13260
tctcccacaa cttcgagggt gttgcttctg ttggacctga tggatctatc acttctatga    13320
ctagaggtgc tagcttcctt aagagacaag ctgagacttc ttctaacgtt ggaggacctc    13380
ttcttgctac tcttaacggt ggactcaact accaaattga gcatcacttg ttccctagag    13440
ttcaccatgg attctaccct agacttgctc tcttgttaa ggcttggct gaggctgaag    13500
gaatcgagta caagcactac cctactatct ggtctaacct tgcttctacc ctcagacata    13560
tgtacgctct tggaagaagg cctagatcta aggctgagta atgacaagct tatgtgacgt    13620
gaaataataa cggtaaaata tatgtaataa taataataat aaagccacaa agtgagaatg    13680
aggggaaggg gaaatgtgta atgagccagt agccggtggt gctaattttg tatcgtattg    13740
tcaataaatc atgaattttg tggtttttat gtgttttttt aaatcatgaa tttttaattt    13800
tataaaataa tctccaatcg gaagaacaac attccatatc catgcatgga tgtttcttta    13860
cccaaatcta gttcttgaga ggatgaagca tcaccgaaca gttctgcaac tatccctcaa    13920
aagctttaaa atgaacaaca aggaacagag caacgttcca aagatcccaa acgaaacata    13980
ttatctatac taatactata ttattaatta ctactgcccg gaatcacaat ccctgaatga    14040
ttcctattaa ctacaagcct tgttggcggc ggagaagtga tcggcgcggc gagaagcagc    14100
ggactcggag acgaggcctt ggaagatctg agtcgaacgg gcagaatcag tattttcctt    14160
cgacgttaat tgatcctaca ctatgtaggt catatccatc gttttaattt ttggccacca    14220
ttcaattctg tcttgccttt agggatgtga atatgaacgg ccaaggtaag agaataaaaa    14280
taatccaaat taaagcaaga gaggccaagt aagataatcc aaatgtacac ttgtcattgc    14340
caaaattagt aaaatactcg gcatattgta ttcccacaca ttattaaaat accgtatatg    14400
tattggctgc atttgcatga ataatactac gtgtaagccc aaaagaaccc acgtgtagcc    14460
catgcaaagt taacactcac gacccccattc ctcagtctcc actatataaa cccaccatcc    14520
ccaatctcac caaacccacc acacaactca caactcactc tcacacctta aagaaccaat    14580
caccaccaaa aattttacaa caattaccaa caacaacaaa caacaaacaa cattacaatt    14640
acatttacaa ttaccatacc atgagcgctg ttaccgttac tggatctgat cctaagaaca    14700
gaggatcttc tagcaacacc gagcaagagg ttccaaaagt tgctatcgat accaacggaa    14760
acgtgttctc tgttcctgat ttcaccatca aggacatcct tggagctatc cctcatgagt    14820
gttacgagag aagattggct acctctctct actacgtgtt cagagatatc ttctgcatgc    14880
ttaccaccgg ataccttacc cataagatcc tttaccctct cctcatctct tacacctcta    14940
acagcatcat caagttcact ttctgggccc tttacactta cgttcaagga cttttcggaa    15000
ccggaatctc ggttctcgct catgagtgtg gacatcaagc tttctctgat tacggtaatcg    15060
tgaacgattt cgttggatgg acccttcact cttaccttat ggttccttac ttcagctgga    15120
agtactctca tggaaagcac cataaggcta ctggacacat gaccagagat atggttttcg    15180
ttcctgccac caaagaggaa ttcaagaagt ctaggaactt cтттcggtaac ctcgctgagt    15240
actctgagga ttctccactt agaacccttt acgagcttct tgttcaacaa cttggaggat    15300
ggatcgctta cctcttcgtt aacgttacag gacaacctta ccctgatgtt ccttcttgga    15360
aatggaacca cttctggctt acctctccac ttttcgagca aagagatgct ctctacatct    15420
tcctttctga tcttggaatc ctcacccagg gaatcgttct tactctttgg tacaagaaat    15480
tcggaggatg gtcccttttc atcaactggt tcgttcctta catctgggtt aaccactggc    15540
tcgttttcat cacattcctt cagcacactg atcctactat gcctcattac aacgctgagg    15600
aatggacttt cgctaagggt gctgctgcta ctatcgatag aaagttcgga ttcatcggac    15660
```

-continued

```
ctcacatctt ccatgatatc atcgagactc atgtgcttca ccactactgt tctaggatcc   15720
cattctacaa cgctagacct gcttctgagg ctatcaagaa agttatggga aagcactaca   15780
ggtctagcga cgagaacatg tggaagtcac tttggaagtc tttcaggtct tgccaatacg   15840
ttgacggtga taacggtgtt ctcatgttcc gtaacatcaa caactgcgga gttggagctg   15900
ctgagaagta atgaaggggg gatcgattat gagatcgtac aaagacactg ctaggtgtta   15960
aggatggata ataataataa taatgagatg aatgtgtttt aagttagtgt aacagctgta   16020
ataaagagag agagagagag agagagagag agagagagag agagagagag agagaggctg   16080
atgaaatgtt atgtatgttt cttggttttt aaaataaatg aaagcacatg ctcgtgtggt   16140
tctatcgaat tattcggcgg ttcctgtggg aaaaagtcca gaagggccgc cgcagctact   16200
actacaacca aggccgtgga ggagggcaac agagccagca cttcgatagc tgctgcgatg   16260
atcttaagca attgagggagc gagtgcacat gcaggggact ggagcgtgca atcggccaga   16320
tgaggcagga catccagcag cagggacagc agcaggaagt tgagaggtgg tcccatcaat   16380
ctaaacaagt cgctagggac cttccgggac agtgcggcac ccagcctagc cgatgccagc   16440
tccaggggca gcagcagtct gcatggtttt gaagtggtga tcgatgagat cgtataaaga   16500
cactgctagg tgttaaggat gggataataa gatgtgtttt aagtcattaa ccgtaataaa   16560
aagagagaga ggctgatgga atgttatgta tgtatgtttc ttggttttta aaattaaatg   16620
gaaagcacat gctcgtgtgg gttctatctc gattaaaaat cccaattata tttggtctaa   16680
tttagtttgg tattgagtaa aacaaattcg aaccaaacca aaatataaat atatagtttt   16740
tatatatatg cctttaagac tttttataga attttctttta aaaaatatct agaaatattt   16800
gcgactcttc tggcatgtaa tatttcgtta aatatgaagt gctccatttt tattaactttt   16860
aaataattgg ttgtacgatc actttcttat caagtgttac taaaatgcgt caatctcttt   16920
gttcttccat attcatatgt caaaatctat caaaattctt atatatcttt ttcgaatttg   16980
aagtgaaatt tcgataattt aaaattaaat agaacatatc attatttagg tatcatattg   17040
attttttatac ttaattacta aatttggtta actttgaaag tgtacatcaa cgaaaaatta   17100
gtcaaacgac taaaataaat aaatatcatg tgttattaag aaaattctcc tataagaata   17160
ttttaataga tcatatgttt gtaaaaaaaa ttaattttta ctaacacata tatttactta   17220
tcaaaaattt gacaaagtaa gattaaaata atattcatct aacaaaaaaa aaaccagaaa   17280
atgctgaaaa cccggcaaaa ccgaaccaat ccaaaccgat atagttggtt tggtttgatt   17340
ttgatataaa ccgaaccaac tcggtccatt tgcaccccta atcataatag ctttaatatt   17400
tcaagatatt attaagttaa cgttgtcaat atcctgcaaa ttttgcaaaa tgaatcaagc   17460
ctatatggct gtaatatgaa tttaaaagca gctcgatgtg gtggtaatat gtaatttact   17520
tgattctaaa aaaatatccc aagtattaat aatttctgct aggaagaagg ttagctacga   17580
tttacagcaa agccagaata caaagaacca taaagtgatt gaagctcgaa atatacgaag   17640
gaacaaatat ttttaaaaaa atacgcaatg acttggaaca aaagaaagtg atatatttttt   17700
tgttcttaaa caagcatccc ctctaaagaa tggcagtttt cctttgcatg taactattat   17760
gctcccttcg ttacaaaaat tttgactac tattgggaac ttcttctgaa aatagtcctg   17820
caggctagta gattggttgg ttggtttcca tgtaccagaa ggcttaccct attagttgaa   17880
agttgaaact ttgttcccta ctcaattcct agttgtgtaa atgtatgtat atgtaatgtg   17940
tataaaacgt agtacttaaa tgactaggag tggttcttga gaccgatgag agatgggagc   18000
agaactaaag atgatgacat aattaagaac gaatttgaaa ggctcttagg tttgaatcct   18060
attcgagaat gttttttgtca aagatagtgg cgatttgaa ccaaagaaaa catttaaaaa   18120
atcagtatcc ggttacgttc atgcaaatag aaagtggtct aggatctgat tgtaatttta   18180
gacttaaaga gtctcttaag attcaatcct ggctgtgtac aaaactacaa ataatatatt   18240
ttagactatt tggccttaac taaacttcca ctcattattt actgaggtta gagaatagac   18300
ttgcgaataa acacattccc gagaaatact catgatccca taattagtca gagggtatgc   18360
caatcagatc taagaacaca cattccctca aattttaatg cacatgtaat catagtttag   18420
cacaattcaa aaataatgta gtattaaaga cagaaatttg tagacttttt tttggcgtta   18480
aaagaagact aagtttatac gtacatttta tttttaagtgg aaaaccgaaa ttttccatcg   18540
aaatatatga atttagtata tatatttctg caatgtacta ttttgctatt ttggcaactt   18600
tcagtggact actactttat tacaatgtgt atggatgcat gagtttgagt atacacatgt   18660
ctaaatgcat gctttgtaaa acgtaacgga ccacaaaaga ggatccatac aaatacatct   18720
catagcttcc tccattattt tccgacacaa acagagcatt ttacaacaat taccaacaac   18780
aacaaacaac aaacaacatt acaattacat ttacaattac cataccatgg cctctatcgc   18840
tatccctgct gctcttgctg gaactcttgg atacgttacc tacaatgtgg ctaaccctga   18900
tatcccagct tctgagaaag ttcctgctta cttcatgcag gttgagtact ggggaccctac   18960
tatcggaact attggatacc tcctcttcat ctacttcgga aagcgtatca tgcagaacag   19020
atctcaacct ttcggactca agaacgctat gctcgtttac aacttctacc agaccttctt   19080
caacagctac tgcatctacc ttttcgttac ttctcatagg gctcagggac ttaaggtttg   19140
gggaaacatc cctgatatga ctgctaactc ttggggaatc tctcaggtta tctggcttca   19200
ctacaacaac aagtacgttg agcttctcga caccttcttc atggtgatga ggaagaagtt   19260
cgaccagctt tctttccttc acatctacca ccacactctt ctcatctggt catggttcgt   19320
tgttatgaag cttgagcctg ttggagattg ctacttcgga tcttctgtta acaccttcgt   19380
gcacgtgatc atgtactctt actacggact tgctgctctt ggagttaact gtttctggaa   19440
gaagtacatc acccagatcc agatgcttca gttctgtcttc tgtgcttctc actctatcta   19500
caccgcttac gttcagaata ccgctttctg gcttccttac cttcaactct gggttatggt   19560
gaacatgttc gttctcttcg ccaacttcta ccgtaagagg tacaagtcta agggtgctaa   19620
gaagcagtga taagggccgc cgccatgtga cagatcgaag gaagaaagt taataagacg   19680
actctcacta ctcgatcgct agtgattgtc attgttatat ataataatgt tatctttcac   19740
aacttatcgt aatgcatgtg aaactataac acattaatcc tacttgtcat atgataacac   19800
tctccccatt taaaactctt gtcaatttaa agatataaga ttcttaaat gattaaaaaa   19860
aatatattat aaattcaatc actcctacta ataaattatt aattattatt tattgattaa   19920
aaaaatactt atactaattt agtctgaata gaataattag attctagcct gcaggcggc   19980
cgcggatccc atggagtcaa agattcaaat agaggaccta acagaactcg ccgtaaagac   20040
tggcgaacag ttcatacaga gtctcttacg actcaatgac aagaagaaaa tcttcgtcaa   20100
catggtggag cacgcacac ttgtctactc caaaaatatc aaagatacag tctcagaaga   20160
ccaaagggca attgagactt ttcaacaaag ggtaatatcc ggaaacctcc tcggattcca   20220
ttgcccagct atctgtcact ttattgtgaa gatagtggaa aaggaaggtg ctcctacaa   20280
atgccatcat tgcgataaag gaaaggccat cgttgaagat gcctctgccg acagtggtcc   20340
caaagatgga cccccaccca cgaggagcat cgtggaaaaa gaagacgttc caaccacgtc   20400
```

-continued

```
ttcaaagcaa gtggattgat gtgatatctc cactgacgta agggatgacg cacaatccca  20460
ctatccttcg caagaccctt cctctatata aggaagttca tttcatttgg agagaacacg  20520
ggggactgaa ttaaatatga gccctgagag gcgtcctgtt gaaatcagac ctgctactgc  20580
tgctgatatg gctgctgttt gtgatatcgt gaaccactac atcgagactt ctaccgttaa  20640
cttcagaact gagcctcaaa ctcctcaaga gtggatcgat gatcttgaga gactccaaga  20700
tagataccct tggcttgttg ctgaggttga gggtgttgtt gctggaatcg cttacgctgg  20760
accttggaag gctagaaacg cttacgattg gactgttgag tctaccgttt acgtttcaca  20820
cagacatcag agacttggac ttggatctac cctttacact caccttctca agtctatgga  20880
agctcaggga ttcaagtctg ttgttgctgt tatcggactc cctaacgatc cttctgttag  20940
acttcatgag gctcttggat acactgctag aggaactctt agagctgctg gatacaagca  21000
cggtggatgg catgatgttg gattctggca aagagatttc gagcttcctg ctcctcctag  21060
acctgttaga ccagttactc agatctgaat ttgcgtgatc gttcaaacat ttggcaataa  21120
agtttcttaa gattgaatcc tgttgccggt cttgcgatga ttatcatata atttctgttg  21180
aattacgtta agcatgtaat aattaacatg taatgcatca cgttatttat gagatgggtt  21240
tttatgatta gagtcccgca attatacatt taatacgcga tagaaaacaa aatatagcgc  21300
gcaaactagg ataaattatc gcgcgcggtg tcatctatgt tactagatca ctagtgatgt  21360
acggttaaaa ccaccccagt acattaaaaa cgtccgcaat gtgttattaa gttgtctaag  21420
cgtcaatttg tttacaccac aatatatcct gccaccagcc agcaacagc tccccgaccg  21480
gcagctcggc acaaaatcac cactcgatac aggcagccca tcagtcc                 21527
```

SEQ ID NO: 2            moltype = DNA  length = 23512
FEATURE                 Location/Qualifiers
misc_feature            1..23512
                        note = pGA7- mod_B nucleotide sequence
source                  1..23512
                        mol_type = other DNA
                        organism = synthetic construct
SEQUENCE: 2

```
tcctgtggtt ggcatgcaca tacaaatgga cgaacggata aaccttttca cgcccttta   60
aatatccgat tattctaata aacgctcttt tctcttaggt ttacccgcca atatatcctg   120
tcaaacactg atagtttaaa ctgaaggcgg gaaacgacaa tctgctagtg gatctcccag   180
tcacgacgtt gtaaaacggg cgccccgcgg aaagcttgcg gccgcggtac cgcccgttcg   240
actcagatct tccaaggcct cgtctccgag tccgctgctt ctcgccgcgc cgatcacttc   300
tccgccgcca acaaggcttg tagttaatag gaatcattca gggattgtga ttccggggcag  360
tagtaattaa taatatagta ttagtataga taatatgttt cgtttgggat ctttggaacg   420
ttgctctgtt ccttgttgtt cattttaaag cttttgaggg atagttgcag aactgttcgg   480
tgatgcttca tcctctcaag aactagattt gggtaaagaa acatccatgc atggatatgt   540
aatgttgttc ttccgattgg agattatttt ataaaattta aaattcatga tttaaaaaaa   600
cacataaaaa ccacaaaatt catgatttat tgacaatacg atacaaaatt agcaccaccg   660
gctactggct cattacacat ttcccccttcc cctcattctc actttgtggc tttattatta   720
ttattattac atatatttta ccgttattat ttcacgtcac ataagcttgt taattaatca   780
ttagtgagcc ttctcagcct ttccgttaac gtagtagtgc tgtcccacct tatcaaggtt   840
agagaaagta gccttccaag caccgtagta agagagcacc ttgtagttga gtccccactt   900
cttagcgaaa ggaacgaatc ttctgctaac ctcaggctgt ctgaattgag gcatatcagg   960
gaagaggtgg tggataacct gacagttaag gtatcccata agccagttca cgtatcctct   1020
agaaggatcg atatcaacgg tgtgatcaac agcgtagtta acccaagaaa ggtgcttatc   1080
agatggaaca acagggaggt gagtatgaga agtagagaag tgagcgaaaa ggtacatgta   1140
agcgatccag tttccgaaag tgaaccacca gtaagcaaca ggccaagagt atccagtagc   1200
aagcttgata acagcggttc taacaacatg agaaacgagc atccaagaag cctcttcgta   1260
gttcttctta cggagaactt gtctagggtg gagaacgtag atccagaaag cttgaacaag   1320
aagtccagag gtaacaggaa cgaaagtcca agcttgaagt ctagcccaag ctctagagaa   1380
tcctctaggt ctgttatcct caacagcagt gttgaagaaa gccacagcag gagtggtatc   1440
aagatccata tcgtgtctaa ccttttgagg ggtagcatgg tgcttgttat gcatctggtt   1500
ccacatctca ccagaagtag aaagtccgaa tccacaagtc atagcctgaa gtctcttgtc   1560
cacgtaaaca gatccggtaa gagagttatg tccaccctca tgttgaaccc atccacatct   1620
agctccgaag aaagcaccgt aaacaacaga agcaatgata gggtatccag cgtacataag   1680
agcagttcca agagcgaatg tagcaagaag ctcgagaagt ctgtaagcca catgggtgat   1740
agaaggcttg aagaatccat ctctctcaag ctcagcacgc catctagcga aatcctcaag   1800
cataggagca tcctcagact cagatctctt gatctcagca ggtctagaag gcaaagctct   1860
aagcatcttc caagccttga gagaacgcat gtggaattct ttgaaagcct cagtagcatc   1920
agcaccagtg ttagcaagca tgtagaagat cacagatcca ccagggtgct tgaagttagt   1980
cacatcgtac tcaacgtcct caactctaac ccatcagtc tcgaaagtag cagcaagctc    2040
atgaggctca agagtcttaa gatcaacagg agcagtagaa gcatccttag catcaagagc   2100
ctcagcagaa gatttagacc tggtaagtgg agatctagga gagatcttca tcagtcttt    2160
aggagggcac atggtatggt aattgtaaat gtaattgtaa tgttgtttgt tgtttgttgt   2220
tgttggtaat tgttgtaaaa ttaattaagt gggtatcttt tggatggata agcaagtagt   2280
gatgatgttc taggtgaagt gatgggggtg ttttatagcg ggagatggtg aaatggatgg   2340
tcgccacata agaaatggag gggaagggt cttgcgccat tcttcagttt gcatggatgc   2400
atgggtttca tttttgtaaca cgtaataagg acaatgaagt gcaggtgtct ctcaagttc    2460
agaggggata tgtggacaga agaagaacg cgatgatatt gatggaaatg gccatccagt    2520
gtgaatctat tcggttgata atactagtgc attttggccg ttaatccctt caattaactg    2580
cacaaacttc agttgagtat tgattatttg attataggt ctgtaaacac aataccaagt    2640
ttatttagag gggagacata caaatagttt cgatataaat aatagagtgg ttaaacttag    2700
ttattaaaac tatatataaa gtctaaaagt taaattattt ttttaattgc aaatatataa    2760
agtctaaagg ggttacatta tttcttaaga gatgtaactc tgttggaatc tgacttaatc   2820
cgtctcatca ctctggtttc cagttctaat ctaatgaatt gtttttctgcc aaagaatttg    2880
aagcaagaag taaattgatc aatgccgtca acccacacca aaccgtcaac ccactaccat    2940
cgccgcggag accccaaac tcaacctcca cccatcggta agaagcacag ggcagcccgc    3000
accaccacca atttggcgtg catgacacct agggacttgg cacgggaggc ggcgcacgtg    3060
```

```
gatgcaaatg acgggatatc agatgacagg aaacgacgtt gagagaccat acgatgtaga   3120
atatgagctc accatcaacg agaaactagg aaaatcacaa aaaaaacaac tctcgtaatt   3180
gtacgagtgg cacagatggg tctgcctcaa catatctcta atacggcgaa gcctgcccaa   3240
cacgtagttg ccggaatccg gtgtggagct cacgactctg aaagataggc gcttcctgtt   3300
tcgtttcgct cacccactgg acgtccgtca tgtgatggat ttcggtcatt ggtttgctga   3360
caaccacatt ctgaagctcc atgagatgag tcttcacaat aggtcctgct caataccgtg   3420
gagttatggt tgcaagtcca taacttgccg ttcgaatatt ttgcggagcc agtcggacgg   3480
gaattggcga gctcggctga cacctataaa ggccatgaca agaagaacca aaagttcttc   3540
cctaatgctt tcatgaggct tcgggtcgtt atggatgtcg gaaaacccct cttgaaggaa   3600
cgagacgtta ttatgcatga cggtaagact attacttgtc agtataagta tgaaagatta   3660
cctgtcttct gctttgtttg tggattgatt ggacacgttg aaaaaaaatg tgcacttcga   3720
tttcaatact cagagatcga cttccctttt ctctaggagt attcgatcaa ggcattaaca   3780
tggaaggaag ctcaagctct aaaggcttca caatggaacc tgaaaaattt caacaagcct   3840
aaactgaaat cgaagtcaaa tcacccaacc gggagctcta aatcagcaaa cactcctcct   3900
ccacagtatc caatcatcgt gcacgatgct ccaggtattg caagccaggt attgcaagct   3960
aggagtagga tagagacctt aaacgtcgtt ggtgtgaaga gtcatcttca gacctaatgg   4020
agatagatgt agacggcggc acgaagactc tgaaacacca gaaaggctag tccaggataa   4080
ggatctgcta tcccaactga cctctcgtta gtcccaaggc ctctcaacta gagcaggagg   4140
aaggatggtc acaagactag gataatgatg tttccaatat gaacctgaat gtccatagct   4200
aatttttta gtcttgcttc tgcacttttt gtttattatg ttctggtgac tatgttattt   4260
acccttgtcc gtatgcttga gggtacccta gtagattggt tggttggttt ccatgtacca   4320
gaaggcttac cctattagtt gaaagttgaa actttgttcc ctactcaatt cctagttgtg   4380
taaatgtatg tatatgtaat gtgtataaaa cgtagtactt aaatgactag gagtggttct   4440
tgagaccgat gagagatggg agcagaacta aagatgatga cataattaag aacgaatttg   4500
aaaggctctt aggtttgaat cctattcgag aatgtttttg tcaaagatag tggcgatttt   4560
gaaccaaaga aaacatttaa aaaatcagta tccggttacg ttcatgcaaa tagaaagtgg   4620
tctaggatct gattgtaatt ttagacttaa agagtctctt aagattcaat cctggctgtg   4680
tacaaaacta caaataatat attttagact atttggcctt aactaaactt ccactcatta   4740
tttactgagg ttagagaata gacttgcgaa taaacacatt cccgagaaat actcatgatc   4800
ccataattag tcagagggta tgccaatcag atctaagaac acacattccc tcaaatttta   4860
atgcacatgt aatcatagtt tagcacaatt caaaaataat gtagtattaa agacagaaat   4920
ttgtagactt tttttttggcg ttaaaagaag actaagttta tacgtacatt ttattttaag   4980
tggaaaaccg aaattttcca tcgaaatata tgaatttagt atatatattt ctgcaatgta   5040
ctattttgct attttggcaa cttttcagtgg actactactt tattacaatg tgtatggatg   5100
catgagtttg agtatacaca tgtctaaatg catgctttgt aaaacgtaac ggaccacaaa   5160
agaggatcca tacaaataca tctcatagct tcctccatta tttttccgaca caaacagagc   5220
atttttacaac aattaccaac aacaacaaac aacaaacaac attacaatta catttacaat   5280
taccatacca tggcctctat cgctatccct gctgctcttg ctggaactct tggatacgtt   5340
acctacaatg tggctaaccc tgatatccca gcttctgaga aagttcctgc ttacttcatg   5400
caggttgagt actgggggacc tactatcgga actattggat acctcctctt catctacttc   5460
ggaaagcgta tcatgcagaa cagatctcaa ccttttcggac tcaagaacgc tatgctcgtt   5520
tacaacttct accagacctt cttcaacagc tactgcatct accttttcgt tacttctcat   5580
agggctcagg gacttaaggt ttggggaaac atccctgata ctcttgggga   5640
atctctcagg ttatctggct tcactacaac aacaagtacg ttgagcttct cgacaccttc   5700
ttcatggtga tgaggaagaa gttcgaccag ctttctttcc ttcacatcta ccaccacact   5760
cttctcatct ggtcatggtt cgttgttatg aagcttgagc ctgttggaga ttgctacttc   5820
ggatcttctg ttaacacctt cgtgcacgtg atcatgtact cttactacgg acttgctgct   5880
cttggagtta actgtttctg gaagaagtac atcacccaga tccagatgct tcagttctgt   5940
atctgtgctt ctcactctat ctacaccgct tacgttcaga ataccgcttt ctggcttcct   6000
taccttcaac tctgggttat ggtgaacatg ttcgttctct tcgccaactt ctaccgtaag   6060
aggtacaagt ctaagggtgc taagaagcag tgataagagcg cgcggccgcgc gggccgccaa   6120
ccatgtgaca gatcgaagga agaaagtgta ataagacgac tctcactact cgatcgctag   6180
tgattgtcat tgttatatat aataatgtta tctttcacaa cttatcgtaa tgcatgtgaa   6240
actataacac attaatccta cttgtcatat gataacactc tccccattta aaactcttgt   6300
caatttaaag ataaagatt ctttaaatga ttaaaaaaaa tatattataa attcaatcac   6360
tcctactaat aaattattaa ttattattta ttgattaaaa aaatacttat actaatttag   6420
tctgaataga ataattagat tctagtctca tccccttta aaccaactta gtaaacgttt   6480
tttttttaa ttttatgaag ttaagttttt accttgtttt taaaaagaat cgttcataag   6540
atgccatgcc agaacattag ctacacgtta cacatagcat gcagccgcgg agaattgttt   6600
ttcttcgcca cttgtcactc ccttcaaaca cctaagagct tctctctcac agcacacaca   6660
tacaatcaca tgcgtgcatg cattattaca cgtgatcgcc atgcaaatct cctttatagc   6720
ctataaatta actcatccgc ttcactcttt actcaaacca aaactcatcg atacaaacaa   6780
gattaaaaac atacacgagg atcttttaca acaattacca acaacaacaa acaacaaaca   6840
acattacaat tacatttaca attaccatac catgcctcca agggactctt actcttatgc   6900
tgctcctcct tctgctcaac ttcacgaagt tgatactcct caagagcacg acaagaaaga   6960
gcttgttatc ggagataggg cttacgatgt taccaacttc gttaagagac accctggtgg   7020
aaagatcatt gcttaccaag ttggaactga tgctaccgat gcttacaagc agttccatgt   7080
tagatctgct aaggctgaca agatgcttaa gtctcttcct tctcgtcctg ttcacaaggg   7140
atactctcca agaagggctg atcttatcgc tgatttccaa gagttcacca agcaacttga   7200
ggctgaggga atgttcgagc cttctcttcc tcatgttgct tacagacttg ctgaggttat   7260
cgctatgcat gttgctggtg ctgctcttat ctggcatgga tacactttcg ctggaatcgc   7320
tatgcttgga gttgttcagg gaagatgtgg atggcttatg catgagggtg gacattactc   7380
tctcactgga aacattgctt tcgacagagc tatccaagtc gcttgttacg gacttggatg   7440
tggaatgtct ggtgcttggt ggcgtaacca gcataacaag caccatgcta ctcctcaaaa   7500
gcttcagcac gatgttgatc ttgataccct tcctctcgtt gctttccatg agagaatcgc   7560
tgctaaggtt aagtctcctg ctatgaaggc ttggctttct atgcaagcta gcttttcgc   7620
tcctgttacc actcttcttg ttgctcttgg atggcagctt taccttcatc ctagacacat   7680
gctcaggact aagcactacg atgagcttgc tatgctcgga atcagatacg gacttgttgg   7740
ataccttgct gctaactacg gtgctggata cgttctcgct tgttaccttc tttacgttca   7800
```

-continued

```
gcttggagct atgtacatct tctgcaactt cgctgtttct catactcacc tccctgttgt   7860
tgagcctaac gagcatgcta cttgggttga gtacgctgct aaccacacta ctaactgttc   7920
tccatcttgg tggtgtgatt ggtggdatgtc ttaccttaac taccagatcg agcaccacct   7980
ttaccmttct atgcctcaat tcagacaccc taagatcgct cctagagtta agcagctttt   8040
cgagaagcac ggacttcact acgatgttag aggatacttc gaggctatgg ctgatacttt   8100
cgctaacctt gataacgttg cccatgctcc tgagaagaaa atgcagtaat gagatcgttc   8160
aaacatttgg caataaagtt tcttaagatt gaatcctgtt gccggtcttg cgatgattat   8220
catataattt ctgttgaatt acgttaagca cgtaataatt aacatgtaat gcatgacgtt   8280
atttatgaga tgggtttta tgattagagt cccgcaatta tcatttaat acgcgataga   8340
aaacaaaata tagcgcgcaa actaggataa attatcgcgc gcggtgtcat ctatgttact   8400
agatcggtcg attaaaaatc ccaattatat ttggtctaat ttagtttggt attgagtaaa   8460
acaaattcga accaaaccaa aatataaata tatagttttt atatatatgc ctttaagact   8520
ttttatagaa ttttctttaa aaaatatcta gaaatatttg cgactcttct ggcatgtaat   8580
atttcgttaa atatgaagtg ctccattttt attaacttta aataattggt tgtacgatca   8640
ctttcttatc aagtgttact aaaatgcgtc aatctctttg ttcttccata ttcatatgtc   8700
aaaatctatc aaaattctta tatatctttt tcgaatttga agtgaaattt cgataaattta   8760
aaattaaata gaacatatca ttatttaggt atcatattga tttttatact taattactaa   8820
atttggttaa ctttgaaagt gtacatcaac gaaaaattag tcaaacgact aaaataaata   8880
aatatcatgt gttattaaga aaattctcct ataagaatat tttaatagat catatgtttg   8940
taaaaaaaat taatttttac taacacatat atttacttat caaaaatttg acaaagtaag   9000
attaaaataa tattcatcta acaaaaaaaa aaccagaaaa tgctgaaaac ccggcaaaac   9060
cgaaccaatc caaaccgata tagttggttt ggtttgattt tgatataaac cgaaccaact   9120
cggtccattt gcaccctaa tcataatagc tttaatattt caagatatta ttaagttaac   9180
gttgtcaata tcctggaaat tttgcaaaat gaatcaagcc tatatggctg taatatgaat   9240
ttaaaagcag ctcgatgtgg tggtaatatg taatttactt gattctaaaa aaatatccca   9300
agtattaata atttctgcta ggaagaaggt tagctacgat ttacagcaaa gccagaatac   9360
aaagaaccat aaagtgattg aagctcgaaa tatacgaagg aacaaatatt tttaaaaaaa   9420
tacgcaatga cttggaacaa aagaaagtga tatatttttt gttcttaaac aagcatcccc   9480
tctaaagaat ggcagttttc ctttgcatgt aactattatg ctcccttcgt tacaaaaatt   9540
ttggactact attgggaact tcttctgaaa atagtgataag aacccacacg agcatgtgct   9600
ttccatttaa ttttaaaaac caagaaacat acatacataa cattccatca gcctctctct   9660
cttttattta cggttaatga cttaaaacac atcttattat cccatcctta acacctagca   9720
gtgtctttat acgatctcat cgatcaccac ttcaaaacca tgcagactgc tgctgccect   9780
ggagctggca tcggctaggc tgggtgccgc actgtcccgg aaggtccota gcgacttgtt   9840
tagattgatg ggaccacctc tcaacttcct gctgctgtcc ctgctgctgg atgtcctgcc   9900
tcatctggcc gattgcacgc tccagtcccc tgcatgtgca ctcgctcctc aattgcttaa   9960
gatcatcgca gcagctatcg aagtgctggc tctgttgccc tcctccacgg ccttggttgt   10020
agtagtagct gccgccgccc ttctggactt tttcccacag gaaccgccga ataattcgat   10080
agaaccacac gagcatgtgc tttcatttat tttaaaaacc aagaaacata cataacattt   10140
catcagcctc tctctctctc tctctctctc tctctctctc tctctctctc tctctctctt   10200
tattacagct gttacactaa cttaaaacac attcatctca ttattattat tattatccat   10260
ccttaacacc tagcagtgtc tttgtacgat ctcataatcg atcacccctt catcaggtat   10320
cctaggctt cactccaacg ttgttgcagt tacggaacat gtacacacca tcatggttct   10380
caacgaactg gcaagatctc caagtttcc aaaggctaac ccacatgttc tcatcggtgt   10440
gtctgtagtg ctctcccata actttcttga tgcactcggt agcttctcta gcatggtaga   10500
atgggatcct tgaaacgtag tgatggagca catgagtctc gatgatgtca tggaagatga   10560
ttccgaggat tccgaactct ctatcgatag tagcagcagc acccttagcg aaagtccact   10620
cttgagcatc gtaatgaggc atagaagaat cggtgtgctg aaggaaggta acgaaaacaa   10680
gccagtggtt aacaaggatc caaggacaga accatgtgat gaaagtaggc cagaatccga   10740
aaaccttgta agcggtgtaa acagaagtga gggtagcaag gattccaaga tcagaaagaa   10800
cgatgtacca gtagtccttc ttatcgaaaa cagggctaga aggccagtag tgagacttga   10860
agaacttaga aacaccaggg taaggttgtc cagtagcgtt agtagcaagg taaagagaaa   10920
gtcctccaag ctgttggaac aagagagcga aaacagagta gataggagtt tcctcagcga   10980
tatcgtgaag gctggtaact tggtgcttct ctttgaattc ctcggcggtg taaggaacga   11040
aaaccatatc tctggtcatg tgtccagtag ccttatggtg cttagcatga gagaacttcc   11100
agctgaagta aggaaccata acaagagagt ggagaaccca tccaacggta tcgttaaccc   11160
atccgtagtt agagaaagca gaatgtccac actcatgtcc aaggatccag attccgaatc   11220
cgaaacaaga gatagagaac acgtaagcag accaagcagc gaatctaagg aattcgttag   11280
ggagaagagg gatgtaggta agtccaacgt aagcgatagc agagatagcc acgatatctc   11340
tcaccacgta agacatagac ttcacgagag atctctcgta acagtgctta gggatagcgt   11400
caaggatatc cttgatggtg taatctggca ccttgaaaac gtttccgaag gtatccgatag   11460
cggtcttttg ctgcttgaaa gatgcaacgt ttccagaacg cctaacggtc ttagtagatc   11520
cctcaaggat ctcagatcca gacacggtaa ccttagacat ggtatggtaa ttgtaaatgt   11580
aattgtaatg ttgtttgttg tttgttgttg ttggtaatg ttgtaaaatt tttggtggtg   11640
attggttctt taaggtgtga gagtgagttg tgagttgtgt ggtgggtttg gtgagattgg   11700
ggatggtggg tttatatagt ggagactgag gaatggggtc gtgagtgtta actttgcatg   11760
ggctacacgt gggttctttt gggcttacac gtagtattat tcatgcaaat gcagccaata   11820
catatacggt attttaataa tgtgtgggaa tacaatatgc cgagtatttt actaattttg   11880
gcaatgacaa gtgtacattt ggattatctt acttggcctc tcttgctttta atttggatta   11940
tttttattct cttaccttgg ccgttcatat tcacatccct aaaggcaaga cagaattgaa   12000
tggtggccaa aaattaaaac gatggatatg acctacatag tgtaggatca attaacgtcg   12060
aaggaaaata ctgattctct caagcatacg gacaagggta aataacatag tcaccagaac   12120
ataataaaca aaaagtgcag aagcaagact aaaaaaaatta gctatggaca ttcaggttca   12180
tattgaaac atcattatcc tagtcttgtg accatcctct ctcctgcctct agttgagagg   12240
ccttgggact aacgagaggt cagttgggat agcagatcct tatcctggac tagcctttct   12300
ggtgtttcag agtcttcgtg ccgccgtcta catctatctc cattaggtct gaagatgact   12360
cttcacacca acgacgttta aggtctctat cctactccta gcttgcaata cctggcttgc   12420
aatacctgga gcatcgtgca cgatgattgg atactgtgga ggaggagtgt ttgctgattt   12480
agagctcccg gttgggtgat ttgacttcga tttcagttta ggcttgttga aattttttcag   12540
```

-continued

```
gttccattgt gaagccttta gagcttgagc ttccttccat gttaatgcct tgatcgaata   12600
ctcctagaga aaagggaagt cgatctctga gtattgaaat cgaagtgcac attttttttc   12660
aacgtgtcca atcaatccac aaacaaagca gaagacaggt aatctttcat acttatactg   12720
acaagtaata gtcttaccgt catgcataat aacgtctcgt tccttcaaga ggggtttttcc   12780
gacatccata acgacccgaa gcctcatgaa agcattaggg aagaactttt ggttcttctt   12840
gtcatggcct ttataggtgt cagccgagct cgccaattcc cgtccgactg gctccgcaaa   12900
atattcgaac ggcaagttat ggacttgcaa ccataactcc acggtattga gcaggaccta   12960
ttgtgaagac tcatctcatg gagcttcaga atgtggttgt cagcaaacca atgaccgaaa   13020
tccatcacat gacggacgtc cagtgggtga gcgaaacgaa acaggaagcg cctatctttc   13080
agagtcgtga gctccacacc ggattccggc aactacgtgt tgggcaggct tcgccgtatt   13140
agagatatgt tgaggcagac ccatctgtgc cactcgtaca attacgagag ttgtttttt    13200
tgtgattttc ctagtttctc gttgatggtg agctcatatt ctacatcgta tggtctctca   13260
acgtcgtttc ctgtcatctg atatcccgtc atttgcatcc acgtgcgccg cctcccgtgc   13320
caagtcccta ggtgtcatgc acgccaaatt ggtggtggtg cgggctgacc tgtgcttctt   13380
accgatgggt ggaggttgag tttggggggtc tccgcggcga tggtagtggg ttgacggttt   13440
ggtgtgggtt gacggcattg atcaatttac ttcttgcttc aaattctttg gcagaaaaca   13500
attcattaga ttagaactgg aaaccagagt gatgagacgg attaagtcag attccaacag   13560
agttacatct cttaagaaat aatgtaaccc ctttagactt tatatattg caattaaaaa   13620
aataatttaa cttttagact ttatatatag ttttaataac taagtttaac cactctatta   13680
tttatatcga aactatttgt atgtctcccc tctaaataaa cttggtattg tgtttacaga   13740
acctataatc aaataatcaa tactcaactg aagtttgtgc agttaattga agggattaac   13800
ggccaaaatg cactagtatt atcaaccgaa tagattcaca ctagatggcc atttccatca   13860
atatcatcgc cgttcttctt ctgtccacat atccccctctg aaacttgaga gacacctgca   13920
cttcattgtc cttattacgt gttacaaaat gaaacccatg catccatgca aactgaagaa   13980
tggcgcaaga accccttcccc tccatttctt atgtggcgac catccatttc accatctccc   14040
gctataaaac accccccatca cttcacctag aacatcatca ctacttgctt atccatccaa   14100
aagatacccca cttttacaac aattaccaac aacaacaaac aacaaacaac attacaatta   14160
catttacaat taccatacca tgccacctag cgctgctaag caaatgggag cttctactgg   14220
tgttcatgct ggtgttactg actcttctgc tttcaccaga aaggatgttg ctgatagacc   14280
tgatctcacc atcgttggag attctgttta cgatgctaag gctttcagat ctgagcatcc   14340
tggtggtgct catttcgttt ctttgttcgg aggaagagat gctactgagg ctttcatgga   14400
ataccataga agggcttggc ctaagtctag aatgtctaga ttccacgttg gatctcttgc   14460
ttctactgag gaacctgttg ctgctgatga gggatacctt caactttgtg ctaggatcgc   14520
taagatggtg ccttctgttt cttctggatt cgctcctgct tcttactggg ttaaggctag   14580
acttatcctt ggatctgcta tcgctcttga ggcttacatg ctttacgctg gaaagagact   14640
tctcccttct atcgttcttg gatggctttt cgctcttatc ggtcttaaca tccagcatga   14700
tgctaaccat ggtgctttgt ctaagtctgc ttctgttaac cttgctcttg gactttgtca   14760
ggattggatc ggaggatcta tgatcctttg gcttcaagag catgttgtta tgcaccacct   14820
ccacactaac gatgttgata aggatcctga tcaaaaggct cacggtgctc ttagactcaa   14880
gcctactgat gcttggtcac ctatgcattg gcttcagcat ctttaccttt tgcctggtca   14940
gactatgtac gcttttcaagc ttttgttcct cgacatctct gagcttgtta tgtggcgttg   15000
ggagggtgag cctatctcta agcttgctgg atacctcttt atgccttctt tgcttctcaa   15060
gcttaccttc tgggctagat tcgttgcttt gcctctttac cttgttcatac   15120
tgctgtgtgt atcgctgcta ctgttatgac tggatctttc tacctcgctt tcttcttctt   15180
catctcccac aacttcgagg gtgttgcttc tgttggacct gatggatcta tcacttctat   15240
gactagaggt gctagcttcc ttaagagaca agctgagact tcttctaacg ttggaggacc   15300
tcttcttgct actcttaacg gtggactcaa ctaccaaatt gagcatcact tgttccctag   15360
agttcaccat ggattctacc ctagacttgc tcctcttgtt aaggctgagc ttgaggctag   15420
aggaatcgag tacaagcact accctactat ctggtctaac cttgcttcta ccctcagaca   15480
tatgtacgct cttggaagaa ggcctagatc taaggctgag taatgacaag cttatgtgac   15540
gtgaaataat aacggtaaaa tatatgtaat aataataata ataaagccac aaagtgagaa   15600
tgaggggaag gggaaatgtg taatgagcca gtagccggtg gtgctaattt tgtatcgtat   15660
tgtcaataaa tcatgaattt tgtggttttt atgtgttttt ttaaatcatg aattttaaat   15720
tttataaaat aatctccaat cggaagaaca acattccata tccatgcatg gatgtttctt   15780
tacccaaatc tagttcttga gaggatgaag catcaccgaa cagttctgca actatccctc   15840
aaaagcttta aaatgaacaa caaggaacag agcaacgttc caaagatccc aaacgaaaca   15900
tattatctat actaatacta tattattaat tactactgcc cggaatcaca atccctgaat   15960
gattcctatt aactacaagc cttgttggcg gcggagaagt gatcggcgcg gcgagaagca   16020
gcggactcgg agacgaggcc ttggaagatc tgagtcgaac gggcagaatc agtatttttcc   16080
ttcgacgtta attgatccta cactatgtag gtcatatcca tcgtttttaat ttttggccac   16140
cattcaattc tgtcttgcct ttagggatgt gaatatgaac ggccaaggta agagaataaa   16200
aataatccaa attaaagcaa gagaggccaa gtaagataat ccaaatgtac acttgtcatt   16260
gccaaaatta gtaaaatact cggcatattg tattcccaca cattattaaa ataccgtata   16320
tgtattggct gcatttgcat gaataatact acgtgtaagc ccaaaagaac ccacgtgtag   16380
cccatgcaaa gttaacactc acgaccccat tcctcagtct ccactatata aacccaccat   16440
ccccaatctc accaaaccca ccacacaact cacaactcac tctcacacct taaagaacca   16500
atcaccacca aaaattttac aacaattacc aacaacaaca aacaacaaac aacattacaa   16560
ttacatttac aattaccata ccatgagcgc tgttaccgtt actggatctg atcctaagaa   16620
cagaggatct tctagcaaca ccgagcaaga ggttccaaaa gttgctatcg ataccaacgg   16680
aaacgtgttc tctgttcctg atttcaccat caaggacatc cttggagcta tccctcatga   16740
gtgttacgag agaagattgg ctacctctct ctactacgtg ttcagagata tcttctgcat   16800
gcttaccacc ggatacctta cccataagat ccttacccct ctcctcatct cttacacctc   16860
taacagcatc atcaagttca ctttctctggc cctttacact tacgttcaag gacttttcgg   16920
aaccggaatc tgggttctcg ctcatgagtg tggacataca ttacacggat tacgggaat    16980
cgtgaacgat ttcgttggat ggaccccttca ctcttacctt atggttcctt acttcagctg   17040
gaagtactct catggaaagc accataaggc tactggacac atgaccagag atatggttttt   17100
cgttcctgcc accaaagagg aattcaagaa gtctaggaac ttcttcggta acctcgctga   17160
gtactctgag gattctccac ttagaaccct ttacgagctt cttgttcaac aacttggagg   17220
atggatcgct tacctcttcg ttaacgttac aggacaacct taccctgatg ttccttcttg   17280
```

-continued

```
gaaatggaac cacttctggc ttacctctcc acttttcgag caaagagatg ctctctacat   17340
cttcctttct gatcttggaa tcctcaccca gggaatcgtt cttactcttt ggtacaagaa   17400
attcggagga tggtcccttt tcatcaactg gttcgttcct tacatctggg ttaaccactg   17460
gctcgttttc atcacattcc ttcagcacac tgatcctact atgcctcatt acaacgctga   17520
ggaatggact ttcgctaagg gtgctgctgc tactatcgat agaaagttcg gattcatcgg   17580
acctcacatc ttccatgata tcatcgagac tcatgtgctt caccactact gttctaggat   17640
cccattctac aacgctagac ctgcttctga ggctatcaag aaagttatgg gaaagcacta   17700
caggtctagc gacgagaaca tgtggaagtc actttggaag tctttcaggt cttgccaata   17760
cgttgacggt gataacggtg ttctcatgtt ccgtaacatc acaactgcg gagttggagc    17820
tgctgagaag taatgaaggg gtgatcgatt atgagatcgt acaaagacac tgctaggtgt   17880
taaggatgga taataataat aataatgaga tgaatgtgtt ttaagttagt gtaacagctg   17940
taataaagag agagagagag agagagagag agagagagag agagagaggc               18000
tgatgaaatg ttatgtatgt ttcttggttt ttaaaataaa tgaaagcaca tgctcgtgtg   18060
gttctatcga attattcggc ggttcctgtg ggaaaaagtc cagaagggcc gccgcagcta   18120
ctactacaac caaggccgtg gaggagggca acagagccag cacttcgata gctgctgcga   18180
tgatcttaag caattgagga gcgagtgcac atgcagggga ctggagcgtg caatcggcca   18240
gatgaggcag gacatccagc agcagggaca gcagcaggaa gttgagaggt ggtcccatca   18300
atctaaacaa gtcgctaggg accttccggg acagtgcggc acccagccca gccgatgcca   18360
gctccagggg cagcagcagt ctgcatggtt ttgaagtggt gatcgatgag atcgtataaa   18420
gacactgcta ggtgttaagg atgggataat aagatgtgtt ttaagtcatt aaccgtaata   18480
aaaagagaga gaggctgatg gaatgttatg tatgtatgtt tcttggtttt taaaattaaa   18540
tggaaagcac atgctcgtgt gggttctatc tcgattaaaa atcccaatta tatttggtct   18600
aatttagttt ggtattgagt aaaacaaatt cgaaccaaac caaaatataa atatatagtt   18660
tttatatata tgcctttaag acttttttata gaattttctt taaaaaatat ctagaaatat   18720
ttgcgactct tctggcatgt aatatttcgt taaatatgaa gtgctccatt tttattaact   18780
ttaaataatt ggttgtacga tcactttctt atcaagtgtt actaaaatgc gtcaatctct   18840
ttgttcttcc atattcatat gtcaaaatct atcaaaattc ttatatatct ttttcgaatt   18900
tgaagtgaaa tttcgataat ttaaaattaa atagaacata tcattattta ggtatcatat   18960
tgattttat acttaattac taaatttggt taactttgaa agtgtacatc aacgaaaaat    19020
tagtcaaacg actaaaataa aaaatatca tgtgttatta agaaaattct cctataagaa    19080
tattttaata gatcatatgt ttgtaaaaaa aattaatttt tactaacaca tatatttact   19140
tatcaaaaat ttgacaaagt aagattaaaa taatattcat ctaacaaaaa aaaaaccaga   19200
aaatgctgaa aacccggcaa aaccgaacca atccaaaccg atatagttgg tttggtttga   19260
ttttgatata aaccgaacca actcggtcca tttgcacccc taatcataat agctttaata   19320
tttcaagata ttattaagtt aacgttgtca atatcctgga aattttgcaa aatgaatcaa   19380
gcctatatgg ctgtaaatatg aatttaaaag cagctcgatg tggtggtaat atgtaattta   19440
cttgattcta aaaaaaatatc ccaagtatta ataatttctg ctaggaagaa ggttagctac  19500
gatttacagc aaagccagaa tacaaagaac cataaagtga ttgaagctcg aaatatacga   19560
aggaacaaat atttttaaaa aaatacgcaa tgacttggaa caaaagaaag tgatatattt   19620
tttgttctta aacaagcatc ccctctaaag aatggcagtt ttcctttgca tgtaactatt   19680
atgctccctt cgttacaaaa attttggact actattggga acttcttctg aaaatagtcc   19740
tgcaggctag tagattggtt ggttggtttc catgtaccag aaggcttacc ctattagttg   19800
aaagttgaaa ctttgttccc tactcaattc ctagttgtat aaatgtatgt atatgtaatg   19860
tgtataaaac gtagtactta aatgactagg agtggttctt gagaccgatg agagatggga   19920
gcagaactaa agatgatgac ataattaaga acgaatttga aaggctctta ggtttgaatc   19980
ctattcgaga atgtttttgt caaagatagt ggcgattttg aaccaaagaa aacatttaaa   20040
aaatcagtat ccggttacgt tcatgcaaat agaaagtggt ctaggatctg attgtaattt   20100
tagacttaaa gagtctctta agattcaatc ctggctgtgt acaaaactac aaataatata   20160
ttttagacta tttggcctta actaaacttc cactcattat ttactgaggt tagagaaatag  20220
acttgcgaat aaacacattc ccgagaaata ctcatgatcc cataattagt cagagggtat   20280
gccaatcaga tctaagaaca cacattccct caaattttaa tgcacatgta atcatagttt   20340
agcacaattc aaaaataatg tagtattaaa gacagaaatt tgtagacttt tttttggcgt   20400
taaaagaaga ctaagtttat acgtacattt tattttaagt ggaaaaccga aattttccat   20460
cgaaatatat gaatttagta tatatatttc tgcaatgtac tattttgcta ttttggcaac   20520
tttcagtgga ctactacttt attacaatgt gtatggatgc atgagtttga gtatacacat   20580
gtctaaatgc atgctttgta aaacgtaacg gaccacaaaa gaggatccat acaaatacat   20640
ctcatagctt cctccattat tttccgacac aaacagagca ttttacaaca attaccaaca   20700
acaacaaaca acaaacaaca ttacaattac atttacaatt accataccat ggaatttgct   20760
caacctctcg ttgctatggc tcaagacag tacgctgcta tcgatgctgt tgttgctcct   20820
gctatcttct ctgctaccga ctctcattgga tggggactca agcctatctc ttctgctact   20880
aaggatctcc ctctcgttga atctcctacc cctcttatcc tttctctcct cgcttacttc   20940
gctatcgttg gttctggact cgtttaccgt aaagtgttcc ctagaaccgt taagggacag   21000
gatcctttcc ttctcaaggc tcttatgctc gctcacaacg ttttccttat cggactcagc   21060
ctttacatgt gcctcaagct cgtttacgag gcttacgtga acaagtactc cttctgggga   21120
aacgcttaca accctgctca aaccgagatg gctaaggtga tctggatctt ctacgtgtcc   21180
aagatctacg agttcatgga caccttcatc atgcttctca agggaaacgt taaccaggtt   21240
tccttcctcc atgtttacca ccacggatct atctctggaa tctggtggat gatcactta    21300
gctgctccag gtgagatgc ttacttctct gctgctctca actcttgggt tcatgtgtgc   21360
atgtacacct actacttcat ggctggtctg tt cttcctaagg acgaaaagac caagagaaag  21420
tacctttggt ggggaagata ccttacccag atgcaaatgt tccagttctt catgaacctt   21480
ctccaggctg tttacctcct ctactcttct tctccttacc ctaagttcat tgctcaactc   21540
ctcgttgttt acatggttac cctcctcatg cttttcggaa acttctacta tatgaagcac   21600
cacgcttcta gtgataagg gccgccgcca tgtgacagat cgaaggaaga aagtgtaata   21660
agacgactct cactactcga tcgctagtga ttgtcattgt tatataat aatgttatct   21720
ttcacaactt atcgtaatgc atgtgaaact ataacacatt aatcctactt gtcatatgat   21780
aacactctcc ccatttaaaa ctcttgtcaa tttaaagata taagattctt taaatgatta   21840
aaaaaaatat attataaatt caatcactcc tactaataaa ttattaatta ttatttattg   21900
attaaaaaaa tacttatact aatttagtct gaatagaata attagattct agcctgcagg   21960
gcggccgcgg atcccatgga gtcaaagatt caaatagagg acctaacaga actcgccgta   22020
```

```
aagactggcg aacagttcat acagagtctc ttacgactca atgacaagaa gaaaatcttc 22080
gtcaacatgg tggagcacga cacacttgtc tactccaaaa atatcaaaga tacagtctca 22140
gaagaccaaa gggcaattga gacttttcaa caaagggtaa tatccggaaa cctcctcgga 22200
ttccattgcc cagctatctg tcactttatt gtgaagatag tggaaaagga aggtggctcc 22260
tacaaatgcc atcattgcga taaaggaaag gccatcgttg aagatgcctc tgccgacagt 22320
ggtcccaaag atggaccccc acccacgagg agcatcgtgg aaaaagaaga cgttccaacc 22380
acgtcttcaa agcaagtgga ttgatgtgat atctccactg acgtaaggga tgacgcacaa 22440
tcccactatc cttcgcaaga cccttcctct atataaggaa gttcatttca tttggagaga 22500
acacgggggga ctgaattaaa tatgagccct gagaggcgtc ctgttgaaat cagacctgct 22560
actgctgctg atatggctgc tgtttgtgat atcgtgaacc actacatcga gacttctacc 22620
gttaacttca gaactgagcc tcaaactcct caagagtgga tcgatgatct tgagagactc 22680
caagatagat acccttggct tgttgctgag gttgagggtg ttgttgctgg aatcgcttac 22740
gctggacctt ggaaggctag aaacgcttac gattggactg ttgagtctac cgtttacgtt 22800
tcacacagac atcagagact tggacttgga tctacccttt acactcacct tctcaagtct 22860
atggaagctc agggattcaa gtctgttgtt gctgttatcg gactccctaa cgatccttct 22920
gttagacttc atgaggctct tggatacact gctagaggaa ctcttagagc tgctggatac 22980
aagcacggtg gatggcatga tgttggattc tggcaaaagg atttcgagct tcctgctcct 23040
cctagacctg ttagaccagt tactcagatc tgaatttgcc tgatcgttca aacatttggc 23100
aataaagttt cttaagattg aatcctgttg ccggtcttgc gatgattatc atataatttc 23160
tgttgaatta cgttaagcat gtaataatta acatgtaatg catgacgtta tttatgagat 23220
gggttttat gattagagtc ccgcaattat acatttaata cgcgatagaa aacaaaatat 23280
agcgcgcaaa ctaggataaa ttatcgcgcg cggtgtcatc tatgttacta gatcactagt 23340
gatgtacggt taaaaccacc ccagtacatt aaaaacgtcc gcaatgtgtt attaagttgt 23400
ctaagcgtca atttgtttac accacaatat atcctgccac cagccagcca acagctcccc 23460
gaccggcagc tcggcacaaa atcaccactc gatacaggca gcccatcagt cc         23512
```

```
SEQ ID NO: 3           moltype = DNA  length = 1254
FEATURE                Location/Qualifiers
misc_feature           1..1254
                       note = Codon-optimized open reading frame for expression of
                        Lachanceakluyveri12 desaturase in plants
source                 1..1254
                       mol_type = other DNA
                       organism = synthetic construct
SEQUENCE: 3
atgagcgctg ttaccgttac tggatctgat cctaagaaca gaggatcttc tagcaacacc 60
gagcaagagg ttccaaaagt tgctatcgat accaacggaa acgtgttctc tgttcctgat 120
ttcaccatca aggacatcct tggagctatc cctcatgagt gttacgagag aagattggct 180
acctctctct actacgtgtt cagagatatc ttctgcatgc ttaccaccgg ataccttacc 240
cataagatcc tttaccctct cctcatctct tacacctcta acagcatcat caagttcact 300
ttctgggccc tttacactta cgttcaagga ctttttcggaa ccggaatctg ggttctcgct 360
catgagtgtg gacatcaagc tttctctgat tacggaatcg tgaacgattt cgttggatgg 420
acccttcact cttaccttat ggttccttac ttcagctgga agtactctca tggaaagcac 480
cataaggcta ctggacacat gaccagagat atggtttcg ttcctgccac caaagaggaa 540
ttcaagaagt ctaggaactt cttcggtaac ctcgctgagt actctgagga ttctccactt 600
agaacccttt acgagcttct tgttcaacaa cttggaggat ggatcgctta cctcttcgtt 660
aacgttacag gacaacctta ccctgatgtt ccttcttgga aatggaacca cttctggctt 720
acctctccac ttttcgagca aagagatgct ctctacatct tcctttctga tcttggaatc 780
ctcacccagg gaatcgttct tactctttgg tacaagaaat cggaggatg gtcccttttc 840
atcaactggt tcgttcctta catctgggtt aaccactggc tcgttttcat cacattcctt 900
cagcacacag atcctactat gcctcattac aacgctgagg aatggacttt cgctaaggct 960
gctgctgcta ctatcgatag aaagttcgga ttcatcggac ctcacatctt ccatgatatc 1020
atcgagactc atgtgcttca ccactactgt tctaggatcc cattctacaa cgctagacct 1080
gcttctgagg ctatcaagaa agttatggga aagcactaca ggtctagcga cgagaacatg 1140
tggagtcac tttggaagtc tttcaggtct tgccaatacg ttgacggtga taacggtgtt 1200
ctcatgttcc gtaacatcaa caactgcgga gttggagctg ctgagaagta atga        1254
```

```
SEQ ID NO: 4           moltype = AA  length = 416
FEATURE                Location/Qualifiers
source                 1..416
                       mol_type = protein
                       organism = Lachancea kluyveri
SEQUENCE: 4
MSAVTVTGSD PKNRGSSSNT EQEVPKVAID TNGNVFSVPD FTIKDILGAI PHECYERRLA 60
TSLYYVFRDI FCMLTTGYLT HKILYPLLIS YTSNSIIKFT FWALYTYVQG LFGTGIWVLA 120
HECGHQAFSD YGIVNDFVGW TLHSYLMVPY FSWKYSHGKH HKATGHMTRD MVFVPATKEE 180
FKKSRNFFGN LAEYSEDSPL RTLYELLVQQ LGGWIAYLFV NVTGQPYPDV PSWKWNHFWL 240
TSPLFEQRDA LYIFLSDLGI LTQGIVLTLW YKKFGGWSLF INWFVPYIWV NHWLVFITFL 300
QHTDPTMPHY NAEEWTFAKG AAATIDRKFG FIGPHIFHDI IETHVLHHYC SRIPFYNARP 360
ASEAIKKVMG KHYRSSDENM WKSLWKSFRS CQYVDGDNGV LMFRNINNCG VGAAEK      416
```

```
SEQ ID NO: 5           moltype = DNA  length = 1251
FEATURE                Location/Qualifiers
source                 1..1251
                       mol_type = other DNA
                       organism = Pichia pastoris
SEQUENCE: 5
atgtctaagg ttaccgtgtc tggatctgag atccttgagg gatctactaa gaccgttagg 60
cgttctggaa acgttgcatc tttcaagcag caaaagaccg ctatcgatac cttcggaaac 120
```

```
gttttcaagg tgccagatta caccatcaag gatatccttg acgctatccc taagcactgt   180
tacgagagat ctctcgtgaa gtctatgtct tacgtggtga gagatatcgt ggctatctct   240
gctatcgctt acgttggact tacctacatc cctcttctcc ctaacgaatt ccttagattc   300
gctgcttggt ctgcttacgt gttctctatc tcttgtttcg gattcggaat ctggatcctt   360
ggacatgagt gtggacattc tgctttctct aactacggat gggttaacga taccgttgga   420
tgggttctcc actctcttgt tatggttcct tacttcagct ggaagttctc tcatgctaag   480
caccataagg ctactggaca catgaccaga gatatggttt tcgttcctta caccgccgag   540
gaattcaaag agaagcacca agttaccagc cttcacgata tcgctgagga aactcctatc   600
tactctgttt tcgctctctt gttccaacag cttggaggac tttctcttta ccttgctact   660
aacgctactg gacaacctta ccctggtgtt tctaagttct tcaagtctca ctactggcct   720
tctagccctg ttttcgataa gaaggactac tggtacatcg ttctttctga tcttggaatc   780
cttgctaccc tcacttctgt ttacaccgct tacaaggttt tcggattctg gcctactttc   840
atcacatggt tctgtccttg gatccttgtt aaccactggc ttgttttcgt taccttcctt   900
cagcacaccg attcttctat gcctcattac gatgctcaag agtggacttt cgctaagggt   960
gctgctgcta ctatcgatag agagttcgga atcctcggaa tcatcttcca tgacatcatc   1020
gagactcatg tgctccatca ctacgtttca aggatcccat tctaccatgc tagagaagct   1080
accgagtgca tcaagaaagt tatgggagag cactacagac acaccgatga aacatgtgg   1140
gttagccttt ggaaaacttg gagatcttgc cagttcgttg agaaccatga tggtgtgtac   1200
atgttccgta actgcaacaa cgttggagtg aagcctaagg atacctgatg a   1251
```

```
SEQ ID NO: 6             moltype = AA  length = 415
FEATURE                  Location/Qualifiers
source                   1..415
                         mol_type = protein
                         organism = Pichia pastoris
SEQUENCE: 6
MSKVTVSGSE ILEGSTKTVR RSGNVASFKQ QKTAIDTFGN VFKVPDYTIK DILDAIPKHC    60
YERSLVKSMS YVVRDIVAIS AIAYVGLTYI PLLPNEFLRF AAWSAYVFSI SCFGFGIWIL   120
GHECGHSAFS NYGWVNDTVG WVLHSLVMVP YFSWKFSHAK HHKATGHMTR DMVFVPYTAE   180
EFKEKHQVTS LHDIAEETPI YSVFALLFQQ LGGLSLYLAT NATGQPYPGV SKFFKSHYWP   240
SSPVFDKKDY WYIVLSDLGI LATLTSVYTA YKVFGFWPTF ITWFCPWILV NHWLVFVTFL   300
QHTDSSMPHY DAQEWTFAKG AAATIDREFG ILGIIFHDII ETHVLHHYVS RIPFYHAREA   360
TECIKKVMGE HYRHTDENMW VSLWKTWRSC QFVENHDGVY MFRNCNNVGV KPKDT   415
```

```
SEQ ID NO: 7             moltype = DNA  length = 1392
FEATURE                  Location/Qualifiers
source                   1..1392
                         mol_type = other DNA
                         organism = Micromonas pusilla
SEQUENCE: 7
atgtgcccgc cgaagacgga cggccgatcg tccccgcgat cgccgctgac gcgcagcaaa    60
tcctccgcgc aggcgctcga cgccaaggac gcgtcgaccg cgcccgtcga tctcaaaacg   120
ctcgagccgc acgagctcgc ggcgacgttc gagacgcgat gggtgcgcgt ggaggacgtc   180
gagtacgacg tcacaaactt caaacacccg ggaggcagcg tgatattcta catgctcgcg   240
aacacgggcg cggacgccac ggaggcgttc aaggagttcc acatgcgatc gcttaaggcg   300
tggaagatgc tcagagcgct gccgtcgcgc cccgcgagag tcaaacgcag cgagagcgag   360
gacgcgccga tgttggagga tttcgcgcgg tggcgcgcag agtcgaacg cgacgggttc   420
tttaagcccct cgataacgca cgtcgcgtat cggttactcg agctcctcgc gaccttcgc   480
ctcggcaccg ccctcatgta cgccgggtac ccgatcatcg cgtccgtcgt gtacggcgcg   540
ttcttcggcg ctcggtgcgg ttgggtccag cacgagggcg ggcacaactc gctcacgggg   600
tccgtctacg tcgacaagcg cctccaagcg atgacgtgcg ggttcgggct gtccacgagc   660
ggggagatgt ggaaccagat gcacaataag caccacgcga cgccgcagaa agtgaggcac   720
gacatggacc tggacacgac ccccgcggtg gcgtttttta acaccgccgt ggaggacaac   780
cggccgaggg ggttctcccg cgcgtgggct cggcttcagg cgtggacgtt cgtcccggtg   840
acctccggc tgctcgtcca ggcgttctgg atctacgtcc tgcacccgcg gcaggtgttg   900
cgaaagaaga actacgagga ggcgtcgtgg atgctcgtct ctcacgtcgt caggaccgcg   960
gtgattaaac tcgcgacggg gtactcgtgg cccgtcgcgt actggtggt caccttcggc   1020
aactggatcg cgtacatgta cctcttcgcg cacttctcca cgagccacac gcacctcccg   1080
gtcgtgccct cggataagca cctgagctgg gtgaactacg cggtcgatca caccgtggac   1140
atcgaccgt cgcgcgggta cgtgaactgg ttgatgggat atctgaactg ccaggtcatt   1200
catcacctgt tcccggacat gccgcagttt cgccagccgg aggtgagccg cgcggttcgtc  1260
ccgttcgcga agaagtgggg gctgaactac aaggtgctgt cctattacgg cgcctggaag   1320
gcgacgttct cgaacttgga taaggtcggg cagcactact acgtcaacgg caaggcggag   1380
aaggcgcact ga   1392
```

```
SEQ ID NO: 8             moltype = DNA  length = 1395
FEATURE                  Location/Qualifiers
misc_feature             1..1395
                         note = Codon-optimized open reading frame for expression of
                         Micromonaspusilla6 desaturase in plants (version 1)
source                   1..1395
                         mol_type = other DNA
                         organism = synthetic construct
SEQUENCE: 8
atgtgccctc ctaagactga tggaagatct tctcctagat ctccacttac caggtctaaa    60
tcttctgctg aggctcttga tgctaaggat gcttctactg ctcctgttga tcttaagact   120
cttgagcctc atgagcttgc tgctactttc gagactagag ggttagagt tgaggacgtt   180
gagtacgatg tgactaactt caagcaccct ggtggatctg tgatcttcta catgcttgct   240
aacactggtg ctgatgctac tgaggctttc aaagaattcc acatgcgttc tctcaaggct   300
```

-continued

```
tggaagatgc ttagagcttt gccttctaga cctgctgaga tcaagagatc tgagtctgag    360
gatgctccta tgcttgagga tttcgctaga tggcgtgctg agcttgagag agatggattc    420
ttcaagcctt ctatcaccca tgtggcttac agacttctcg agcttcttgc tacattcgct    480
cttgaactg ctcttatgta cgctggatac cctatcattg cttctgttgt ttacggtgct    540
ttcttcggag ctagatgtgg atgggttcaa catgagggtg gacataactc tcttaccgga    600
tctgtttacg tggacaagag acttcaggct atgacttgtg gattcggact ttctacttct    660
ggtgagatgt ggaaccagat gcataacaag caccatgcta cccctcaaaa ggttagacac    720
gatatggatc ttgataccac tcctgctgtg gctttcttca acactgctgt tgaggataac    780
agacctagag gattctctag agcttgggct agacttcaag cttggacttt cgttcctgtt    840
acctctggac ttcttgttca agctttctgg atctacgttc tccaccctag acaagttctc    900
cgtaagaaga actacgaaga ggcttcttgg atgctcgttt ctcatgttgt tagaaccgct    960
gttatcaagc ttgctactgg atactcttgg cctgttgctt actggtggtt cactttcgga   1020
aactggatcg cttacatgta ccttttcgct cacttctcta cttctcatac tcacctccct   1080
gttgttccat ctgataagca cctttcttgg gttaactacg ctgttgatca caccgttgat   1140
atcgatcctt ctagaggata cgtgaactgg cttatgggat accttaactg tcaggttatc   1200
caccacctct tccctgatat gcctcaattc agacagcctg aggttagcag aagattcgtt   1260
cctttcgcta gaagtggggg actcaactac aaggtgctct cttactacgg tgcttggaag   1320
gctactttct ctaaccttga taaggtggga cagcactact acgttaacgg aaaggctgag   1380
aaggctcact aatga                                                     1395
```

```
SEQ ID NO: 9               moltype = AA  length = 463
FEATURE                    Location/Qualifiers
source                     1..463
                           mol_type = protein
                           organism = Micromonas pusilla
SEQUENCE: 9
MCPPKTDGRS SPRSPLTRSK SSAEALDAKD ASTAPVDLKT LEPHELAATF ETRWVRVEDV     60
EYDVTNFKHP GGSVIFYMLA NTGADATEAF KEFHMRSLKA WKMLRALPSR PAEIKRSESE    120
DAPMLEDFAR WRAELERDGF FKPSITHVAY RLLELLATFA LGTALMYAGY PIIASVVYGA    180
FFGARCGWVQ HEGGHNSLTG SVYVDKRLQA MTCGFGLSTS GEMWNQMHNK HHATPQKVRH    240
DMDLDTTPAV AFFNTAVEDN RPRGFSRAWA RLQAWTFVPV TSGLLVQAFW IYVLHPRQVL    300
RKKNYEEASW MLVSHVVRTA VIKLATGYSW PVAYWWFTFG NWIAYMYLFA HFSTSHTHLP    360
VVPSDKHLSW VNYAVDHTVD IDPSRGYVNW LMGYLNCQVI HHLFPDMPQF RQPEVSRRFV    420
PFAKKWGLNY KVLSYYGAWK ATFSNLDKVG QHYYVNGKAE KAH                      463
```

```
SEQ ID NO: 10              moltype = DNA  length = 1449
FEATURE                    Location/Qualifiers
source                     1..1449
                           mol_type = other DNA
                           organism = Ostreococcus lucimarinus
SEQUENCE: 10
atgtgcgtcg aaacgaccga aggcacatcg cgaacgatgg cgaacgaacg cacgagctcg     60
tcgtcgtcgc tgagcgaagg cggaacgccg acggtgacgg tcgggatggg aagcgaagac    120
gcggggaaga agactcgaaa cgcgagcgtc acggcgtgga cgaaagagtt ggagccgcac    180
gcgatcgcga agacgttcga acggcggtac gtgacgatcg aaggcgtgga atacgatgtg    240
acggattta agcatcccgg aggatcggtt atttattaca tgctgtcgaa cacgggagcg    300
gacgcgacgg aggcttttaa agagtttcat tatcggtcga aaaaggcgcg caaggcgttg    360
gcggcgttgc cgcataagcc agtggacgcg gcgacgcggg aaccgatcga agatgaggcg    420
atgctgaagg atttcgcgca gtggcgcaag gaattggagc gtgagggatt ttttaagccc    480
tcgccggcgc acgtggcgta tcgattcgcc gagctcgcgg cgatgttcgc gctcggcacg    540
gcgttgatcg acgcgcgttg gcacgtcgct tccgtgatcg tgtactcgtg tttcttcggc    600
gcgcgatgcg gttgggtgca gcacgagggt gggcacaatt cgttgactgg aaacatttgg    660
tgggacaagc gaatccaagc cttcgccgcg gggttcggct tggcgtcgag tggcgacatg    720
tggaacaaca tgcacaacaa gcatcacgcg acgccccaaa aggtgcgaca cgatatggat    780
ctcgacacca ctcccacggt ggcgttcttc aactccgcgg ttgaagaaaa tcgcccgcgg    840
ggattcagta agttgtggtt gcgccttcaa gcgtggacct tcgtgcccgt gacgtccggt    900
atggttttgt tcttctggat gttcgtcttg cacccgcgta acgcgctgcg acgcaaaagc    960
ttcgaagaag cggcttggat gttttccgcg cacgtcattc gcacggcggt tatcaaagcc   1020
gtcaccggct actcctggat cgcctcgtac ggcttgttcg cggcgacgat gtgggcgagc   1080
ggatgttact tgttcgcgca cttttccacg tctcacacgc acttggatgt cgtgccgagc   1140
gataaacacc tctcgtgggt gcgatacgcc gtcgatcaca cgatcgacat caatccgaac   1200
aacagcgtcg tcaactggtt gatgggctac ttgaactgcc aagtcatcca tcacctgttc   1260
ccggatatgc ctcagttccg ccaacccgaa gtctcccgcc gattcgtccc gtttgcgaag   1320
aagtggaact aaaactacaa ggtcttgacg tattatgggg cctggaaggc gacgttcggc   1380
aacttgaacg acgtcgggaa gcactattac gtgcacggat ctcagcgcgt caaatcaaag   1440
tcggcgtga                                                            1449
```

```
SEQ ID NO: 11              moltype = DNA  length = 1449
FEATURE                    Location/Qualifiers
misc_feature               1..1449
                           note = Codon-optimized open reading frame for expression of
                           Ostreococcuslucimarinus6-desaturase in plants
source                     1..1449
                           mol_type = other DNA
                           organism = synthetic construct
SEQUENCE: 11
atgtgtgttg agactactga gggaaccctc agaactatgg ctaacgagag gacctcttct     60
tcttcttcac tctctgaggg tggaactcct actgttactg tgggaatggg atctgaggat    120
gctgaaagaa aaaccagaaa cgcttctgtt actgcttgga ccaaagagct tgagcctcac    180
```

```
gctatcgcta agaccttcga gagaagatac gttaccatcg aggatgttga gtacgatgtg   240
accgatttca aacaccctgg tggatctgtg atctactaca tgctctctaa cactggtgct   300
gatgctactg aggctttcaa agagttccac taccgttcta agaaggctag aaaggctctt   360
gctgctcttc ctcacaagcc tgttgatgct gctactagag agcctattga ggacgaggct   420
atgcttaagg atttcgctca gtggagaaaa gagttggaga gagagggatt cttcaagcct   480
tctcctgctc atgttgctta ccgtttcgct gaactcgctg ctatgttcgc tcttggaacc   540
gctcttatgc atgctagatg gcacgttgct agcgttatcg tgtactcctg tttcttcgga   600
gctagatgtg gatgggttca acatgagggt ggacacaact ctcttaccgg aaacatctgg   660
tgggataaga gaatccaagc tttcgctgct ggattcggac ttgcttcttc tggtgacatg   720
tggaacaaca tgcacaacaa gcaccatgct actcctcaga aagtgagaca cgatatggat   780
cttgatacca cccctaccgt tgctttcttc aactctgctg tggaggaaaa cagacctagg   840
ggattctcta agctttggct cagacttcaa gcttggacct tcgttcctgt tacctctgga   900
atggtgctct tcttctggat gttcgttctc catcctagaa acgctctccg tcgtaagtct   960
ttcgaagagg ctgcttggat gttctctgct cacgttatca gaaccgctgt tatcaaggct  1020
gttaccggat actcttggat cgctagctac ggacttttcg ctgctactat gtgggcttcc  1080
ggatgctacc ttttcgctca cttctctact tctcacaccc acctcgatgt tgttccatct  1140
gataagcacc ttagctgggt taggtacgct gttgatcaca ccatcgacat caaccctaac  1200
aactctgttg tgaactggct tatgggatac cttaactgcc aggttatcca ccatctcttc  1260
cctgatatgc ctcaattcag acagcctgag gtgtcaagaa gattcgtccc tttcgctaag  1320
aagtggaacc tcaactacaa ggtgctcact tactacggtg cttggaaggc tactttcgga  1380
aacctcaacg atgttggaaa gcactactac gttcacggat ctcagagagt gaagagcaag  1440
agcgcttga                                                         1449
```

```
SEQ ID NO: 12              moltype = AA   length = 482
FEATURE                    Location/Qualifiers
source                     1..482
                           mol_type = protein
                           organism = Ostreococcus lucimarinus
SEQUENCE: 12
MCVETTEGTS RTMANERTSS SSSLSEGGTP TVTVGMGSED AGKKTRNASV TAWTKELEPH   60
AIAKTFERRY VTIEGVEYDV TDFKHPGGSV IYYMLSNTGA DATEAFKEFH YRSKKARKAL  120
AALPHKPVDA ATREPIEDEA MLKDFAQWRK ELEREGFFKP SPAHVAYRFA ELAAMFALGT  180
ALMHARWHVA SVIVYSCFFG ARCGWVQHEG GHNSLTGNIW WDKRIQAFAA GFGLASSGDM  240
WNNMHNKHHA TPQKVRHDMD LDTTPTVAFF NSAVEENRPR GFSKLWLRLQ AWTFVPVTSG  300
MVLFFWMFVL HPRNALRRKS FEEAAWMFSA HVIRTAVIKA VTGYSWIASY GLFAATMWAS  360
GCYLFAHFST SHTHLDVVPS DKHLSWVRYA VDHTIDINPN NSVVNWLMGY LNCQVIHHLF  420
PDMPQFRQPE VSRRFVPFAK KWNLNYKVLT YYGAWKATFG NLNDVGKHYY VHGSQRVKSK  480
SA                                                                482
```

```
SEQ ID NO: 13              moltype = AA   length = 456
FEATURE                    Location/Qualifiers
source                     1..456
                           mol_type = protein
                           organism = Ostreococcus tauri
SEQUENCE: 13
MCVETENNDG IPTVEIAFDG ERERAEANVK LSAEKMEPAA LAKTFARRYV VIEGVEYDVT   60
DFKHPGGTVI FYALSNTGAD ATEAFKEFHH RSRKARKALA ALPSRPAKTA KVDDAEMLQD  120
FAKWRKELER DGFFKPSPAH VAYRFAELAA MYALGTYLMY ARYVVSSVLV YACFFGARCG  180
WVQHEGGHSS LTGNIWWDKR IQAFTAGFGL AGSGDMWNSM HNKHHATPQK VRHDMDLDTT  240
PAVAFFNTAV EDNRPRGFSK YWLRLQAWTF IPVTSGLVLL FWMFFLHPSK ALKGGKYEEL  300
VWMLAAHVIR TWTIKAVTGF TAMQSYGLFL ATSWVSGCYL FAHFSTSHTH LDVVPADEHL  360
SWVRYAVDHT IDIDPSQGWV NWLMGYLNCQ VIHHLFPSMP QFRQPEVSRR FVAFAKKWNL  420
NYKVMTYAGA WKATLGNLDN VGKHYYVHGQ HSGKTA                           456
```

```
SEQ ID NO: 14              moltype = DNA   length = 894
FEATURE                    Location/Qualifiers
source                     1..894
                           mol_type = other DNA
                           organism = Pyramimonas cordata
SEQUENCE: 14
atggagttcg ctcagcctct tgtggctatg gcacaggagc agtatgccgc aattgacgcg    60
gtggtagccc ctgcaatttt ctcagctacc gacagcatcg gttggggtct taagcccatt   120
agcagcgcga caaaggatct tcctctcgtt gagagtccga cgccgctcat actgagcctg   180
ttggcctatt ttgcgatcgt cggctctggg ctggtgtacc gcaaagtatt ccctcgcaca   240
gtaaaggggc aagacccctt cctgctgaag gcgctcatcg ttgcgcacaa cgtgttcctc   300
attggcctca gtctatacat gtgcttgaag cttgtctacg aggcttacgt caacaagtac   360
tccttctggg gaaacgccta caaccccgca cagaccgaga tggcgaaggt catctggatt   420
ttctacgtct ccaagatcta tgagttcatg gacacgttca tcatgctctt gaagggcaac   480
gtcaaccagg tctcttttcct gcatgtgtac catcatggct ccatctctgg tatctggtgg   540
atgatcacct acgctgcccc tggcggtgac gcgtacttct cggcggcgct caactcgtgg   600
gtgcacgtgt gcatgtacac gtactacttc atggcggcgg tgctgcccaa ggacgagaag   660
accaagcgca gtacctctg tgtggggccgc tacctgaccc agatgcagat gttccagttc   720
ttcatgaacc tgctccaggc ggtctacctc ctctactcct ctagccccta ccccaagttc   780
atcgcccagc tgctggtggt gtacatggtc acgctgctga tgctcttcgg caacttctac   840
tacatgaagc accacgcgag caagaagcag aagctggcca gcaagaagca gtag          894
```

```
SEQ ID NO: 15              moltype = DNA   length = 870
FEATURE                    Location/Qualifiers
misc_feature               1..870
```

```
                            note = Codon-optimized open reading frame for expression of
                             Pyramimonascordata6 elongase in plants (truncated at 3'
                             end and encodingfunctional elongase) (version 1)
source                      1..870
                            mol_type = other DNA
                            organism = synthetic construct
SEQUENCE: 15
atggaattcg cccagcctct tgttgctatg gctcaagagc aatacgctgc tatcgatgct   60
gttgttgctc ctgctatctt ctctgctact gattctatcg gatggggact taagcctatc  120
tcttctgcta ctaaggactt gcctcttgtt gagtctccta cacctctcat cctttctttg  180
cttgcttact tcgctatcgt tggatctgga ctcgtttaca gaaaggtttt ccctagaacc  240
gtgaagggac aagatccatt ccttttgaag gctcttatgc ttgctcacaa cgtgttcctt  300
atcggacttt ctctttacat gtgcctcaag cttgtgtacg aggcttacgt taacaagtac  360
tctttctggg gaaacgctta caaccctgct caaactgaga tggctaaggt tatctggatc  420
ttctacgtga gcaagatcta cgagttcatg gataccttca tcatgctcct caagggaaat  480
gttaaccagg ttagcttcct tcacgtttac catcacggat ctatctctgg aatctggtgg  540
atgattactt acgctgctcc tggtggtgat gcttacttct ctgctgctct taactcttgg  600
gttcacgtgt gtatgtacac ctactatttt atggctgccg tgcttcctaa ggacgagaaa  660
actaagagaa agtacctctg gtggggaaga taccttactc aaatgcagat gttccagttc  720
ttcatgaacc ttctccaggc tgtttacctt ctctactctt catctcctta ccctaagttt  780
atcgctcagc tcctcgtggt gtacatggtt actcttctca tgcttttcgg aaacttctac  840
tacatgaagc accacgctag caagtgatga                                   870

SEQ ID NO: 16              moltype = AA  length = 297
FEATURE                    Location/Qualifiers
source                     1..297
                           mol_type = protein
                           organism = Pyramimonas cordata
SEQUENCE: 16
MEFAQPLVAM AQEQYAAIDA VVAPAIFSAT DSIGWGLKPI SSATKDLPLV ESPTPLILSL   60
LAYFAIVGSG LVYRKVFPRT VKGQDPFLLK ALMLAHNVFL IGLSLYMCLK LVYEAYVNKY  120
SFWGNAYNPA QTEMAKVIWI FYVSKIYEFM DTFIMLLKGN VNQVSFLHVY HHGSISGIWW  180
MITYAAPGGD AYFSAALNSW VHVCMYTYYF MAAVLPKDEK TKRKYLWWGR YLTQMQMFQF  240
FMNLLQAVYL LYSSSPYPKF IAQLLVVYMV TLLMLFGNFY YMKHHASKKQ KLASKKQ     297

SEQ ID NO: 17              moltype = AA  length = 288
FEATURE                    Location/Qualifiers
source                     1..288
                           mol_type = protein
                           organism = Pyramimonas cordata
SEQUENCE: 17
MEFAQPLVAM AQEQYAAIDA VVAPAIFSAT DSIGWGLKPI SSATKDLPLV ESPTPLILSL   60
LAYFAIVGSG LVYRKVFPRT VKGQDPFLLK ALMLAHNVFL IGLSLYMCLK LVYEAYVNKY  120
SFWGNAYNPA QTEMAKVIWI FYVSKIYEFM DTFIMLLKGN VNQVSFLHVY HHGSISGIWW  180
MITYAAPGGD AYFSAALNSW VHVCMYTYYF MAAVLPKDEK TKRKYLWWGR YLTQMQMFQF  240
FMNLLQAVYL LYSSSPYPKF IAQLLVVYMV TLLMLFGNFY YMKHHASK             288

SEQ ID NO: 18              moltype = DNA  length = 1278
FEATURE                    Location/Qualifiers
source                     1..1278
                           mol_type = other DNA
                           organism = Pavlova salina
SEQUENCE: 18
atgccgccgc gcgatagcta ctcgtacgcc gccccgccgt cggcccagct gcacgaggtc   60
gataccccgc aggagcatga taagaaggag ctcgtcatcg gtgaccgcgc gtacgacgtg  120
accaactttg tgaagcgcca cccgggtggc aagatcatcg cataccaggt tggcacagat  180
gcgacggacg cgtacaagca gttccatgtg cggtctgcca aggcggacaa gatgctcaag  240
tcgctgcctt cgcgcccggt gcacaagggc tactcgcccc gccgcgctga cctcattgcc  300
gacttccagg agttcaccaa gcagctggag cggagggca tgtttgagcc gtcgctgccg  360
cacgtggcat accgcctggc ggaggtgatc gcgatgcacg tggccggcgc cgcgctcatc  420
tggcacgggt acaccttcgc gggcattgcc atgctcggcg ttgtgcaggg ccgctgcgcg  480
tggctcatgc acgagggcgg ccactactcg ctcacgggca acattgcttt tgaccgtgcc  540
atccaagtcg cgtgctacgg ccttggctgc ggcatgtcgg gcgcgtggtg gcgcaaccag  600
cacaacaagc accacgcgac gccgcagaag ttgcagcacg acgtcgacct cgacaccctc  660
ccgctcgtcg ccttccacga gcggatagcc gccaaggtga agagccccgc gatgaaggcg  720
tggcttagta tgcaggcgaa gctcttcgcg ccagtgacca cgctgctggt cgcgctgggc  780
tggcagctgt acctgcaccc gcgccatatg ctgcgcacca gcactacga cgagctcgcg  840
atgctcggca ttcgctacgg ccttgtcggc tacctcgcgg cgaactacgg cgcgggggtac  900
gtgctcgtgt gctacctgct gtacgtgcag ctcggcgca tgtacatctt ctgcaacttt  960
gccgtgtcgc acacacacct gccggttgtc gagcctaacg agcacgcaac gtgggtggag  1020
tacgccgcga accacgacga caactgctcg ccctcgtggt ggtgcgactg gtgggatgtcg  1080
tacctcaact accagatcga gcaccacctc tacccgtcca tgccgcagtt ccgccacccg  1140
aagattgcgc gcgggggtgaa gcagctcttc gagaagcacg gcctgcacta cgacgtgcgt  1200
ggctacttcg aggccatggc ggacacgttt gccaaccttg acaacgtcgc gcacgcgccg  1260
gagaagaaga tgcagtga                                                1278

SEQ ID NO: 19              moltype = DNA  length = 1281
FEATURE                    Location/Qualifiers
misc_feature              1..1281
```

```
                          note = Codon-optimized open reading frame for expression of
                          Pavlovasalina5 desaturase in plants (version 1)
source                    1..1281
                          mol_type = other DNA
                          organism = synthetic construct
SEQUENCE: 19
atgcctccaa gggactctta ctcttatgct gctcctcctt ctgctcaact tcacgaagtt      60
gatactcctc aagagcacga caagaaagag cttgttatcg gagatagggc ttacgatgtt     120
accaacttcg ttaagagaca ccctggtgga aagatcattg cttaccaagt tggaactgat     180
gctaccgatg cttacaagca gttccatgtt agatctgcta aggctgacaa gatgcttaag     240
tctcttcctt ctcgtcctgt tcacaaggga tactctccaa gaagggctga tcttatcgct     300
gatttccaag agttcaccaa gcaacttgag gctgagggaa tgttcgagcc ttctcttcct     360
catgttgctt acagacttgc tgaggttatc gctatgcatg ttgctggtgc tgctcttatc     420
tggcatggat acacttttcgc tggaatcgct atgcttggag ttgttcaggg aagatgtgga     480
tggcttatgc atgagggtgg acattactct ctcactggaa acattgcttt cgacagagct     540
atccaagttg cttgttacgg acttggatgt ggaatgtctg gtgcttggtg gcgtaaccag     600
cataacaagc accatgctac tcctcaaaag cttcagcacg atgttgatct tgataccctt     660
cctctcgttg ctttccatga gagaatcgct gctaaggtta agtctcctgc tatgaaggct     720
tggctttcta tgcaagctaa gcttttcgct cctgttacca ctcttcttgt tgctcttgga     780
tggcagcttt accttcatcc tagacacatg ctcaggacta agcactacga tgagcttgct     840
atgctcggaa tcagatacgg acttgttgga taccttgctg ctaactacgg tgctggatac     900
gttctcgctt gttaccttct ttacgttcag cttggagcta tgtacatctt ctgcaacttc     960
gctgtttctc atactcacct ccctgttgtt gagcctaacg agcatgctac ttgggttgag    1020
tacgctgcta accacactac taactgttct ccatcttggt ggtgtgattg gtggatgtct    1080
taccttaact accagatcga gcaccaccacctt tacccttcta tgcctcaatt cagacaccct    1140
aagatcgctc ctagagttaa gcagctttc gagaagcacg gacttcacta cgatgttaga    1200
ggatacttcg aggctatggc tgatactttc gctaaccttg ataacgttgc ccatgctcct    1260
gagaagaaaa tgcagtaatg a                                               1281

SEQ ID NO: 20             moltype = AA  length = 425
FEATURE                   Location/Qualifiers
source                    1..425
                          mol_type = protein
                          organism = Pavlova salina
SEQUENCE: 20
MPPRDSYSYA APPSAQLHEV DTPQEHDKKE LVIGDRAYDV TNFVKRHPGG KIIAYQVGTD      60
ATDAYKQFHV RSAKADKMLK SLPSRPVHKG YSPRRADLIA DFQEFTKQLE AEGMFEPSLP     120
HVAYRLAEVI AMHVAGAALI WHGYTFAGIA MLGVVQGRCG WLMHEGGHYS LTGNIAFDRA     180
IQVACYGLGC GMSGAWWRNQ HNKHHATPQK LQHDVDLDTL PLVAFHERIA AKVKSPAMKA     240
WLSMQAKLFA PVTTLLVALG WQLYLHPRHM LRTKHYDELA MLGIRYGLVG YLAANYGAGY     300
VLACYLLYVQ LGAMYIFCNF AVSHTHLPVV EPNEHATWVE YAANHTTNCS PSWWCDWWMS     360
YLNYQIEHHL YPSMPQFRHP KIAPRVKQLF EKHGLHYDVR GYFEAMADTF ANLDNVAHAP     420
EKKMQ                                                                 425

SEQ ID NO: 21             moltype = DNA  length = 1329
FEATURE                   Location/Qualifiers
source                    1..1329
                          mol_type = other DNA
                          organism = Pyramimonas cordata
SEQUENCE: 21
atgggaaagg gaggcaatgc tagcgctcct actgcgaaga aggaggtgtt gatcgagggg      60
aagtttttacg atgtcaccga cttcaggcac cccggtggtt cgatcatcaa gtttctctcg     120
ggttctggtg ctgacgccac cgcttcctac cgcgagttcc acgttaggtc agcgaaggca     180
gacaagttct tgaagacgct gccctcccgc gaagccactc cccaggagct gaagcaggcg     240
gttgagttct ccaagctcaa cccgccctcc gcggagagtg cctctgctcc cctgaccgac     300
cttgccaagg tggaagcgct gaacaaggac ttcgaggctt ccgtgagca gctcattcag     360
gagggcttct ttaagcccaa tatcccgcat gtggtcaagc gcatcacgga agtcgtggcg     420
atgatggccg tagcctcctg gatgatggtg cagaccaacg ctcttgttgt gaccctcgga     480
gttctgatcc gcggcattgc acagggccgg tgcggttggc ttatgcacga gggcggccac     540
tatagtctta ctgggaagat ctccattgat aggcgtctgc aggagtcaat ttacggattc     600
ggctgtggaa tgtccggcgc ctggtggcgc aaccagcaca acaagcacca cgcaacccca     660
cagaagctgc agcatgacgt cgacctggag acccttcctc tgatggcttt caacaacgct     720
gttaccgata gacgcaaggt gaagcctggt agtctccagg ctctgtggct caagtaccag     780
gccttcctct tcttccccgt gacctccctt ctggtcaggc tcggttggac caccgtcctc     840
cacccccaggc acagcttgcg caccaagcac tatttcgagc tgctctgcat ggctgctcgt     900
tacgcgagtt tcgctgctct tttcgctccc aagtacggac ttgcaggagc tgccgggctc     960
tacctcgcca ccttcgctgt cgggtgcaac tatattttca tcaacttctc ggtctctcac    1020
actcacctgc ccgtgagcgg tgcgagcgag tacctgcatt gggtcgtgta ttcggccatc    1080
cacaccacta acatcaaatc cagcatgctg tgcgattggt ggatgtcatt cctcaacttc    1140
cagatcgagc atcacctgtt cccttcaatg ccccagttcc gccacaagat tatctccccg    1200
cgtgtaaagg ccttgtttga gaagcacggt cttgtgtatg atgtgcgccc ctattggggg    1260
gccatggctg acaccttcaa gaacttgaat gacgttggca ctcacgcatc tcactccaag    1320
gcgcactag                                                            1329

SEQ ID NO: 22             moltype = AA  length = 442
FEATURE                   Location/Qualifiers
source                    1..442
                          mol_type = protein
                          organism = Pyramimonas cordata
```

```
SEQUENCE: 22
MGKGGNASAP  TAKKEVLIEG  KFYDVTDFRH  PGGSIIKFLS  GSGADATASY  REFHVRSAKA  60
DKFLKTLPSR  EATPQELKQA  VEFSKLNPPS  AESASAPLTD  LAKVEALNKD  FEAFREQLIQ  120
EGFFKPNIPH  VVKRITEVVA  MMAVASWMMV  QTNALVVTLG  VLIRGIAQGR  CGWLMHEGGH  180
YSLTGKISID  RRLQESIYGF  GCGMSGAWWR  NQHNKHHATP  QKLQHDVDLE  TLPLMAFNNA  240
VTDRRKVKPG  SLQALWLKYQ  AFLFFPVTSL  LVGLGWTTVL  HPRHSLRTKH  YFELLCMAAR  300
YASFAALFAP  KYGLAGAAGL  YLATFAVGCN  YIFINFSVSH  THLPVSGASE  YLHWVVYSAI  360
HTTNIKSSML  CDWWMSFLNF  QIEHHLFPSM  PQFRHKIISP  RVKALFEKHG  LVYDVRPYWG  420
AMADTFKNLN  DVGTHASHSK  AH                                              442

SEQ ID NO: 23              moltype = DNA  length = 804
FEATURE                    Location/Qualifiers
source                     1..804
                           mol_type = other DNA
                           organism = Pyramimonas cordata
SEQUENCE: 23
atggcgtcta ttgcgattcc ggctgcgctg gcagggactc ttggttatgt gacgtacaat  60
gtcgcaaacc cagatattcc tgcatccgag aaggtgcctg cttactttat gcaggtcgag  120
tattgggggc caacgattgg gaccatcggt tatcttctgt tcatctactt tggtaaacgg  180
attatgcaaa acaggagcca gccgtttggc ctgaagaacg ctatgctggt gtacaacttc  240
tatcagactt tcttcaactc gtactgcata tacctttttg tcacgtcgca ccgcgctcag  300
gggctgaaag tttgggggaaa catccccgat atgactgctg acagctgggg gatctcacag  360
gtgatctggc tgcactacaa caacaagtac gttgagctgc tggacacgtt cttcatggtc  420
atgcgcaaga agtttgacca gctttcgttc ctgcacattt accatcatac cctgttgatc  480
tggtcttggt tcgtggtgat gaaattggag cccgttgggg actgctactt tggctctagc  540
gtcaacacgt ttgtgcacgt cattatgtac tcgtactatg gcttgccgc ctgcggggtg  600
aattgcttct ggaagaagta cattacgcag attcagatgc tgcagttctg tatctgcgct  660
tcgcactcga tttataccgc ctatgtgcag aacaccgcgt tctggttgcc ttacttgcag  720
ctgtgggtga tggtgaacat gttcgtgttg ttcgccaact tctatcgcaa gcgctacaag  780
agcaaggggtg ccaagaagca gtaa                                          804

SEQ ID NO: 24              moltype = DNA  length = 807
FEATURE                    Location/Qualifiers
misc_feature               1..807
                           note = Codon-optimized open reading frame for expression of
                           Pyramimonascordata5 elongase in plants (version 1)
source                     1..807
                           mol_type = other DNA
                           organism = synthetic construct
SEQUENCE: 24
atggcctcta tcgctatccc tgctgctctt gctggaactc ttggatacgt tacctacaat  60
gtggctaacc ctgatatccc agcttctgag aaagttcctg cttacttcat gcaggttgag  120
tactggggac ctactatcgg aactattgga tacctcctct tcatctactt cggaaagcgt  180
atcatgcaga acagatctca acctttcgga ctcaagaacg ctatgctcgt ttacaacttc  240
taccagacct tcttcaacag ctactgcatc tacctttttcg ttacttctca tagggctcag  300
ggacttaagg tttggggaaa catccctgat atgactgcta actcttgggg aatctctcag  360
gttatctggc ttcactacaa caacaagtac gttgagctcc tcgacacctt cttcatggtg  420
atgaggaaga agttcgacca gctttctttc cttcacatct accaccacac tcttctcatc  480
tggtcatggt tcgttgttat gaagcttgag cctgttggag attgctactt cggatcttct  540
gttaacacct tcgtgcacgt gatcatgtac tcttactacg gacttgctgc tcttggagtt  600
aactgtttct ggaagaagta catcacccag atccagatgc ttcagttctg tatctgtgct  660
tctcactcta tctacaccgc ttacgttcag aataccgctt ctggcttcc ttaccttcaa  720
ctctgggtta tggtgaacat gttcgttctc ttcgccaact ctaccgtaa gaggtacaag  780
tctaagggtg ctaagaagca gtgataa                                        807

SEQ ID NO: 25              moltype = AA  length = 267
FEATURE                    Location/Qualifiers
source                     1..267
                           mol_type = protein
                           organism = Pyramimonas cordata
SEQUENCE: 25
MASIAIPAAL  AGTLGYVTYN  VANPDIPASE  KVPAYFMQVE  YWGPTIGTIG  YLLFIYFGKR  60
IMQNRSQPFG  LKNAMLVYNF  YQTFFNSYCI  YLFVTSHRAQ  GLKVWGNIPD  MTANSWGISQ  120
VIWLHYNNKY  VELLDTFFMV  MRKKFDQLSF  LHIYHHTLLI  WSWFVVMKLE  PVGDCYFGSS  180
VNTFVHVIMY  SYYGLAALGV  NCFWKKYITQ  IQMLQFCICA  SHSIYTAYVQ  NTAFWLPYLQ  240
LWVMVNMFVL  FANFYRKRYK  SKGAKKQ                                       267

SEQ ID NO: 26              moltype = DNA  length = 1344
FEATURE                    Location/Qualifiers
source                     1..1344
                           mol_type = other DNA
                           organism = Pavlova salina
SEQUENCE: 26
atgcctccga gcgcggcgaa gcagatgggc gcgagcacgg gcgtgcatgc gggcgtcaca  60
gattcgtcgg ccttcacgcg caaggatgtc gccgacaggc cggacctcac gatcgtgggt  120
gacagcgtgt acgatgcgaa ggcgttccgc tccgagcatc cgggtggcgc gcactttgtg  180
tcgctgttcg gcgggcgcga tgccacggag gcgttcatgg agtaccaccg cgcgcctgg  240
cccaagtcgc gcatgtcgcg cttccacgtc ggctctctgg catcgaccga ggagcccgtc  300
gccgccgatg agggctacct ccagctgtgc gctcgcatcc ccaagatggt gccgtcggtc  360
```

```
agcagcgggt tcgcgccggc gtcgtactgg gtgaaggccg ggctgatcct cggctccgcg    420
atcgcgctcg aggcgtacat gctgtacgcg ggcaagcgcc tgctcccgtc gatcgtgctc    480
gggtggctgt ttgcgctgat tggcctgaac atccagcacg atgccaacca cggcgcgctc    540
tccaagtcgg cctcggtcaa cctggcgctc gggttgtgcc aggactggat cggcgggagc    600
atgatcctct ggctgcagga gcacgttgtc atgcaccact tgcacaccaa cgacgttgac    660
aaggacccgg accagaaggc cacggcgcgc ctgcggctca agccgaccga cgcgtggagc    720
ccgatgcact ggctgcagca cctctacctg ctgcctgggg agacgatgta cgcctttcaag   780
ctgctgtttc tcgacatcag cgagctggtg atgtggcggt gggagggcga gcccatcagc    840
aagctggccg ggtacctctt catgcccctcg ctgctcctca agctcaccttt ctgggcgcgc   900
tttgtcgcgc tgccgctgta cctcgcgccc agcgtgcaca cggcggtgtg catcgcggcg    960
acggtaatga cggggagctt ctacctcgcc ttcttcttct tcatctcgca caacttcgag   1020
ggcgtggcga gcgtcggacc ggacggcagc atcaccagca tgacgcgcgg cgcatccttc   1080
ctcaagcggc aggccgagac ctcgtccaac gtgggcggcc cgctgctcgc cacgctcaac   1140
ggcggcctca actaccaaat cgagcaccac ctcttcccca gggtgcacca cggcttctac   1200
cctcgcctcg cgccgttggt caaggcggag ctcgaggcgc gcggcattga gtacaagcac   1260
tacccccacca tatggagcaa cctggcatcc acgctgaggc acatgtacgc gctcggccgc   1320
aggccgcgca gcaaggcgga gtga                                          1344
```

```
SEQ ID NO: 27              moltype = DNA   length = 1347
FEATURE                    Location/Qualifiers
misc_feature               1..1347
                           note = Codon-optimized open reading frame for expression of
                            Pavlovasalina4 desaturase in plants (version 1)
source                     1..1347
                           mol_type = other DNA
                           organism = synthetic construct
SEQUENCE: 27
atgccaccta gcgctgctaa gcaaatggga gcttctactg gtgttcatgc tggtgttact    60
gactcttctg cttttcaccag aaaggatgtt gctgatagac ctgatctcac catcgttgga   120
gattctgttt acgatgctaa ggctttcaga tctgagcatc ctggtggtgc tcatttcgtt   180
tctttgttcg gaggaagaga tgctactgag gctttcatgg aataccatag aagggcttgg   240
cctaagtcta gaatgtctag attccacgtt ggatctcttg cttctactga ggaacctgtt   300
gctgctgatg agggatacct tcaactttgt gctaggatcg ctaagatggt gccttctgtt   360
tcttctggat tcgctcctgc ttcttactgg gttaaggctg gacttatcct tggatctgct   420
atcgctcttg aggcttacat gctttacgct ggaaagagac ttctccttc tatcgttctt   480
ggatggcttt tcgctcttat cggtcttaac atccagcatg atgctaacca tggtgctttg   540
tctaagtctg cttctgttaa ccttgctctt ggactttgtc aggattggat cggaggatct   600
atgatccttt ggcttcaaga gcatgttgtt atgcaccacc tccacactaa cgatgttgat   660
aaggatcctg atcaaaaggc tcacggtgct cttagactca agcctactga tgcttggtca   720
cctatgcatt ggcttcagca tctttacctt ttgcctggtg agactatgta cgcttttcaag   780
cttttgttcc tcgacatctc tgagcttgtt atgtggcgtt gggagggtga gcctatctct   840
aagcttgctg atacctcttt tatgccttct ttgcttctca gcttaccttt ctgggctaga   900
ttcgttgctt tgcctcttta ccttgctcct tctgttcaca ctgctgtgtg tatcgctgct   960
actgttatga ctggatcttt ctacctcgct ttcttcttct tcatctccca caacttcgag   1020
ggtgttgctt ctgttggacc tgatggatct atcacttcta tgactagagg tgctagcttc   1080
cttaagagac aagctgagac ttcttctaac gttggaggac ctcttcttgc tactcttaac   1140
ggtggactca actaccaaat tgagcatcac cttgttccca gagttcacca tggattctac   1200
cctagacttg ctcctcttgt taaggctgag cttgaggcga gaggaatcga gtacaagcac   1260
taccctacta tctggtctaa ccttgcttct accctcagac atatgtacgc tcttggaaga   1320
aggcctagat ctaaggctga gtaatga                                       1347
```

```
SEQ ID NO: 28              moltype = AA   length = 447
FEATURE                    Location/Qualifiers
source                     1..447
                           mol_type = protein
                           organism = Pavlova salina
SEQUENCE: 28
MPPSAAKQMG ASTGVHAGVT DSSAFTRKDV ADRPDLTIVG DSVYDAKAFR SEHPGGAHFV    60
SLFGGRDATE AFMEYHRRAW PKSRMSRFHV GSLASTEEPV AADEGYLQLC ARIAKMVPSV   120
SSGFAPASYW VKAGLILGSA IALEAYMLYA GKRLLPSIVL GWLFALIGLN IQHDANHGAL   180
SKSASVNLAL GLCQDWIGGS MILWLQEHVV MHHLHTNDVD KDPDQKAHGA LRLKPTDAWS   240
PMHWLQHLYL LPGETMYAFK LLFLDISELV MWRWEGEPIS KLAGYLFMPS LLLKLTFWAR   300
FVALPLYLAP SVHTAVCIAA TVMTGSFYLA FFFFISHNFE GVASVGPDGS ITSMTRGASF   360
LKRQAETSSN VGGPLLATLN GGLNYQIEHH LFPRVHHGFY PRLAPLVKAE LEARGIEYKH   420
YPTIWSNLAS TLRHMYALGR RPRSKAE                                       447
```

```
SEQ ID NO: 29              moltype = AA   length = 263
FEATURE                    Location/Qualifiers
source                     1..263
                           mol_type = protein
                           organism = Isochrysis galbana
SEQUENCE: 29
MALANDAGER IWAAVTDPEI LIGTFSYLLL KPLLRNSGLV DEKKGAYRTS MIWYNVLLAL    60
FSALSFYVTA TALGWDYGTG AWLRRQTGDT PQPLFQCPSP VWDSKLFTWT AKAFYYSKYV   120
EYLDTAWLVL KGKRVSFLQA FHHFGAPWDV YLGIRLHNEG VWIFMFFNSF IHTIMYTYYG   180
LTAAGYKFKA KPLITAMQIC QFVGGFLLVW DYINVPCFNS DKGKLFSWAF NYAYVGSVFL   240
LFCHFFYQDN LATKKSAKAG KQL                                           263
```

```
SEQ ID NO: 30              moltype = DNA   length = 801
```

```
FEATURE             Location/Qualifiers
misc_feature        1..801
                    note = Codon-optimized open reading frame for expression of
                    Emilianiahuxleyi9 elongase in plants
source              1..801
                    mol_type = other DNA
                    organism = synthetic construct
SEQUENCE: 30
atgcttgata gagcttcatc tgatgctgct atttggagcg ctgtttctga tcctgagatc   60
cttatcggaa ccttctctta cctttttgctt aagcctctcc tcagaaactc tggacttgtg  120
gatgagagaa agggagctta ccgtacttct atgatctggt acaacgttgt tcttgctctt  180
ttctctgcta cctctttcta cgttactgct actgctcttg gatgggataa gggaactggt  240
gagtggctta gatctcttac tggtgattct cctcaacaac tttggcagtg cccttctaga  300
gtttgggaca gcaaactctt cttgtggact gctaaagcct tctactactc caagtacgtt  360
gagtaccttg atactgcttg gcttgttctc aagggaaaga aggtttcatt cctccaggga  420
ttccatcatt tcggtgctcc atgggatgtt taccttggaa tcaggcttaa gaacgaggga  480
gtttggatct tcatgttctt caacagcttc atccacactg ttatgtacac ttactacgga  540
cttactgctg ctggatacaa gatcagagga aagcctatca tcaccgctat gcaaatctct  600
caattcgttg gtggattcgt tcttgtgtgg gactacatca acgttccttg tttccatgct  660
gatgctggac aagttttctc ttgggtgttc aactacgctt atgtgggatc tgttttcctt  720
cttttctgcc acttcttcta catggacaac attgctaagg ctaaggctaa aaaggctgtt  780
gctaccagaa aggctctttg a                                             801

SEQ ID NO: 31         moltype = AA   length = 266
FEATURE               Location/Qualifiers
source                1..266
                      mol_type = protein
                      organism = Emiliania huxleyi
SEQUENCE: 31
MLDRASSDAA IWSAVSDPEI LIGTFSYLLL KPLLRNSGLV DERKGAYRTS MIWYNVVLAL   60
FSATSFYVTA TALGWDKGTG EWLRSLTGDS PQQLWQCPSR VWDSKLFLWT AKAFYYSKYV  120
EYLDTAWLVL KGKKVSFLQG FHHFGAPWDV YLGIRLKNEG VWIFMFFNSF IHTVMYTYYG  180
LTAAGYKIRG KPIITAMQIS QFVGGFVLVW DYINVPCFHA DAGQVFSWVF NYAYVGSVFL  240
LFCHFFYMDN IAKAKAKKAV ATRKAL                                        266

SEQ ID NO: 32         moltype = DNA   length = 819
FEATURE               Location/Qualifiers
source                1..819
                      mol_type = other DNA
                      organism = Pavlova pinguis
SEQUENCE: 32
atggttgcgc cacccatcac gctcgagtgg ctgctttcgc cgaagctcaa ggatgcagtg   60
ttcggtgggg aggtgctcta cttctccatt gcctacctgt ttcttgcgcc catttttgaag  120
cgcacccccgt tggtggacac gcggaagggc gcgtataaga gtggtatgat cgcgtacaac  180
gtgatcatgt gcgtgttctc gctggtgtgc ttcatctgcc agctcgcagc cctgggctat  240
gacatgggct acttgcagtg ggtgcgtgac ctcacagggg acgagattgt cccctctac  300
caggacgtgt ccccgtcccc cgccttctcc aacaagctct tcaagtattc gtctattgcc  360
ttccactact ccaagtatgt tgagtacatg gacaccgcat ggctggtgat gaagggcaag  420
cccgtgtcct tgctccaggg cttccaccac tttggcgccg cctgggacac ctactttggc  480
atcaccttcc agaacgaggg catctacgtg ttcgtggtgc tcaacgcctt catccacacg  540
atcatgtacg catactacgc ggccactgcg gcgggtctca agttctcact gaagttcgtc  600
atcacgctca tgcagatcac ccaattcaac gtgggcttcg taatggtgta tcactacatc  660
accctggagt acttccgcaa ctcaccggag ctcgtcttct cctacctttt caactatgcg  720
tacgtctgca cggttctcct cctcttcatg cagttcttct acatggacaa ctttggcaag  780
aagaaggccg ctgccgccgc gggcaagaag aagaagtag                          819

SEQ ID NO: 33         moltype = AA   length = 272
FEATURE               Location/Qualifiers
source                1..272
                      mol_type = protein
                      organism = Pavlova pinguis
SEQUENCE: 33
MVAPPITLEW LLSPKLKDAV FGGEVLYFSI AYLFLAPILK RTPLVDTRKG AYKSGMIAYN   60
VIMCVFSLVC FICQLAALGY DMGYLQWVRD LTGDEIVPLY QDVSPSPAFS NKLFKYSSIA  120
FHYSKYVEYM DTAWLVMKGK PVSLLQGFHH FGAAWDTYFG ITFQNEGIYV FVVLNAFIHT  180
IMYAYYAATA AGLKFSLKFV ITLMQITQFN VGFVMVYHYI TLEYFRNSPE LVFSYLFNYA  240
YVCTVLLLFM QFFYMDNFGK KKAAAAAGKK KK                                 272

SEQ ID NO: 34         moltype = DNA   length = 840
FEATURE               Location/Qualifiers
source                1..840
                      mol_type = other DNA
                      organism = Pavlova salina
SEQUENCE: 34
atggcgactg aagggatgcc ggcgataacg ctggactggc tgctctcgcc cgggctgaag   60
gatgccgtaa ttgcgcggga ggtgctctac ttttcgcttg ggtatctgct gctcgagccc  120
atcctcaagc gctcaccgtt tgtggacaag cgcaagggcg cataccgcaa cggcatgatc  180
gcgtacaaca tcctcatgtg cggtttctcg ctggtatgct cgtgtgcca gatggcggcg  240
ctcggccttg atcgcggcca cctgcagttt gtccgcgacc tcacgggcga cagcgtggtg  300
```

-continued

```
cagctctacc aggacgtgag cccatcccct gcattcgcga acaagctctt ccggtactca    360
gcggtggcgt tccactactc aaagtacgtg gagtacatgg acacagcgtg gcttgtgctg    420
aagggcaagc ccgtctcgtt cctgcagggc ttccaccact tcggcgccgc gtgggacacc    480
tactttggca tcacgtttca gaacgagggc acctacgtct ttgtgctgct caacgcattc    540
atccacacaa tcatgtacac ctactacggc gcgacggcag cgggcatcaa aatctcgatg    600
aagccgctga tcaccctcat gcagatcacg cagttcctgc tgggcttcgc gctcgtctac    660
ccgtacattg acctcggcta cttccgtgcg tcgcccgagc tcgtgtggag ctacctgttc    720
aactatgcgt acgtactcat ggtgctcttc ctcttcatgc gcttcttcta ccacgacaac    780
tttagcaagc acaagccaat ctcgcgcatc gactccagca accgcatgaa aaccgagtag    840
```

SEQ ID NO: 35             moltype = AA   length = 279
FEATURE                   Location/Qualifiers
source                    1..279
                          mol_type = protein
                          organism = Pavlova salina SEQUENCE: 35
```
MATEGMPAIT LDWLLSPGLK DAVIGGEVLY FSLGYLLLEP ILKRSPFVDK RKGAYRNGMI     60
AYNILMCGFS LVCFVCQMAA LGLDRGHLQF VRDLTGDSVV QLYQDVSPSP AFANKLFRYS    120
AVAFHYSKYV EYMDTAWLVL KGKPVSFLQG FHHFGAAWDT YFGITFQNEG TYVFVLLNAF    180
IHTIMYTYYG ATAAGIKISM KPLITLMQIT QFLLGFALVY PYIDLGYFRA SPELVWSYLF    240
NYAYVLMVLF LFMRFFYHDN FSKHKPISRI DSSNRMKTE                          279
```

SEQ ID NO: 36             moltype = DNA   length = 1284
FEATURE                   Location/Qualifiers
source                    1..1284
                          mol_type = other DNA
                          organism = Pavlova salina SEQUENCE: 36
```
atgggacgcg gcggagacag cagtgggcag gcgcatccgg cggcggagct ggcggtcccg     60
agcgaccgcg cggaggtgag caacgctgac agcaaagcgc tgcacatcgt gctgtatggc    120
aagcgcgtgg atgtgaccaa gttccaacgc acgcacccgg gtggtagcaa ggtcttccgg    180
atcttccagg accgcgatgc gacggagcag ttcgagtcct accactcgaa gcgcgcgatc    240
aagatgatgg agggcatgct caagaagtct gaggatgctc ccgccgacac gcccttgccc    300
tcccagtcac cgatggggaa ggacttcaag gcgatgatcg agcggcacgt tgcagcgggt    360
tactacgatc catgcccgct cgatgagctg ttcaagctca gcctcgtgct cctcccgacc    420
tttgcgggca tgtacatgct caaggcgggc gtcggctccc cgctctgcgg cgccctcatg    480
gtgagctttg gctggtacct cgatggctgg ctcgcgcacg actatctgca ccactccgtc    540
ttcaaggggg ccgtcgcacg caccgtcggg tggaacaacg cggcgggcta cttcctcggc    600
ttcgtgcagg ggtatgcggt cgagtggtgg cgcgcgcggc ataacacgca ccacgtgtgc    660
accaatgagg acggctcgga ccccgacatc aaaacggcgc cgctgctcat atacgtgcgc    720
aacaagccga gcatcgccaa gcgcctgaac gccttccagc gctaccagca gtactactat    780
gtgccggtga tggcaatcct cgacctgtac tggcggctcg agtcgatcgc ctacgtcgcg    840
atgcgcctgc cgaagatgct gccgcaggcc ctcgcactcg tcgcgcacta cgccatcgtc    900
gcgtgggtct ttgcgggcaa ctaccacctg ctcccgctcg tgacggttct gcgcgggttt    960
ggcactggga tcaccgtttt cgcgacgcac tacggtgagg acattctcga cgcggaccag   1020
gtgcgtcaca tgacgctcgt cgagcagacg gcactcacct cgcgcaacat ctcgggcggc   1080
tggctcgtga acgtgctcac cggcttcatc tcactgcaga cggagcacca cctgttcccg   1140
atgatgccaa ccggcaacct catgactatc cagcccgagg tgcgcgcctt cttcaagaag   1200
cacggacttg agtaccgcga gggcaacctc attgagtgcg tgcggcagaa catccgtgcg   1260
cttgcattcg agcacctgct ttga                                         1284
```

SEQ ID NO: 37             moltype = AA   length = 427
FEATURE                   Location/Qualifiers
source                    1..427
                          mol_type = protein
                          organism = Pavlova salina SEQUENCE: 37
```
MGRGGDSSGQ AHPAAELAVP SDRAEVSNAD SKALHIVLYG KRVDVTKFQR THPGGSKVFR     60
IFQDRDATEQ FESYHSKRAI KMMEGMLKKS EDAPADTPLP SQSPMGKDFK AMIERHVAAG    120
YYDPCPLDEL FKLSLVLLPT FAGMYMLKAG VGSPLCGALM VSFGWYLDGW LAHDYLHHSV    180
FKGSVARTVG WNNAAGYFLG FVQGYAVEWW RARHNTHHVC TNEDGSDPDI KTAPLLIYVR    240
NKPSIAKRLN AFQRYQQYYY VPVMAILDLY WRLESIAYVA MRLPKMLPQA LALVAHYAIV    300
AWVFAGNYHL LPLVTVLRGF GTGITVFATH YGEDILDADQ VRHMTLVEQT ALTSRNISGG    360
WLVNVLTGFI SLQTEHHLFP MMPTGNLMTI QPEVRAFFKK HGLEYREGNL IECVRQNIRA    420
LAFEHLL                                                             427
```

SEQ ID NO: 38             moltype = AA   length = 116
FEATURE                   Location/Qualifiers
source                    1..116
                          mol_type = protein
                          organism = Tomato yellow leaf curl virus SEQUENCE: 38
```
MWDPLLNEFP ESVHGFRCML AIKYLQSVEE TYEPNTLGHD LIRDLISVVR ARDYVEATRR     60
YNHFHARLEG SPKAELRQPI QQPCCCPHCP RHKQATIMDV QAHVPEAQNI QNVSKP        116
```

SEQ ID NO: 39             moltype = DNA   length = 351
FEATURE                   Location/Qualifiers
source                    1..351
                          mol_type = other DNA

```
                      organism = Tomato yellow leaf curl virus
SEQUENCE: 39
atgtgggatc cacttctaaa tgaatttcct gaatctgttc acggatttcg ttgtatgtta    60
gctattaaat atttgcagtc cgttgaggaa acttacgagc ccaatacatt gggccacgat   120
ttaattaggg atcttatatc tgttgtaagg gcccgtgact atgtcgaagc gaccaggcga   180
tataatcatt tccacgcccg cctcgaaggt cgccgaagg ctgaacttcg acagcccata    240
cagcagccgt gctgctgtcc ccattgtcca aggcacaaac aagcgacgat catggacgta   300
caggcccatg taccggaagc ccagaatata cagaatgtat cgaagccctg a            351

SEQ ID NO: 40            moltype = AA   length = 389
FEATURE                  Location/Qualifiers
source                   1..389
                         mol_type = protein
                         organism = Arabidopsis thaliana
SEQUENCE: 40
MVIAAAVIVP LGLLFFISGL AVNLFQAVCY VLIRPLSKNT YRKINRVVAE TLWLELVWIV    60
DWWAGVKIQV FADNETFNRM GKEHALVVCN HRSDIDWLVG WILAQRSGCL GSALAVMKKS   120
SKFLPVIGWS MWFSEYLFLE RNWAKDESTL KSGLQRLSDF PRPFWLALFV EGTRFTEAKL   180
KAAQEYAASS ELPIPRNVLI PRTKGFVSAV SNMRSFVPAI YDMTVTIPKT SPPPTMLRLF   240
KGQPSVVHVH IKCHSMKDLP ESDDAIAQWC RDQFVAKDAL LDKHIAADTF PGQQEQNIGR   300
PIKSLAVVLS WACVLTLGAI KFLHWAQLFS SWKGITISAL GLGIITLCMQ ILIRSSQSER   360
STPAKVVPAK PKDNHHPESS SQTETEKEK                                     389

SEQ ID NO: 41            moltype = AA   length = 281
FEATURE                  Location/Qualifiers
source                   1..281
                         mol_type = protein
                         organism = Limnanthes alba
SEQUENCE: 41
MAKTRTSSLR NRRQLKTAVA ATADDDKDGI FMVLLSCFKI FVCFAIVLIT AVAWGLIMVL    60
LLPWPYMRIR LGNLYGHIIG GLVIWLYGIP IEIQGSEHTK KRAIYISNHA SPIDAFFVMW   120
LAPIGTVGVA KKEVIWYPLL GQLYTLAHHI RIDRSNPAAA IQSMKEAVRV ITEKNLSLIM   180
FPEGTRSGDG RLLPFKKGFV HLALQSHLPI VPMILTGTHL AWRKGTFRVR PVPITVKYLP   240
PINTDDWTVD KIDDYVKMIH DIYVRNLPAS QKPLGSTNRS K                       281

SEQ ID NO: 42            moltype = AA   length = 303
FEATURE                  Location/Qualifiers
source                   1..303
                         mol_type = protein
                         organism = Saccharomyces cerevisiae
SEQUENCE: 42
MSVIGRFLYY LRSVLVVLAL AGCGFYGVIA SILCTLIGKQ HLAQWITARC FYHVMKLMLG    60
LDVKVVGEEN LAKKPYIMIA NHQSTLDIFM LGRIFPPGCT VTAKKSLKYV PFLGWFMALS   120
GTYFLDRSKR QEAIDTLNKG LENVKKNKRA LWVFPEGTRS YTSELTMLPF KKGAFHLAQQ   180
GKIPIVPVVV SNTSTLVSPK YGVFNRGCMI VRILKPISTE NLTKDKIGEF AEKVRDQMVD   240
TLKEIGYSPA INDTTLPPQA IEYAALQHDK KVNKKIKNEP VPSVSISNDV NTHNEGSSVK   300
KMH                                                                303

SEQ ID NO: 43            moltype = AA   length = 373
FEATURE                  Location/Qualifiers
source                   1..373
                         mol_type = protein
                         organism = Micromonas pusilla
SEQUENCE: 43
MTPYQWFNVV SSLGYVLFTA TTSTVTMLVP AIILLRPVSA NLYARCTSWI FACWWTSCLF    60
ITERLNGVKV RVTGDALPLN APLLIMSNHK CNLDWMFLWS SAIRTGSMFH VGVFKAVAKS   120
EIRVIPIFGW GCKLNGFAYV RRRWSSDASH LTSWIQSQIR RRLNANWTLI FPEGTRYTDR   180
NKERSDLSCA KDGLEPMAGE ILRPRTKGLA LLLRESAKGG GYYRKIVDMT IQYTDADGKP   240
LKGAALGTRC FGQLAKGQLP VATCHVHFDV FSHKDVPAGE DEDEVEAWVW KRWRKKANML   300
EACASAGQFE GVREWSTSGT AVPLKTQTAL RCFFVLQGLV CVGVACSSTA FLAYVACAAV   360
GAAVIAQTDP AWW                                                     373

SEQ ID NO: 44            moltype = AA   length = 314
FEATURE                  Location/Qualifiers
source                   1..314
                         mol_type = protein
                         organism = Mortierella alpina
SEQUENCE: 44
MSIGSSNPVL LAAIPFVYLF VLPRVLAFLP QKAQFLAKCI VVLIATLIMS VAGCFISIVC    60
ALLDKRYVIN YVVSRLFSFL AARPCGVTYK IVGEEHLDKY PAIVVCNHQS SMDMMVLGRV   120
FPKHCVVMAK KELLYFPFLG MFMKLSNAIF IDRKNHKKAI ESTTQAVADM KKHNSGIWIF   180
PEGTRSRLDK ADLLPFKKGA FHLAIQAQLP ILPIISQGYS HIYDSSKRYF PGGELEIRVL   240
EPIPTTGLTT DDVNDLMDKT RNLMLKHLKE MDSQYSSSTA ENGSTHIDAD IAKSTATSIG   300
NTDDAITKRR TPKE                                                    314

SEQ ID NO: 45            moltype = AA   length = 391
FEATURE                  Location/Qualifiers
source                   1..391
                         mol_type = protein
```

-continued

```
                     organism = Braccisa napus
SEQUENCE: 45
MAMAAAAVIV PLGILFFISG LVVNLLQAVC YVLIRPLSKN TYRKINRVVA ETLWLELVWI   60
VDWWAGVKIQ VFADDETFNR MGKEHALVVC NHRSDIDWLV GWILAQRSGC LGSALAVMKK  120
SSKFLPVIGW SMWFSEYLFL ERNWAKDEST LKSGLQRLND FPRPFWLALF VEGTRFTEAK  180
LKAAQEYAAS SQLPVPRNVL IPRTKGFVSA VSNMRSFVPA IYDMTVAIPK TSPPPTMLRL  240
FKGQPSVVHV HIKCHSMKDL PESDDAIAQW CRDQFVAKDA LLDKHIAADT FPGQKEHNIG  300
RPIKSLAVVV SWACLLTLGA MKFLHWSNLF SSLKGIALSA LGLGIITLCM QILIRSSQSE  360
RSTPAKVAPA KPKDKHQSGS SSQTEVEEKQ K                                  391

SEQ ID NO: 46          moltype = AA   length = 390
FEATURE                Location/Qualifiers
source                 1..390
                       mol_type = protein
                       organism = Braccisa napus
SEQUENCE: 46
MAMAAAVIVP LGILFFISGL VVNLLQAICY VLIRPLSKNT YRKINRVVAE TLWLELVWIV   60
DWWAGVKIQV FADNETFNRM GKEHALVVCN HRSDIDWLVG WILAQRSGCL GSALAVMKKS  120
SKFLPVIGWS MWFSEYLFLE RNWAKDESTL KSGLQRLNDF PRPFWLALFV EGTRFTEAKL  180
KAAQEYAASS ELPVPRNVLI PRTKGFVSAV SNMRSFVPAI YDMTVAIPKT SPPPTMLRLF  240
KGQPSVVHVH IKCHSMKDLP ESDDAIAQWC RDQFVAKDAL LDKHIAADTF PGQQEQNIGR  300
PIKSLAVVLS WSCLLILGAM KFLHWSNLFS SWKGIAFSAL GLGIITLCMQ ILIRSSQSER  360
STPAKVVPAK PKDNHNDSGS SSQTEVEKQK                                    390

SEQ ID NO: 47          moltype = AA   length = 361
FEATURE                Location/Qualifiers
source                 1..361
                       mol_type = protein
                       organism = Phytophthora infestans
SEQUENCE: 47
MATKEAYVFP TLTEIKRSLP KDCFEASVPL SLYYTVRCLV IAVALTFGLN YARALPEVES   60
FWALDAALCT GYILLQGIVF WGFFTVGHDA GHGAFSRYHL LNPVVGTFMH SLILTPFESW  120
KLTHRHHHKN TGNIDRDEVF YPQRKADDHP LSRNLILALG AAWLAYLVEG FPPRKVNHFN  180
PFEPLFVRQV SAVVISLLAH FFVAGLSIYL SLQLGLKTMA IYYYGPVFVF GSMLVITTFL  240
HHNDEETPWY ADSEWTYVKG NLSSVDRSYG ALIDNLSHNI GTHQIHHLFP IIPHYKLKKA  300
TAAFHQAFPE LVRKSDEPII KAFFRVGRLY ANYGVVDQEA KLFTLKEAKA ATEAAAKTKS  360
T                                                                   361

SEQ ID NO: 48          moltype = AA   length = 418
FEATURE                Location/Qualifiers
source                 1..418
                       mol_type = protein
                       organism = Thalassiosira pseudonana
SEQUENCE: 48
MYRLTSTFLI ALAFSSSINA FSPQRPPRTI TKSKVQSTVL PIPTKDDLNF LQPQLDENDL   60
YLDDVNTPPR AGTIMKMLPK ETFNIDTATS LGYFGMDMAA VVSSMTLLNA IVTSDQYHAL  120
PLPLQAATVI PFQLLAGFAM WCMWCIGHDA GHSTVSKTKW INRVVGEVAH SVVCLTPFVP  180
WQMSHRKHHL NHNHIEKDYS HKWYSRDEFD DIPQLYKTFG YNPRMMQLPF LYFMYLALGI  240
PDGGHVVFYG RMWEGVSLQK KFDAAISVAV SCATAGSLWM NMGTADFTVV CMVPWLVLSW  300
WLFMVTYLQH HSEDGKLYTD ETFTFEKGAF ETVDRSYGKL INRMSHHMMD GHVVHHLFFE  360
RVPHYRLEAA TEALVKGMDE TGQKHLYKYI DTPDFNAEIV NGFRDNWFLV EEENIKRE    418

SEQ ID NO: 49          moltype = AA   length = 363
FEATURE                Location/Qualifiers
source                 1..363
                       mol_type = protein
                       organism = Pythium irregulare
SEQUENCE: 49
MASTSAAQDA APYEFPPSLTE IKRALPSECF EASVPLSLYY TARSLALAGS LAVALSYARA   60
LPLVQANALL DATLCTGYVL LQGIVFWGFF TVGHDCGHGA FSRSHVLNFS VGTLMHSIIL  120
TPFESWKLSH RHHHKNTGNI DKDEIFYPQR EADSHPVSRH LVMSLGSAWF AYLFAGFPPR  180
TMNHFNPWEA MYVRRVAAVI ISLGVLFAFA GLYSYLTFVL GFTTMAIYYF GPLFIFATML  240
VVTTFLHHND EETPWYADSE WTYVKGNLSS VDRSYGALID NLSHNIGTHQ IHHLFPIIPH  300
YKLNDATAAF AKAFPPELVRK NAAPIIPTFF RMAAMYAKYG VVDTDAKTFT LKEAKAAAKT  360
KSS                                                                 363

SEQ ID NO: 50          moltype = DNA   length = 18
FEATURE                Location/Qualifiers
misc_feature           1..18
                       note = Oligonucleotide primer
source                 1..18
                       mol_type = other DNA
                       organism = synthetic construct
SEQUENCE: 50
gcgaagcaca tcgagtca                                                 18

SEQ ID NO: 51          moltype = DNA   length = 20
FEATURE                Location/Qualifiers
misc_feature           1..20
```

-continued

```
                              note = Oligonucleotide primer
source                        1..20
                              mol_type = other DNA
                              organism = synthetic construct
SEQUENCE: 51
ggttgaggtg gtagctgagg                                        20

SEQ ID NO: 52       moltype = DNA  length = 23
FEATURE             Location/Qualifiers
misc_feature        1..23
                    note = Oligonucleotide primer
source              1..23
                    mol_type = other DNA
                    organism = synthetic construct
SEQUENCE: 52
tctctacccg tctcacatga cgc                                    23

SEQ ID NO: 53       moltype = DNA  length = 19
FEATURE             Location/Qualifiers
misc_feature        1..19
                    note = Oligonucleotide primer
source              1..19
                    mol_type = other DNA
                    organism = synthetic construct
SEQUENCE: 53
atacaagcac ggtggatgg                                         19

SEQ ID NO: 54       moltype = DNA  length = 22
FEATURE             Location/Qualifiers
misc_feature        1..22
                    note = Oligonucleotide primer
source              1..22
                    mol_type = other DNA
                    organism = synthetic construct
SEQUENCE: 54
tggtctaaca ggtctaggag ga                                     22

SEQ ID NO: 55       moltype = DNA  length = 26
FEATURE             Location/Qualifiers
misc_feature        1..26
                    note = Oligonucleotide primer
source              1..26
                    mol_type = other DNA
                    organism = synthetic construct
SEQUENCE: 55
tggcaaagag atttcgagct tcctgc                                 26

SEQ ID NO: 56       moltype = DNA  length = 22
FEATURE             Location/Qualifiers
misc_feature        1..22
                    note = Oligonucleotide primer
source              1..22
                    mol_type = other DNA
                    organism = synthetic construct
SEQUENCE: 56
caagcaccgt agtaagagag ca                                     22

SEQ ID NO: 57       moltype = DNA  length = 20
FEATURE             Location/Qualifiers
misc_feature        1..20
                    note = Oligonucleotide primer
source              1..20
                    mol_type = other DNA
                    organism = synthetic construct
SEQUENCE: 57
cagacagcct gaggttagca                                        20

SEQ ID NO: 58       moltype = DNA  length = 26
FEATURE             Location/Qualifiers
misc_feature        1..26
                    note = Oligonucleotide primer
source              1..26
                    mol_type = other DNA
                    organism = synthetic construct
SEQUENCE: 58
tccccacttc ttagcgaaag gaacga                                 26
```